United States Patent
Geneste et al.

(10) Patent No.: US 9,840,495 B2
(45) Date of Patent: Dec. 12, 2017

(54) OXINDOLE DERIVATIVES CARRYING A PIPERIDYL-SUBSTITUTED AZETIDINYL SUBSTITUENT AND USE THEREOF FOR TREATING VASOPRESSINE-RELATED DISEASES

(71) Applicants: AbbVie Deutschland GmbH & Co. KG, Wiesbaden (DE); AbbVie Inc., North Chicago, IL (US)

(72) Inventors: Hervé Geneste, Ludwigshafen (DE); Wilfried Hornberger, Ludwigshafen (DE); Charles W. Hutchins, Green Oaks, IL (US); Katja Jantos, Ludwigshafen (DE); Andreas Kling, Ludwigshafen (DE); Loic Laplanche, Ludwigshafen (DE); Marcel Van Gaalen, Ludwigshafen (DE)

(73) Assignees: ABBVIE DEUTSCHLAND GMBH & CO. KG, Wiesbaden (DE); ABBVIE INC., North Chicago, IL (US)

( * ) Notice: Subject to any disclaimer, the term of this patent is extended or adjusted under 35 U.S.C. 154(b) by 0 days.

(21) Appl. No.: 15/106,670

(22) PCT Filed: Dec. 19, 2014

(86) PCT No.: PCT/EP2014/078699
§ 371 (c)(1),
(2) Date: Jun. 20, 2016

(87) PCT Pub. No.: WO2015/091931
PCT Pub. Date: Jun. 25, 2015

(65) Prior Publication Data
US 2017/0008875 A1    Jan. 12, 2017

Related U.S. Application Data

(60) Provisional application No. 61/919,281, filed on Dec. 20, 2013.

(51) Int. Cl.
| | |
|---|---|
| *A01N 43/00* | (2006.01) |
| *A61K 31/00* | (2006.01) |
| *C07D 401/14* | (2006.01) |
| *C07D 401/04* | (2006.01) |
| *C07B 59/00* | (2006.01) |
| *C07D 405/14* | (2006.01) |
| *C07D 491/107* | (2006.01) |

(52) U.S. Cl.
CPC .......... *C07D 401/14* (2013.01); *C07B 59/002* (2013.01); *C07D 401/04* (2013.01); *C07D 405/14* (2013.01); *C07D 491/107* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 2008/0318923 A1 | 12/2008 | Sekiguchi et al. | |
| 2011/0065720 A1* | 3/2011 | Netz ................... | C07D 401/04 514/253.09 |
| 2011/0092516 A1 | 4/2011 | Hager-Wernet et al. | |
| 2011/0257194 A1 | 10/2011 | Hager-Wernet et al. | |
| 2014/0275110 A1 | 9/2014 | Oost et al. | |

(Continued)

FOREIGN PATENT DOCUMENTS

| | | |
|---|---|---|
| WO | 2005030755 | 4/2005 |
| WO | 2006005609 | 1/2006 |
| WO | 2006080574 | 8/2006 |

(Continued)

OTHER PUBLICATIONS

Thibonnier, M., "Development and therapeutic indications of orally-active non-peptide vasopressin receptor antagonists." Expert Opinion on Investigational Drugs, 1998, 7(5), 729-740.

(Continued)

*Primary Examiner* — Dennis Heyer
*Assistant Examiner* — Daniel M Podgorski
(74) *Attorney, Agent, or Firm* — Neal, Gerber & Eisenberg LLP

(57) ABSTRACT

The present invention relates to novel substituted oxindole derivatives of formula (I) wherein the variables are as defined in the claims and description; to pharmaceutical compositions comprising them, and to their use for treatment of vasopressin-related disorders.

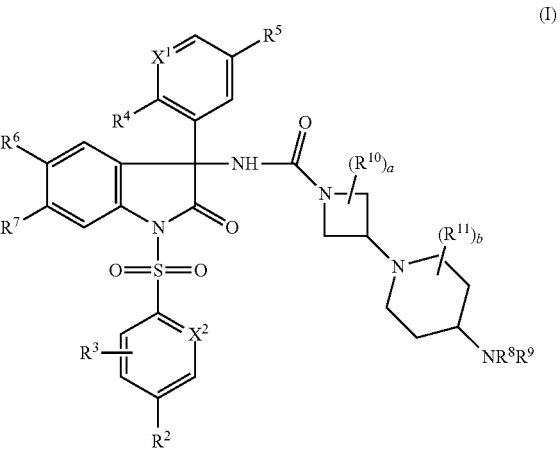

29 Claims, No Drawings

(56) References Cited

U.S. PATENT DOCUMENTS

2014/0303138 A1   10/2014   Braje et al.

FOREIGN PATENT DOCUMENTS

| WO | 2008080970 | 7/2008 |
| WO | 2008080971 | 7/2008 |
| WO | 2008080972 | 7/2008 |
| WO | 2008080973 | 7/2008 |
| WO | 2009071687 | 6/2009 |
| WO | 2009071689 | 6/2009 |
| WO | 2009071690 | 6/2009 |
| WO | 2009071691 | 6/2009 |
| WO | 2009083559 | 7/2009 |
| WO | 2010009775 | 1/2010 |
| WO | 2010142739 | 12/2010 |

OTHER PUBLICATIONS

Ryckmans, T. "Modulation of the vasopressin system for the treatment of CNS diseases" Current Opinion in Drug Discovery & Development, 2010, 13 (5), 538-547.

Decaux, G. et al., "Non-peptide arginine-vasopressin antagonists: the vaptans," Lancet, 2010, 371, 1624-1632.

Lemmens-Gruber, R. et al. "Vasopressin antagonists," Cellular and Molecular Life Sciences, 2006, 63, 1766-1779.

Diaz, G. J. et al., "The [3H]dofetilide binding assay is a predictive screening tool for hERG blockade and proarrhythmia: Comparison of intact cell and membrane preparations and effects of altering [K-F]o," Journal of Pharmacological and Toxicological Methods, 2004, 50, 187-199.

International Report on Patentability for PCT Application PCT/EP2014/078699 dated Jun. 21, 2016.

* cited by examiner

OXINDOLE DERIVATIVES CARRYING A PIPERIDYL-SUBSTITUTED AZETIDINYL SUBSTITUENT AND USE THEREOF FOR TREATING VASOPRESSINE-RELATED DISEASES

CROSS-REFERENCE TO RELATED APPLICATIONS

This is a National Stage of International Patent Application No. PCT/EP2014/078699 filed on Dec. 19, 2014, which claims priority to U.S. Patent Application No. 61/919,281, filed on Dec. 20, 2013, the entire contents of which are incorporated herein by reference.

The present invention relates to novel substituted oxindole derivatives, pharmaceutical compositions comprising them, and their use for the treatment of vasopressin-related disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3 and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740; T. Ryckmans, Current Opinion in Drug Discovery & Development 13 (2010), 538-547; G. Decaux et al., Lancet 371 (2008), 1624-1632; R. Lemmens-Gruber, M. Kamyar, Cell. Mol. Life Sci. 63 (2006), 1766-1779).

1-(Het)Arylsulfonyl-1,3-dihydro-2H-indol-2-ones have previously been described as ligands of vasopressin receptors, for example in WO 2005/030755, WO 2006/005609, WO 2006/080574, WO 2008/080970, WO 2008/080971, WO 2008/080972, WO 2008/080973, WO 2009/071687, WO 2009/071689, WO 2009/071690, WO2009/071691, WO 2009/083559, WO 2010/009775 or WO 2010/142739.

Besides the binding affinity for the vasopressin V1b receptor, further properties may be advantageous for the treatment and/or prophylaxis of vasopressin-related disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)"). A larger quotient Ki(V1a)/Ki(V1b) means a greater V1b selectivity;

2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)"). A larger quotient Ki(V2)/Ki(V1b) means a greater V1b selectivity;

3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)"). A larger quotient Ki(OT)/Ki(V1b) means a greater V1b selectivity.

4.) the metabolic stability, for example determined from the half-lives, measured in vitro, in liver microsomes from various species (e.g. rat or human);

5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

6.) a suitable solubility in water (in mg/ml);

7.) suitable pharmacokinetics (time course of the concentration of the compound of the invention in plasma or in tissue, for example brain). The pharmacokinetics can be described by the following parameters: half-life (in h), volume of distribution (in 1·kg−1), plasma clearance (in 1·h−1·kg−1), AUC (area under the curve, area under the concentration-time curve, in ng·h·1−1), oral bioavailability (the dose-normalized ratio of AUC after oral administration and AUC after intravenous administration), the so-called brain-plasma ratio (the ratio of AUC in brain tissue and AUC in plasma);

8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187 199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was therefore an object of the present invention to provide compounds for the treatment or prophylaxis of various vasopressin-related diseases. The compounds were intended to have a high activity and selectivity, especially a high affinity and selectivity vis-à-vis the vasopressin V1b receptor. In addition, the substance of the invention was intended to have one or more of the aforementioned advantages 1.) to 8.).

The object is achieved by compounds of the formula I

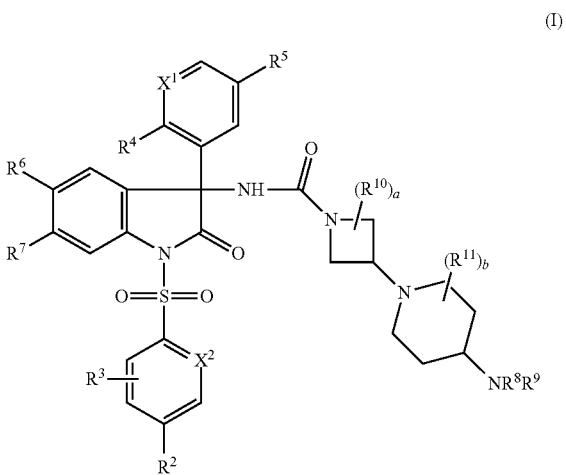

wherein $X^1$ is N or CH;

$X^2$ is C—$R^1$ or N;

$R^1$ and $R^2$, independently of each other, are selected from hydrogen, halogen, cyano, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^3$ is selected from hydrogen, halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^4$ is selected from $C_1$-$C_3$-alkoxy;

$R^5$ is selected from hydrogen and $C_1$-$C_3$-alkoxy;

$R^6$ is selected from cyano and halogen;

$R^7$ is selected from hydrogen, halogen and cyano;

$R^8$ is selected from hydrogen, cyano, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_7$-cycloalkyl, $C_3$-$C_7$-halocycloalkyl and phenyl which may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

$R^9$ is selected from $C_1$-$C_4$-alkoxy-$C_1$-$C_4$-alkyl, $C_1$-$C_4$-haloalkoxy-$C_1$-$C_4$-alkyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, phenoxy, where the phenyl moiety may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or $R^8$ and $R^9$, together with the nitrogen atom they are bound to, form a 3-, 4-, 5-, 6- or 7-membered saturated, partially unsaturated or maximally unsaturated heterocyclic ring, where the heterocyclic ring may contain 1 or 2 further heteroatoms or heteroatom groups selected from O, N, S, NO, SO and $SO_2$ as ring members, and where the heterocyclic ring may carry 1 or 2 substituents $R^{12}$ and/or 1 or 2 substituents $R^{13}$; where in case that the heterocyclic ring does not contain 1 or 2 further heteroatoms or heteroatom groups as ring members, the heterocyclic ring carries 1 or 2 substituents $R^{12}$ and optionally 1 or 2 substituents $R^{13}$;

$R^{10}$ and $R^{11}$, independently of each other and independently of each occurrence, are selected from halogen, $C_1$-$C_4$-alkyl, $C_1$-$C_4$-haloalkyl, $C_1$-$C_4$-alkoxy and $C_1$-$C_4$-haloalkoxy, with the proviso that $R^{10}$ and $R^{11}$ are not halogen, $C_1$-$C_4$-alkoxy or $C_1$-$C_4$-haloalkoxy if they are bound to a carbon atom in α-position to a nitrogen ring atom; or two non-geminal radicals $R^{10}$ form together a group —$(CH_2)_n$—, where n is 1, 2, 3 or 4, where 1 or 2 hydrogen atoms in this group may be replaced a methyl group; or two non-geminal radicals $R^{11}$ form together a group —$(CH_2)_n$—, where n is 1, 2, 3 or 4, where 1 or 2 hydrogen atoms in this group may be replaced a methyl group;

each $R^{12}$ is independently selected from halogen, hydroxyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, phenoxy, benzyloxy, where the phenyl moiety in the two last-mentioned radicals may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

or two radicals $R^{12}$, together with the atom(s) they are bound to, form a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

each $R^{13}$ is independently selected from halogen, hydroxyl, cyano, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_7$-cycloalkyl, $C_3$-$C_7$-halocycloalkyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, phenyl, phenoxy and a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the phenyl moieties or the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

a is 0, 1 or 2; and b is 0, 1, 2, 3 or 4;

and the N-oxides, stereoisomers and pharmaceutically acceptable salts thereof, and the compound of the formula I, wherein at least one of the atoms has been replaced by its stable, non-radioactive isotope.

Accordingly, the present invention relates to compounds of the formula I (also "compounds I" hereinafter) and the N-oxides, stereoisomers and the pharmaceutically acceptable salts of the compounds I of the compounds I.

In another aspect, the invention relates to a pharmaceutical composition comprising a therapeutically effective amount of at least one compound of formula I or an N-oxide, a stereoisomer or a pharmaceutically acceptable salt thereof, or comprising at least one compound as defined above or below wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

In yet another aspect, the invention relates to a compound of formula I or an N-oxide, a stereoisomer or a pharmaceutically acceptable salt thereof for use as a medicament.

In yet another aspect, the invention relates to a compound of formula I or an N-oxide, a stereoisomer or a pharmaceutically acceptable salt thereof for the treatment and/or prophylaxis of vasopressin-related diseases, especially of disorders which respond to the modulation of the vasopressin receptor, in particular of the V1b receptor.

In yet another aspect, the invention relates to the use of a compound of formula I or of an N-oxide, a stereoisomer or a pharmaceutically acceptable salt thereof for the manufacture of a medicament for the treatment and/or prophylaxis of vasopressin-related diseases; especially of disorders which respond to the modulation of the vasopressin receptor, in particular of the V1b receptor.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhauser Verlag, vol. 10, pp. 224-285. These include for example hydrochloric acid, citric acid, tartaric acid, lactic acid, phosphoric acid, methanesulfonic acid, acetic acid, trifluoroacetic acid, formic acid, maleic acid and fumaric acid.

Halogen in the terms of the present invention is fluorine, chlorine, bromine or iodine, preferably fluorine, chlorine or bromine and especially fluorine or chlorine.

$C_1$-$C_3$-Alkyl is a linear or branched alkyl radical having 1 to 3 carbon atoms, such as methyl, ethyl, n-propyl or isopropyl. $C_1$-$C_4$-Alkyl is a linear or branched alkyl radical having 1 to 4 carbon atoms, such as methyl, ethyl, n-propyl, isopropyl, n-butyl, sec-butyl, isobutyl or tert-butyl.

Fluorinated alkyl is a straight-chain or branched alkyl group having from 1 to 4 (=fluorinated $C_1$-$C_4$-alkyl), in particular 1 to 3 carbon atoms (=fluorinated $C_1$-$C_3$-alkyl), more preferably 1 or 2 carbon atoms (=fluorinated $C_1$-$C_2$-alkyl), wherein at least one, e.g. 1, 2, 3, 4 or all of the hydrogen atoms are replaced by fluorine atoms. Examples for fluorinated $C_1$-$C_2$-alkyl are fluoromethyl, difluoromethyl, trifluoromethyl, 1-fluoroethyl, (R)-1-fluoroethyl, (S)-1-fluoroethyl, 2-fluoroethyl, 1,1-difluoroethyl, 2,2-difluoroethyl, 2,2,2-trifluoroethyl, pentafluoroethyl and the like. Examples for fluorinated $C_1$-$C_3$-alkyl are, apart those mentioned above for fluorinated $C_1$-$C_2$-alkyl, 1-fluoropropyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, 2-fluoropropyl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl and the like. Examples for fluorinated $C_1$-$C_4$-alkyl are, apart those mentioned above for fluorinated $C_1$-$C_3$-alkyl, 1-fluorobutyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

$C_1$-$C_4$-Haloalkyl is $C_1$-$C_4$-alkyl as defined above wherein at least one, e.g. 1, 2, 3, 4 or all of the hydrogen atoms are replaced by a halogen atom. Examples are, apart those mentioned above for fluorinated $C_1$-$C_4$-alkyl, chloromethyl, bromomethyl, dichloromethyl, trichloromethyl, chlorofluoromethyl, dichlorofluoromethyl, chlorodifluoromethyl, 1-chloroethyl, 1-bromoethyl, 2-chloro-2-fluoroethyl, 2-chloro-2,2-difluoroethyl, 2,2-dichloro-2-fluoroethyl, 2,2,2-trichloroethyl, 3-chloropropyl, 4-chlorobutyl and the like.

$C_1$-$C_3$-Hydroxyalkyl is $C_1$-$C_3$-alkyl as defined above wherein one of the hydrogen atoms is replaced by a hydroxyl group. Examples are hydroxymethyl, 1- and 2-hydroxyethyl, 1-, 2- and 3-hydroxy-n-propyl, 1-(hydroxymethyl)-ethyl and the like.

$C_3$-$C_7$-Cycloalkyl is a monocyclic saturated hydrocarbon radical having 3 to 7, in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of $C_3$-$C_4$-cycloalkyl comprise cyclopropyl and cyclobutyl. Examples of $C_3$-$C_5$-cycloalkyl comprise cyclopropyl, cyclobutyl and cyclopentyl. Examples of $C_3$-$C_6$-cycloalkyl comprise cyclopropyl, cyclobutyl, cyclopentyl and cyclohexyl. Examples of $C_3$-$C_7$-cycloalkyl comprise cyclopropyl, cyclobutyl, cyclopentyl, cyclohexyl and cycloheptyl.

$C_3$-$C_7$-Halocycloalkyl is a monocyclic saturated hydrocarbon radical having 3 to 7, in particular 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

$C_1$-$C_3$-Alkoxy is a linear or branched alkyl radical linked via an oxygen atom and having 1 to 3 carbon atoms. Examples are methoxy, ethoxy, n-propoxy and isopropoxy. $C_1$-$C_4$-Alkoxy is a linear or branched alkyl radical linked via an oxygen atom and having 1 to 4 carbon atoms. Examples are methoxy, ethoxy, n-propoxy, isopropoxy, n-butoxy, sec-butoxy, isobutoxy and tert-butoxy.

$C_1$-$C_4$-Haloalkoxy is $C_1$-$C_4$-alkoxy as defined above wherein at least one, e.g. 1, 2, 3, 4 or all of the hydrogen atoms are replaced by a halogen atom. Preferably, $C_1$-$C_4$-haloalkoxy is fluorinated $C_1$-$C_4$-alkoxy. This is a straight-chain or branched alkoxy group having from 1 to 4, in particular 1 to 3 carbon atoms (=fluorinated $C_1$-$C_3$-alkoxy), more preferably 1 or 2 carbon atoms (=fluorinated $C_1$-$C_2$-alkoxy), wherein at least one, e.g. 1, 2, 3, 4 or all of the hydrogen atoms are replaced by fluorine atoms, such as in fluoromethoxy, difluoromethoxy, trifluoromethoxy, 1-fluoroethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1-fluoropropoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, 2-fluoro-1-methylethoxy, (R)-2-fluoro-1-methylethoxy, (S)-2-fluoro-1-methylethoxy, 2,2-difluoro-1-methylethoxy, (R)-2,2-difluoro-1-methylethoxy, (S)-2,2-difluoro-1-methylethoxy, 1,2-difluoro-1-methylethoxy, (R)-1,2-difluoro-1-methylethoxy, (S)-1,2-difluoro-1-methylethoxy, 2,2,2-trifluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc $C_3$-$C_7$-Cycloalkoxy is a monocyclic saturated hydrocarbon radical linked via an oxygen atom and having 3 to 7, in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of $C_3$-$C_4$-cycloalkoxy comprise cyclopropoxy and cyclobutoxy. Examples of $C_3$-$C_5$-cycloalkoxy comprise cyclopropoxy, cyclobutoxy and cyclopentoxy. Examples of $C_3$-$C_6$-cycloalkoxy comprise cyclopropoxy, cyclobutoxy, cyclopentoxy and cyclohexoxy. Examples of $C_3$-$C_7$-cycloalkoxy comprise cyclopropoxy, cyclobutoxy, cyclopentoxy, cyclohexoxy and cycloheptoxy.

$C_3$-$C_7$-Halocycloalkoxy is a monocyclic saturated hydrocarbon radical linked via an oxygen atom and having 3 to 7, in particular 3 to 6 ("$C_3$-$C_6$-halocycloalkoxy") or 3 to 5 ("$C_3$-$C_5$-halocycloalkoxy") or 3 to 4 ("$C_3$-$C_4$-halocycloalkoxy") carbon ring members (as mentioned above) in which some or all of the hydrogen atoms are replaced by halogen atoms as mentioned above, in particular fluorine, chlorine and bromine.

"$C_1$-$C_4$-Alkoxy-$C_1$-$C_4$-alkyl" refers to a straight-chain or branched alkyl group having 1 to 4 carbon atoms, as defined above, where one hydrogen atom is replaced by a $C_1$-$C_4$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

$C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

$C_1$-$C_4$-Alkylthio is a $C_1$-$C_4$-alkyl group, as defined above, attached via a sulfur atom. Examples are methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio).

$C_1$-$C_4$-Haloalkylthio is a $C_1$-$C_4$-haloalkyl group, as defined above, attached via a sulfur atom. Examples are $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio.

$C_1$-$C_4$-Alkylsulfinyl is a $C_1$-$C_1$-alkyl group, as defined above, attached via a sulfinyl [S(O)] group. Examples are methylsulfinyl, ethylsulfinyl, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl).

$C_1$-$C_4$-Haloalkylsulfinyl is a $C_1$-$C_4$-haloalkyl group, as defined above, attached via a sulfinyl [S(O)] group. Examples are $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, $S(O)C_2F_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl.

$C_1$-$C_4$-Alkylsulfonyl is a $C_1$-$C_4$-alkyl group, as defined above, attached via a sulfonyl [S(O)$_2$] group. Examples are methylsulfonyl, ethylsulfonyl, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl).

$C_1$-$C_4$-Haloalkylsulfonyl is a $C_1$-$C_4$-haloalkyl group, as defined above, attached via a sulfonyl [S(O)$_2$] group. Examples are $S(O)_2CH_2F$, $S(O)_2CHF_2$, $S(O)_2CF_3$, $S(O)_2CH_2Cl$, $S(O)_2CHCl_2$, $S(O)_2CCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, $S(O)_2C_2F_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonyl, 1-($CH_2Br$)-2-bromoethylsulfonyl, 4-fluorobutylsulfonyl, 4-chlorobutylsulfonyl, 4-bromobutylsulfonyl or nonafluorobutylsulfonyl.

$C_1$-$C_4$-Alkylcarbonyl is a $C_1$-$C_4$-alkyl group, as defined above, attached via a carbonyl [C(=O)] group. Examples are acetyl (methylcarbonyl), propionyl (ethylcarbonyl), propylcarbonyl, isopropylcarbonyl, n-butylcarbonyl and the like.

$C_1$-$C_4$-Haloalkylcarbonyl is a $C_1$-$C_4$-haloalkyl group, as defined above, attached via a carbonyl [C(=O)] group. Examples are trifluoromethylcarbonyl, 2,2,2-trifluoroethylcarbonyl and the like.

The term "3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members" denotes a 3-, 4-, 5-, 6- or 7-membered saturated, partially unsaturated or maximum unsaturated heteromonocyclic ring containing 1, 2 or 3 heteroatoms or heteroatom groups selected from O, N, S, NO, SO and $SO_2$, as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

The term "3-, 4-, 5-, 6- or 7-membered saturated, partially unsaturated or maximum unsaturated heterocyclic ring containing 1, 2 or 3 heteroatoms or heteroatom groups selected from O, N, S, NO, SO and $SO_2$, as ring members" [wherein "maximum unsaturated" includes also "aromatic"] as used herein denotes monocyclic radicals, the monocyclic radicals being saturated, partially unsaturated or maximum unsaturated (including aromatic). 7-membered rings cannot be aromatic; they are homoaromatic if maximally unsaturated (3 double bonds).

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl-, -2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

The compounds of the invention of the formula I and their N-oxides, stereoisomers and pharmacologically acceptable salts may also be present in the form of solvates or hydrates. Solvates mean in the context of the present invention crystalline forms of the compounds I or of their pharmaceutically acceptable salts which comprise solvent molecules incorporated in the crystal lattice. The solvent molecules are preferably incorporated in stoichiometric ratios. Hydrates are a specific form of solvates; the solvent in this case being water.

The statements made hereinafter concerning suitable and preferred features of the invention, especially concerning the radicals $R^1$, $R^2$, $R^3$, $R^4$, $R^5$, $R^6$, $R^7$, $R^8$, $R^9$, $R^{10}$, $R^{11}$, $R^{12}$, $R^{13}$, $X^1$, $X^2$, a and b in the compound I, but also concerning the features of the process of the invention and of the use according to the invention apply both taken on their own as well as preferably in any possible combination with one another.

The compounds I are preferably provided in the form of the free base (i.e. according to structural formula I) or in the form of their acid addition salts.

In a preferred embodiment, $X^2$ is C—$R^1$ and $R^1$, $R^2$ and $R^3$, independently of each other, are selected from hydrogen, halogen, $C_1$-$C_3$-alkyl, fluorinated $C_1$-$C_3$-alkyl, $C_1$-$C_3$-alkoxy and fluorinated $C_1$-$C_3$-alkoxy. More preferably, $R^1$, $R^2$ and $R^3$, independently of each other, are selected from hydrogen, fluorine and methoxy.

In particular, $R^1$ is selected from hydrogen, fluorine and methoxy.

In particular, $R^2$ is selected from hydrogen, fluorine and methoxy.

In particular, $R^3$ is selected from hydrogen and fluorine.

$R^3$ is preferably bound in 3- or 5-position, in particular in 5-position, relative to the 2- and 4-positions of $R^1$ and $R^2$.

In another preferred embodiment, $X^2$ is N and $R^2$ and $R^3$, independently of each other, are selected from hydrogen, halogen, $C_1$-$C_3$-alkyl, fluorinated $C_1$-$C_3$-alkyl, $C_1$-$C_3$-alkoxy and fluorinated $C_1$-$C_3$-alkoxy. More preferably, $R^1$, $R^2$ and $R^3$, independently of each other, are selected from hydrogen, fluorine and methoxy.

In this case, $R^2$ is preferably selected from hydrogen, fluorine and methoxy, and is in particular methoxy.

In this case, $R^3$ is preferably selected from hydrogen, fluorine and methoxy, and is in particular hydrogen.

Preferably, $R^4$ is selected from methoxy and ethoxy.

Preferably, $R^5$ is hydrogen or methoxy, and in particular hydrogen.

Preferably, $R^6$ is selected from cyano, fluorine and chlorine.

Preferably, $R^7$ is selected from hydrogen and fluorine.

In a preferred embodiment, $R^8$ is selected from hydrogen, $C_1$-$C_4$-alkyl, $C_1$-$C_4$-haloalkyl, $C_3$-$C_6$-cycloalkyl and $C_3$-$C_6$-halocycloalkyl;

$R^9$ is selected from $C_1$-$C_4$-alkoxy-$C_1$-$C_4$-alkyl, $C_1$-$C_4$-haloalkoxy-$C_1$-$C_4$-alkyl, $C_1$-$C_4$-alkoxy, $C_1$-$C_4$-haloalkoxy, $C_3$-$C_6$-cycloalkoxy, $C_3$-$C_6$-halocycloalkoxy, and a 3-, 4-, 5- or 6-membered saturated, partially unsaturated or maximally unsaturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or $R^8$ and $R^9$, together with the nitrogen atom they are bound to, form a 3-, 4-, 5- or 6-membered saturated, partially unsaturated or maximally unsaturated heterocyclic ring, where the heterocyclic ring may contain 1 or 2 further heteroatoms or heteroatom groups selected from O, N, S, NO, SO and $SO_2$ as ring members, and where the heterocyclic ring may carry 1 or 2 substituents $R^{12}$ and/or 1 substituent $R^{13}$; where in case that the heterocyclic ring does not contain 1 or 2 further heteroatoms or heteroatom groups as ring members, the heterocyclic ring carries 1 or 2 substituents $R^{12}$ and optionally 1 substituent $R^{13}$;

each $R^{12}$ is independently selected from halogen, hydroxyl, $C_1$-$C_4$-alkoxy, $C_1$-$C_4$-haloalkoxy, $C_3$-$C_6$-cycloalkoxy, $C_3$-$C_6$-halocycloalkoxy, and a 3-, 4-, 5- or 6-membered saturated, partially unsaturated or maximally unsaturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;
or two radicals $R^{12}$, together with the atom(s) they are bound to, form a 3-, 4-, 5- or 6-membered saturated, partially unsaturated or maximally unsaturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and $R^{13}$ is selected from halogen, hydroxyl, cyano, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl, $C_3$-$C_6$-halocycloalkyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, phenyl, phenoxy and a 3-, 4-, 5- or 6-membered saturated, partially unsaturated or maximally unsaturated heterocyclic ring containing 1, 2 or 3 heteroatoms or heteroatom groups selected from O, N, S, NO, SO and $SO_2$ as ring members, where the phenyl moieties or the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy.

More preferably, $R^8$ is selected from hydrogen, $C_1$-$C_4$-alkyl, fluorinated $C_1$-$C_4$-alkyl, $C_3$-$C_6$-cycloalkyl and fluorinated $C_3$-$C_6$-cycloalkyl;

$R^9$ is selected from $C_1$-$C_4$-alkoxy-$C_1$-$C_4$-alkyl, fluorinated $C_1$-$C_4$-alkoxy-$C_1$-$C_4$-alkyl, $C_1$-$C_4$-alkoxy, fluorinated $C_1$-$C_4$-alkoxy, and a 3-, 4-, 5- or 6-membered saturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or $R^8$ and $R^9$, together with the nitrogen atom they are bound to, form a 3-, 4-, 5- or 6-membered saturated heterocyclic ring, where the heterocyclic ring may contain 1 or 2 further heteroatoms or heteroatom groups selected from O, N, S, NO, SO and $SO_2$ as ring members, and where the heterocyclic ring may carry 1 or 2 substituents $R^{12}$ and/or 1 substituent $R^{13}$; where in case that the heterocyclic ring does not contain 1 or 2 further heteroatoms or heteroatom groups as ring members, the heterocyclic ring carries 1 or 2 substituents $R^{12}$ and optionally 1 substituent $R^{13}$;

each $R^{12}$ is independently selected from halogen, hydroxyl, $C_1$-$C_4$-alkoxy, fluorinated $C_1$-$C_4$-alkoxy, and a 3-, 4-, 5- or 6-membered saturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or two radicals $R^{12}$, together with the atom(s) they are bound to, form a 3-, 4-, 5- or 6-membered saturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and $R^{13}$ is selected halogen, hydroxyl, cyano, $C_1$-$C_4$-alkyl, fluorinated $C_1$-$C_4$-alkyl, $C_1$-$C_4$-alkoxy-$C_1$-$C_4$-alkyl, fluorinated $C_1$-$C_4$-alkoxy-$C_1$-$C_4$-alkyl, $C_3$-$C_6$-cycloalkyl, fluorinated $C_3$-$C_6$-cycloalkyl, $C_1$-$C_4$-alkoxy, fluorinated $C_1$-$C_4$-alkoxy, and a 3-, 4-, 5- or 6-membered saturated, partially unsaturated or maximally unsaturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy.

In particular, $R^8$ is selected from hydrogen, $C_1$-$C_4$-alkyl and $C_3$-$C_6$-cycloalkyl;

$R^9$ is selected from $C_1$-$C_4$-alkoxy-$C_1$-$C_4$-alkyl, fluorinated $C_1$-$C_4$-alkoxy-$C_1$-$C_4$-alkyl, $C_1$-$C_4$-alkoxy, fluorinated $C_1$-$C_4$-alkoxy, and a 3-, 4-, 5- or 6-membered saturated heterocyclic ring containing 1 oxygen atom as ring member; or $R^8$ and $R^9$, together with the nitrogen atom they are bound to form a 3-, 4-, 5- or 6-membered saturated heterocyclic ring, where the heterocyclic ring contains 1 further oxygen atom as ring member, and where the heterocyclic ring may carry 1 or 2 substituents $R^{12}$; or form a 3-, 4-, 5- or 6-membered saturated heterocyclic ring which carries 1 or 2 substituents $R^{12}$; and each $R^{12}$ is independently selected from halogen, hydroxyl, $C_1$-$C_4$-alkoxy, and a 3-, 4-, 5- or 6-membered saturated heterocyclic ring containing 1 oxygen atom as ring member; or two radicals $R^{12}$ bound to the same carbon ring atom, together with this carbon atom they are bound to, form a 3-, 4-, 5- or 6-membered saturated heterocyclic ring containing 1 oxygen atom as ring member.

The saturated heterocyclic ring formed by $R^8$ and $R^9$ together with the nitrogen atom they are bound to is preferably selected from azetidin-1-yl carrying in the 3-position (relative to the 1-position of the nitrogen ring atom) 1 or 2 substituents $R^{12}$; isoxazolidin-2-yl, piperidin-1-yl carrying in the 4-position (relative to the 1-position of the nitrogen ring atom) 1 or 2 substituents $R^{12}$; and morpholin-1-yl, where $R^{12}$ is as defined above or, in particular, as defined below.

If two radicals $R^{12}$ bound to the same carbon ring atom together with this carbon ring atom form a ring, this is preferably a spiro-bound oxetan-3-yl ring; i.e. preferably the two radicals $R^{12}$ bound to the same carbon atom together form a group —$CH_2$—O—$CH_2$—.

Preferably, each $R^{10}$ is independently selected from halogen and $C_1$-$C_4$-alkyl, preferably from F, Cl and $CH_3$, with the proviso that $R^{10}$ is not halogen if it is bound to a carbon atom in α-position to a nitrogen ring atom; and is in particular $CH_3$.

Preferably, each $R^{11}$ is independently selected from halogen and $C_1$-$C_4$-alkyl, preferably from F, Cl and $CH_3$, with the proviso that $R^{11}$ is not halogen if it is bound to a carbon atom in α-position to a nitrogen ring atom; and is in particular $CH_3$;

or two non-geminal radicals $R^{11}$ form together a group —$CH_2$—.

In one embodiment, $X^1$ is N.
In another embodiment, $X^1$ is CH.
In one embodiment, $X^2$ is C—$R^1$.
In another embodiment, $X^2$ is N.
a is preferably 0 or 1, in particular 0.
b is preferably 0, 1 or 2, in particular 0.

The invention preferably relates to compounds of the formula I in which $R^1$ (if present), $R^2$ and $R^3$, independently of each other, are selected from hydrogen, halogen, $C_1$-$C_3$-alkyl, fluorinated $C_1$-$C_3$-alkyl, $C_1$-$C_3$-alkoxy and fluorinated $C_1$-$C_3$-alkoxy;
$R^4$ is selected from methoxy and ethoxy;
$R^5$ is hydrogen or methoxy;
$R^6$ is selected from cyano, fluorine and chlorine;
$R^7$ is hydrogen or fluorine;
$R^8$ is selected from hydrogen, $C_1$-$C_4$-alkyl, fluorinated $C_1$-$C_4$-alkyl, $C_3$-$C_6$-cycloalkyl and fluorinated $C_3$-$C_6$-cycloalkyl;
$R^9$ is selected from $C_1$-$C_4$-alkoxy-$C_1$-$C_4$-alkyl, fluorinated $C_1$-$C_4$-alkoxy-$C_1$-$C_4$-alkyl, $C_1$-$C_4$-alkoxy, fluorinated $C_1$-$C_4$-alkoxy, and a 3-, 4-, 5- or 6-membered saturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or $R^8$ and $R^9$, together with the nitrogen atom they are bound to, form a 3-, 4-, 5- or 6-membered saturated heterocyclic ring, where the heterocyclic ring may contain 1 or 2 further heteroatoms or heteroatom groups selected from O, N, S, NO, SO and $SO_2$ as ring members, and where the heterocyclic ring may carry 1 or 2 substituents $R^{12}$ and/or 1 substituent $R^{13}$; where in case that the heterocyclic ring does not contain 1 or 2 further heteroatoms or heteroatom groups as ring members, the heterocyclic ring carries 1 or 2 substituents $R^{12}$ and optionally 1 substituent $R^{13}$;

each $R^{12}$ is independently selected from halogen, hydroxyl, $C_1$-$C_4$-alkoxy, fluorinated $C_1$-$C_4$-alkoxy, and a 3-, 4-, 5- or 6-membered saturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or two radicals $R^{12}$, together with the atom(s) they are bound to, form a 3-, 4-, 5- or 6-membered saturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and $R^{13}$ is selected halogen, hydroxyl, cyano, $C_1$-$C_4$-alkyl, fluorinated $C_1$-$C_4$-alkyl, $C_1$-$C_4$-alkoxy-$C_1$-$C_4$-alkyl, fluorinated $C_1$-$C_4$-alkoxy-$C_1$-$C_4$-alkyl, $C_3$-$C_6$-cycloalkyl, fluorinated $C_3$-$C_6$-cycloalkyl, $C_1$-$C_4$-alkoxy, fluorinated $C_1$-$C_4$-alkoxy, and a 3-, 4-, 5- or 6-membered saturated, partially unsaturated or maximally unsaturated heterocyclic ring containing 1 or 2 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

each $R^{10}$ is independently selected from halogen and $C_1$-$C_4$-alkyl or two non-geminal radicals $R^{10}$ form together a group —$CH_2$— or —$CH_2CH_2$—;

each $R^{11}$ is independently selected from halogen and $C_1$-$C_4$-alkyl or two non-geminal radicals $R^{11}$ form together a group —$CH_2$— or —$CH_2CH_2$—;

a is 0, 1 or 2;
b is 0, 1 or 2;
and the pharmaceutically acceptable salts thereof.

The invention more preferably relates to compounds of the formula I in which $R^1$ (if present), $R^2$ and $R^3$, independently of each other, are selected from hydrogen, fluorine and methoxy;
$R^4$ is selected from methoxy and ethoxy;
$R^5$ is hydrogen or methoxy;
$R^6$ is selected from cyano, fluorine and chlorine;
$R^7$ is hydrogen or fluorine;
$R^8$ is selected from hydrogen, $C_1$-$C_4$-alkyl and $C_3$-$C_6$-cycloalkyl;
$R^9$ is selected from $C_1$-$C_4$-alkoxy-$C_1$-$C_4$-alkyl, fluorinated $C_1$-$C_4$-alkoxy-$C_1$-$C_4$-alkyl, $C_1$-$C_4$-alkoxy, fluorinated $C_1$-$C_4$-alkoxy, and a 3-, 4-, 5- or 6-membered saturated heterocyclic ring containing 1 oxygen atom as ring member; or $R^8$ and $R^9$, together with the nitrogen atom they are bound to form a 3-, 4-, 5- or 6-membered saturated heterocyclic ring, where the heterocyclic ring contains 1 further oxygen atom as ring member, and where the heterocyclic ring may carry 1 or 2 substituents $R^{12}$; or form a 3-, 4-, 5- or 6-membered saturated heterocyclic ring which carries 1 or 2 substituents $R^{12}$; and each $R^{12}$ is independently selected from halogen, hydroxyl, $C_1$-$C_4$-alkoxy, and a 3-, 4-, 5- or 6-membered saturated heterocyclic ring containing 1 oxygen atom as ring member; or two radicals $R^{12}$ bound to the same carbon ring atom, together with this carbon atom they are bound to, form a 3-, 4-, 5- or 6-membered saturated heterocyclic ring containing 1 oxygen atom as ring member;

each $R^1$ is independently selected from F, Cl and methyl or two non-geminal radicals $R^{10}$ form together a group —$CH_2$—;

each $R^{11}$ is independently selected from F, Cl and methyl or two non-geminal radicals $R^{11}$ form together a group —$CH_2$—;

$X^1$ is N or CH;
$X^2$ is C—$R^1$ or N;
a is 0, 1 or 2, preferably 0 or 1;
b is 0, 1 or 2, preferably 0 or 2;
and the pharmaceutically acceptable salts thereof.

The invention even more preferably relates to compounds of the formula I in which $R^1$ (if present) is selected from hydrogen, fluorine and methoxy;
$R^2$ is selected from hydrogen, fluorine and methoxy;
$R^3$ is selected from hydrogen and fluorine;
$R^4$ is selected from methoxy and ethoxy;
$R^5$ is hydrogen or methoxy;
$R^6$ is selected from cyano, fluorine and chlorine;
$R^7$ is hydrogen or fluorine;
$R^8$ is selected from hydrogen, $C_1$-$C_4$-alkyl and $C_3$-$C_6$-cycloalkyl;
$R^9$ is selected from $C_1$-$C_4$-alkoxy-$C_1$-$C_4$-alkyl, $C_1$-$C_4$-alkoxy, and a 3-, 4-, 5- or 6-membered saturated heterocyclic ring containing 1 oxygen atom as ring member; or $R^8$ and $R^9$, together with the nitrogen atom they are bound to form a 3-, 4-, 5- or 6-membered saturated heterocyclic ring, where the heterocyclic ring contains 1 further oxygen atom as ring member, and where the heterocyclic ring may carry 1 or 2 substituents $R^{12}$; or form a 3-, 4-, 5- or 6-membered saturated heterocyclic ring which carries 1 or 2 substituents $R^{12}$; and each $R^{12}$ is independently selected from halogen, hydroxyl, $C_1$-$C_4$-alkoxy, and a 3-, 4-, 5- or 6-membered saturated heterocyclic ring containing 1 oxygen atom as ring member; or two radicals $R^{12}$ bound to the same carbon ring atom, together with this carbon atom they are bound to, form a 3-, 4-, 5- or 6-membered saturated heterocyclic ring containing 1 oxygen atom as ring member;

$X^1$ is N or CH;
$X^2$ is C—$R^1$ or N;
a is 0;
b is 0;
and the pharmaceutically acceptable salts thereof.

The invention even in particular relates to compounds of the formula I in which $R^1$ (if present) is selected from hydrogen, fluorine and methoxy;
$R^2$ is selected from hydrogen, fluorine and methoxy;
$R^3$ is selected from hydrogen and fluorine;
$R^4$ is selected from methoxy and ethoxy;
$R^5$ is hydrogen or methoxy;
$R^6$ is selected from cyano, fluorine and chlorine;
$R^7$ is hydrogen or fluorine;
$R^8$ is selected from hydrogen, $C_1$-$C_4$-alkyl and $C_3$-$C_6$-cycloalkyl;
$R^9$ is selected from $C_1$-$C_4$-alkoxy-$C_1$-$C_4$-alkyl, $C_1$-$C_4$-alkoxy, oxetan-3-yl and tetrahydropyran-4-yl; or $R^8$ and $R^9$, together with the nitrogen atom they are bound to form a saturated heterocyclic ring selected from azetidin-1-yl carrying in the 3-position (relative to the 1-position of the nitrogen ring atom) 1 or 2 substituents $R^{12}$; isoxazolidin-2-yl, piperidin-1-yl carrying in the 4-position (relative to the 1-position of the nitrogen ring atom) 1 or 2 substituents $R^{12}$; and morpholin-1-yl; and each $R^{12}$ is independently selected from halogen, hydroxyl, $C_1$-$C_4$-alkoxy, and oxetan-3-yl; or two radicals $R^{12}$ bound to the same carbon ring atom together form a group —$CH_2$—O—$CH_2$— (i.e. together with the carbon atom they are bound to form a spiro-bound oxetan-3-yl ring);

$X^1$ is N or CH;
$X^2$ is C—$R^1$ or N;
a is 0;
b is 0;
and the pharmaceutically acceptable salts thereof.

Examples of preferred embodiment of the present invention are compounds of the formulae I.1 to I.40 and the N-oxides, stereoisomers and the pharmaceutically acceptable salts thereof, in which the radicals $R^1$, $R^2$, $R^3$, $R^6$, $R^7$, $R^8$ and $R^9$ have one of the above general or preferred meanings. In particular, preferred compounds are the individual compounds compiled in the tables 1 to 28600 below. Moreover, the meanings mentioned below for the individual variables in the tables are per se, independently of the combination in which they are mentioned, a particularly preferred embodiment of the substituents in question.

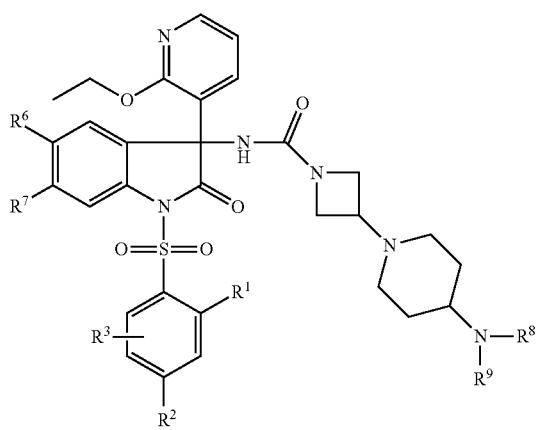

1.1

1.2
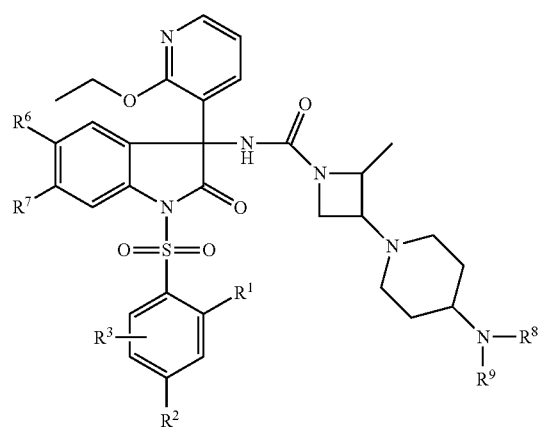
1.3
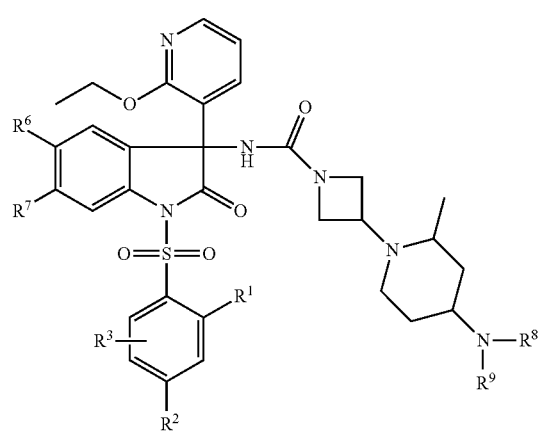
1.4
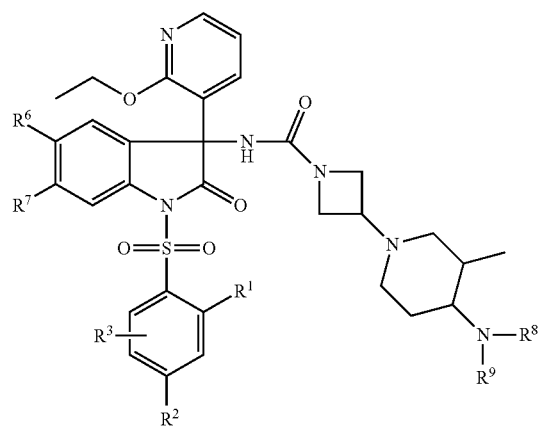
1.5
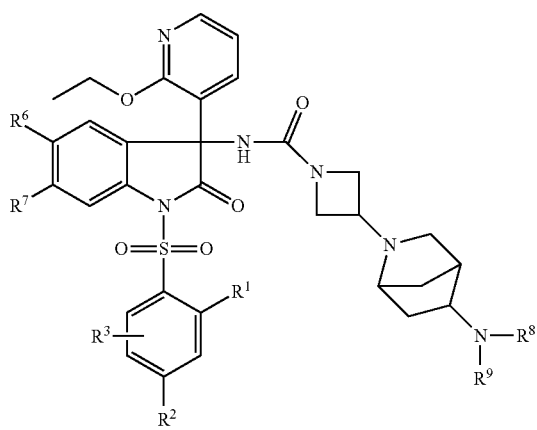
1.6
1.7

1.8
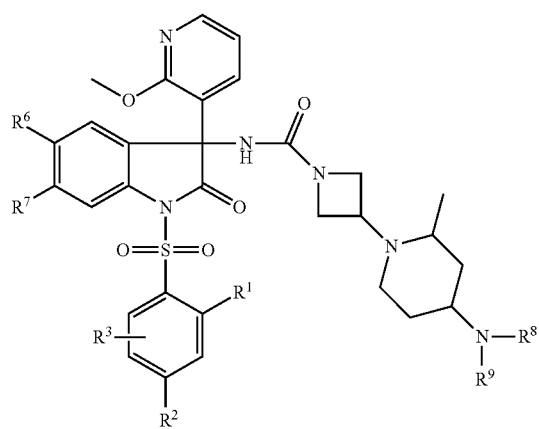
1.9
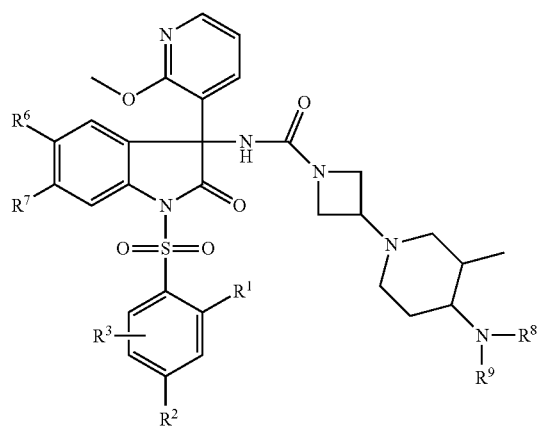
1.10
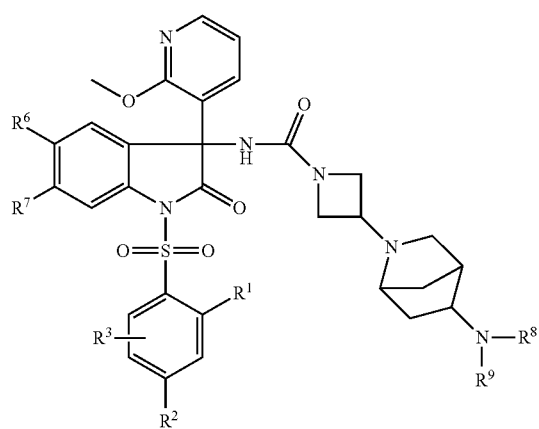
1.11
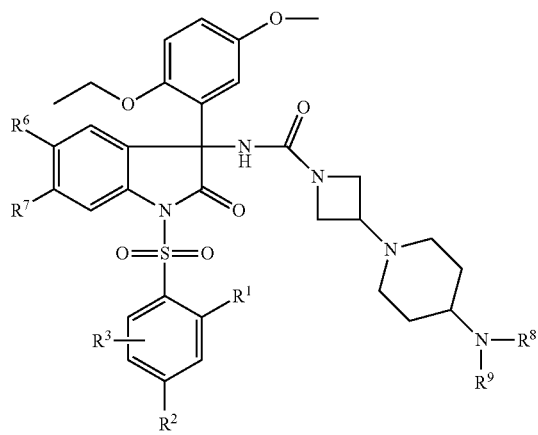
1.12
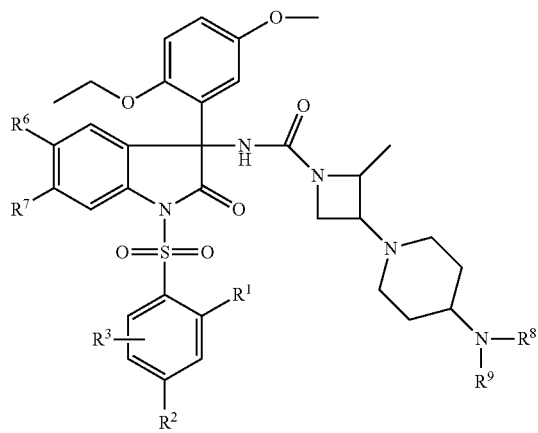
1.13
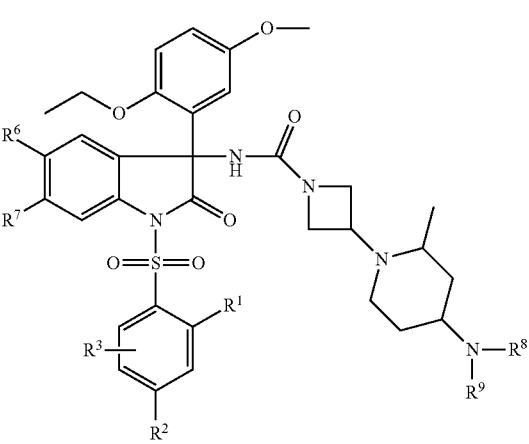

1.14
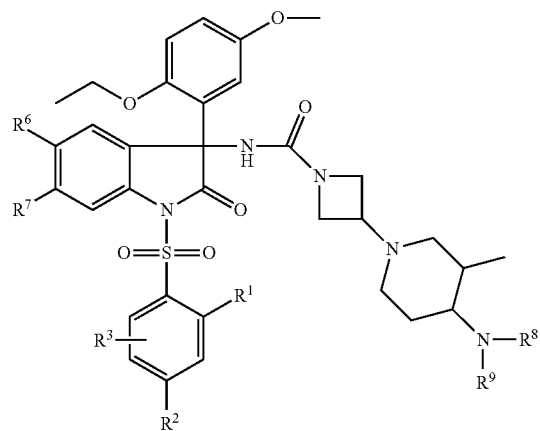
1.15
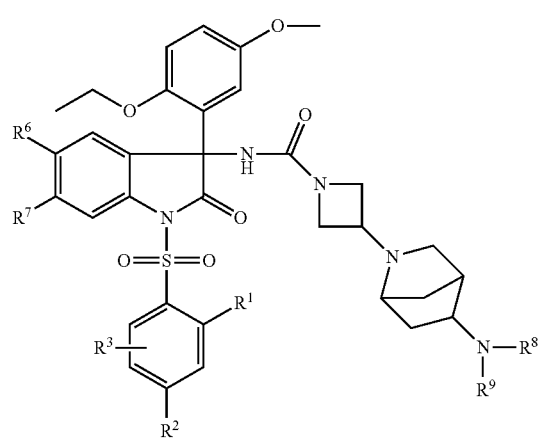
1.16
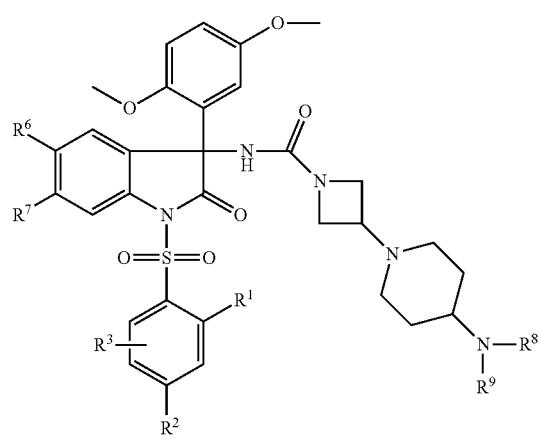
1.17
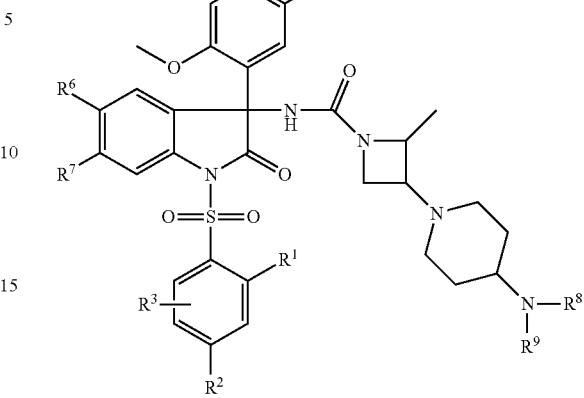
1.18
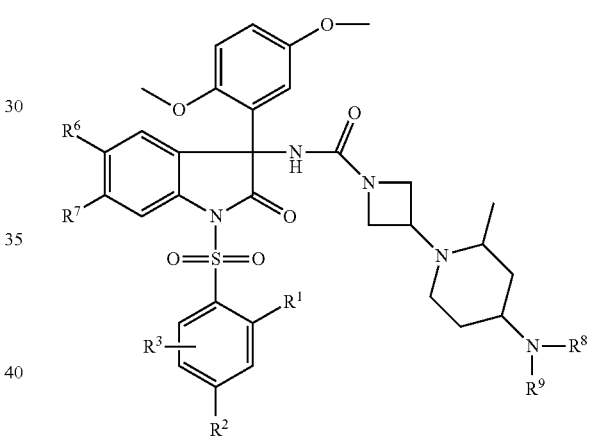
1.19
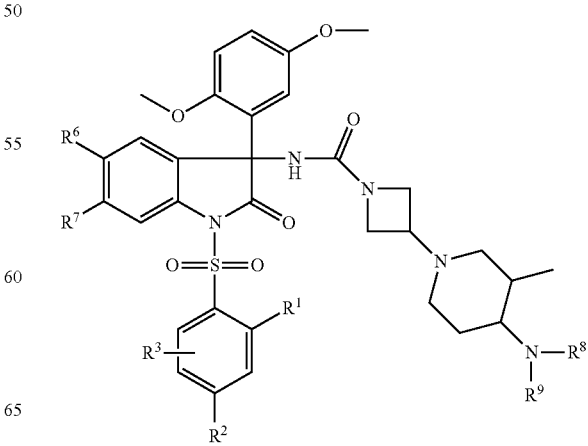

1.20
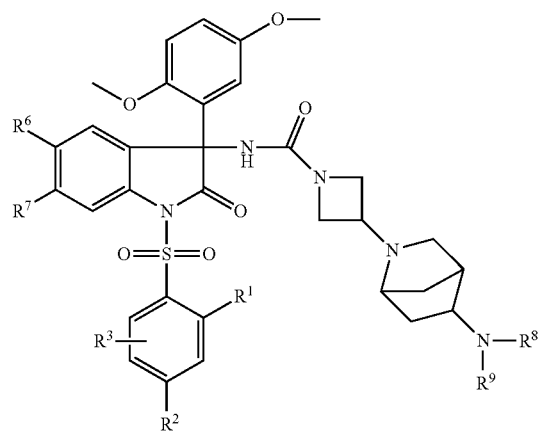
1.21
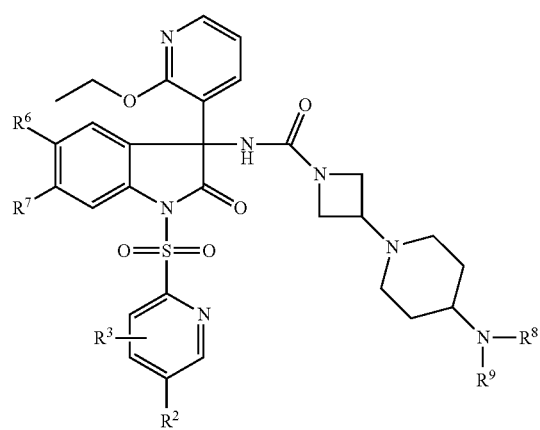
1.22
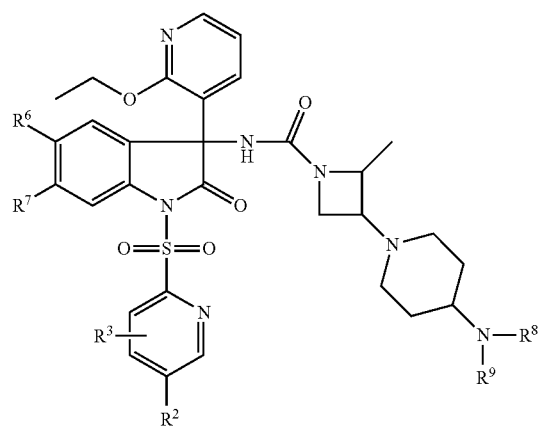
1.23
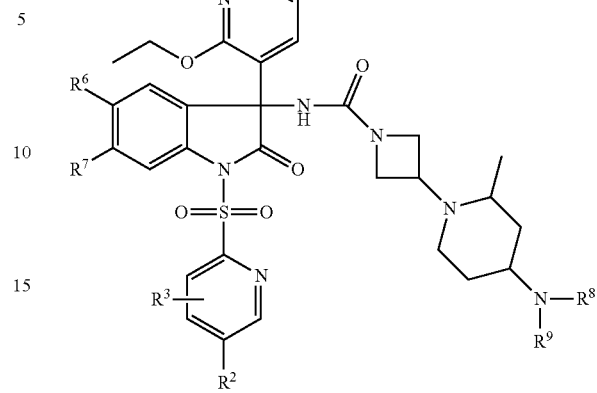
1.24
1.25
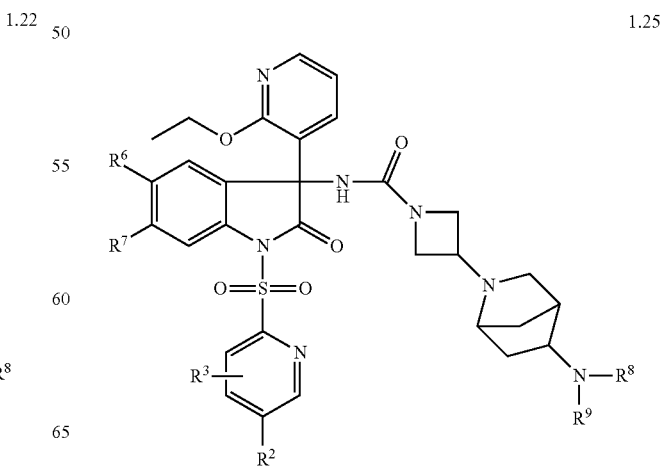

-continued
1.26
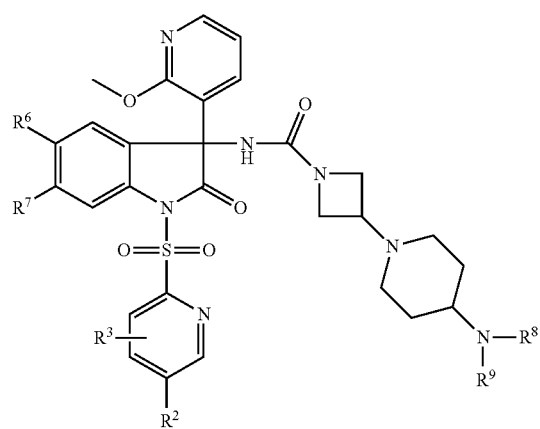
1.27
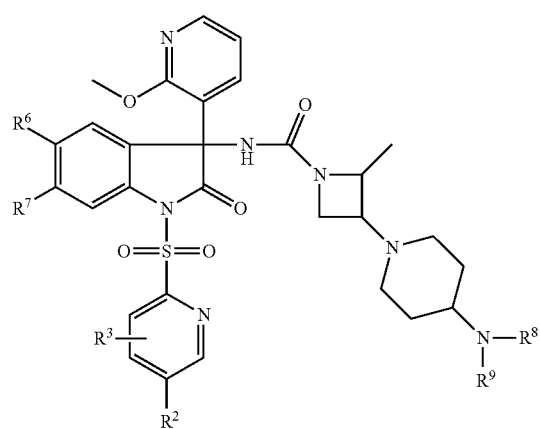
1.28
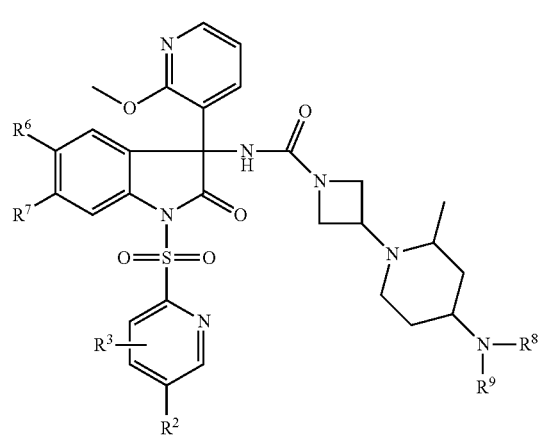
-continued
1.29
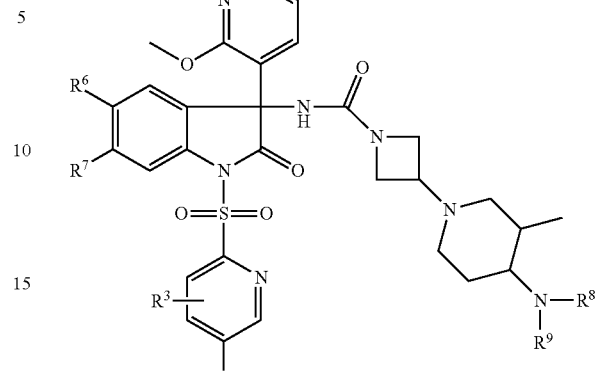
1.30
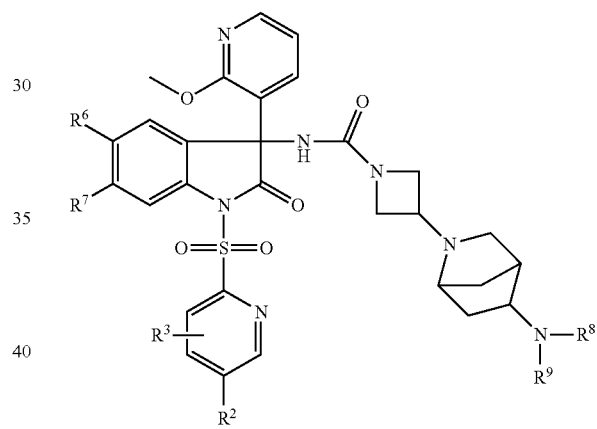
1.31
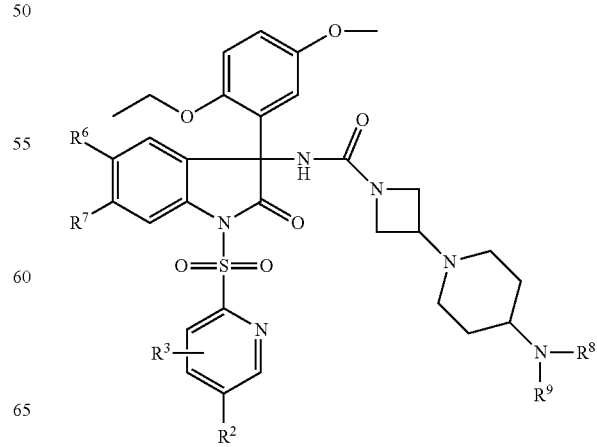

-continued
1.32
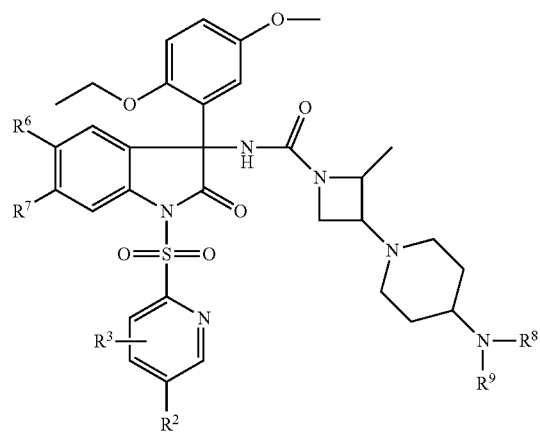
1.33
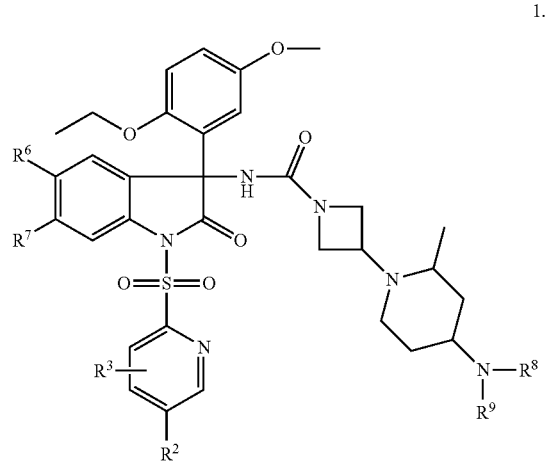
1.34
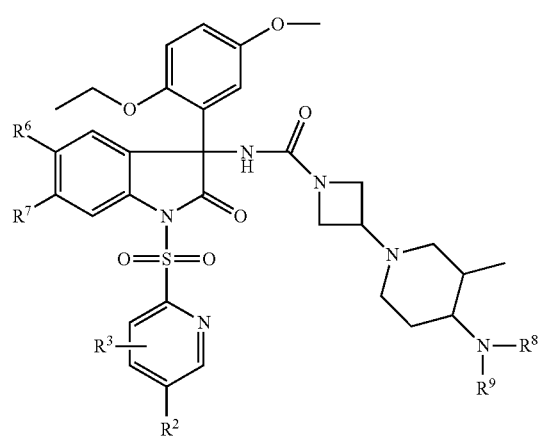
-continued
1.35
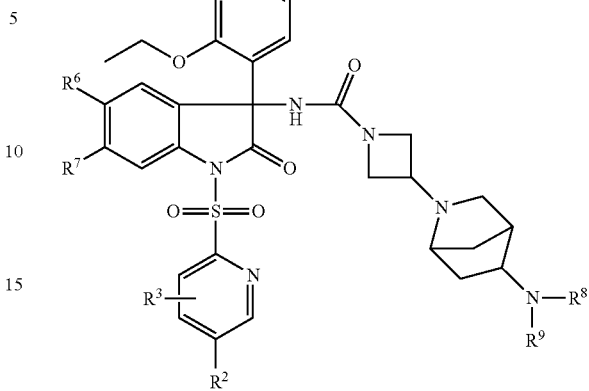
1.36
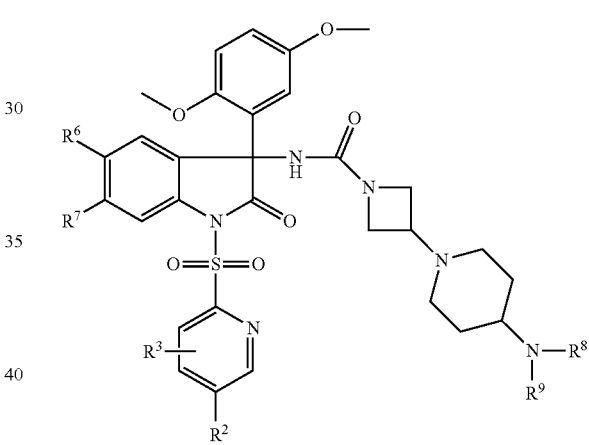
1.37
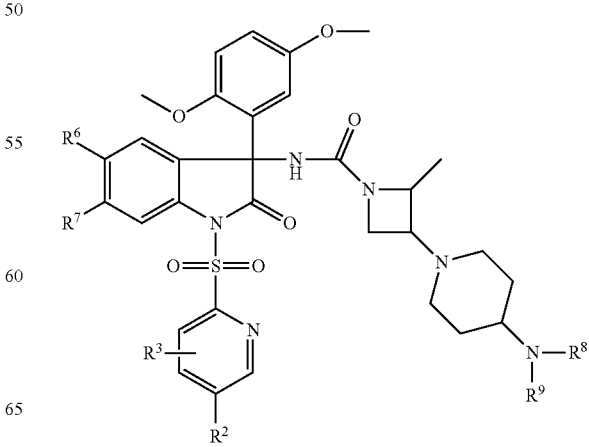

-continued 1.38
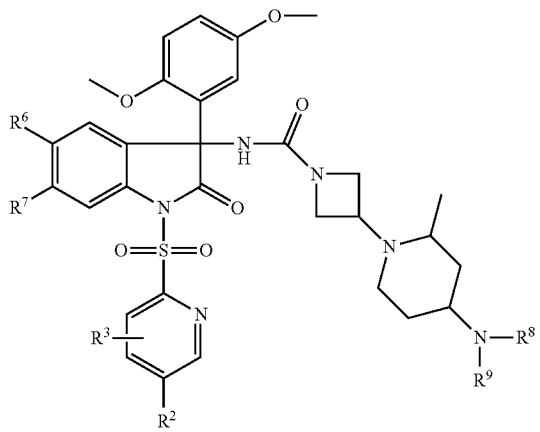

1.39
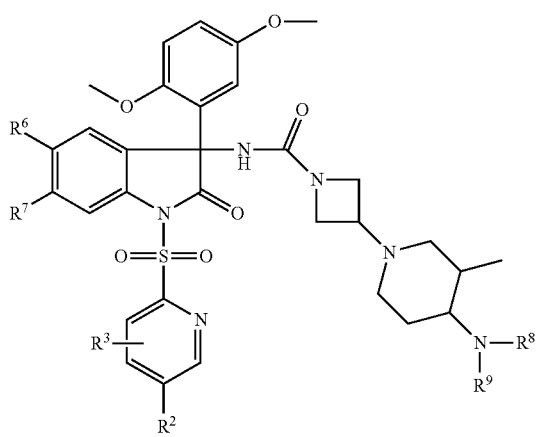

1.40
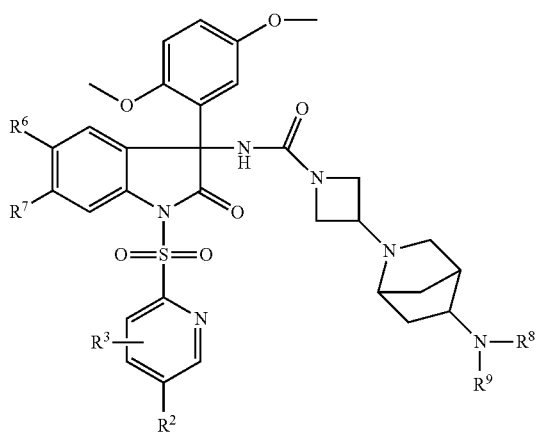

Table 1
Compounds of the formula I.1 in which $R^8$ is hydrogen, $R^9$ is methoxy, and $R^1$, $R^2$, $R^3$, $R^6$ and $R^7$ for a compound corresponds in each case to one row of Table A Table 2
Compounds of the formula I.1 in which $R^8$ is hydrogen, $R^9$ is ethoxy, and $R^1$, $R^2$, $R^3$, $R^6$ and $R^7$ for a compound corresponds in each case to one row of Table A Table 3
Compounds of the formula I.1 in which $R^8$ is hydrogen, $R^9$ is n-propoxy, and $R^1$, $R^2$, $R^3$, $R^6$ and $R^7$ for a compound corresponds in each case to one row of Table A Table 4
Compounds of the formula I.1 in which $R^8$ is hydrogen, $R^9$ is isopropoxy, and $R^1$, $R^2$, $R^3$, $R^6$ and $R^7$ for a compound corresponds in each case to one row of Table A Table 5
Compounds of the formula I.1 in which $R^8$ is hydrogen, $R^9$ is n-butoxy, and $R^1$, $R^2$, $R^3$, $R^6$ and $R^7$ for a compound corresponds in each case to one row of Table A Table 6
Compounds of the formula I.1 in which $R^8$ is hydrogen, $R^9$ is sec-butoxy, and $R^1$, $R^2$, $R^3$, $R^6$ and $R^7$ for a compound corresponds in each case to one row of Table A Table 7
Compounds of the formula I.1 in which $R^8$ is hydrogen, $R^9$ is isobutoxy, and $R^1$, $R^2$, $R^3$, $R^6$ and $R^7$ for a compound corresponds in each case to one row of Table A Table 8
Compounds of the formula I.1 in which $R^8$ is hydrogen, $R^9$ is tert-butoxy, and $R^1$, $R^2$, $R^3$, $R^6$ and $R^7$ for a compound corresponds in each case to one row of Table A Table 9
Compounds of the formula I.1 in which $R^8$ is hydrogen, $R^9$ is fluoromethoxy, and $R^1$, $R^2$, $R^3$, $R^6$ and $R^7$ for a compound corresponds in each case to one row of Table A Table 10
Compounds of the formula I.1 in which $R^8$ is hydrogen, $R^9$ is difluoromethoxy, and $R^1$, $R^2$, $R^3$, $R^6$ and $R^7$ for a compound corresponds in each case to one row of Table A Table 11
Compounds of the formula I.1 in which $R^8$ is hydrogen, $R^9$ is trifluoromethoxy, and $R^1$, $R^2$, $R^3$, $R^6$ and $R^7$ for a compound corresponds in each case to one row of Table A Table 12
Compounds of the formula I.1 in which $R^8$ is hydrogen, $R^9$ is 2-fluoroethoxy, and $R^1$, $R^2$, $R^3$, $R^6$ and $R^7$ for a compound corresponds in each case to one row of Table A Table 13
Compounds of the formula I.1 in which $R^8$ is hydrogen, $R^9$ is 2,2-difluoroethoxy, and $R^1$, $R^2$, $R^3$, $R^6$ and $R^7$ for a compound corresponds in each case to one row of Table A Table 14
Compounds of the formula I.1 in which $R^8$ is hydrogen, $R^9$ is 2,2,2-trifluoroethoxy, and $R^1$, $R^2$, $R^3$, $R^6$ and $R^7$ for a compound corresponds in each case to one row of Table A Table 15
Compounds of the formula I.1 in which $R^8$ is hydrogen, $R^9$ is pentafluoroethoxy, and $R^1$, $R^2$, $R^3$, $R^6$ and $R^7$ for a compound corresponds in each case to one row of Table A Table 16
Compounds of the formula I.1 in which $R^8$ is hydrogen, $R^9$ is methoxymethyl, and $R^1$, $R^2$, $R^3$, $R^6$ and $R^7$ for a compound corresponds in each case to one row of Table A Table 17
Compounds of the formula I.1 in which $R^8$ is hydrogen, $R^9$ is ethoxymethyl, and $R^1$, $R^2$, $R^3$, $R^6$ and $R^7$ for a compound corresponds in each case to one row of Table A Table 18
Compounds of the formula I.1 in which $R^8$ is hydrogen, $R^9$ is n-propoxymethyl, and $R^1$, $R^2$, $R^3$, $R^6$ and $R^7$ for a compound corresponds in each case to one row of Table A Table 19
Compounds of the formula I.1 in which $R^8$ is hydrogen, $R^9$ is isopropoxymethyl, and $R^1$, $R^2$, $R^3$, $R^6$ and $R^7$ for a compound corresponds in each case to one row of Table A Table 20
Compounds of the formula I.1 in which $R^8$ is hydrogen, $R^9$ is methoxy-1-ethyl, and $R^1$, $R^2$, $R^3$, $R^6$ and $R^7$ for a compound corresponds in each case to one row of Table A Table 21
Compounds of the formula I.1 in which $R^8$ is hydrogen, $R^9$ is ethoxy-1-ethyl, and $R^1$, $R^2$, $R^3$, $R^6$ and $R^7$ for a compound corresponds in each case to one row of Table A Table 22
Compounds of the formula I.1 in which $R^8$ is hydrogen, $R^9$ is n-propoxy-1-ethyl, and $R^1$, $R^2$, $R^3$, $R^6$ and $R^7$ for a compound corresponds in each case to one row of Table A Table 23
Compounds of the formula I.1 in which $R^8$ is hydrogen, $R^9$ is isopropoxy-1-ethyl, and $R^1$, $R^2$, $R^3$, $R^6$ and $R^7$ for a compound corresponds in each case to one row of Table A Table 24
Compounds of the formula I.1 in which $R^8$ is hydrogen, $R^9$ is methoxy-2-ethyl, and $R^1$, $R^2$, $R^3$, $R^6$ and $R^7$ for a compound corresponds in each case to one row of Table A Table 25
Compounds of the formula I.1 in which $R^8$ is hydrogen, $R^9$ is ethoxy-2-ethyl, and $R^1$, $R^2$, $R^3$, $R^6$ and $R^7$ for a compound corresponds in each case to one row of Table A Table 26
Compounds of the formula I.1 in which $R^8$ is hydrogen, $R^9$ is n-propoxy-2-ethyl, and $R^1$, $R^2$, $R^3$, $R^6$ and $R^7$ for a compound corresponds in each case to one row of Table A Table 27
Compounds of the formula I.1 in which $R^8$ is hydrogen, $R^9$ is isopropoxy-2-ethyl, and $R^1$, $R^2$, $R^3$, $R^6$ and $R^7$ for a compound corresponds in each case to one row of Table A Table 28
Compounds of the formula I.1 in which $R^8$ is hydrogen, $R^9$ is methoxy-1-propyl, and $R^1$, $R^2$, $R^3$, $R^6$ and $R^7$ for a compound corresponds in each case to one row of Table A Table 29
Compounds of the formula I.1 in which $R^8$ is hydrogen, $R^9$ is ethoxy-1-propyl, and $R^1$, $R^2$, $R^3$, $R^6$ and $R^7$ for a compound corresponds in each case to one row of Table A Table 30
Compounds of the formula I.1 in which $R^8$ is hydrogen, $R^9$ is n-propoxy-1-propyl, and $R^1$, $R^2$, $R^3$, $R^6$ and $R^7$ for a compound corresponds in each case to one row of Table A Table 31
Compounds of the formula I.1 in which $R^8$ is hydrogen, $R^9$ is isopropoxy-1-propyl, and $R^1$, $R^2$, $R^3$, $R^6$ and $R^7$ for a compound corresponds in each case to one row of Table A Table 32
Compounds of the formula I.1 in which $R^8$ is hydrogen, $R^9$ is methoxy-2-propyl, and $R^1$, $R^2$, $R^3$, $R^6$ and $R^7$ for a compound corresponds in each case to one row of Table A Table 33
Compounds of the formula I.1 in which $R^8$ is hydrogen, $R^9$ is ethoxy-2-propyl, and $R^1$, $R^2$, $R^3$, $R^6$ and $R^7$ for a compound corresponds in each case to one row of Table A Table 34
Compounds of the formula I.1 in which $R^8$ is hydrogen, $R^9$ is n-propoxy-2-propyl, and $R^1$, $R^2$, $R^3$, $R^6$ and $R^7$ for a compound corresponds in each case to one row of Table A Table 35
Compounds of the formula I.1 in which $R^8$ is hydrogen, $R^9$ is isopropoxy-2-propyl, and $R^1$, $R^2$, $R^3$, $R^6$ and $R^7$ for a compound corresponds in each case to one row of Table A Table 36
Compounds of the formula I.1 in which $R^8$ is hydrogen, $R^9$ is methoxy-3-propyl, and $R^1$, $R^2$, $R^3$, $R^6$ and $R^7$ for a compound corresponds in each case to one row of Table A Table 37
Compounds of the formula I.1 in which $R^8$ is hydrogen, $R^9$ is ethoxy-3-propyl, and $R^1$, $R^2$, $R^3$, $R^6$ and $R^7$ for a compound corresponds in each case to one row of Table A Table 38
Compounds of the formula I.1 in which $R^8$ is hydrogen, $R^9$ is n-propoxy-3-propyl, and $R^1$, $R^2$, $R^3$, $R^6$ and $R^7$ for a compound corresponds in each case to one row of Table A Table 39
Compounds of the formula I.1 in which $R^8$ is hydrogen, $R^9$ is isopropoxy-3-propyl, and $R^1$, $R^2$, $R^3$, $R^6$ and $R^7$ for a compound corresponds in each case to one row of Table A Table 40
Compounds of the formula I.1 in which $R^8$ is hydrogen, $R^9$ is oxetan-2-yl, and $R^1$, $R^2$, $R^3$, $R^6$ and $R^7$ for a compound corresponds in each case to one row of Table A Table 41
Compounds of the formula I.1 in which $R^8$ is hydrogen, $R^9$ is oxetan-3-yl, and $R^1$, $R^2$, $R^3$, $R^6$ and $R^7$ for a compound corresponds in each case to one row of Table A Table 42
Compounds of the formula I.1 in which $R^8$ is hydrogen, $R^9$ is tetrahydrofuran-2-yl, and $R^1$, $R^2$, $R^3$, $R^6$ and $R^7$ for a compound corresponds in each case to one row of Table A Table 43
Compounds of the formula I.1 in which $R^8$ is hydrogen, $R^9$ is tetrahydrofuran-3-yl, and $R^1$, $R^2$, $R^3$, $R^6$ and $R^7$ for a compound corresponds in each case to one row of Table A Table 44
Compounds of the formula I.1 in which $R^8$ is hydrogen, $R^9$ is tetrahydropyran-2-yl, and $R^1$, $R^2$, $R^3$, $R^6$ and $R^7$ for a compound corresponds in each case to one row of Table A Table 45
Compounds of the formula I.1 in which $R^8$ is hydrogen, $R^9$ is tetrahydropyran-3-yl, and $R^1$, $R^2$, $R^3$, $R^6$ and $R^7$ for a compound corresponds in each case to one row of Table A Table 46
Compounds of the formula I.1 in which $R^8$ is hydrogen, $R^9$ is tetrahydropyran-4-yl, and $R^1$, $R^2$, $R^3$, $R^6$ and $R^7$ for a compound corresponds in each case to one row of Table A Table 47
Compounds of the formula I.1 in which $R^8$ is hydrogen, $R^9$ is thietan-2-yl, and $R^1$, $R^2$, $R^3$, $R^6$ and $R^7$ for a compound corresponds in each case to one row of Table A Table 48
Compounds of the formula I.1 in which $R^8$ is hydrogen, $R^9$ is thietan-3-yl, and $R^1$, $R^2$, $R^3$, $R^6$ and $R^7$ for a compound corresponds in each case to one row of Table A Table 49
Compounds of the formula I.1 in which $R^8$ is hydrogen, $R^9$ is 1-oxothietan-3-yl, and $R^1$, $R^2$, $R^3$, $R^6$ and $R^7$ for a compound corresponds in each case to one row of Table A Table 50
Compounds of the formula I.1 in which $R^8$ is hydrogen, $R^9$ is 1,1-dioxothietan-3-yl, and $R^1$, $R^2$, $R^3$, $R^6$ and $R^7$ for a compound corresponds in each case to one row of Table A Table 51
Compounds of the formula I.1 in which $R^8$ is methyl, $R^9$ is methoxy, and $R^1$, $R^2$, $R^3$, $R^6$ and $R^7$ for a compound corresponds in each case to one row of Table A Table 52
Compounds of the formula I.1 in which $R^8$ is methyl, $R^9$ is ethoxy, and $R^1$, $R^2$, $R^3$, $R^6$ and $R^7$ for a compound corresponds in each case to one row of Table A Table 53
Compounds of the formula I.1 in which $R^8$ is methyl, $R^9$ is n-propoxy, and $R^1$, $R^2$, $R^3$, $R^6$ and $R^7$ for a compound corresponds in each case to one row of Table A Table 54
Compounds of the formula I.1 in which $R^8$ is methyl, $R^9$ is isopropoxy, and $R^1$, $R^2$, $R^3$, $R^6$ and $R^7$ for a compound corresponds in each case to one row of Table A Table 55
Compounds of the formula I.1 in which $R^8$ is methyl, $R^9$ is n-butoxy, and $R^1$, $R^2$, $R^3$, $R^6$ and $R^7$ for a compound corresponds in each case to one row of Table A Table 56
Compounds of the formula I.1 in which $R^8$ is methyl, $R^9$ is sec-butoxy, and $R^1$, $R^2$, $R^3$, $R^6$ and $R^7$ for a compound corresponds in each case to one row of Table A Table 57
Compounds of the formula I.1 in which $R^8$ is methyl, $R^9$ is isobutoxy, and $R^1$, $R^2$, $R^3$, $R^6$ and $R^7$ for a compound corresponds in each case to one row of Table A Table 58
Compounds of the formula I.1 in which $R^8$ is methyl, $R^9$ is tert-butoxy, and $R^1$, $R^2$, $R^3$, $R^6$ and $R^7$ for a compound corresponds in each case to one row of Table A Table 59
Compounds of the formula I.1 in which $R^8$ is methyl, $R^9$ is fluoromethoxy, and $R^1$, $R^2$, $R^3$, $R^6$ and $R^7$ for a compound corresponds in each case to one row of Table A Table 60
Compounds of the formula I.1 in which $R^8$ is methyl, $R^9$ is difluoromethoxy, and $R^1$, $R^2$, $R^3$, $R^6$ and $R^7$ for a compound corresponds in each case to one row of Table A Table 61
Compounds of the formula I.1 in which $R^8$ is methyl, $R^9$ is trifluoromethoxy, and $R^1$, $R^2$, $R^3$, $R^6$ and $R^7$ for a compound corresponds in each case to one row of Table A Table 62
Compounds of the formula I.1 in which $R^8$ is methyl, $R^9$ is 2-fluoroethoxy, and $R^1$, $R^2$, $R^3$, $R^6$ and $R^7$ for a compound corresponds in each case to one row of Table A Table 63
Compounds of the formula I.1 in which $R^8$ is methyl, $R^9$ is 2,2-difluoroethoxy, and $R^1$, $R^2$, $R^3$, $R^6$ and $R^7$ for a compound corresponds in each case to one row of Table A Table 64
Compounds of the formula I.1 in which $R^8$ is methyl, $R^9$ is 2,2,2-trifluoroethoxy, and $R^1$, $R^2$, $R^3$, $R^6$ and $R^7$ for a compound corresponds in each case to one row of Table A Table 65
Compounds of the formula I.1 in which $R^8$ is methyl, $R^9$ is pentafluoroethoxy, and $R^1$, $R^2$, $R^3$, $R^6$ and $R^7$ for a compound corresponds in each case to one row of Table A Table 66
Compounds of the formula I.1 in which $R^8$ is methyl, $R^9$ is methoxymethyl, and $R^1$, $R^2$, $R^3$, $R^6$ and $R^7$ for a compound corresponds in each case to one row of Table A Table 67
Compounds of the formula I.1 in which $R^8$ is methyl, $R^9$ is ethoxymethyl, and $R^1$, $R^2$, $R^3$, $R^6$ and $R^7$ for a compound corresponds in each case to one row of Table A Table 68
Compounds of the formula I.1 in which $R^8$ is methyl, $R^9$ is n-propoxymethyl, and $R^1$, $R^2$, $R^3$, $R^6$ and $R^7$ for a compound corresponds in each case to one row of Table A Table 69
Compounds of the formula I.1 in which $R^8$ is methyl, $R^9$ is isopropoxymethyl, and $R^1$, $R^2$, $R^3$, $R^6$ and $R^7$ for a compound corresponds in each case to one row of Table A Table 70
Compounds of the formula I.1 in which $R^8$ is methyl, $R^9$ is methoxy-1-ethyl, and $R^1$, $R^2$, $R^3$, $R^6$ and $R^7$ for a compound corresponds in each case to one row of Table A Table 71
Compounds of the formula I.1 in which $R^8$ is methyl, $R^9$ is ethoxy-1-ethyl, and $R^1$, $R^2$, $R^3$, $R^6$ and $R^7$ for a compound corresponds in each case to one row of Table A Table 72
Compounds of the formula I.1 in which $R^8$ is methyl, $R^9$ is n-propoxy-1-ethyl, and $R^1$, $R^2$, $R^3$, $R^6$ and $R^7$ for a compound corresponds in each case to one row of Table A Table 73
Compounds of the formula I.1 in which $R^8$ is methyl, $R^9$ is isopropoxy-1-ethyl, and $R^1$, $R^2$, $R^3$, $R^6$ and $R^7$ for a compound corresponds in each case to one row of Table A Table 74
Compounds of the formula I.1 in which $R^8$ is methyl, $R^9$ is methoxy-2-ethyl, and $R^1$, $R^2$, $R^3$, $R^6$ and $R^7$ for a compound corresponds in each case to one row of Table A Table 75
Compounds of the formula I.1 in which $R^8$ is methyl, $R^9$ is ethoxy-2-ethyl, and $R^1$, $R^2$, $R^3$, $R^6$ and $R^7$ for a compound corresponds in each case to one row of Table A Table 76
Compounds of the formula I.1 in which $R^8$ is methyl, $R^9$ is n-propoxy-2-ethyl, and $R^1$, $R^2$, $R^3$, $R^6$ and $R^7$ for a compound corresponds in each case to one row of Table A Table 77
Compounds of the formula I.1 in which $R^8$ is methyl, $R^9$ is isopropoxy-2-ethyl, and $R^1$, $R^2$, $R^3$, $R^6$ and $R^7$ for a compound corresponds in each case to one row of Table A Table 78
Compounds of the formula I.1 in which $R^8$ is methyl, $R^9$ is methoxy-1-propyl, and $R^1$, $R^2$, $R^3$, $R^6$ and $R^7$ for a compound corresponds in each case to one row of Table A Table 79
Compounds of the formula I.1 in which $R^8$ is methyl, $R^9$ is ethoxy-1-propyl, and $R^1$, $R^2$, $R^3$, $R^6$ and $R^7$ for a compound corresponds in each case to one row of Table A Table 80
Compounds of the formula I.1 in which $R^8$ is methyl, $R^9$ is n-propoxy-1-propyl, and $R^1$, $R^2$, $R^3$, $R^6$ and $R^7$ for a compound corresponds in each case to one row of Table A Table 81
Compounds of the formula I.1 in which $R^8$ is methyl, $R^9$ is isopropoxy-1-propyl, and $R^1$, $R^2$, $R^3$, $R^6$ and $R^7$ for a compound corresponds in each case to one row of Table A Table 82
Compounds of the formula I.1 in which $R^8$ is methyl, $R^9$ is methoxy-2-propyl, and $R^1$, $R^2$, $R^3$, $R^6$ and $R^7$ for a compound corresponds in each case to one row of Table A Table 83
Compounds of the formula I.1 in which $R^8$ is methyl, $R^9$ is ethoxy-2-propyl, and $R^1$, $R^2$, $R^3$, $R^6$ and $R^7$ for a compound corresponds in each case to one row of Table A Table 84
Compounds of the formula I.1 in which $R^8$ is methyl, $R^9$ is n-propoxy-2-propyl, and $R^1$, $R^2$, $R^3$, $R^6$ and $R^7$ for a compound corresponds in each case to one row of Table A Table 85
Compounds of the formula I.1 in which $R^8$ is methyl, $R^9$ is isopropoxy-2-propyl, and $R^1$, $R^2$, $R^3$, $R^6$ and $R^7$ for a compound corresponds in each case to one row of Table A Table 86
Compounds of the formula I.1 in which $R^8$ is methyl, $R^9$ is methoxy-3-propyl, and $R^1$, $R^2$, $R^3$, $R^6$ and $R^7$ for a compound corresponds in each case to one row of Table A Table 87
Compounds of the formula I.1 in which $R^8$ is methyl, $R^9$ is ethoxy-3-propyl, and $R^1$, $R^2$, $R^3$, $R^6$ and $R^7$ for a compound corresponds in each case to one row of Table A Table 88
Compounds of the formula I.1 in which $R^8$ is methyl, $R^9$ is n-propoxy-3-propyl, and $R^1$, $R^2$, $R^3$, $R^6$ and $R^7$ for a compound corresponds in each case to one row of Table A Table 89
Compounds of the formula I.1 in which $R^8$ is methyl, $R^9$ is isopropoxy-3-propyl, and $R^1$, $R^2$, $R^3$, $R^6$ and $R^7$ for a compound corresponds in each case to one row of Table A Table 90
Compounds of the formula I.1 in which $R^8$ is methyl, $R^9$ is oxetan-2-yl, and $R^1$, $R^2$, $R^3$, $R^6$ and $R^7$ for a compound corresponds in each case to one row of Table A Table 91
Compounds of the formula I.1 in which $R^8$ is methyl, $R^9$ is oxetan-3-yl, and $R^1$, $R^2$, $R^3$, $R^6$ and $R^7$ for a compound corresponds in each case to one row of Table A Table 92
Compounds of the formula I.1 in which $R^8$ is methyl, $R^9$ is tetrahydrofuran-2-yl, and $R^1$, $R^2$, $R^3$, $R^6$ and $R^7$ for a compound corresponds in each case to one row of Table A Table 93
Compounds of the formula I.1 in which $R^8$ is methyl, $R^9$ is tetrahydrofuran-3-yl, and $R^1$, $R^2$, $R^3$, $R^6$ and $R^7$ for a compound corresponds in each case to one row of Table A Table 94
Compounds of the formula I.1 in which $R^8$ is methyl, $R^9$ is tetrahydropyran-2-yl, and $R^1$, $R^2$, $R^3$, $R^6$ and $R^7$ for a compound corresponds in each case to one row of Table A Table 95
Compounds of the formula I.1 in which $R^8$ is methyl, $R^9$ is tetrahydropyran-3-yl, and $R^1$, $R^2$, $R^3$, $R^6$ and $R^7$ for a compound corresponds in each case to one row of Table A Table 96
Compounds of the formula I.1 in which $R^8$ is methyl, $R^9$ is tetrahydropyran-4-yl, and $R^1$, $R^2$, $R^3$, $R^6$ and $R^7$ for a compound corresponds in each case to one row of Table A Table 97
Compounds of the formula I.1 in which $R^8$ is methyl, $R^9$ is thietan-2-yl, and $R^1$, $R^2$, $R^3$, $R^6$ and $R^7$ for a compound corresponds in each case to one row of Table A Table 98
Compounds of the formula I.1 in which $R^8$ is methyl, $R^9$ is thietan-3-yl, and $R^1$, $R^2$, $R^3$, $R^6$ and $R^7$ for a compound corresponds in each case to one row of Table A Table 99
Compounds of the formula I.1 in which $R^8$ is methyl, $R^9$ is 1-oxothietan-3-yl, and $R^1$, $R^2$, $R^3$, $R^6$ and $R^7$ for a compound corresponds in each case to one row of Table A Table 100
Compounds of the formula I.1 in which $R^8$ is methyl, $R^9$ is 1,1-dioxothietan-3-yl, and $R^1$, $R^2$, $R^3$, $R^6$ and $R^7$ for a compound corresponds in each case to one row of Table A Table 101
Compounds of the formula I.1 in which $R^8$ is ethyl, $R^9$ is methoxy, and $R^1$, $R^2$, $R^3$, $R^6$ and $R^7$ for a compound corresponds in each case to one row of Table A Table 102
Compounds of the formula I.1 in which $R^8$ is ethyl, $R^9$ is ethoxy, and $R^1$, $R^2$, $R^3$, $R^6$ and $R^7$ for a compound corresponds in each case to one row of Table A Table 103
Compounds of the formula I.1 in which $R^8$ is ethyl, $R^9$ is n-propoxy, and $R^1$, $R^2$, $R^3$, $R^6$ and $R^7$ for a compound corresponds in each case to one row of Table A Table 104
Compounds of the formula I.1 in which $R^8$ is ethyl, $R^9$ is isopropoxy, and $R^1$, $R^2$, $R^3$, $R^6$ and $R^7$ for a compound corresponds in each case to one row of Table A Table 105
Compounds of the formula I.1 in which $R^8$ is ethyl, $R^9$ is n-butoxy, and $R^1$, $R^2$, $R^3$, $R^6$ and $R^7$ for a compound corresponds in each case to one row of Table A Table 106
Compounds of the formula I.1 in which $R^8$ is ethyl, $R^9$ is sec-butoxy, and $R^1$, $R^2$, $R^3$, $R^6$ and $R^7$ for a compound corresponds in each case to one row of Table A Table 107
Compounds of the formula I.1 in which $R^8$ is ethyl, $R^9$ is isobutoxy, and $R^1$, $R^2$, $R^3$, $R^6$ and $R^7$ for a compound corresponds in each case to one row of Table A Table 108
Compounds of the formula I.1 in which $R^8$ is ethyl, $R^9$ is tert-butoxy, and $R^1$, $R^2$, $R^3$, $R^6$ and $R^7$ for a compound corresponds in each case to one row of Table A Table 109
Compounds of the formula I.1 in which $R^8$ is ethyl, $R^9$ is fluoromethoxy, and $R^1$, $R^2$, $R^3$, $R^6$ and $R^7$ for a compound corresponds in each case to one row of Table A Table 110
Compounds of the formula I.1 in which $R^8$ is ethyl, $R^9$ is difluoromethoxy, and $R^1$, $R^2$, $R^3$, $R^6$ and $R^7$ for a compound corresponds in each case to one row of Table A Table 111
Compounds of the formula I.1 in which $R^8$ is ethyl, $R^9$ is trifluoromethoxy, and $R^1$, $R^2$, $R^3$, $R^6$ and $R^7$ for a compound corresponds in each case to one row of Table A Table 112
Compounds of the formula I.1 in which $R^8$ is ethyl, $R^9$ is 2-fluoroethoxy, and $R^1$, $R^2$, $R^3$, $R^6$ and $R^7$ for a compound corresponds in each case to one row of Table A Table 113
Compounds of the formula I.1 in which $R^8$ is ethyl, $R^9$ is 2,2-difluoroethoxy, and $R^1$, $R^2$, $R^3$, $R^6$ and $R^7$ for a compound corresponds in each case to one row of Table A Table 114
Compounds of the formula I.1 in which $R^8$ is ethyl, $R^9$ is 2,2,2-trifluoroethoxy, and $R^1$, $R^2$, $R^3$, $R^6$ and $R^7$ for a compound corresponds in each case to one row of Table A Table 115
Compounds of the formula I.1 in which $R^8$ is ethyl, $R^9$ is pentafluoroethoxy, and $R^1$, $R^2$, $R^3$, $R^6$ and $R^7$ for a compound corresponds in each case to one row of Table A Table 116
Compounds of the formula I.1 in which $R^8$ is ethyl, $R^9$ is methoxymethyl, and $R^1$, $R^2$, $R^3$, $R^6$ and $R^7$ for a compound corresponds in each case to one row of Table A Table 117
Compounds of the formula I.1 in which $R^8$ is ethyl, $R^9$ is ethoxymethyl, and $R^1$, $R^2$, $R^3$, $R^6$ and $R^7$ for a compound corresponds in each case to one row of Table A Table 118
Compounds of the formula I.1 in which $R^8$ is ethyl, $R^9$ is n-propoxymethyl, and $R^1$, $R^2$, $R^3$, $R^6$ and $R^7$ for a compound corresponds in each case to one row of Table A Table 119
Compounds of the formula I.1 in which $R^8$ is ethyl, $R^9$ is isopropoxymethyl, and $R^1$, $R^2$, $R^3$, $R^6$ and $R^7$ for a compound corresponds in each case to one row of Table A Table 120
Compounds of the formula I.1 in which $R^8$ is ethyl, $R^9$ is methoxy-1-ethyl, and $R^1$, $R^2$, $R^3$, $R^6$ and $R^7$ for a compound corresponds in each case to one row of Table A Table 121
Compounds of the formula I.1 in which $R^8$ is ethyl, $R^9$ is ethoxy-1-ethyl, and $R^1$, $R^2$, $R^3$, $R^6$ and $R^7$ for a compound corresponds in each case to one row of Table A Table 122
Compounds of the formula I.1 in which $R^8$ is ethyl, $R^9$ is n-propoxy-1-ethyl, and $R^1$, $R^2$, $R^3$, $R^6$ and $R^7$ for a compound corresponds in each case to one row of Table A Table 123
Compounds of the formula I.1 in which $R^8$ is ethyl, $R^9$ is isopropoxy-1-ethyl, and $R^1$, $R^2$, $R^3$, $R^6$ and $R^7$ for a compound corresponds in each case to one row of Table A Table 124
Compounds of the formula I.1 in which $R^8$ is ethyl, $R^9$ is methoxy-2-ethyl, and $R^1$, $R^2$, $R^3$, $R^6$ and $R^7$ for a compound corresponds in each case to one row of Table A Table 125
Compounds of the formula I.1 in which $R^8$ is ethyl, $R^9$ is ethoxy-2-ethyl, and $R^1$, $R^2$, $R^3$, $R^6$ and $R^7$ for a compound corresponds in each case to one row of Table A Table 126
Compounds of the formula I.1 in which $R^8$ is ethyl, $R^9$ is n-propoxy-2-ethyl, and $R^1$, $R^2$, $R^3$, $R^6$ and $R^7$ for a compound corresponds in each case to one row of Table A Table 127
Compounds of the formula I.1 in which $R^8$ is ethyl, $R^9$ is isopropoxy-2-ethyl, and $R^1$, $R^2$, $R^3$, $R^6$ and $R^7$ for a compound corresponds in each case to one row of Table A Table 128
Compounds of the formula I.1 in which $R^8$ is ethyl, $R^9$ is methoxy-1-propyl, and $R^1$, $R^2$, $R^3$, $R^6$ and $R^7$ for a compound corresponds in each case to one row of Table A Table 129
Compounds of the formula I.1 in which $R^8$ is ethyl, $R^9$ is ethoxy-1-propyl, and $R^1$, $R^2$, $R^3$, $R^6$ and $R^7$ for a compound corresponds in each case to one row of Table A Table 130
Compounds of the formula I.1 in which $R^8$ is ethyl, $R^9$ is n-propoxy-1-propyl, and $R^1$, $R^2$, $R^3$, $R^6$ and $R^7$ for a compound corresponds in each case to one row of Table A Table 131
Compounds of the formula I.1 in which $R^8$ is ethyl, $R^9$ is isopropoxy-1-propyl, and $R^1$, $R^2$, $R^3$, $R^6$ and $R^7$ for a compound corresponds in each case to one row of Table A Table 132
Compounds of the formula I.1 in which $R^8$ is ethyl, $R^9$ is methoxy-2-propyl, and $R^1$, $R^2$, $R^3$, $R^6$ and $R^7$ for a compound corresponds in each case to one row of Table A Table 133
Compounds of the formula I.1 in which $R^8$ is ethyl, $R^9$ is ethoxy-2-propyl, and $R^1$, $R^2$, $R^3$, $R^6$ and $R^7$ for a compound corresponds in each case to one row of Table A Table 134
Compounds of the formula I.1 in which $R^8$ is ethyl, $R^9$ is n-propoxy-2-propyl, and $R^1$, $R^2$, $R^3$, $R^6$ and $R^7$ for a compound corresponds in each case to one row of Table A Table 135
Compounds of the formula I.1 in which $R^8$ is ethyl, $R^9$ is isopropoxy-2-propyl, and $R^1$, $R^2$, $R^3$, $R^6$ and $R^7$ for a compound corresponds in each case to one row of Table A Table 136
Compounds of the formula I.1 in which $R^8$ is ethyl, $R^9$ is methoxy-3-propyl, and $R^1$, $R^2$, $R^3$, $R^6$ and $R^7$ for a compound corresponds in each case to one row of Table A Table 137
Compounds of the formula I.1 in which $R^8$ is ethyl, $R^9$ is ethoxy-3-propyl, and $R^1$, $R^2$, $R^3$, $R^6$ and $R^7$ for a compound corresponds in each case to one row of Table A Table 138
Compounds of the formula I.1 in which $R^8$ is ethyl, $R^9$ is n-propoxy-3-propyl, and $R^1$, $R^2$, $R^3$, $R^6$ and $R^7$ for a compound corresponds in each case to one row of Table A Table 139
Compounds of the formula I.1 in which $R^8$ is ethyl, $R^9$ is isopropoxy-3-propyl, and $R^1$, $R^2$, $R^3$, $R^6$ and $R^7$ for a compound corresponds in each case to one row of Table A Table 140
Compounds of the formula I.1 in which $R^8$ is ethyl, $R^9$ is oxetan-2-yl, and $R^1$, $R^2$, $R^3$, $R^6$ and $R^7$ for a compound corresponds in each case to one row of Table A Table 141
Compounds of the formula I.1 in which $R^8$ is ethyl, $R^9$ is oxetan-3-yl, and $R^1$, $R^2$, $R^3$, $R^6$ and $R^7$ for a compound corresponds in each case to one row of Table A Table 142
Compounds of the formula I.1 in which $R^8$ is ethyl, $R^9$ is tetrahydrofuran-2-yl, and $R^1$, $R^2$, $R^3$, $R^6$ and $R^7$ for a compound corresponds in each case to one row of Table A Table 143
Compounds of the formula I.1 in which $R^8$ is ethyl, $R^9$ is tetrahydrofuran-3-yl, and $R^1$, $R^2$, $R^3$, $R^6$ and $R^7$ for a compound corresponds in each case to one row of Table A Table 144
Compounds of the formula I.1 in which $R^8$ is ethyl, $R^9$ is tetrahydropyran-2-yl, and $R^1$, $R^2$, $R^3$, $R^6$ and $R^7$ for a compound corresponds in each case to one row of Table A Table 145
Compounds of the formula I.1 in which $R^8$ is ethyl, $R^9$ is tetrahydropyran-3-yl, and $R^1$, $R^2$, $R^3$, $R^6$ and $R^7$ for a compound corresponds in each case to one row of Table A Table 146
Compounds of the formula I.1 in which $R^8$ is ethyl, $R^9$ is tetrahydropyran-4-yl, and $R^1$, $R^2$, $R^3$, $R^6$ and $R^7$ for a compound corresponds in each case to one row of Table A Table 147
Compounds of the formula I.1 in which $R^8$ is ethyl, $R^9$ is thietan-2-yl, and $R^1$, $R^2$, $R^3$, $R^6$ and $R^7$ for a compound corresponds in each case to one row of Table A Table 148
Compounds of the formula I.1 in which $R^8$ is ethyl, $R^9$ is thietan-3-yl, and $R^1$, $R^2$, $R^3$, $R^6$ and $R^7$ for a compound corresponds in each case to one row of Table A Table 149
Compounds of the formula I.1 in which $R^8$ is ethyl, $R^9$ is 1-oxothietan-3-yl, and $R^1$, $R^2$, $R^3$, $R^6$ and $R^7$ for a compound corresponds in each case to one row of Table A Table 150
Compounds of the formula I.1 in which $R^8$ is ethyl, $R^9$ is 1,1-dioxothietan-3-yl, and $R^1$, $R^2$, $R^3$, $R^6$ and $R^7$ for a compound corresponds in each case to one row of Table A Table 151
Compounds of the formula I.1 in which $R^8$ is n-propyl, $R^9$ is methoxy, and $R^1$, $R^2$, $R^3$, $R^6$ and $R^7$ for a compound corresponds in each case to one row of Table A Table 152
Compounds of the formula I.1 in which $R^8$ is n-propyl, $R^9$ is ethoxy, and $R^1$, $R^2$, $R^3$, $R^6$ and $R^7$ for a compound corresponds in each case to one row of Table A Table 153
Compounds of the formula I.1 in which $R^8$ is n-propyl, $R^9$ is n-propoxy, and $R^1$, $R^2$, $R^3$, $R^6$ and $R^7$ for a compound corresponds in each case to one row of Table A Table 154
Compounds of the formula I.1 in which $R^8$ is n-propyl, $R^9$ is isopropoxy, and $R^1$, $R^2$, $R^3$, $R^6$ and $R^7$ for a compound corresponds in each case to one row of Table A Table 155
Compounds of the formula I.1 in which $R^8$ is n-propyl, $R^9$ is n-butoxy, and $R^1$, $R^2$, $R^3$, $R^6$ and $R^7$ for a compound corresponds in each case to one row of Table A Table 156
Compounds of the formula I.1 in which $R^8$ is n-propyl, $R^9$ is sec-butoxy, and $R^1$, $R^2$, $R^3$, $R^6$ and $R^7$ for a compound corresponds in each case to one row of Table A Table 157
Compounds of the formula I.1 in which $R^8$ is n-propyl, $R^9$ is isobutoxy, and $R^1$, $R^2$, $R^3$, $R^6$ and $R^7$ for a compound corresponds in each case to one row of Table A Table 158
Compounds of the formula I.1 in which $R^8$ is n-propyl, $R^9$ is tert-butoxy, and $R^1$, $R^2$, $R^3$, $R^6$ and $R^7$ for a compound corresponds in each case to one row of Table A Table 159
Compounds of the formula I.1 in which $R^8$ is n-propyl, $R^9$ is fluoromethoxy, and $R^1$, $R^2$, $R^3$, $R^6$ and $R^7$ for a compound corresponds in each case to one row of Table A Table 160
Compounds of the formula I.1 in which $R^8$ is n-propyl, $R^9$ is difluoromethoxy, and $R^1$, $R^2$, $R^3$, $R^6$ and $R^7$ for a compound corresponds in each case to one row of Table A Table 161
Compounds of the formula I.1 in which $R^8$ is n-propyl, $R^9$ is trifluoromethoxy, and $R^1$, $R^2$, $R^3$, $R^6$ and $R^7$ for a compound corresponds in each case to one row of Table A Table 162
Compounds of the formula I.1 in which $R^8$ is n-propyl, $R^9$ is 2-fluoroethoxy, and $R^1$, $R^2$, $R^3$, $R^6$ and $R^7$ for a compound corresponds in each case to one row of Table A Table 163
Compounds of the formula I.1 in which $R^8$ is n-propyl, $R^9$ is 2,2-difluoroethoxy, and $R^1$, $R^2$, $R^3$, $R^6$ and $R^7$ for a compound corresponds in each case to one row of Table A Table 164
Compounds of the formula I.1 in which $R^8$ is n-propyl, $R^9$ is 2,2,2-trifluoroethoxy, and $R^1$, $R^2$, $R^3$, $R^6$ and $R^7$ for a compound corresponds in each case to one row of Table A Table 165
Compounds of the formula I.1 in which $R^8$ is n-propyl, $R^9$ is pentafluoroethoxy, and $R^1$, $R^2$, $R^3$, $R^6$ and $R^7$ for a compound corresponds in each case to one row of Table A Table 166
Compounds of the formula I.1 in which $R^8$ is n-propyl, $R^9$ is methoxymethyl, and $R^1$, $R^2$, $R^3$, $R^6$ and $R^7$ for a compound corresponds in each case to one row of Table A Table 167
Compounds of the formula I.1 in which $R^8$ is n-propyl, $R^9$ is ethoxymethyl, and $R^1$, $R^2$, $R^3$, $R^6$ and $R^7$ for a compound corresponds in each case to one row of Table A Table 168
Compounds of the formula I.1 in which $R^8$ is n-propyl, $R^9$ is n-propoxymethyl, and $R^1$, $R^2$, $R^3$, $R^6$ and $R^7$ for a compound corresponds in each case to one row of Table A Table 169
Compounds of the formula I.1 in which $R^8$ is n-propyl, $R^9$ is isopropoxymethyl, and $R^1$, $R^2$, $R^3$, $R^6$ and $R^7$ for a compound corresponds in each case to one row of Table A Table 170
Compounds of the formula I.1 in which $R^8$ is n-propyl, $R^9$ is methoxy-1-ethyl, and $R^1$, $R^2$, $R^3$, $R^6$ and $R^7$ for a compound corresponds in each case to one row of Table A Table 171
Compounds of the formula I.1 in which $R^8$ is n-propyl, $R^9$ is ethoxy-1-ethyl, and $R^1$, $R^2$, $R^3$, $R^6$ and $R^7$ for a compound corresponds in each case to one row of Table A Table 172
Compounds of the formula I.1 in which $R^8$ is n-propyl, $R^9$ is n-propoxy-1-ethyl, and $R^1$, $R^2$, $R^3$, $R^6$ and $R^7$ for a compound corresponds in each case to one row of Table A Table 173
Compounds of the formula I.1 in which $R^8$ is n-propyl, $R^9$ is isopropoxy-1-ethyl, and $R^1$, $R^2$, $R^3$, $R^6$ and $R^7$ for a compound corresponds in each case to one row of Table A Table 174
Compounds of the formula I.1 in which $R^8$ is n-propyl, $R^9$ is methoxy-2-ethyl, and $R^1$, $R^2$, $R^3$, $R^6$ and $R^7$ for a compound corresponds in each case to one row of Table A Table 175
Compounds of the formula I.1 in which $R^8$ is n-propyl, $R^9$ is ethoxy-2-ethyl, and $R^1$, $R^2$, $R^3$, $R^6$ and $R^7$ for a compound corresponds in each case to one row of Table A Table 176
Compounds of the formula I.1 in which $R^8$ is n-propyl, $R^9$ is n-propoxy-2-ethyl, and $R^1$, $R^2$, $R^3$, $R^6$ and $R^7$ for a compound corresponds in each case to one row of Table A Table 177
Compounds of the formula I.1 in which $R^8$ is n-propyl, $R^9$ is isopropoxy-2-ethyl, and $R^1$, $R^2$, $R^3$, $R^6$ and $R^7$ for a compound corresponds in each case to one row of Table A Table 178
Compounds of the formula I.1 in which $R^8$ is n-propyl, $R^9$ is methoxy-1-propyl, and $R^1$, $R^2$, $R^3$, $R^6$ and $R^7$ for a compound corresponds in each case to one row of Table A Table 179
Compounds of the formula I.1 in which $R^8$ is n-propyl, $R^9$ is ethoxy-1-propyl, and $R^1$, $R^2$, $R^3$, $R^6$ and $R^7$ for a compound corresponds in each case to one row of Table A Table 180
Compounds of the formula I.1 in which $R^8$ is n-propyl, $R^9$ is n-propoxy-1-propyl, and $R^1$, $R^2$, $R^3$, $R^6$ and $R^7$ for a compound corresponds in each case to one row of Table A Table 181
Compounds of the formula I.1 in which $R^8$ is n-propyl, $R^9$ is isopropoxy-1-propyl, and $R^1$, $R^2$, $R^3$, $R^6$ and $R^7$ for a compound corresponds in each case to one row of Table A Table 182
Compounds of the formula I.1 in which $R^8$ is n-propyl, $R^9$ is methoxy-2-propyl, and $R^1$, $R^2$, $R^3$, $R^6$ and $R^7$ for a compound corresponds in each case to one row of Table A Table 183
Compounds of the formula I.1 in which $R^8$ is n-propyl, $R^9$ is ethoxy-2-propyl, and $R^1$, $R^2$, $R^3$, $R^6$ and $R^7$ for a compound corresponds in each case to one row of Table A Table 184
Compounds of the formula I.1 in which $R^8$ is n-propyl, $R^9$ is n-propoxy-2-propyl, and $R^1$, $R^2$, $R^3$, $R^6$ and $R^7$ for a compound corresponds in each case to one row of Table A Table 185
Compounds of the formula I.1 in which $R^8$ is n-propyl, $R^9$ is isopropoxy-2-propyl, and $R^1$, $R^2$, $R^3$, $R^6$ and $R^7$ for a compound corresponds in each case to one row of Table A Table 186
Compounds of the formula I.1 in which $R^8$ is n-propyl, $R^9$ is methoxy-3-propyl, and $R^1$, $R^2$, $R^3$, $R^6$ and $R^7$ for a compound corresponds in each case to one row of Table A Table 187
Compounds of the formula I.1 in which $R^8$ is n-propyl, $R^9$ is ethoxy-3-propyl, and $R^1$, $R^2$, $R^3$, $R^6$ and $R^7$ for a compound corresponds in each case to one row of Table A Table 188
Compounds of the formula I.1 in which $R^8$ is n-propyl, $R^9$ is n-propoxy-3-propyl, and $R^1$, $R^2$, $R^3$, $R^6$ and $R^7$ for a compound corresponds in each case to one row of Table A Table 189
Compounds of the formula I.1 in which $R^8$ is n-propyl, $R^9$ is isopropoxy-3-propyl, and $R^1$, $R^2$, $R^3$, $R^6$ and $R^7$ for a compound corresponds in each case to one row of Table A Table 190
Compounds of the formula I.1 in which $R^8$ is n-propyl, $R^9$ is oxetan-2-yl, and $R^1$, $R^2$, $R^3$, $R^6$ and $R^7$ for a compound corresponds in each case to one row of Table A Table 191
Compounds of the formula I.1 in which $R^8$ is n-propyl, $R^9$ is oxetan-3-yl, and $R^1$, $R^2$, $R^3$, $R^6$ and $R^7$ for a compound corresponds in each case to one row of Table A Table 192
Compounds of the formula I.1 in which $R^8$ is n-propyl, $R^9$ is tetrahydrofuran-2-yl, and $R^1$, $R^2$, $R^3$, $R^6$ and $R^7$ for a compound corresponds in each case to one row of Table A Table 193
Compounds of the formula I.1 in which $R^8$ is n-propyl, $R^9$ is tetrahydrofuran-3-yl, and $R^1$, $R^2$, $R^3$, $R^6$ and $R^7$ for a compound corresponds in each case to one row of Table A Table 194
Compounds of the formula I.1 in which $R^8$ is n-propyl, $R^9$ is tetrahydropyran-2-yl, and $R^1$, $R^2$, $R^3$, $R^6$ and $R^7$ for a compound corresponds in each case to one row of Table A Table 195
Compounds of the formula I.1 in which $R^8$ is n-propyl, $R^9$ is tetrahydropyran-3-yl, and $R^1$, $R^2$, $R^3$, $R^6$ and $R^7$ for a compound corresponds in each case to one row of Table A Table 196
Compounds of the formula I.1 in which $R^8$ is n-propyl, $R^9$ is tetrahydropyran-4-yl, and $R^1$, $R^2$, $R^3$, $R^6$ and $R^7$ for a compound corresponds in each case to one row of Table A Table 197
Compounds of the formula I.1 in which $R^8$ is n-propyl, $R^9$ is thietan-2-yl, and $R^1$, $R^2$, $R^3$, $R^6$ and $R^7$ for a compound corresponds in each case to one row of Table A Table 198
Compounds of the formula I.1 in which $R^8$ is n-propyl, $R^9$ is thietan-3-yl, and $R^1$, $R^2$, $R^3$, $R^6$ and $R^7$ for a compound corresponds in each case to one row of Table A Table 199
Compounds of the formula I.1 in which $R^8$ is n-propyl, $R^9$ is 1-oxothietan-3-yl, and $R^1$, $R^2$, $R^3$, $R^6$ and $R^7$ for a compound corresponds in each case to one row of Table A Table 200
Compounds of the formula I.1 in which $R^8$ is n-propyl, $R^9$ is 1,1-dioxothietan-3-yl, and $R^1$, $R^2$, $R^3$, $R^6$ and $R^7$ for a compound corresponds in each case to one row of Table A Table 201
Compounds of the formula I.1 in which $R^8$ is isopropyl, $R^9$ is methoxy, and $R^1$, $R^2$, $R^3$, $R^6$ and $R^7$ for a compound corresponds in each case to one row of Table A Table 202
Compounds of the formula I.1 in which $R^8$ is isopropyl, $R^9$ is ethoxy, and $R^1$, $R^2$, $R^3$, $R^6$ and $R^7$ for a compound corresponds in each case to one row of Table A Table 203
Compounds of the formula I.1 in which $R^8$ is isopropyl, $R^9$ is n-propoxy, and $R^1$, $R^2$, $R^3$, $R^6$ and $R^7$ for a compound corresponds in each case to one row of Table A Table 204
Compounds of the formula I.1 in which $R^8$ is isopropyl, $R^9$ is isopropoxy, and $R^1$, $R^2$, $R^3$, $R^6$ and $R^7$ for a compound corresponds in each case to one row of Table A Table 205
Compounds of the formula I.1 in which $R^8$ is isopropyl, $R^9$ is n-butoxy, and $R^1$, $R^2$, $R^3$, $R^6$ and $R^7$ for a compound corresponds in each case to one row of Table A Table 206
Compounds of the formula I.1 in which $R^8$ is isopropyl, $R^9$ is sec-butoxy, and $R^1$, $R^2$, $R^3$, $R^6$ and $R^7$ for a compound corresponds in each case to one row of Table A Table 207
Compounds of the formula I.1 in which $R^8$ is isopropyl, $R^9$ is isobutoxy, and $R^1$, $R^2$, $R^3$, $R^6$ and $R^7$ for a compound corresponds in each case to one row of Table A Table 208
Compounds of the formula I.1 in which $R^8$ is isopropyl, $R^9$ is tert-butoxy, and $R^1$, $R^2$, $R^3$, $R^6$ and $R^7$ for a compound corresponds in each case to one row of Table A Table 209
Compounds of the formula I.1 in which $R^8$ is isopropyl, $R^9$ is fluoromethoxy, and $R^1$, $R^2$, $R^3$, $R^6$ and $R^7$ for a compound corresponds in each case to one row of Table A Table 210
Compounds of the formula I.1 in which $R^8$ is isopropyl, $R^9$ is difluoromethoxy, and $R^1$, $R^2$, $R^3$, $R^6$ and $R^7$ for a compound corresponds in each case to one row of Table A Table 211
Compounds of the formula I.1 in which $R^8$ is isopropyl, $R^9$ is trifluoromethoxy, and $R^1$, $R^2$, $R^3$, $R^6$ and $R^7$ for a compound corresponds in each case to one row of Table A Table 212
Compounds of the formula I.1 in which $R^8$ is isopropyl, $R^9$ is 2-fluoroethoxy, and $R^1$, $R^2$, $R^3$, $R^6$ and $R^7$ for a compound corresponds in each case to one row of Table A Table 213
Compounds of the formula I.1 in which $R^8$ is isopropyl, $R^9$ is 2,2-difluoroethoxy, and $R^1$, $R^2$, $R^3$, $R^6$ and $R^7$ for a compound corresponds in each case to one row of Table A Table 214
Compounds of the formula I.1 in which $R^8$ is isopropyl, $R^9$ is 2,2,2-trifluoroethoxy, and $R^1$, $R^2$, $R^3$, $R^6$ and $R^7$ for a compound corresponds in each case to one row of Table A Table 215
Compounds of the formula I.1 in which $R^8$ is isopropyl, $R^9$ is pentafluoroethoxy, and $R^1$, $R^2$, $R^3$, $R^6$ and $R^7$ for a compound corresponds in each case to one row of Table A Table 216
Compounds of the formula I.1 in which $R^8$ is isopropyl, $R^9$ is methoxymethyl, and $R^1$, $R^2$, $R^3$, $R^6$ and $R^7$ for a compound corresponds in each case to one row of Table A Table 217
Compounds of the formula I.1 in which $R^8$ is isopropyl, $R^9$ is ethoxymethyl, and $R^1$, $R^2$, $R^3$, $R^6$ and $R^7$ for a compound corresponds in each case to one row of Table A Table 218
Compounds of the formula I.1 in which $R^8$ is isopropyl, $R^9$ is n-propoxymethyl, and $R^1$, $R^2$, $R^3$, $R^6$ and $R^7$ for a compound corresponds in each case to one row of Table A Table 219
Compounds of the formula I.1 in which $R^8$ is isopropyl, $R^9$ is isopropoxymethyl, and $R^1$, $R^2$, $R^3$, $R^6$ and $R^7$ for a compound corresponds in each case to one row of Table A Table 220
Compounds of the formula I.1 in which $R^8$ is isopropyl, $R^9$ is methoxy-1-ethyl, and $R^1$, $R^2$, $R^3$, $R^6$ and $R^7$ for a compound corresponds in each case to one row of Table A Table 221
Compounds of the formula I.1 in which $R^8$ is isopropyl, $R^9$ is ethoxy-1-ethyl, and $R^1$, $R^2$, $R^3$, $R^6$ and $R^7$ for a compound corresponds in each case to one row of Table A Table 222
Compounds of the formula I.1 in which $R^8$ is isopropyl, $R^9$ is n-propoxy-1-ethyl, and $R^1$, $R^2$, $R^3$, $R^6$ and $R^7$ for a compound corresponds in each case to one row of Table A Table 223
Compounds of the formula I.1 in which $R^8$ is isopropyl, $R^9$ is isopropoxy-1-ethyl, and $R^1$, $R^2$, $R^3$, $R^6$ and $R^7$ for a compound corresponds in each case to one row of Table A Table 224
Compounds of the formula I.1 in which $R^8$ is isopropyl, $R^9$ is methoxy-2-ethyl, and $R^1$, $R^2$, $R^3$, $R^6$ and $R^7$ for a compound corresponds in each case to one row of Table A Table 225
Compounds of the formula I.1 in which $R^8$ is isopropyl, $R^9$ is ethoxy-2-ethyl, and $R^1$, $R^2$, $R^3$, $R^6$ and $R^7$ for a compound corresponds in each case to one row of Table A Table 226
Compounds of the formula I.1 in which $R^8$ is isopropyl, $R^9$ is n-propoxy-2-ethyl, and $R^1$, $R^2$, $R^3$, $R^6$ and $R^7$ for a compound corresponds in each case to one row of Table A Table 227
Compounds of the formula I.1 in which $R^8$ is isopropyl, $R^9$ is isopropoxy-2-ethyl, and $R^1$, $R^2$, $R^3$, $R^6$ and $R^7$ for a compound corresponds in each case to one row of Table A Table 228
Compounds of the formula I.1 in which $R^8$ is isopropyl, $R^9$ is methoxy-1-propyl, and $R^1$, $R^2$, $R^3$, $R^6$ and $R^7$ for a compound corresponds in each case to one row of Table A Table 229
Compounds of the formula I.1 in which $R^8$ is isopropyl, $R^9$ is ethoxy-1-propyl, and $R^1$, $R^2$, $R^3$, $R^6$ and $R^7$ for a compound corresponds in each case to one row of Table A Table 230
Compounds of the formula I.1 in which $R^8$ is isopropyl, $R^9$ is n-propoxy-1-propyl, and $R^1$, $R^2$, $R^3$, $R^6$ and $R^7$ for a compound corresponds in each case to one row of Table A Table 231
Compounds of the formula I.1 in which $R^8$ is isopropyl, $R^9$ is isopropoxy-1-propyl, and $R^1$, $R^2$, $R^3$, $R^6$ and $R^7$ for a compound corresponds in each case to one row of Table A Table 232
Compounds of the formula I.1 in which $R^8$ is isopropyl, $R^9$ is methoxy-2-propyl, and $R^1$, $R^2$, $R^3$, $R^6$ and $R^7$ for a compound corresponds in each case to one row of Table A Table 233
Compounds of the formula I.1 in which $R^8$ is isopropyl, $R^9$ is ethoxy-2-propyl, and $R^1$, $R^2$, $R^3$, $R^6$ and $R^7$ for a compound corresponds in each case to one row of Table A Table 234
Compounds of the formula I.1 in which $R^8$ is isopropyl, $R^9$ is n-propoxy-2-propyl, and $R^1$, $R^2$, $R^3$, $R^6$ and $R^7$ for a compound corresponds in each case to one row of Table A Table 235
Compounds of the formula I.1 in which $R^8$ is isopropyl, $R^9$ is isopropoxy-2-propyl, and $R^1$, $R^2$, $R^3$, $R^6$ and $R^7$ for a compound corresponds in each case to one row of Table A Table 236
Compounds of the formula I.1 in which $R^8$ is isopropyl, $R^9$ is methoxy-3-propyl, and $R^1$, $R^2$, $R^3$, $R^6$ and $R^7$ for a compound corresponds in each case to one row of Table A Table 237
Compounds of the formula I.1 in which $R^8$ is isopropyl, $R^9$ is ethoxy-3-propyl, and $R^1$, $R^2$, $R^3$, $R^6$ and $R^7$ for a compound corresponds in each case to one row of Table A Table 238
Compounds of the formula I.1 in which $R^8$ is isopropyl, $R^9$ is n-propoxy-3-propyl, and $R^1$, $R^2$, $R^3$, $R^6$ and $R^7$ for a compound corresponds in each case to one row of Table A Table 239
Compounds of the formula I.1 in which $R^8$ is isopropyl, $R^9$ is isopropoxy-3-propyl, and $R^1$, $R^2$, $R^3$, $R^6$ and $R^7$ for a compound corresponds in each case to one row of Table A Table 240
Compounds of the formula I.1 in which $R^8$ is isopropyl, $R^9$ is oxetan-2-yl, and $R^1$, $R^2$, $R^3$, $R^6$ and $R^7$ for a compound corresponds in each case to one row of Table A Table 241
Compounds of the formula I.1 in which $R^8$ is isopropyl, $R^9$ is oxetan-3-yl, and $R^1$, $R^2$, $R^3$, $R^6$ and $R^7$ for a compound corresponds in each case to one row of Table A Table 242
Compounds of the formula I.1 in which $R^8$ is isopropyl, $R^9$ is tetrahydrofuran-2-yl, and $R^1$, $R^2$, $R^3$, $R^6$ and $R^7$ for a compound corresponds in each case to one row of Table A Table 243
Compounds of the formula I.1 in which $R^8$ is isopropyl, $R^9$ is tetrahydrofuran-3-yl, and $R^1$, $R^2$, $R^3$, $R^6$ and $R^7$ for a compound corresponds in each case to one row of Table A Table 244
Compounds of the formula I.1 in which $R^8$ is isopropyl, $R^9$ is tetrahydropyran-2-yl, and $R^1$, $R^2$, $R^3$, $R^6$ and $R^7$ for a compound corresponds in each case to one row of Table A Table 245
Compounds of the formula I.1 in which $R^8$ is isopropyl, $R^9$ is tetrahydropyran-3-yl, and $R^1$, $R^2$, $R^3$, $R^6$ and $R^7$ for a compound corresponds in each case to one row of Table A Table 246
Compounds of the formula I.1 in which $R^8$ is isopropyl, $R^9$ is tetrahydropyran-4-yl, and $R^1$, $R^2$, $R^3$, $R^6$ and $R^7$ for a compound corresponds in each case to one row of Table A Table 247
Compounds of the formula I.1 in which $R^8$ is isopropyl, $R^9$ is thietan-2-yl, and $R^1$, $R^2$, $R^3$, $R^6$ and $R^7$ for a compound corresponds in each case to one row of Table A Table 248
Compounds of the formula I.1 in which $R^8$ is isopropyl, $R^9$ is thietan-3-yl, and $R^1$, $R^2$, $R^3$, $R^6$ and $R^7$ for a compound corresponds in each case to one row of Table A Table 249
Compounds of the formula I.1 in which $R^8$ is isopropyl, $R^9$ is 1-oxothietan-3-yl, and $R^1$, $R^2$, $R^3$, $R^6$ and $R^7$ for a compound corresponds in each case to one row of Table A Table 250
Compounds of the formula I.1 in which $R^8$ is isopropyl, $R^9$ is 1,1-dioxothietan-3-yl, and $R^1$, $R^2$, $R^3$, $R^6$ and $R^7$ for a compound corresponds in each case to one row of Table A Table 251
Compounds of the formula I.1 in which $R^8$ is n-butyl, $R^9$ is methoxy, and $R^1$, $R^2$, $R^3$, $R^6$ and $R^7$ for a compound corresponds in each case to one row of Table A Table 252
Compounds of the formula I.1 in which $R^8$ is n-butyl, $R^9$ is ethoxy, and $R^1$, $R^2$, $R^3$, $R^6$ and $R^7$ for a compound corresponds in each case to one row of Table A Table 253
Compounds of the formula I.1 in which $R^8$ is n-butyl, $R^9$ is n-propoxy, and $R^1$, $R^2$, $R^3$, $R^6$ and $R^7$ for a compound corresponds in each case to one row of Table A Table 254
Compounds of the formula I.1 in which $R^8$ is n-butyl, $R^9$ is isopropoxy, and $R^1$, $R^2$, $R^3$, $R^6$ and $R^7$ for a compound corresponds in each case to one row of Table A Table 255
Compounds of the formula I.1 in which $R^8$ is n-butyl, $R^9$ is n-butoxy, and $R^1$, $R^2$, $R^3$, $R^6$ and $R^7$ for a compound corresponds in each case to one row of Table A Table 256
Compounds of the formula I.1 in which $R^8$ is n-butyl, $R^9$ is sec-butoxy, and $R^1$, $R^2$, $R^3$, $R^6$ and $R^7$ for a compound corresponds in each case to one row of Table A Table 257
Compounds of the formula I.1 in which $R^8$ is n-butyl, $R^9$ is isobutoxy, and $R^1$, $R^2$, $R^3$, $R^6$ and $R^7$ for a compound corresponds in each case to one row of Table A Table 258
Compounds of the formula I.1 in which $R^8$ is n-butyl, $R^9$ is tert-butoxy, and $R^1$, $R^2$, $R^3$, $R^6$ and $R^7$ for a compound corresponds in each case to one row of Table A Table 259
Compounds of the formula I.1 in which $R^8$ is n-butyl, $R^9$ is fluoromethoxy, and $R^1$, $R^2$, $R^3$, $R^6$ and $R^7$ for a compound corresponds in each case to one row of Table A Table 260
Compounds of the formula I.1 in which $R^8$ is n-butyl, $R^9$ is difluoromethoxy, and $R^1$, $R^2$, $R^3$, $R^6$ and $R^7$ for a compound corresponds in each case to one row of Table A Table 261
Compounds of the formula I.1 in which $R^8$ is n-butyl, $R^9$ is trifluoromethoxy, and $R^1$, $R^2$, $R^3$, $R^6$ and $R^7$ for a compound corresponds in each case to one row of Table A Table 262
Compounds of the formula I.1 in which $R^8$ is n-butyl, $R^9$ is 2-fluoroethoxy, and $R^1$, $R^2$, $R^3$, $R^6$ and $R^7$ for a compound corresponds in each case to one row of Table A Table 263
Compounds of the formula I.1 in which $R^8$ is n-butyl, $R^9$ is 2,2-difluoroethoxy, and $R^1$, $R^2$, $R^3$, $R^6$ and $R^7$ for a compound corresponds in each case to one row of Table A Table 264
Compounds of the formula I.1 in which $R^8$ is n-butyl, $R^9$ is 2,2,2-trifluoroethoxy, and $R^1$, $R^2$, $R^3$, $R^6$ and $R^7$ for a compound corresponds in each case to one row of Table A Table 265
Compounds of the formula I.1 in which $R^8$ is n-butyl, $R^9$ is pentafluoroethoxy, and $R^1$, $R^2$, $R^3$, $R^6$ and $R^7$ for a compound corresponds in each case to one row of Table A Table 266
Compounds of the formula I.1 in which $R^8$ is n-butyl, $R^9$ is methoxymethyl, and $R^1$, $R^2$, $R^3$, $R^6$ and $R^7$ for a compound corresponds in each case to one row of Table A Table 267
Compounds of the formula I.1 in which $R^8$ is n-butyl, $R^9$ is ethoxymethyl, and $R^1$, $R^2$, $R^3$, $R^6$ and $R^7$ for a compound corresponds in each case to one row of Table A Table 268
Compounds of the formula I.1 in which $R^8$ is n-butyl, $R^9$ is n-propoxymethyl, and $R^1$, $R^2$, $R^3$, $R^6$ and $R^7$ for a compound corresponds in each case to one row of Table A Table 269
Compounds of the formula I.1 in which $R^8$ is n-butyl, $R^9$ is isopropoxymethyl, and $R^1$, $R^2$, $R^3$, $R^6$ and $R^7$ for a compound corresponds in each case to one row of Table A Table 270
Compounds of the formula I.1 in which $R^8$ is n-butyl, $R^9$ is methoxy-1-ethyl, and $R^1$, $R^2$, $R^3$, $R^6$ and $R^7$ for a compound corresponds in each case to one row of Table A Table 271
Compounds of the formula I.1 in which $R^8$ is n-butyl, $R^9$ is ethoxy-1-ethyl, and $R^1$, $R^2$, $R^3$, $R^6$ and $R^7$ for a compound corresponds in each case to one row of Table A Table 272
Compounds of the formula I.1 in which $R^8$ is n-butyl, $R^9$ is n-propoxy-1-ethyl, and $R^1$, $R^2$, $R^3$, $R^6$ and $R^7$ for a compound corresponds in each case to one row of Table A Table 273
Compounds of the formula I.1 in which $R^8$ is n-butyl, $R^9$ is isopropoxy-1-ethyl, and $R^1$, $R^2$, $R^3$, $R^6$ and $R^7$ for a compound corresponds in each case to one row of Table A Table 274
Compounds of the formula I.1 in which $R^8$ is n-butyl, $R^9$ is methoxy-2-ethyl, and $R^1$, $R^2$, $R^3$, $R^6$ and $R^7$ for a compound corresponds in each case to one row of Table A Table 275
Compounds of the formula I.1 in which $R^8$ is n-butyl, $R^9$ is ethoxy-2-ethyl, and $R^1$, $R^2$, $R^3$, $R^6$ and $R^7$ for a compound corresponds in each case to one row of Table A Table 276
Compounds of the formula I.1 in which $R^8$ is n-butyl, $R^9$ is n-propoxy-2-ethyl, and $R^1$, $R^2$, $R^3$, $R^6$ and $R^7$ for a compound corresponds in each case to one row of Table A Table 277
Compounds of the formula I.1 in which $R^8$ is n-butyl, $R^9$ is isopropoxy-2-ethyl, and $R^1$, $R^2$, $R^3$, $R^6$ and $R^7$ for a compound corresponds in each case to one row of Table A Table 278
Compounds of the formula I.1 in which $R^8$ is n-butyl, $R^9$ is methoxy-1-propyl, and $R^1$, $R^2$, $R^3$, $R^6$ and $R^7$ for a compound corresponds in each case to one row of Table A Table 279
Compounds of the formula I.1 in which $R^8$ is n-butyl, $R^9$ is ethoxy-1-propyl, and $R^1$, $R^2$, $R^3$, $R^6$ and $R^7$ for a compound corresponds in each case to one row of Table A Table 280
Compounds of the formula I.1 in which $R^8$ is n-butyl, $R^9$ is n-propoxy-1-propyl, and $R^1$, $R^2$, $R^3$, $R^6$ and $R^7$ for a compound corresponds in each case to one row of Table A Table 281
Compounds of the formula I.1 in which $R^8$ is n-butyl, $R^9$ is isopropoxy-1-propyl, and $R^1$, $R^2$, $R^3$, $R^6$ and $R^7$ for a compound corresponds in each case to one row of Table A Table 282
Compounds of the formula I.1 in which $R^8$ is n-butyl, $R^9$ is methoxy-2-propyl, and $R^1$, $R^2$, $R^3$, $R^6$ and $R^7$ for a compound corresponds in each case to one row of Table A Table 283
Compounds of the formula I.1 in which $R^8$ is n-butyl, $R^9$ is ethoxy-2-propyl, and $R^1$, $R^2$, $R^3$, $R^6$ and $R^7$ for a compound corresponds in each case to one row of Table A Table 284
Compounds of the formula I.1 in which $R^8$ is n-butyl, $R^9$ is n-propoxy-2-propyl, and $R^1$, $R^2$, $R^3$, $R^6$ and $R^7$ for a compound corresponds in each case to one row of Table A Table 285
Compounds of the formula I.1 in which $R^8$ is n-butyl, $R^9$ is isopropoxy-2-propyl, and $R^1$, $R^2$, $R^3$, $R^6$ and $R^7$ for a compound corresponds in each case to one row of Table A Table 286
Compounds of the formula I.1 in which $R^8$ is n-butyl, $R^9$ is methoxy-3-propyl, and $R^1$, $R^2$, $R^3$, $R^6$ and $R^7$ for a compound corresponds in each case to one row of Table A Table 287
Compounds of the formula I.1 in which $R^8$ is n-butyl, $R^9$ is ethoxy-3-propyl, and $R^1$, $R^2$, $R^3$, $R^6$ and $R^7$ for a compound corresponds in each case to one row of Table A Table 288
Compounds of the formula I.1 in which $R^8$ is n-butyl, $R^9$ is n-propoxy-3-propyl, and $R^1$, $R^2$, $R^3$, $R^6$ and $R^7$ for a compound corresponds in each case to one row of Table A Table 289
Compounds of the formula I.1 in which $R^8$ is n-butyl, $R^9$ is isopropoxy-3-propyl, and $R^1$, $R^2$, $R^3$, $R^6$ and $R^7$ for a compound corresponds in each case to one row of Table A Table 290
Compounds of the formula I.1 in which $R^8$ is n-butyl, $R^9$ is oxetan-2-yl, and $R^1$, $R^2$, $R^3$, $R^6$ and $R^7$ for a compound corresponds in each case to one row of Table A Table 291
Compounds of the formula I.1 in which $R^8$ is n-butyl, $R^9$ is oxetan-3-yl, and $R^1$, $R^2$, $R^3$, $R^6$ and $R^7$ for a compound corresponds in each case to one row of Table A Table 292
Compounds of the formula I.1 in which $R^8$ is n-butyl, $R^9$ is tetrahydrofuran-2-yl, and $R^1$, $R^2$, $R^3$, $R^6$ and $R^7$ for a compound corresponds in each case to one row of Table A Table 293
Compounds of the formula I.1 in which $R^8$ is n-butyl, $R^9$ is tetrahydrofuran-3-yl, and $R^1$, $R^2$, $R^3$, $R^6$ and $R^7$ for a compound corresponds in each case to one row of Table A Table 294
Compounds of the formula I.1 in which $R^8$ is n-butyl, $R^9$ is tetrahydropyran-2-yl, and $R^1$, $R^2$, $R^3$, $R^6$ and $R^7$ for a compound corresponds in each case to one row of Table A Table 295
Compounds of the formula I.1 in which $R^8$ is n-butyl, $R^9$ is tetrahydropyran-3-yl, and $R^1$, $R^2$, $R^3$, $R^6$ and $R^7$ for a compound corresponds in each case to one row of Table A Table 296
Compounds of the formula I.1 in which $R^8$ is n-butyl, $R^9$ is tetrahydropyran-4-yl, and $R^1$, $R^2$, $R^3$, $R^6$ and $R^7$ for a compound corresponds in each case to one row of Table A Table 297
Compounds of the formula I.1 in which $R^8$ is n-butyl, $R^9$ is thietan-2-yl, and $R^1$, $R^2$, $R^3$, $R^6$ and $R^7$ for a compound corresponds in each case to one row of Table A Table 298
Compounds of the formula I.1 in which $R^8$ is n-butyl, $R^9$ is thietan-3-yl, and $R^1$, $R^2$, $R^3$, $R^6$ and $R^7$ for a compound corresponds in each case to one row of Table A Table 299
Compounds of the formula I.1 in which $R^8$ is n-butyl, $R^9$ is 1-oxothietan-3-yl, and $R^1$, $R^2$, $R^3$, $R^6$ and $R^7$ for a compound corresponds in each case to one row of Table A Table 300
Compounds of the formula I.1 in which $R^8$ is n-butyl, $R^9$ is 1,1-dioxothietan-3-yl, and $R^1$, $R^2$, $R^3$, $R^6$ and $R^7$ for a compound corresponds in each case to one row of Table A Table 301
Compounds of the formula I.1 in which $R^8$ is sec-butyl, $R^9$ is methoxy, and $R^1$, $R^2$, $R^3$, $R^6$ and $R^7$ for a compound corresponds in each case to one row of Table A Table 302
Compounds of the formula I.1 in which $R^8$ is sec-butyl, $R^9$ is ethoxy, and $R^1$, $R^2$, $R^3$, $R^6$ and $R^7$ for a compound corresponds in each case to one row of Table A Table 303
Compounds of the formula I.1 in which $R^8$ is sec-butyl, $R^9$ is n-propoxy, and $R^1$, $R^2$, $R^3$, $R^6$ and $R^7$ for a compound corresponds in each case to one row of Table A Table 304
Compounds of the formula I.1 in which $R^8$ is sec-butyl, $R^9$ is isopropoxy, and $R^1$, $R^2$, $R^3$, $R^6$ and $R^7$ for a compound corresponds in each case to one row of Table A Table 305
Compounds of the formula I.1 in which $R^8$ is sec-butyl, $R^9$ is n-butoxy, and $R^1$, $R^2$, $R^3$, $R^6$ and $R^7$ for a compound corresponds in each case to one row of Table A Table 306
Compounds of the formula I.1 in which $R^8$ is sec-butyl, $R^9$ is sec-butoxy, and $R^1$, $R^2$, $R^3$, $R^6$ and $R^7$ for a compound corresponds in each case to one row of Table A Table 307
Compounds of the formula I.1 in which $R^8$ is sec-butyl, $R^9$ is isobutoxy, and $R^1$, $R^2$, $R^3$, $R^6$ and $R^7$ for a compound corresponds in each case to one row of Table A Table 308
Compounds of the formula I.1 in which $R^8$ is sec-butyl, $R^9$ is tert-butoxy, and $R^1$, $R^2$, $R^3$, $R^6$ and $R^7$ for a compound corresponds in each case to one row of Table A Table 309
Compounds of the formula I.1 in which $R^8$ is sec-butyl, $R^9$ is fluoromethoxy, and $R^1$, $R^2$, $R^3$, $R^6$ and $R^7$ for a compound corresponds in each case to one row of Table A Table 310
Compounds of the formula I.1 in which $R^8$ is sec-butyl, $R^9$ is difluoromethoxy, and $R^1$, $R^2$, $R^3$, $R^6$ and $R^7$ for a compound corresponds in each case to one row of Table A Table 311
Compounds of the formula I.1 in which $R^8$ is sec-butyl, $R^9$ is trifluoromethoxy, and $R^1$, $R^2$, $R^3$, $R^6$ and $R^7$ for a compound corresponds in each case to one row of Table A Table 312
Compounds of the formula I.1 in which $R^8$ is sec-butyl, $R^9$ is 2-fluoroethoxy, and $R^1$, $R^2$, $R^3$, $R^6$ and $R^7$ for a compound corresponds in each case to one row of Table A Table 313
Compounds of the formula I.1 in which $R^8$ is sec-butyl, $R^9$ is 2,2-difluoroethoxy, and $R^1$, $R^2$, $R^3$, $R^6$ and $R^7$ for a compound corresponds in each case to one row of Table A Table 314
Compounds of the formula I.1 in which $R^8$ is sec-butyl, $R^9$ is 2,2,2-trifluoroethoxy, and $R^1$, $R^2$, $R^3$, $R^6$ and $R^7$ for a compound corresponds in each case to one row of Table A Table 315
Compounds of the formula I.1 in which $R^8$ is sec-butyl, $R^9$ is pentafluoroethoxy, and $R^1$, $R^2$, $R^3$, $R^6$ and $R^7$ for a compound corresponds in each case to one row of Table A Table 316
Compounds of the formula I.1 in which $R^8$ is sec-butyl, $R^9$ is methoxymethyl, and $R^1$, $R^2$, $R^3$, $R^6$ and $R^7$ for a compound corresponds in each case to one row of Table A Table 317
Compounds of the formula I.1 in which $R^8$ is sec-butyl, $R^9$ is ethoxymethyl, and $R^1$, $R^2$, $R^3$, $R^6$ and $R^7$ for a compound corresponds in each case to one row of Table A Table 318
Compounds of the formula I.1 in which $R^8$ is sec-butyl, $R^9$ is n-propoxymethyl, and $R^1$, $R^2$, $R^3$, $R^6$ and $R^7$ for a compound corresponds in each case to one row of Table A Table 319
Compounds of the formula I.1 in which $R^8$ is sec-butyl, $R^9$ is isopropoxymethyl, and $R^1$, $R^2$, $R^3$, $R^6$ and $R^7$ for a compound corresponds in each case to one row of Table A Table 320
Compounds of the formula I.1 in which $R^8$ is sec-butyl, $R^9$ is methoxy-1-ethyl, and $R^1$, $R^2$, $R^3$, $R^6$ and $R^7$ for a compound corresponds in each case to one row of Table A Table 321
Compounds of the formula I.1 in which $R^8$ is sec-butyl, $R^9$ is ethoxy-1-ethyl, and $R^1$, $R^2$, $R^3$, $R^6$ and $R^7$ for a compound corresponds in each case to one row of Table A Table 322
Compounds of the formula I.1 in which $R^8$ is sec-butyl, $R^9$ is n-propoxy-1-ethyl, and $R^1$, $R^2$, $R^3$, $R^6$ and $R^7$ for a compound corresponds in each case to one row of Table A Table 323
Compounds of the formula I.1 in which $R^8$ is sec-butyl, $R^9$ is isopropoxy-1-ethyl, and $R^1$, $R^2$, $R^3$, $R^6$ and $R^7$ for a compound corresponds in each case to one row of Table A Table 324
Compounds of the formula I.1 in which $R^8$ is sec-butyl, $R^9$ is methoxy-2-ethyl, and $R^1$, $R^2$, $R^3$, $R^6$ and $R^7$ for a compound corresponds in each case to one row of Table A Table 325
Compounds of the formula I.1 in which $R^8$ is sec-butyl, $R^9$ is ethoxy-2-ethyl, and $R^1$, $R^2$, $R^3$, $R^6$ and $R^7$ for a compound corresponds in each case to one row of Table A Table 326
Compounds of the formula I.1 in which $R^8$ is sec-butyl, $R^9$ is n-propoxy-2-ethyl, and $R^1$, $R^2$, $R^3$, $R^6$ and $R^7$ for a compound corresponds in each case to one row of Table A Table 327
Compounds of the formula I.1 in which $R^8$ is sec-butyl, $R^9$ is isopropoxy-2-ethyl, and $R^1$, $R^2$, $R^3$, $R^6$ and $R^7$ for a compound corresponds in each case to one row of Table A Table 328
Compounds of the formula I.1 in which $R^8$ is sec-butyl, $R^9$ is methoxy-1-propyl, and $R^1$, $R^2$, $R^3$, $R^6$ and $R^7$ for a compound corresponds in each case to one row of Table A Table 329
Compounds of the formula I.1 in which $R^8$ is sec-butyl, $R^9$ is ethoxy-1-propyl, and $R^1$, $R^2$, $R^3$, $R^6$ and $R^7$ for a compound corresponds in each case to one row of Table A Table 330
Compounds of the formula I.1 in which $R^8$ is sec-butyl, $R^9$ is n-propoxy-1-propyl, and $R^1$, $R^2$, $R^3$, $R^6$ and $R^7$ for a compound corresponds in each case to one row of Table A Table 331
Compounds of the formula I.1 in which $R^8$ is sec-butyl, $R^9$ is isopropoxy-1-propyl, and $R^1$, $R^2$, $R^3$, $R^6$ and $R^7$ for a compound corresponds in each case to one row of Table A Table 332
Compounds of the formula I.1 in which $R^8$ is sec-butyl, $R^9$ is methoxy-2-propyl, and $R^1$, $R^2$, $R^3$, $R^6$ and $R^7$ for a compound corresponds in each case to one row of Table A Table 333
Compounds of the formula I.1 in which $R^8$ is sec-butyl, $R^9$ is ethoxy-2-propyl, and $R^1$, $R^2$, $R^3$, $R^6$ and $R^7$ for a compound corresponds in each case to one row of Table A Table 334
Compounds of the formula I.1 in which $R^8$ is sec-butyl, $R^9$ is n-propoxy-2-propyl, and $R^1$, $R^2$, $R^3$, $R^6$ and $R^7$ for a compound corresponds in each case to one row of Table A Table 335
Compounds of the formula I.1 in which $R^8$ is sec-butyl, $R^9$ is isopropoxy-2-propyl, and $R^1$, $R^2$, $R^3$, $R^6$ and $R^7$ for a compound corresponds in each case to one row of Table A Table 336
Compounds of the formula I.1 in which $R^8$ is sec-butyl, $R^9$ is methoxy-3-propyl, and $R^1$, $R^2$, $R^3$, $R^6$ and $R^7$ for a compound corresponds in each case to one row of Table A Table 337
Compounds of the formula I.1 in which $R^8$ is sec-butyl, $R^9$ is ethoxy-3-propyl, and $R^1$, $R^2$, $R^3$, $R^6$ and $R^7$ for a compound corresponds in each case to one row of Table A Table 338
Compounds of the formula I.1 in which $R^8$ is sec-butyl, $R^9$ is n-propoxy-3-propyl, and $R^1$, $R^2$, $R^3$, $R^6$ and $R^7$ for a compound corresponds in each case to one row of Table A Table 339
Compounds of the formula I.1 in which $R^8$ is sec-butyl, $R^9$ is isopropoxy-3-propyl, and $R^1$, $R^2$, $R^3$, $R^6$ and $R^7$ for a compound corresponds in each case to one row of Table A Table 340
Compounds of the formula I.1 in which $R^8$ is sec-butyl, $R^9$ is oxetan-2-yl, and $R^1$, $R^2$, $R^3$, $R^6$ and $R^7$ for a compound corresponds in each case to one row of Table A Table 341
Compounds of the formula I.1 in which $R^8$ is sec-butyl, $R^9$ is oxetan-3-yl, and $R^1$, $R^2$, $R^3$, $R^6$ and $R^7$ for a compound corresponds in each case to one row of Table A Table 342
Compounds of the formula I.1 in which $R^8$ is sec-butyl, $R^9$ is tetrahydrofuran-2-yl, and $R^1$, $R^2$, $R^3$, $R^6$ and $R^7$ for a compound corresponds in each case to one row of Table A Table 343
Compounds of the formula I.1 in which $R^8$ is sec-butyl, $R^9$ is tetrahydrofuran-3-yl, and $R^1$, $R^2$, $R^3$, $R^6$ and $R^7$ for a compound corresponds in each case to one row of Table A Table 344
Compounds of the formula I.1 in which $R^8$ is sec-butyl, $R^9$ is tetrahydropyran-2-yl, and $R^1$, $R^2$, $R^3$, $R^6$ and $R^7$ for a compound corresponds in each case to one row of Table A Table 345
Compounds of the formula I.1 in which $R^8$ is sec-butyl, $R^9$ is tetrahydropyran-3-yl, and $R^1$, $R^2$, $R^3$, $R^6$ and $R^7$ for a compound corresponds in each case to one row of Table A Table 346
Compounds of the formula I.1 in which $R^8$ is sec-butyl, $R^9$ is tetrahydropyran-4-yl, and $R^1$, $R^2$, $R^3$, $R^6$ and $R^7$ for a compound corresponds in each case to one row of Table A Table 347
Compounds of the formula I.1 in which $R^8$ is sec-butyl, $R^9$ is thietan-2-yl, and $R^1$, $R^2$, $R^3$, $R^6$ and $R^7$ for a compound corresponds in each case to one row of Table A Table 348
Compounds of the formula I.1 in which $R^8$ is sec-butyl, $R^9$ is thietan-3-yl, and $R^1$, $R^2$, $R^3$, $R^6$ and $R^7$ for a compound corresponds in each case to one row of Table A Table 349
Compounds of the formula I.1 in which $R^8$ is sec-butyl, $R^9$ is 1-oxothietan-3-yl, and $R^1$, $R^2$, $R^3$, $R^6$ and $R^7$ for a compound corresponds in each case to one row of Table A Table 350
Compounds of the formula I.1 in which $R^8$ is sec-butyl, $R^9$ is 1,1-dioxothietan-3-yl, and $R^1$, $R^2$, $R^3$, $R^6$ and $R^7$ for a compound corresponds in each case to one row of Table A Table 351
Compounds of the formula I.1 in which $R^8$ is isobutyl, $R^9$ is methoxy, and $R^1$, $R^2$, $R^3$, $R^6$ and $R^7$ for a compound corresponds in each case to one row of Table A Table 352
Compounds of the formula I.1 in which $R^8$ is isobutyl, $R^9$ is ethoxy, and $R^1$, $R^2$, $R^3$, $R^6$ and $R^7$ for a compound corresponds in each case to one row of Table A Table 353
Compounds of the formula I.1 in which $R^8$ is isobutyl, $R^9$ is n-propoxy, and $R^1$, $R^2$, $R^3$, $R^6$ and $R^7$ for a compound corresponds in each case to one row of Table A Table 354
Compounds of the formula I.1 in which $R^8$ is isobutyl, $R^9$ is isopropoxy, and $R^1$, $R^2$, $R^3$, $R^6$ and $R^7$ for a compound corresponds in each case to one row of Table A Table 355
Compounds of the formula I.1 in which $R^8$ is isobutyl, $R^9$ is n-butoxy, and $R^1$, $R^2$, $R^3$, $R^6$ and $R^7$ for a compound corresponds in each case to one row of Table A Table 356
Compounds of the formula I.1 in which $R^8$ is isobutyl, $R^9$ is sec-butoxy, and $R^1$, $R^2$, $R^3$, $R^6$ and $R^7$ for a compound corresponds in each case to one row of Table A Table 357
Compounds of the formula I.1 in which $R^8$ is isobutyl, $R^9$ is isobutoxy, and $R^1$, $R^2$, $R^3$, $R^6$ and $R^7$ for a compound corresponds in each case to one row of Table A Table 358
Compounds of the formula I.1 in which $R^8$ is isobutyl, $R^9$ is tert-butoxy, and $R^1$, $R^2$, $R^3$, $R^6$ and $R^7$ for a compound corresponds in each case to one row of Table A Table 359
Compounds of the formula I.1 in which $R^8$ is isobutyl, $R^9$ is fluoromethoxy, and $R^1$, $R^2$, $R^3$, $R^6$ and $R^7$ for a compound corresponds in each case to one row of Table A Table 360
Compounds of the formula I.1 in which $R^8$ is isobutyl, $R^9$ is difluoromethoxy, and $R^1$, $R^2$, $R^3$, $R^6$ and $R^7$ for a compound corresponds in each case to one row of Table A Table 361
Compounds of the formula I.1 in which $R^8$ is isobutyl, $R^9$ is trifluoromethoxy, and $R^1$, $R^2$, $R^3$, $R^6$ and $R^7$ for a compound corresponds in each case to one row of Table A Table 362
Compounds of the formula I.1 in which $R^8$ is isobutyl, $R^9$ is 2-fluoroethoxy, and $R^1$, $R^2$, $R^3$, $R^6$ and $R^7$ for a compound corresponds in each case to one row of Table A Table 363
Compounds of the formula I.1 in which $R^8$ is isobutyl, $R^9$ is 2,2-difluoroethoxy, and $R^1$, $R^2$, $R^3$, $R^6$ and $R^7$ for a compound corresponds in each case to one row of Table A Table 364
Compounds of the formula I.1 in which $R^8$ is isobutyl, $R^9$ is 2,2,2-trifluoroethoxy, and $R^1$, $R^2$, $R^3$, $R^6$ and $R^7$ for a compound corresponds in each case to one row of Table A Table 365
Compounds of the formula I.1 in which $R^8$ is isobutyl, $R^9$ is pentafluoroethoxy, and $R^1$, $R^2$, $R^3$, $R^6$ and $R^7$ for a compound corresponds in each case to one row of Table A Table 366
Compounds of the formula I.1 in which $R^8$ is isobutyl, $R^9$ is methoxymethyl, and $R^1$, $R^2$, $R^3$, $R^6$ and $R^7$ for a compound corresponds in each case to one row of Table A Table 367
Compounds of the formula I.1 in which $R^8$ is isobutyl, $R^9$ is ethoxymethyl, and $R^1$, $R^2$, $R^3$, $R^6$ and $R^7$ for a compound corresponds in each case to one row of Table A Table 368
Compounds of the formula I.1 in which $R^8$ is isobutyl, $R^9$ is n-propoxymethyl, and $R^1$, $R^2$, $R^3$, $R^6$ and $R^7$ for a compound corresponds in each case to one row of Table A Table 369
Compounds of the formula I.1 in which $R^8$ is isobutyl, $R^9$ is isopropoxymethyl, and $R^1$, $R^2$, $R^3$, $R^6$ and $R^7$ for a compound corresponds in each case to one row of Table A Table 370
Compounds of the formula I.1 in which $R^8$ is isobutyl, $R^9$ is methoxy-1-ethyl, and $R^1$, $R^2$, $R^3$, $R^6$ and $R^7$ for a compound corresponds in each case to one row of Table A Table 371
Compounds of the formula I.1 in which $R^8$ is isobutyl, $R^9$ is ethoxy-1-ethyl, and $R^1$, $R^2$, $R^3$, $R^6$ and $R^7$ for a compound corresponds in each case to one row of Table A Table 372
Compounds of the formula I.1 in which $R^8$ is isobutyl, $R^9$ is n-propoxy-1-ethyl, and $R^1$, $R^2$, $R^3$, $R^6$ and $R^7$ for a compound corresponds in each case to one row of Table A Table 373
Compounds of the formula I.1 in which $R^8$ is isobutyl, $R^9$ is isopropoxy-1-ethyl, and $R^1$, $R^2$, $R^3$, $R^6$ and $R^7$ for a compound corresponds in each case to one row of Table A Table 374
Compounds of the formula I.1 in which $R^8$ is isobutyl, $R^9$ is methoxy-2-ethyl, and $R^1$, $R^2$, $R^3$, $R^6$ and $R^7$ for a compound corresponds in each case to one row of Table A Table 375
Compounds of the formula I.1 in which $R^8$ is isobutyl, $R^9$ is ethoxy-2-ethyl, and $R^1$, $R^2$, $R^3$, $R^6$ and $R^7$ for a compound corresponds in each case to one row of Table A Table 376
Compounds of the formula I.1 in which $R^8$ is isobutyl, $R^9$ is n-propoxy-2-ethyl, and $R^1$, $R^2$, $R^3$, $R^6$ and $R^7$ for a compound corresponds in each case to one row of Table A Table 377
Compounds of the formula I.1 in which $R^8$ is isobutyl, $R^9$ is isopropoxy-2-ethyl, and $R^1$, $R^2$, $R^3$, $R^6$ and $R^7$ for a compound corresponds in each case to one row of Table A Table 378
Compounds of the formula I.1 in which $R^8$ is isobutyl, $R^9$ is methoxy-1-propyl, and $R^1$, $R^2$, $R^3$, $R^6$ and $R^7$ for a compound corresponds in each case to one row of Table A Table 379
Compounds of the formula I.1 in which $R^8$ is isobutyl, $R^9$ is ethoxy-1-propyl, and $R^1$, $R^2$, $R^3$, $R^6$ and $R^7$ for a compound corresponds in each case to one row of Table A Table 380
Compounds of the formula I.1 in which $R^8$ is isobutyl, $R^9$ is n-propoxy-1-propyl, and $R^1$, $R^2$, $R^3$, $R^6$ and $R^7$ for a compound corresponds in each case to one row of Table A Table 381
Compounds of the formula I.1 in which $R^8$ is isobutyl, $R^9$ is isopropoxy-1-propyl, and $R^1$, $R^2$, $R^3$, $R^6$ and $R^7$ for a compound corresponds in each case to one row of Table A Table 382
Compounds of the formula I.1 in which $R^8$ is isobutyl, $R^9$ is methoxy-2-propyl, and $R^1$, $R^2$, $R^3$, $R^6$ and $R^7$ for a compound corresponds in each case to one row of Table A Table 383
Compounds of the formula I.1 in which $R^8$ is isobutyl, $R^9$ is ethoxy-2-propyl, and $R^1$, $R^2$, $R^3$, $R^6$ and $R^7$ for a compound corresponds in each case to one row of Table A Table 384
Compounds of the formula I.1 in which $R^8$ is isobutyl, $R^9$ is n-propoxy-2-propyl, and $R^1$, $R^2$, $R^3$, $R^6$ and $R^7$ for a compound corresponds in each case to one row of Table A Table 385
Compounds of the formula I.1 in which $R^8$ is isobutyl, $R^9$ is isopropoxy-2-propyl, and $R^1$, $R^2$, $R^3$, $R^6$ and $R^7$ for a compound corresponds in each case to one row of Table A Table 386
Compounds of the formula I.1 in which $R^8$ is isobutyl, $R^9$ is methoxy-3-propyl, and $R^1$, $R^2$, $R^3$, $R^6$ and $R^7$ for a compound corresponds in each case to one row of Table A Table 387
Compounds of the formula I.1 in which $R^8$ is isobutyl, $R^9$ is ethoxy-3-propyl, and $R^1$, $R^2$, $R^3$, $R^6$ and $R^7$ for a compound corresponds in each case to one row of Table A Table 388
Compounds of the formula I.1 in which $R^8$ is isobutyl, $R^9$ is n-propoxy-3-propyl, and $R^1$, $R^2$, $R^3$, $R^6$ and $R^7$ for a compound corresponds in each case to one row of Table A Table 389
Compounds of the formula I.1 in which $R^8$ is isobutyl, $R^9$ is isopropoxy-3-propyl, and $R^1$, $R^2$, $R^3$, $R^6$ and $R^7$ for a compound corresponds in each case to one row of Table A Table 390
Compounds of the formula I.1 in which $R^8$ is isobutyl, $R^9$ is oxetan-2-yl, and $R^1$, $R^2$, $R^3$, $R^6$ and $R^7$ for a compound corresponds in each case to one row of Table A Table 391
Compounds of the formula I.1 in which $R^8$ is isobutyl, $R^9$ is oxetan-3-yl, and $R^1$, $R^2$, $R^3$, $R^6$ and $R^7$ for a compound corresponds in each case to one row of Table A Table 392
Compounds of the formula I.1 in which $R^8$ is isobutyl, $R^9$ is tetrahydrofuran-2-yl, and $R^1$, $R^2$, $R^3$, $R^6$ and $R^7$ for a compound corresponds in each case to one row of Table A Table 393
Compounds of the formula I.1 in which $R^8$ is isobutyl, $R^9$ is tetrahydrofuran-3-yl, and $R^1$, $R^2$, $R^3$, $R^6$ and $R^7$ for a compound corresponds in each case to one row of Table A Table 394
Compounds of the formula I.1 in which $R^8$ is isobutyl, $R^9$ is tetrahydropyran-2-yl, and $R^1$, $R^2$, $R^3$, $R^6$ and $R^7$ for a compound corresponds in each case to one row of Table A Table 395
Compounds of the formula I.1 in which $R^8$ is isobutyl, $R^9$ is tetrahydropyran-3-yl, and $R^1$, $R^2$, $R^3$, $R^6$ and $R^7$ for a compound corresponds in each case to one row of Table A Table 396
Compounds of the formula I.1 in which $R^8$ is isobutyl, $R^9$ is tetrahydropyran-4-yl, and $R^1$, $R^2$, $R^3$, $R^6$ and $R^7$ for a compound corresponds in each case to one row of Table A Table 397
Compounds of the formula I.1 in which $R^8$ is isobutyl, $R^9$ is thietan-2-yl, and $R^1$, $R^2$, $R^3$, $R^6$ and $R^7$ for a compound corresponds in each case to one row of Table A Table 398
Compounds of the formula I.1 in which $R^8$ is isobutyl, $R^9$ is thietan-3-yl, and $R^1$, $R^2$, $R^3$, $R^6$ and $R^7$ for a compound corresponds in each case to one row of Table A Table 399
Compounds of the formula I.1 in which $R^8$ is isobutyl, $R^9$ is 1-oxothietan-3-yl, and $R^1$, $R^2$, $R^3$, $R^6$ and $R^7$ for a compound corresponds in each case to one row of Table A Table 400
Compounds of the formula I.1 in which $R^8$ is isobutyl, $R^9$ is 1,1-dioxothietan-3-yl, and $R^1$, $R^2$, $R^3$, $R^6$ and $R^7$ for a compound corresponds in each case to one row of Table A Table 401
Compounds of the formula I.1 in which $R^8$ is tert-butyl, $R^9$ is methoxy, and $R^1$, $R^2$, $R^3$, $R^6$ and $R^7$ for a compound corresponds in each case to one row of Table A Table 402
Compounds of the formula I.1 in which $R^8$ is tert-butyl, $R^9$ is ethoxy, and $R^1$, $R^2$, $R^3$, $R^6$ and $R^7$ for a compound corresponds in each case to one row of Table A Table 403
Compounds of the formula I.1 in which $R^8$ is tert-butyl, $R^9$ is n-propoxy, and $R^1$, $R^2$, $R^3$, $R^6$ and $R^7$ for a compound corresponds in each case to one row of Table A Table 404
Compounds of the formula I.1 in which $R^8$ is tert-butyl, $R^9$ is isopropoxy, and $R^1$, $R^2$, $R^3$, $R^6$ and $R^7$ for a compound corresponds in each case to one row of Table A Table 405
Compounds of the formula I.1 in which $R^8$ is tert-butyl, $R^9$ is n-butoxy, and $R^1$, $R^2$, $R^3$, $R^6$ and $R^7$ for a compound corresponds in each case to one row of Table A Table 406
Compounds of the formula I.1 in which $R^8$ is tert-butyl, $R^9$ is sec-butoxy, and $R^1$, $R^2$, $R^3$, $R^6$ and $R^7$ for a compound corresponds in each case to one row of Table A Table 407
Compounds of the formula I.1 in which $R^8$ is tert-butyl, $R^9$ is isobutoxy, and $R^1$, $R^2$, $R^3$, $R^6$ and $R^7$ for a compound corresponds in each case to one row of Table A Table 408
Compounds of the formula I.1 in which $R^8$ is tert-butyl, $R^9$ is tert-butoxy, and $R^1$, $R^2$, $R^3$, $R^6$ and $R^7$ for a compound corresponds in each case to one row of Table A Table 409
Compounds of the formula I.1 in which $R^8$ is tert-butyl, $R^9$ is fluoromethoxy, and $R^1$, $R^2$, $R^3$, $R^6$ and $R^7$ for a compound corresponds in each case to one row of Table A Table 410
Compounds of the formula I.1 in which $R^8$ is tert-butyl, $R^9$ is difluoromethoxy, and $R^1$, $R^2$, $R^3$, $R^6$ and $R^7$ for a compound corresponds in each case to one row of Table A Table 411
Compounds of the formula I.1 in which $R^8$ is tert-butyl, $R^9$ is trifluoromethoxy, and $R^1$, $R^2$, $R^3$, $R^6$ and $R^7$ for a compound corresponds in each case to one row of Table A Table 412
Compounds of the formula I.1 in which $R^8$ is tert-butyl, $R^9$ is 2-fluoroethoxy, and $R^1$, $R^2$, $R^3$, $R^6$ and $R^7$ for a compound corresponds in each case to one row of Table A Table 413
Compounds of the formula I.1 in which $R^8$ is tert-butyl, $R^9$ is 2,2-difluoroethoxy, and $R^1$, $R^2$, $R^3$, $R^6$ and $R^7$ for a compound corresponds in each case to one row of Table A Table 414
Compounds of the formula I.1 in which $R^8$ is tert-butyl, $R^9$ is 2,2,2-trifluoroethoxy, and $R^1$, $R^2$, $R^3$, $R^6$ and $R^7$ for a compound corresponds in each case to one row of Table A Table 415
Compounds of the formula I.1 in which $R^8$ is tert-butyl, $R^9$ is pentafluoroethoxy, and $R^1$, $R^2$, $R^3$, $R^6$ and $R^7$ for a compound corresponds in each case to one row of Table A Table 416
Compounds of the formula I.1 in which $R^8$ is tert-butyl, $R^9$ is methoxymethyl, and $R^1$, $R^2$, $R^3$, $R^6$ and $R^7$ for a compound corresponds in each case to one row of Table A Table 417
Compounds of the formula I.1 in which $R^8$ is tert-butyl, $R^9$ is ethoxymethyl, and $R^1$, $R^2$, $R^3$, $R^6$ and $R^7$ for a compound corresponds in each case to one row of Table A Table 418
Compounds of the formula I.1 in which $R^8$ is tert-butyl, $R^9$ is n-propoxymethyl, and $R^1$, $R^2$, $R^3$, $R^6$ and $R^7$ for a compound corresponds in each case to one row of Table A Table 419
Compounds of the formula I.1 in which $R^8$ is tert-butyl, $R^9$ is isopropoxymethyl, and $R^1$, $R^2$, $R^3$, $R^6$ and $R^7$ for a compound corresponds in each case to one row of Table A Table 420
Compounds of the formula I.1 in which $R^8$ is tert-butyl, $R^9$ is methoxy-1-ethyl, and $R^1$, $R^2$, $R^3$, $R^6$ and $R^7$ for a compound corresponds in each case to one row of Table A Table 421
Compounds of the formula I.1 in which $R^8$ is tert-butyl, $R^9$ is ethoxy-1-ethyl, and $R^1$, $R^2$, $R^3$, $R^6$ and $R^7$ for a compound corresponds in each case to one row of Table A Table 422
Compounds of the formula I.1 in which $R^8$ is tert-butyl, $R^9$ is n-propoxy-1-ethyl, and $R^1$, $R^2$, $R^3$, $R^6$ and $R^7$ for a compound corresponds in each case to one row of Table A Table 423
Compounds of the formula I.1 in which $R^8$ is tert-butyl, $R^9$ is isopropoxy-1-ethyl, and $R^1$, $R^2$, $R^3$, $R^6$ and $R^7$ for a compound corresponds in each case to one row of Table A Table 424
Compounds of the formula I.1 in which $R^8$ is tert-butyl, $R^9$ is methoxy-2-ethyl, and $R^1$, $R^2$, $R^3$, $R^6$ and $R^7$ for a compound corresponds in each case to one row of Table A Table 425
Compounds of the formula I.1 in which $R^8$ is tert-butyl, $R^9$ is ethoxy-2-ethyl, and $R^1$, $R^2$, $R^3$, $R^6$ and $R^7$ for a compound corresponds in each case to one row of Table A Table 426
Compounds of the formula I.1 in which $R^8$ is tert-butyl, $R^9$ is n-propoxy-2-ethyl, and $R^1$, $R^2$, $R^3$, $R^6$ and $R^7$ for a compound corresponds in each case to one row of Table A Table 427
Compounds of the formula I.1 in which $R^8$ is tert-butyl, $R^9$ is isopropoxy-2-ethyl, and $R^1$, $R^2$, $R^3$, $R^6$ and $R^7$ for a compound corresponds in each case to one row of Table A Table 428
Compounds of the formula I.1 in which $R^8$ is tert-butyl, $R^9$ is methoxy-1-propyl, and $R^1$, $R^2$, $R^3$, $R^6$ and $R^7$ for a compound corresponds in each case to one row of Table A Table 429
Compounds of the formula I.1 in which $R^8$ is tert-butyl, $R^9$ is ethoxy-1-propyl, and $R^1$, $R^2$, $R^3$, $R^6$ and $R^7$ for a compound corresponds in each case to one row of Table A Table 430
Compounds of the formula I.1 in which $R^8$ is tert-butyl, $R^9$ is n-propoxy-1-propyl, and $R^1$, $R^2$, $R^3$, $R^6$ and $R^7$ for a compound corresponds in each case to one row of Table A Table 431
Compounds of the formula I.1 in which $R^8$ is tert-butyl, $R^9$ is isopropoxy-1-propyl, and $R^1$, $R^2$, $R^3$, $R^6$ and $R^7$ for a compound corresponds in each case to one row of Table A Table 432
Compounds of the formula I.1 in which $R^8$ is tert-butyl, $R^9$ is methoxy-2-propyl, and $R^1$, $R^2$, $R^3$, $R^6$ and $R^7$ for a compound corresponds in each case to one row of Table A Table 433
Compounds of the formula I.1 in which $R^8$ is tert-butyl, $R^9$ is ethoxy-2-propyl, and $R^1$, $R^2$, $R^3$, $R^6$ and $R^7$ for a compound corresponds in each case to one row of Table A Table 434
Compounds of the formula I.1 in which $R^8$ is tert-butyl, $R^9$ is n-propoxy-2-propyl, and $R^1$, $R^2$, $R^3$, $R^6$ and $R^7$ for a compound corresponds in each case to one row of Table A Table 435
Compounds of the formula I.1 in which $R^8$ is tert-butyl, $R^9$ is isopropoxy-2-propyl, and $R^1$, $R^2$, $R^3$, $R^6$ and $R^7$ for a compound corresponds in each case to one row of Table A Table 436
Compounds of the formula I.1 in which $R^8$ is tert-butyl, $R^9$ is methoxy-3-propyl, and $R^1$, $R^2$, $R^3$, $R^6$ and $R^7$ for a compound corresponds in each case to one row of Table A Table 437
Compounds of the formula I.1 in which $R^8$ is tert-butyl, $R^9$ is ethoxy-3-propyl, and $R^1$, $R^2$, $R^3$, $R^6$ and $R^7$ for a compound corresponds in each case to one row of Table A Table 438
Compounds of the formula I.1 in which $R^8$ is tert-butyl, $R^9$ is n-propoxy-3-propyl, and $R^1$, $R^2$, $R^3$, $R^6$ and $R^7$ for a compound corresponds in each case to one row of Table A Table 439
Compounds of the formula I.1 in which $R^8$ is tert-butyl, $R^9$ is isopropoxy-3-propyl, and $R^1$, $R^2$, $R^3$, $R^6$ and $R^7$ for a compound corresponds in each case to one row of Table A Table 440
Compounds of the formula I.1 in which $R^8$ is tert-butyl, $R^9$ is oxetan-2-yl, and $R^1$, $R^2$, $R^3$, $R^6$ and $R^7$ for a compound corresponds in each case to one row of Table A Table 441
Compounds of the formula I.1 in which $R^8$ is tert-butyl, $R^9$ is oxetan-3-yl, and $R^1$, $R^2$, $R^3$, $R^6$ and $R^7$ for a compound corresponds in each case to one row of Table A Table 442
Compounds of the formula I.1 in which $R^8$ is tert-butyl, $R^9$ is tetrahydrofuran-2-yl, and $R^1$, $R^2$, $R^3$, $R^6$ and $R^7$ for a compound corresponds in each case to one row of Table A Table 443
Compounds of the formula I.1 in which $R^8$ is tert-butyl, $R^9$ is tetrahydrofuran-3-yl, and $R^1$, $R^2$, $R^3$, $R^6$ and $R^7$ for a compound corresponds in each case to one row of Table A Table 444
Compounds of the formula I.1 in which $R^8$ is tert-butyl, $R^9$ is tetrahydropyran-2-yl, and $R^1$, $R^2$, $R^3$, $R^6$ and $R^7$ for a compound corresponds in each case to one row of Table A Table 445
Compounds of the formula I.1 in which $R^8$ is tert-butyl, $R^9$ is tetrahydropyran-3-yl, and $R^1$, $R^2$, $R^3$, $R^6$ and $R^7$ for a compound corresponds in each case to one row of Table A Table 446
Compounds of the formula I.1 in which $R^8$ is tert-butyl, $R^9$ is tetrahydropyran-4-yl, and $R^1$, $R^2$, $R^3$, $R^6$ and $R^7$ for a compound corresponds in each case to one row of Table A Table 447
Compounds of the formula I.1 in which $R^8$ is tert-butyl, $R^9$ is thietan-2-yl, and $R^1$, $R^2$, $R^3$, $R^6$ and $R^7$ for a compound corresponds in each case to one row of Table A Table 448
Compounds of the formula I.1 in which $R^8$ is tert-butyl, $R^9$ is thietan-3-yl, and $R^1$, $R^2$, $R^3$, $R^6$ and $R^7$ for a compound corresponds in each case to one row of Table A Table 449
Compounds of the formula I.1 in which $R^8$ is tert-butyl, $R^9$ is 1-oxothietan-3-yl, and $R^1$, $R^2$, $R^3$, $R^6$ and $R^7$ for a compound corresponds in each case to one row of Table A Table 450
Compounds of the formula I.1 in which $R^8$ is tert-butyl, $R^9$ is 1,1-dioxothietan-3-yl, and $R^1$, $R^2$, $R^3$, $R^6$ and $R^7$ for a compound corresponds in each case to one row of Table A Table 451
Compounds of the formula I.1 in which $R^8$ is cyclopropyl, $R^9$ is methoxy, and $R^1$, $R^2$, $R^3$, $R^6$ and $R^7$ for a compound corresponds in each case to one row of Table A Table 452
Compounds of the formula I.1 in which $R^8$ is cyclopropyl, $R^9$ is ethoxy, and $R^1$, $R^2$, $R^3$, $R^6$ and $R^7$ for a compound corresponds in each case to one row of Table A Table 453
Compounds of the formula I.1 in which $R^8$ is cyclopropyl, $R^9$ is n-propoxy, and $R^1$, $R^2$, $R^3$, $R^6$ and $R^7$ for a compound corresponds in each case to one row of Table A Table 454
Compounds of the formula I.1 in which $R^8$ is cyclopropyl, $R^9$ is isopropoxy, and $R^1$, $R^2$, $R^3$, $R^6$ and $R^7$ for a compound corresponds in each case to one row of Table A Table 455
Compounds of the formula I.1 in which $R^8$ is cyclopropyl, $R^9$ is n-butoxy, and $R^1$, $R^2$, $R^3$, $R^6$ and $R^7$ for a compound corresponds in each case to one row of Table A Table 456
Compounds of the formula I.1 in which $R^8$ is cyclopropyl, $R^9$ is sec-butoxy, and $R^1$, $R^2$, $R^3$, $R^6$ and $R^7$ for a compound corresponds in each case to one row of Table A Table 457
Compounds of the formula I.1 in which $R^8$ is cyclopropyl, $R^9$ is isobutoxy, and $R^1$, $R^2$, $R^3$, $R^6$ and $R^7$ for a compound corresponds in each case to one row of Table A Table 458
Compounds of the formula I.1 in which $R^8$ is cyclopropyl, $R^9$ is tert-butoxy, and $R^1$, $R^2$, $R^3$, $R^6$ and $R^7$ for a compound corresponds in each case to one row of Table A Table 459
Compounds of the formula I.1 in which $R^8$ is cyclopropyl, $R^9$ is fluoromethoxy, and $R^1$, $R^2$, $R^3$, $R^6$ and $R^7$ for a compound corresponds in each case to one row of Table A Table 460
Compounds of the formula I.1 in which $R^8$ is cyclopropyl, $R^9$ is difluoromethoxy, and $R^1$, $R^2$, $R^3$, $R^6$ and $R^7$ for a compound corresponds in each case to one row of Table A Table 461
Compounds of the formula I.1 in which $R^8$ is cyclopropyl, $R^9$ is trifluoromethoxy, and $R^1$, $R^2$, $R^3$, $R^6$ and $R^7$ for a compound corresponds in each case to one row of Table A Table 462
Compounds of the formula I.1 in which $R^8$ is cyclopropyl, $R^9$ is 2-fluoroethoxy, and $R^1$, $R^2$, $R^3$, $R^6$ and $R^7$ for a compound corresponds in each case to one row of Table A Table 463
Compounds of the formula I.1 in which $R^8$ is cyclopropyl, $R^9$ is 2,2-difluoroethoxy, and $R^1$, $R^2$, $R^3$, $R^6$ and $R^7$ for a compound corresponds in each case to one row of Table A Table 464
Compounds of the formula I.1 in which $R^8$ is cyclopropyl, $R^9$ is 2,2,2-trifluoroethoxy, and $R^1$, $R^2$, $R^3$, $R^6$ and $R^7$ for a compound corresponds in each case to one row of Table A Table 465
Compounds of the formula I.1 in which $R^8$ is cyclopropyl, $R^9$ is pentafluoroethoxy, and $R^1$, $R^2$, $R^3$, $R^6$ and $R^7$ for a compound corresponds in each case to one row of Table A Table 466
Compounds of the formula I.1 in which $R^8$ is cyclopropyl, $R^9$ is methoxymethyl, and $R^1$, $R^2$, $R^3$, $R^6$ and $R^7$ for a compound corresponds in each case to one row of Table A Table 467
Compounds of the formula I.1 in which $R^8$ is cyclopropyl, $R^9$ is ethoxymethyl, and $R^1$, $R^2$, $R^3$, $R^6$ and $R^7$ for a compound corresponds in each case to one row of Table A Table 468
Compounds of the formula I.1 in which $R^8$ is cyclopropyl, $R^9$ is n-propoxymethyl, and $R^1$, $R^2$, $R^3$, $R^6$ and $R^7$ for a compound corresponds in each case to one row of Table A Table 469
Compounds of the formula I.1 in which $R^8$ is cyclopropyl, $R^9$ is isopropoxymethyl, and $R^1$, $R^2$, $R^3$, $R^6$ and $R^7$ for a compound corresponds in each case to one row of Table A Table 470
Compounds of the formula I.1 in which $R^8$ is cyclopropyl, $R^9$ is methoxy-1-ethyl, and $R^1$, $R^2$, $R^3$, $R^6$ and $R^7$ for a compound corresponds in each case to one row of Table A Table 471
Compounds of the formula I.1 in which $R^8$ is cyclopropyl, $R^9$ is ethoxy-1-ethyl, and $R^1$, $R^2$, $R^3$, $R^6$ and $R^7$ for a compound corresponds in each case to one row of Table A Table 472
Compounds of the formula I.1 in which $R^8$ is cyclopropyl, $R^9$ is n-propoxy-1-ethyl, and $R^1$, $R^2$, $R^3$, $R^6$ and $R^7$ for a compound corresponds in each case to one row of Table A Table 473
Compounds of the formula I.1 in which $R^8$ is cyclopropyl, $R^9$ is isopropoxy-1-ethyl, and $R^1$, $R^2$, $R^3$, $R^6$ and $R^7$ for a compound corresponds in each case to one row of Table A Table 474
Compounds of the formula I.1 in which $R^8$ is cyclopropyl, $R^9$ is methoxy-2-ethyl, and $R^1$, $R^2$, $R^3$, $R^6$ and $R^7$ for a compound corresponds in each case to one row of Table A Table 475
Compounds of the formula I.1 in which $R^8$ is cyclopropyl, $R^9$ is ethoxy-2-ethyl, and $R^1$, $R^2$, $R^3$, $R^6$ and $R^7$ for a compound corresponds in each case to one row of Table A Table 476
Compounds of the formula I.1 in which $R^8$ is cyclopropyl, $R^9$ is n-propoxy-2-ethyl, and $R^1$, $R^2$, $R^3$, $R^6$ and $R^7$ for a compound corresponds in each case to one row of Table A Table 477
Compounds of the formula I.1 in which $R^8$ is cyclopropyl, $R^9$ is isopropoxy-2-ethyl, and $R^1$, $R^2$, $R^3$, $R^6$ and $R^7$ for a compound corresponds in each case to one row of Table A Table 478
Compounds of the formula I.1 in which $R^8$ is cyclopropyl, $R^9$ is methoxy-1-propyl, and $R^1$, $R^2$, $R^3$, $R^6$ and $R^7$ for a compound corresponds in each case to one row of Table A Table 479
Compounds of the formula I.1 in which $R^8$ is cyclopropyl, $R^9$ is ethoxy-1-propyl, and $R^1$, $R^2$, $R^3$, $R^6$ and $R^7$ for a compound corresponds in each case to one row of Table A Table 480
Compounds of the formula I.1 in which $R^8$ is cyclopropyl, $R^9$ is n-propoxy-1-propyl, and $R^1$, $R^2$, $R^3$, $R^6$ and $R^7$ for a compound corresponds in each case to one row of Table A Table 481
Compounds of the formula I.1 in which $R^8$ is cyclopropyl, $R^9$ is isopropoxy-1-propyl, and $R^1$, $R^2$, $R^3$, $R^6$ and $R^7$ for a compound corresponds in each case to one row of Table A Table 482
Compounds of the formula I.1 in which $R^8$ is cyclopropyl, $R^9$ is methoxy-2-propyl, and $R^1$, $R^2$, $R^3$, $R^6$ and $R^7$ for a compound corresponds in each case to one row of Table A Table 483
Compounds of the formula I.1 in which $R^8$ is cyclopropyl, $R^9$ is ethoxy-2-propyl, and $R^1$, $R^2$, $R^3$, $R^6$ and $R^7$ for a compound corresponds in each case to one row of Table A Table 484
Compounds of the formula I.1 in which $R^8$ is cyclopropyl, $R^9$ is n-propoxy-2-propyl, and $R^1$, $R^2$, $R^3$, $R^6$ and $R^7$ for a compound corresponds in each case to one row of Table A Table 485
Compounds of the formula I.1 in which $R^8$ is cyclopropyl, $R^9$ is isopropoxy-2-propyl, and $R^1$, $R^2$, $R^3$, $R^6$ and $R^7$ for a compound corresponds in each case to one row of Table A Table 486
Compounds of the formula I.1 in which $R^8$ is cyclopropyl, $R^9$ is methoxy-3-propyl, and $R^1$, $R^2$, $R^3$, $R^6$ and $R^7$ for a compound corresponds in each case to one row of Table A Table 487
Compounds of the formula I.1 in which $R^8$ is cyclopropyl, $R^9$ is ethoxy-3-propyl, and $R^1$, $R^2$, $R^3$, $R^6$ and $R^7$ for a compound corresponds in each case to one row of Table A Table 488
Compounds of the formula I.1 in which $R^8$ is cyclopropyl, $R^9$ is n-propoxy-3-propyl, and $R^1$, $R^2$, $R^3$, $R^6$ and $R^7$ for a compound corresponds in each case to one row of Table A Table 489
Compounds of the formula I.1 in which $R^8$ is cyclopropyl, $R^9$ is isopropoxy-3-propyl, and $R^1$, $R^2$, $R^3$, $R^6$ and $R^7$ for a compound corresponds in each case to one row of Table A Table 490
Compounds of the formula I.1 in which $R^8$ is cyclopropyl, $R^9$ is oxetan-2-yl, and $R^1$, $R^2$, $R^3$, $R^6$ and $R^7$ for a compound corresponds in each case to one row of Table A Table 491
Compounds of the formula I.1 in which $R^8$ is cyclopropyl, $R^9$ is oxetan-3-yl, and $R^1$, $R^2$, $R^3$, $R^6$ and $R^7$ for a compound corresponds in each case to one row of Table A Table 492
Compounds of the formula I.1 in which $R^8$ is cyclopropyl, $R^9$ is tetrahydrofuran-2-yl, and $R^1$, $R^2$, $R^3$, $R^6$ and $R^7$ for a compound corresponds in each case to one row of Table A Table 493
Compounds of the formula I.1 in which $R^8$ is cyclopropyl, $R^9$ is tetrahydrofuran-3-yl, and $R^1$, $R^2$, $R^3$, $R^6$ and $R^7$ for a compound corresponds in each case to one row of Table A Table 494
Compounds of the formula I.1 in which $R^8$ is cyclopropyl, $R^9$ is tetrahydropyran-2-yl, and $R^1$, $R^2$, $R^3$, $R^6$ and $R^7$ for a compound corresponds in each case to one row of Table A Table 495
Compounds of the formula I.1 in which $R^8$ is cyclopropyl, $R^9$ is tetrahydropyran-3-yl, and $R^1$, $R^2$, $R^3$, $R^6$ and $R^7$ for a compound corresponds in each case to one row of Table A Table 496
Compounds of the formula I.1 in which $R^8$ is cyclopropyl, $R^9$ is tetrahydropyran-4-yl, and $R^1$, $R^2$, $R^3$, $R^6$ and $R^7$ for a compound corresponds in each case to one row of Table A Table 497
Compounds of the formula I.1 in which $R^8$ is cyclopropyl, $R^9$ is thietan-2-yl, and $R^1$, $R^2$, $R^3$, $R^6$ and $R^7$ for a compound corresponds in each case to one row of Table A Table 498
Compounds of the formula I.1 in which $R^8$ is cyclopropyl, $R^9$ is thietan-3-yl, and $R^1$, $R^2$, $R^3$, $R^6$ and $R^7$ for a compound corresponds in each case to one row of Table A Table 499
Compounds of the formula I.1 in which $R^8$ is cyclopropyl, $R^9$ is 1-oxothietan-3-yl, and $R^1$, $R^2$, $R^3$, $R^6$ and $R^7$ for a compound corresponds in each case to one row of Table A Table 500
Compounds of the formula I.1 in which $R^8$ is cyclopropyl, $R^9$ is 1,1-dioxothietan-3-yl, and $R^1$, $R^2$, $R^3$, $R^6$ and $R^7$ for a compound corresponds in each case to one row of Table A Table 501
Compounds of the formula I.1 in which $R^8$ is cyclobutyl, $R^9$ is methoxy, and $R^1$, $R^2$, $R^3$, $R^6$ and $R^7$ for a compound corresponds in each case to one row of Table A Table 502
Compounds of the formula I.1 in which $R^8$ is cyclobutyl, $R^9$ is ethoxy, and $R^1$, $R^2$, $R^3$, $R^6$ and $R^7$ for a compound corresponds in each case to one row of Table A Table 503
Compounds of the formula I.1 in which $R^8$ is cyclobutyl, $R^9$ is n-propoxy, and $R^1$, $R^2$, $R^3$, $R^6$ and $R^7$ for a compound corresponds in each case to one row of Table A Table 504
Compounds of the formula I.1 in which $R^8$ is cyclobutyl, $R^9$ is isopropoxy, and $R^1$, $R^2$, $R^3$, $R^6$ and $R^7$ for a compound corresponds in each case to one row of Table A Table 505
Compounds of the formula I.1 in which $R^8$ is cyclobutyl, $R^9$ is n-butoxy, and $R^1$, $R^2$, $R^3$, $R^6$ and $R^7$ for a compound corresponds in each case to one row of Table A Table 506
Compounds of the formula I.1 in which $R^8$ is cyclobutyl, $R^9$ is sec-butoxy, and $R^1$, $R^2$, $R^3$, $R^6$ and $R^7$ for a compound corresponds in each case to one row of Table A Table 507
Compounds of the formula I.1 in which $R^8$ is cyclobutyl, $R^9$ is isobutoxy, and $R^1$, $R^2$, $R^3$, $R^6$ and $R^7$ for a compound corresponds in each case to one row of Table A Table 508
Compounds of the formula I.1 in which $R^8$ is cyclobutyl, $R^9$ is tert-butoxy, and $R^1$, $R^2$, $R^3$, $R^6$ and $R^7$ for a compound corresponds in each case to one row of Table A Table 509
Compounds of the formula I.1 in which $R^8$ is cyclobutyl, $R^9$ is fluoromethoxy, and $R^1$, $R^2$, $R^3$, $R^6$ and $R^7$ for a compound corresponds in each case to one row of Table A Table 510
Compounds of the formula I.1 in which $R^8$ is cyclobutyl, $R^9$ is difluoromethoxy, and $R^1$, $R^2$, $R^3$, $R^6$ and $R^7$ for a compound corresponds in each case to one row of Table A Table 511
Compounds of the formula I.1 in which $R^8$ is cyclobutyl, $R^9$ is trifluoromethoxy, and $R^1$, $R^2$, $R^3$, $R^6$ and $R^7$ for a compound corresponds in each case to one row of Table A Table 512
Compounds of the formula I.1 in which $R^8$ is cyclobutyl, $R^9$ is 2-fluoroethoxy, and $R^1$, $R^2$, $R^3$, $R^6$ and $R^7$ for a compound corresponds in each case to one row of Table A Table 513
Compounds of the formula I.1 in which $R^8$ is cyclobutyl, $R^9$ is 2,2-difluoroethoxy, and $R^1$, $R^2$, $R^3$, $R^6$ and $R^7$ for a compound corresponds in each case to one row of Table A Table 514
Compounds of the formula I.1 in which $R^8$ is cyclobutyl, $R^9$ is 2,2,2-trifluoroethoxy, and $R^1$, $R^2$, $R^3$, $R^6$ and $R^7$ for a compound corresponds in each case to one row of Table A Table 515
Compounds of the formula I.1 in which $R^8$ is cyclobutyl, $R^9$ is pentafluoroethoxy, and $R^1$, $R^2$, $R^3$, $R^6$ and $R^7$ for a compound corresponds in each case to one row of Table A Table 516
Compounds of the formula I.1 in which $R^8$ is cyclobutyl, $R^9$ is methoxymethyl, and $R^1$, $R^2$, $R^3$, $R^6$ and $R^7$ for a compound corresponds in each case to one row of Table A Table 517
Compounds of the formula I.1 in which $R^8$ is cyclobutyl, $R^9$ is ethoxymethyl, and $R^1$, $R^2$, $R^3$, $R^6$ and $R^7$ for a compound corresponds in each case to one row of Table A Table 518
Compounds of the formula I.1 in which $R^8$ is cyclobutyl, $R^9$ is n-propoxymethyl, and $R^1$, $R^2$, $R^3$, $R^6$ and $R^7$ for a compound corresponds in each case to one row of Table A Table 519
Compounds of the formula I.1 in which $R^8$ is cyclobutyl, $R^9$ is isopropoxymethyl, and $R^1$, $R^2$, $R^3$, $R^6$ and $R^7$ for a compound corresponds in each case to one row of Table A Table 520
Compounds of the formula I.1 in which $R^8$ is cyclobutyl, $R^9$ is methoxy-1-ethyl, and $R^1$, $R^2$, $R^3$, $R^6$ and $R^7$ for a compound corresponds in each case to one row of Table A Table 521
Compounds of the formula I.1 in which $R^8$ is cyclobutyl, $R^9$ is ethoxy-1-ethyl, and $R^1$, $R^2$, $R^3$, $R^6$ and $R^7$ for a compound corresponds in each case to one row of Table A Table 522
Compounds of the formula I.1 in which $R^8$ is cyclobutyl, $R^9$ is n-propoxy-1-ethyl, and $R^1$, $R^2$, $R^3$, $R^6$ and $R^7$ for a compound corresponds in each case to one row of Table A Table 523
Compounds of the formula I.1 in which $R^8$ is cyclobutyl, $R^9$ is isopropoxy-1-ethyl, and $R^1$, $R^2$, $R^3$, $R^6$ and $R^7$ for a compound corresponds in each case to one row of Table A Table 524
Compounds of the formula I.1 in which $R^8$ is cyclobutyl, $R^9$ is methoxy-2-ethyl, and $R^1$, $R^2$, $R^3$, $R^6$ and $R^7$ for a compound corresponds in each case to one row of Table A Table 525
Compounds of the formula I.1 in which $R^8$ is cyclobutyl, $R^9$ is ethoxy-2-ethyl, and $R^1$, $R^2$, $R^3$, $R^6$ and $R^7$ for a compound corresponds in each case to one row of Table A Table 526
Compounds of the formula I.1 in which $R^8$ is cyclobutyl, $R^9$ is n-propoxy-2-ethyl, and $R^1$, $R^2$, $R^3$, $R^6$ and $R^7$ for a compound corresponds in each case to one row of Table A Table 527
Compounds of the formula I.1 in which $R^8$ is cyclobutyl, $R^9$ is isopropoxy-2-ethyl, and $R^1$, $R^2$, $R^3$, $R^6$ and $R^7$ for a compound corresponds in each case to one row of Table A Table 528
Compounds of the formula I.1 in which $R^8$ is cyclobutyl, $R^9$ is methoxy-1-propyl, and $R^1$, $R^2$, $R^3$, $R^6$ and $R^7$ for a compound corresponds in each case to one row of Table A Table 529
Compounds of the formula I.1 in which $R^8$ is cyclobutyl, $R^9$ is ethoxy-1-propyl, and $R^1$, $R^2$, $R^3$, $R^6$ and $R^7$ for a compound corresponds in each case to one row of Table A Table 530
Compounds of the formula I.1 in which $R^8$ is cyclobutyl, $R^9$ is n-propoxy-1-propyl, and $R^1$, $R^2$, $R^3$, $R^6$ and $R^7$ for a compound corresponds in each case to one row of Table A Table 531
Compounds of the formula I.1 in which $R^8$ is cyclobutyl, $R^9$ is isopropoxy-1-propyl, and $R^1$, $R^2$, $R^3$, $R^6$ and $R^7$ for a compound corresponds in each case to one row of Table A Table 532
Compounds of the formula I.1 in which $R^8$ is cyclobutyl, $R^9$ is methoxy-2-propyl, and $R^1$, $R^2$, $R^3$, $R^6$ and $R^7$ for a compound corresponds in each case to one row of Table A Table 533
Compounds of the formula I.1 in which $R^8$ is cyclobutyl, $R^9$ is ethoxy-2-propyl, and $R^1$, $R^2$, $R^3$, $R^6$ and $R^7$ for a compound corresponds in each case to one row of Table A Table 534
Compounds of the formula I.1 in which $R^8$ is cyclobutyl, $R^9$ is n-propoxy-2-propyl, and $R^1$, $R^2$, $R^3$, $R^6$ and $R^7$ for a compound corresponds in each case to one row of Table A Table 535
Compounds of the formula I.1 in which $R^8$ is cyclobutyl, $R^9$ is isopropoxy-2-propyl, and $R^1$, $R^2$, $R^3$, $R^6$ and $R^7$ for a compound corresponds in each case to one row of Table A Table 536
Compounds of the formula I.1 in which $R^8$ is cyclobutyl, $R^9$ is methoxy-3-propyl, and $R^1$, $R^2$, $R^3$, $R^6$ and $R^7$ for a compound corresponds in each case to one row of Table A Table 537
Compounds of the formula I.1 in which $R^8$ is cyclobutyl, $R^9$ is ethoxy-3-propyl, and $R^1$, $R^2$, $R^3$, $R^6$ and $R^7$ for a compound corresponds in each case to one row of Table A Table 538
Compounds of the formula I.1 in which $R^8$ is cyclobutyl, $R^9$ is n-propoxy-3-propyl, and $R^1$, $R^2$, $R^3$, $R^6$ and $R^7$ for a compound corresponds in each case to one row of Table A Table 539
Compounds of the formula I.1 in which $R^8$ is cyclobutyl, $R^9$ is isopropoxy-3-propyl, and $R^1$, $R^2$, $R^3$, $R^6$ and $R^7$ for a compound corresponds in each case to one row of Table A Table 540
Compounds of the formula I.1 in which $R^8$ is cyclobutyl, $R^9$ is oxetan-2-yl, and $R^1$, $R^2$, $R^3$, $R^6$ and $R^7$ for a compound corresponds in each case to one row of Table A Table 541
Compounds of the formula I.1 in which $R^8$ is cyclobutyl, $R^9$ is oxetan-3-yl, and $R^1$, $R^2$, $R^3$, $R^6$ and $R^7$ for a compound corresponds in each case to one row of Table A Table 542
Compounds of the formula I.1 in which $R^8$ is cyclobutyl, $R^9$ is tetrahydrofuran-2-yl, and $R^1$, $R^2$, $R^3$, $R^6$ and $R^7$ for a compound corresponds in each case to one row of Table A Table 543
Compounds of the formula I.1 in which $R^8$ is cyclobutyl, $R^9$ is tetrahydrofuran-3-yl, and $R^1$, $R^2$, $R^3$, $R^6$ and $R^7$ for a compound corresponds in each case to one row of Table A Table 544
Compounds of the formula I.1 in which $R^8$ is cyclobutyl, $R^9$ is tetrahydropyran-2-yl, and $R^1$, $R^2$, $R^3$, $R^6$ and $R^7$ for a compound corresponds in each case to one row of Table A Table 545
Compounds of the formula I.1 in which $R^8$ is cyclobutyl, $R^9$ is tetrahydropyran-3-yl, and $R^1$, $R^2$, $R^3$, $R^6$ and $R^7$ for a compound corresponds in each case to one row of Table A Table 546
Compounds of the formula I.1 in which $R^8$ is cyclobutyl, $R^9$ is tetrahydropyran-4-yl, and $R^1$, $R^2$, $R^3$, $R^6$ and $R^7$ for a compound corresponds in each case to one row of Table A Table 547
Compounds of the formula I.1 in which $R^8$ is cyclobutyl, $R^9$ is thietan-2-yl, and $R^1$, $R^2$, $R^3$, $R^6$ and $R^7$ for a compound corresponds in each case to one row of Table A Table 548
Compounds of the formula I.1 in which $R^8$ is cyclobutyl, $R^9$ is thietan-3-yl, and $R^1$, $R^2$, $R^3$, $R^6$ and $R^7$ for a compound corresponds in each case to one row of Table A Table 549
Compounds of the formula I.1 in which $R^8$ is cyclobutyl, $R^9$ is 1-oxothietan-3-yl, and $R^1$, $R^2$, $R^3$, $R^6$ and $R^7$ for a compound corresponds in each case to one row of Table A Table 550
Compounds of the formula I.1 in which $R^8$ is cyclobutyl, $R^9$ is 1,1-dioxothietan-3-yl, and $R^1$, $R^2$, $R^3$, $R^6$ and $R^7$ for a compound corresponds in each case to one row of Table A Table 551
Compounds of the formula I.1 in which $R^8$ is cyclopentyl, $R^9$ is methoxy, and $R^1$, $R^2$, $R^3$, $R^6$ and $R^7$ for a compound corresponds in each case to one row of Table A Table 552
Compounds of the formula I.1 in which $R^8$ is cyclopentyl, $R^9$ is ethoxy, and $R^1$, $R^2$, $R^3$, $R^6$ and $R^7$ for a compound corresponds in each case to one row of Table A Table 553
Compounds of the formula I.1 in which $R^8$ is cyclopentyl, $R^9$ is n-propoxy, and $R^1$, $R^2$, $R^3$, $R^6$ and $R^7$ for a compound corresponds in each case to one row of Table A Table 554
Compounds of the formula I.1 in which $R^8$ is cyclopentyl, $R^9$ is isopropoxy, and $R^1$, $R^2$, $R^3$, $R^6$ and $R^7$ for a compound corresponds in each case to one row of Table A Table 555
Compounds of the formula I.1 in which $R^8$ is cyclopentyl, $R^9$ is n-butoxy, and $R^1$, $R^2$, $R^3$, $R^6$ and $R^7$ for a compound corresponds in each case to one row of Table A Table 556
Compounds of the formula I.1 in which $R^8$ is cyclopentyl, $R^9$ is sec-butoxy, and $R^1$, $R^2$, $R^3$, $R^6$ and $R^7$ for a compound corresponds in each case to one row of Table A Table 557
Compounds of the formula I.1 in which $R^8$ is cyclopentyl, $R^9$ is isobutoxy, and $R^1$, $R^2$, $R^3$, $R^6$ and $R^7$ for a compound corresponds in each case to one row of Table A Table 558
Compounds of the formula I.1 in which $R^8$ is cyclopentyl, $R^9$ is tert-butoxy, and $R^1$, $R^2$, $R^3$, $R^6$ and $R^7$ for a compound corresponds in each case to one row of Table A Table 559
Compounds of the formula I.1 in which $R^8$ is cyclopentyl, $R^9$ is fluoromethoxy, and $R^1$, $R^2$, $R^3$, $R^6$ and $R^7$ for a compound corresponds in each case to one row of Table A Table 560
Compounds of the formula I.1 in which $R^8$ is cyclopentyl, $R^9$ is difluoromethoxy, and $R^1$, $R^2$, $R^3$, $R^6$ and $R^7$ for a compound corresponds in each case to one row of Table A Table 561
Compounds of the formula I.1 in which $R^8$ is cyclopentyl, $R^9$ is trifluoromethoxy, and $R^1$, $R^2$, $R^3$, $R^6$ and $R^7$ for a compound corresponds in each case to one row of Table A Table 562
Compounds of the formula I.1 in which $R^8$ is cyclopentyl, $R^9$ is 2-fluoroethoxy, and $R^1$, $R^2$, $R^3$, $R^6$ and $R^7$ for a compound corresponds in each case to one row of Table A Table 563
Compounds of the formula I.1 in which $R^8$ is cyclopentyl, $R^9$ is 2,2-difluoroethoxy, and $R^1$, $R^2$, $R^3$, $R^6$ and $R^7$ for a compound corresponds in each case to one row of Table A Table 564
Compounds of the formula I.1 in which $R^8$ is cyclopentyl, $R^9$ is 2,2,2-trifluoroethoxy, and $R^1$, $R^2$, $R^3$, $R^6$ and $R^7$ for a compound corresponds in each case to one row of Table A Table 565
Compounds of the formula I.1 in which $R^8$ is cyclopentyl, $R^9$ is pentafluoroethoxy, and $R^1$, $R^2$, $R^3$, $R^6$ and $R^7$ for a compound corresponds in each case to one row of Table A Table 566
Compounds of the formula I.1 in which $R^8$ is cyclopentyl, $R^9$ is methoxymethyl, and $R^1$, $R^2$, $R^3$, $R^6$ and $R^7$ for a compound corresponds in each case to one row of Table A Table 567
Compounds of the formula I.1 in which $R^8$ is cyclopentyl, $R^9$ is ethoxymethyl, and $R^1$, $R^2$, $R^3$, $R^6$ and $R^7$ for a compound corresponds in each case to one row of Table A Table 568
Compounds of the formula I.1 in which $R^8$ is cyclopentyl, $R^9$ is n-propoxymethyl, and $R^1$, $R^2$, $R^3$, $R^6$ and $R^7$ for a compound corresponds in each case to one row of Table A Table 569
Compounds of the formula I.1 in which $R^8$ is cyclopentyl, $R^9$ is isopropoxymethyl, and $R^1$, $R^2$, $R^3$, $R^6$ and $R^7$ for a compound corresponds in each case to one row of Table A Table 570
Compounds of the formula I.1 in which $R^8$ is cyclopentyl, $R^9$ is methoxy-1-ethyl, and $R^1$, $R^2$, $R^3$, $R^6$ and $R^7$ for a compound corresponds in each case to one row of Table A Table 571
Compounds of the formula I.1 in which $R^8$ is cyclopentyl, $R^9$ is ethoxy-1-ethyl, and $R^1$, $R^2$, $R^3$, $R^6$ and $R^7$ for a compound corresponds in each case to one row of Table A Table 572
Compounds of the formula I.1 in which $R^8$ is cyclopentyl, $R^9$ is n-propoxy-1-ethyl, and $R^1$, $R^2$, $R^3$, $R^6$ and $R^7$ for a compound corresponds in each case to one row of Table A Table 573
Compounds of the formula I.1 in which $R^8$ is cyclopentyl, $R^9$ is isopropoxy-1-ethyl, and $R^1$, $R^2$, $R^3$, $R^6$ and $R^7$ for a compound corresponds in each case to one row of Table A Table 574
Compounds of the formula I.1 in which $R^8$ is cyclopentyl, $R^9$ is methoxy-2-ethyl, and $R^1$, $R^2$, $R^3$, $R^6$ and $R^7$ for a compound corresponds in each case to one row of Table A Table 575
Compounds of the formula I.1 in which $R^8$ is cyclopentyl, $R^9$ is ethoxy-2-ethyl, and $R^1$, $R^2$, $R^3$, $R^6$ and $R^7$ for a compound corresponds in each case to one row of Table A Table 576
Compounds of the formula I.1 in which $R^8$ is cyclopentyl, $R^9$ is n-propoxy-2-ethyl, and $R^1$, $R^2$, $R^3$, $R^6$ and $R^7$ for a compound corresponds in each case to one row of Table A Table 577
Compounds of the formula I.1 in which $R^8$ is cyclopentyl, $R^9$ is isopropoxy-2-ethyl, and $R^1$, $R^2$, $R^3$, $R^6$ and $R^7$ for a compound corresponds in each case to one row of Table A Table 578
Compounds of the formula I.1 in which $R^8$ is cyclopentyl, $R^9$ is methoxy-1-propyl, and $R^1$, $R^2$, $R^3$, $R^6$ and $R^7$ for a compound corresponds in each case to one row of Table A Table 579
Compounds of the formula I.1 in which $R^8$ is cyclopentyl, $R^9$ is ethoxy-1-propyl, and $R^1$, $R^2$, $R^3$, $R^6$ and $R^7$ for a compound corresponds in each case to one row of Table A Table 580
Compounds of the formula I.1 in which $R^8$ is cyclopentyl, $R^9$ is n-propoxy-1-propyl, and $R^1$, $R^2$, $R^3$, $R^6$ and $R^7$ for a compound corresponds in each case to one row of Table A Table 581
Compounds of the formula I.1 in which $R^8$ is cyclopentyl, $R^9$ is isopropoxy-1-propyl, and $R^1$, $R^2$, $R^3$, $R^6$ and $R^7$ for a compound corresponds in each case to one row of Table A Table 582
Compounds of the formula I.1 in which $R^8$ is cyclopentyl, $R^9$ is methoxy-2-propyl, and $R^1$, $R^2$, $R^3$, $R^6$ and $R^7$ for a compound corresponds in each case to one row of Table A Table 583
Compounds of the formula I.1 in which $R^8$ is cyclopentyl, $R^9$ is ethoxy-2-propyl, and $R^1$, $R^2$, $R^3$, $R^6$ and $R^7$ for a compound corresponds in each case to one row of Table A Table 584
Compounds of the formula I.1 in which $R^8$ is cyclopentyl, $R^9$ is n-propoxy-2-propyl, and $R^1$, $R^2$, $R^3$, $R^6$ and $R^7$ for a compound corresponds in each case to one row of Table A Table 585
Compounds of the formula I.1 in which $R^8$ is cyclopentyl, $R^9$ is isopropoxy-2-propyl, and $R^1$, $R^2$, $R^3$, $R^6$ and $R^7$ for a compound corresponds in each case to one row of Table A Table 586
Compounds of the formula I.1 in which $R^8$ is cyclopentyl, $R^9$ is methoxy-3-propyl, and $R^1$, $R^2$, $R^3$, $R^6$ and $R^7$ for a compound corresponds in each case to one row of Table A Table 587
Compounds of the formula I.1 in which $R^8$ is cyclopentyl, $R^9$ is ethoxy-3-propyl, and $R^1$, $R^2$, $R^3$, $R^6$ and $R^7$ for a compound corresponds in each case to one row of Table A Table 588
Compounds of the formula I.1 in which $R^8$ is cyclopentyl, $R^9$ is n-propoxy-3-propyl, and $R^1$, $R^2$, $R^3$, $R^6$ and $R^7$ for a compound corresponds in each case to one row of Table A Table 589
Compounds of the formula I.1 in which $R^8$ is cyclopentyl, $R^9$ is isopropoxy-3-propyl, and $R^1$, $R^2$, $R^3$, $R^6$ and $R^7$ for a compound corresponds in each case to one row of Table A Table 590
Compounds of the formula I.1 in which $R^8$ is cyclopentyl, $R^9$ is oxetan-2-yl, and $R^1$, $R^2$, $R^3$, $R^6$ and $R^7$ for a compound corresponds in each case to one row of Table A Table 591
Compounds of the formula I.1 in which $R^8$ is cyclopentyl, $R^9$ is oxetan-3-yl, and $R^1$, $R^2$, $R^3$, $R^6$ and $R^7$ for a compound corresponds in each case to one row of Table A Table 592
Compounds of the formula I.1 in which $R^8$ is cyclopentyl, $R^9$ is tetrahydrofuran-2-yl, and $R^1$, $R^2$, $R^3$, $R^6$ and $R^7$ for a compound corresponds in each case to one row of Table A Table 593
Compounds of the formula I.1 in which $R^8$ is cyclopentyl, $R^9$ is tetrahydrofuran-3-yl, and $R^1$, $R^2$, $R^3$, $R^6$ and $R^7$ for a compound corresponds in each case to one row of Table A Table 594
Compounds of the formula I.1 in which $R^8$ is cyclopentyl, $R^9$ is tetrahydropyran-2-yl, and $R^1$, $R^2$, $R^3$, $R^6$ and $R^7$ for a compound corresponds in each case to one row of Table A Table 595
Compounds of the formula I.1 in which $R^8$ is cyclopentyl, $R^9$ is tetrahydropyran-3-yl, and $R^1$, $R^2$, $R^3$, $R^6$ and $R^7$ for a compound corresponds in each case to one row of Table A Table 596
Compounds of the formula II in which $R^8$ is cyclopentyl, $R^9$ is tetrahydropyran-4-yl, and $R^1$, $R^2$, $R^3$, $R^6$ and $R^7$ for a compound corresponds in each case to one row of Table A Table 597
Compounds of the formula I.1 in which $R^8$ is cyclopentyl, $R^9$ is thietan-2-yl, and $R^1$, $R^2$, $R^3$, $R^6$ and $R^7$ for a compound corresponds in each case to one row of Table A Table 598
Compounds of the formula I.1 in which $R^8$ is cyclopentyl, $R^9$ is thietan-3-yl, and $R^1$, $R^2$, $R^3$, $R^6$ and $R^7$ for a compound corresponds in each case to one row of Table A Table 599
Compounds of the formula II in which $R^8$ is cyclopentyl, $R^9$ is 1-oxothietan-3-yl, and $R^1$, $R^2$, $R^3$, $R^6$ and $R^7$ for a compound corresponds in each case to one row of Table A Table 600
Compounds of the formula I.1 in which $R^8$ is cyclopentyl, $R^9$ is 1,1-dioxothietan-3-yl, and $R^1$, $R^2$, $R^3$, $R^6$ and $R^7$ for a compound corresponds in each case to one row of Table A Table 601
Compounds of the formula I.1 in which $R^8$ is cyclohexyl, $R^9$ is methoxy, and $R^1$, $R^2$, $R^3$, $R^6$ and $R^7$ for a compound corresponds in each case to one row of Table A Table 602
Compounds of the formula II in which $R^8$ is cyclohexyl, $R^9$ is ethoxy, and $R^1$, $R^2$, $R^3$, $R^6$ and $R^7$ for a compound corresponds in each case to one row of Table A Table 603
Compounds of the formula I.1 in which $R^8$ is cyclohexyl, $R^9$ is n-propoxy, and $R^1$, $R^2$, $R^3$, $R^6$ and $R^7$ for a compound corresponds in each case to one row of Table A Table 604
Compounds of the formula I.1 in which $R^8$ is cyclohexyl, $R^9$ is isopropoxy, and $R^1$, $R^2$, $R^3$, $R^6$ and $R^7$ for a compound corresponds in each case to one row of Table A Table 605
Compounds of the formula I.1 in which $R^8$ is cyclohexyl, $R^9$ is n-butoxy, and $R^1$, $R^2$, $R^3$, $R^6$ and $R^7$ for a compound corresponds in each case to one row of Table A Table 606
Compounds of the formula I.1 in which $R^8$ is cyclohexyl, $R^9$ is sec-butoxy, and $R^1$, $R^2$, $R^3$, $R^6$ and $R^7$ for a compound corresponds in each case to one row of Table A Table 607
Compounds of the formula I.1 in which $R^8$ is cyclohexyl, $R^9$ is isobutoxy, and $R^1$, $R^2$, $R^3$, $R^6$ and $R^7$ for a compound corresponds in each case to one row of Table A Table 608
Compounds of the formula I.1 in which $R^8$ is cyclohexyl, $R^9$ is tert-butoxy, and $R^1$, $R^2$, $R^3$, $R^6$ and $R^7$ for a compound corresponds in each case to one row of Table A Table 609
Compounds of the formula I.1 in which $R^8$ is cyclohexyl, $R^9$ is fluoromethoxy, and $R^1$, $R^2$, $R^3$, $R^6$ and $R^7$ for a compound corresponds in each case to one row of Table A Table 610
Compounds of the formula I.1 in which $R^8$ is cyclohexyl, $R^9$ is difluoromethoxy, and $R^1$, $R^2$, $R^3$, $R^6$ and $R^7$ for a compound corresponds in each case to one row of Table A Table 611
Compounds of the formula I.1 in which $R^8$ is cyclohexyl, $R^9$ is trifluoromethoxy, and $R^1$, $R^2$, $R^3$, $R^6$ and $R^7$ for a compound corresponds in each case to one row of Table A Table 612
Compounds of the formula I.1 in which $R^8$ is cyclohexyl, $R^9$ is 2-fluoroethoxy, and $R^1$, $R^2$, $R^3$, $R^6$ and $R^7$ for a compound corresponds in each case to one row of Table A Table 613
Compounds of the formula I.1 in which $R^8$ is cyclohexyl, $R^9$ is 2,2-difluoroethoxy, and $R^1$, $R^2$, $R^3$, $R^6$ and $R^7$ for a compound corresponds in each case to one row of Table A Table 614
Compounds of the formula I.1 in which $R^8$ is cyclohexyl, $R^9$ is 2,2,2-trifluoroethoxy, and $R^1$, $R^2$, $R^3$, $R^6$ and $R^7$ for a compound corresponds in each case to one row of Table A Table 615
Compounds of the formula I.1 in which $R^8$ is cyclohexyl, $R^9$ is pentafluoroethoxy, and $R^1$, $R^2$, $R^3$, $R^6$ and $R^7$ for a compound corresponds in each case to one row of Table A Table 616
Compounds of the formula I.1 in which $R^8$ is cyclohexyl, $R^9$ is methoxymethyl, and $R^1$, $R^2$, $R^3$, $R^6$ and $R^7$ for a compound corresponds in each case to one row of Table A Table 617
Compounds of the formula I.1 in which $R^8$ is cyclohexyl, $R^9$ is ethoxymethyl, and $R^1$, $R^2$, $R^3$, $R^6$ and $R^7$ for a compound corresponds in each case to one row of Table A Table 618
Compounds of the formula I.1 in which $R^8$ is cyclohexyl, $R^9$ is n-propoxymethyl, and $R^1$, $R^2$, $R^3$, $R^6$ and $R^7$ for a compound corresponds in each case to one row of Table A Table 619
Compounds of the formula I.1 in which $R^8$ is cyclohexyl, $R^9$ is isopropoxymethyl, and $R^1$, $R^2$, $R^3$, $R^6$ and $R^7$ for a compound corresponds in each case to one row of Table A Table 620
Compounds of the formula I.1 in which $R^8$ is cyclohexyl, $R^9$ is methoxy-1-ethyl, and $R^1$, $R^2$, $R^3$, $R^6$ and $R^7$ for a compound corresponds in each case to one row of Table A Table 621
Compounds of the formula I.1 in which $R^8$ is cyclohexyl, $R^9$ is ethoxy-1-ethyl, and $R^1$, $R^2$, $R^3$, $R^6$ and $R^7$ for a compound corresponds in each case to one row of Table A Table 622
Compounds of the formula I.1 in which $R^8$ is cyclohexyl, $R^9$ is n-propoxy-1-ethyl, and $R^1$, $R^2$, $R^3$, $R^6$ and $R^7$ for a compound corresponds in each case to one row of Table A Table 623
Compounds of the formula I.1 in which $R^8$ is cyclohexyl, $R^9$ is isopropoxy-1-ethyl, and $R^1$, $R^2$, $R^3$, $R^6$ and $R^7$ for a compound corresponds in each case to one row of Table A Table 624
Compounds of the formula I.1 in which $R^8$ is cyclohexyl, $R^9$ is methoxy-2-ethyl, and $R^1$, $R^2$, $R^3$, $R^6$ and $R^7$ for a compound corresponds in each case to one row of Table A Table 625
Compounds of the formula I.1 in which $R^8$ is cyclohexyl, $R^9$ is ethoxy-2-ethyl, and $R^1$, $R^2$, $R^3$, $R^6$ and $R^7$ for a compound corresponds in each case to one row of Table A Table 626
Compounds of the formula I.1 in which $R^8$ is cyclohexyl, $R^9$ is n-propoxy-2-ethyl, and $R^1$, $R^2$, $R^3$, $R^6$ and $R^7$ for a compound corresponds in each case to one row of Table A Table 627
Compounds of the formula I.1 in which $R^8$ is cyclohexyl, $R^9$ is isopropoxy-2-ethyl, and $R^1$, $R^2$, $R^3$, $R^6$ and $R^7$ for a compound corresponds in each case to one row of Table A Table 628
Compounds of the formula I.1 in which $R^8$ is cyclohexyl, $R^9$ is methoxy-1-propyl, and $R^1$, $R^2$, $R^3$, $R^6$ and $R^7$ for a compound corresponds in each case to one row of Table A Table 629
Compounds of the formula I.1 in which $R^8$ is cyclohexyl, $R^9$ is ethoxy-1-propyl, and $R^1$, $R^2$, $R^3$, $R^6$ and $R^7$ for a compound corresponds in each case to one row of Table A Table 630
Compounds of the formula I.1 in which $R^8$ is cyclohexyl, $R^9$ is n-propoxy-1-propyl, and $R^1$, $R^2$, $R^3$, $R^6$ and $R^7$ for a compound corresponds in each case to one row of Table A Table 631
Compounds of the formula I.1 in which $R^8$ is cyclohexyl, $R^9$ is isopropoxy-1-propyl, and $R^1$, $R^2$, $R^3$, $R^6$ and $R^7$ for a compound corresponds in each case to one row of Table A Table 632
Compounds of the formula I.1 in which $R^8$ is cyclohexyl, $R^9$ is methoxy-2-propyl, and $R^1$, $R^2$, $R^3$, $R^6$ and $R^7$ for a compound corresponds in each case to one row of Table A Table 633
Compounds of the formula I.1 in which $R^8$ is cyclohexyl, $R^9$ is ethoxy-2-propyl, and $R^1$, $R^2$, $R^3$, $R^6$ and $R^7$ for a compound corresponds in each case to one row of Table A Table 634
Compounds of the formula I.1 in which $R^8$ is cyclohexyl, $R^9$ is n-propoxy-2-propyl, and $R^1$, $R^2$, $R^3$, $R^6$ and $R^7$ for a compound corresponds in each case to one row of Table A Table 635
Compounds of the formula I.1 in which $R^8$ is cyclohexyl, $R^9$ is isopropoxy-2-propyl, and $R^1$, $R^2$, $R^3$, $R^6$ and $R^7$ for a compound corresponds in each case to one row of Table A Table 636
Compounds of the formula I.1 in which $R^8$ is cyclohexyl, $R^9$ is methoxy-3-propyl, and $R^1$, $R^2$, $R^3$, $R^6$ and $R^7$ for a compound corresponds in each case to one row of Table A Table 637
Compounds of the formula I.1 in which $R^8$ is cyclohexyl, $R^9$ is ethoxy-3-propyl, and $R^1$, $R^2$, $R^3$, $R^6$ and $R^7$ for a compound corresponds in each case to one row of Table A Table 638
Compounds of the formula I.1 in which $R^8$ is cyclohexyl, $R^9$ is n-propoxy-3-propyl, and $R^1$, $R^2$, $R^3$, $R^6$ and $R^7$ for a compound corresponds in each case to one row of Table A Table 639
Compounds of the formula I.1 in which $R^8$ is cyclohexyl, $R^9$ is isopropoxy-3-propyl, and $R^1$, $R^2$, $R^3$, $R^6$ and $R^7$ for a compound corresponds in each case to one row of Table A Table 640
Compounds of the formula I.1 in which $R^8$ is cyclohexyl, $R^9$ is oxetan-2-yl, and $R^1$, $R^2$, $R^3$, $R^6$ and $R^7$ for a compound corresponds in each case to one row of Table A Table 641
Compounds of the formula I.1 in which $R^8$ is cyclohexyl, $R^9$ is oxetan-3-yl, and $R^1$, $R^2$, $R^3$, $R^6$ and $R^7$ for a compound corresponds in each case to one row of Table A Table 642
Compounds of the formula I.1 in which $R^8$ is cyclohexyl, $R^9$ is tetrahydrofuran-2-yl, and $R^1$, $R^2$, $R^3$, $R^6$ and $R^7$ for a compound corresponds in each case to one row of Table A Table 643
Compounds of the formula I.1 in which $R^8$ is cyclohexyl, $R^9$ is tetrahydrofuran-3-yl, and $R^1$, $R^2$, $R^3$, $R^6$ and $R^7$ for a compound corresponds in each case to one row of Table A Table 644
Compounds of the formula I.1 in which $R^8$ is cyclohexyl, $R^9$ is tetrahydropyran-2-yl, and $R^1$, $R^2$, $R^3$, $R^6$ and $R^7$ for a compound corresponds in each case to one row of Table A Table 645
Compounds of the formula I.1 in which $R^8$ is cyclohexyl, $R^9$ is tetrahydropyran-3-yl, and $R^1$, $R^2$, $R^3$, $R^6$ and $R^7$ for a compound corresponds in each case to one row of Table A Table 646
Compounds of the formula I.1 in which $R^8$ is cyclohexyl, $R^9$ is tetrahydropyran-4-yl, and $R^1$, $R^2$, $R^3$, $R^6$ and $R^7$ for a compound corresponds in each case to one row of Table A Table 647
Compounds of the formula I.1 in which $R^8$ is cyclohexyl, $R^9$ is thietan-2-yl, and $R^1$, $R^2$, $R^3$, $R^6$ and $R^7$ for a compound corresponds in each case to one row of Table A Table 648
Compounds of the formula I.1 in which $R^8$ is cyclohexyl, $R^9$ is thietan-3-yl, and $R^1$, $R^2$, $R^3$, $R^6$ and $R^7$ for a compound corresponds in each case to one row of Table A Table 649
Compounds of the formula I.1 in which $R^8$ is cyclohexyl, $R^9$ is 1-oxothietan-3-yl, and $R^1$, $R^2$, $R^3$, $R^6$ and $R^7$ for a compound corresponds in each case to one row of Table A Table 650
Compounds of the formula I.1 in which $R^8$ is cyclohexyl, $R^9$ is 1,1-dioxothietan-3-yl, and $R^1$, $R^2$, $R^3$, $R^6$ and $R^7$ for a compound corresponds in each case to one row of Table A Table 651
Compounds of the formula I.1 in which $R^8$ and $R^9$, together with the nitrogen atom they are bound to, form (or in other words: $NR^8R^9$ is) 2-fluoroaziridin-1-yl, and $R^1$, $R^2$, $R^3$, $R^6$ and $R^7$ for a compound corresponds in each case to one row of Table A Table 652
Compounds of the formula I.1 in which $R^8$ and $R^9$, together with the nitrogen atom they are bound to, form (or in other words: $NR^8R^9$ is) 2,2-difluoroaziridin-1-yl, and $R^1$, $R^2$, $R^3$, $R^6$ and $R^7$ for a compound corresponds in each case to one row of Table A Table 653
Compounds of the formula I.1 in which $R^8$ and $R^9$, together with the nitrogen atom they are bound to, form (or in other words: $NR^8R^9$ is) 2-methoxyaziridin-1-yl, and $R^1$, $R^2$, $R^3$, $R^6$ and $R^7$ for a compound corresponds in each case to one row of Table A Table 654
Compounds of the formula I.1 in which $R^8$ and $R^9$, together with the nitrogen atom they are bound to, form (or in other words: $NR^8R^9$ is) 2-fluoroazetidin-1-yl, and $R^1$, $R^2$, $R^3$, $R^6$ and $R^7$ for a compound corresponds in each case to one row of Table A Table 655
Compounds of the formula I.1 in which $R^8$ and $R^9$, together with the nitrogen atom they are bound to, form (or in other words: $NR^8R^9$ is) 2,2-difluoroazetidin-1-yl, and $R^1$, $R^2$, $R^3$, $R^6$ and $R^7$ for a compound corresponds in each case to one row of Table A Table 656
Compounds of the formula I.1 in which $R^8$ and $R^9$, together with the nitrogen atom they are bound to, form (or in other words: $NR^8R^9$ is) 3-fluoroazetidin-1-yl, and $R^1$, $R^2$, $R^3$, $R^6$ and $R^7$ for a compound corresponds in each case to one row of Table A Table 657
Compounds of the formula I.1 in which $R^8$ and $R^9$, together with the nitrogen atom they are bound to, form (or in other words: $NR^8R^9$ is) 3,3-difluoroazetidin-1-yl, and $R^1$, $R^2$, $R^3$, $R^6$ and $R^7$ for a compound corresponds in each case to one row of Table A Table 658
Compounds of the formula I.1 in which $R^8$ and $R^9$, together with the nitrogen atom they are bound to, form (or in other words: $NR^8R^9$ is) 2-hydroxyazetidin-1-yl, and $R^1$, $R^2$, $R^3$, $R^6$ and $R^7$ for a compound corresponds in each case to one row of Table A Table 659
Compounds of the formula I.1 in which $R^8$ and $R^9$, together with the nitrogen atom they are bound to, form (or in other words: $NR^8R^9$ is) 3-hydroxyazetidin-1-yl, and $R^1$, $R^2$, $R^3$, $R^6$ and $R^7$ for a compound corresponds in each case to one row of Table A Table 660
Compounds of the formula I.1 in which $R^8$ and $R^9$, together with the nitrogen atom they are bound to, form (or in other words: $NR^8R^9$ is) 2-methoxyazetidin-1-yl, and $R^1$, $R^2$, $R^3$, $R^6$ and $R^7$ for a compound corresponds in each case to one row of Table A Table 661
Compounds of the formula I.1 in which $R^8$ and $R^9$, together with the nitrogen atom they are bound to, form (or in other words: $NR^8R^9$ is) 3-methoxyazetidin-1-yl, and $R^1$, $R^2$, $R^3$, $R^6$ and $R^7$ for a compound corresponds in each case to one row of Table A Table 662
Compounds of the formula I.1 in which $R^8$ and $R^9$, together with the nitrogen atom they are bound to, form (or in other words: $NR^8R^9$ is) 2-ethoxyazetidin-1-yl, and $R^1$, $R^2$, $R^3$, $R^6$ and $R^7$ for a compound corresponds in each case to one row of Table A Table 663
Compounds of the formula I.1 in which $R^8$ and $R^9$, together with the nitrogen atom they are bound to, form (or in other words: $NR^8R^9$ is) 3-ethoxyazetidin-1-yl, and $R^1$, $R^2$, $R^3$, $R^6$ and $R^7$ for a compound corresponds in each case to one row of Table A Table 664
Compounds of the formula I.1 in which $R^8$ and $R^9$, together with the nitrogen atom they are bound to, form (or in other words: $NR^8R^9$ is) 2-trifluoromethoxyazetidin-1-yl, and $R^1$, $R^2$, $R^3$, $R^6$ and $R^7$ for a compound corresponds in each case to one row of Table A Table 665
Compounds of the formula I.1 in which $R^8$ and $R^9$, together with the nitrogen atom they are bound to, form (or in other words: $NR^8R^9$ is) 3-trifluoromethoxyazetidin-1-yl, and $R^1$, $R^2$, $R^3$, $R^6$ and $R^7$ for a compound corresponds in each case to one row of Table A Table 666
Compounds of the formula I.1 in which $R^8$ and $R^9$, together with the nitrogen atom they are bound to, form (or in other words: $NR^8R^9$ is) 2-(oxetan-3-yl)-azetidin-1-yl, and $R^1$, $R^2$, $R^3$, $R^6$ and $R^7$ for a compound corresponds in each case to one row of Table A Table 667
Compounds of the formula I.1 in which $R^8$ and $R^9$, together with the nitrogen atom they are bound to, form (or in other words: $NR^8R^9$ is) 3-(oxetan-3-yl)-azetidin-1-yl, and $R^1$, $R^2$, $R^3$, $R^6$ and $R^7$ for a compound corresponds in each case to one row of Table A Table 668
Compounds of the formula I.1 in which $R^8$ and $R^9$, together with the nitrogen atom they are bound to, form (or in other words: $NR^8R^9$ is) [1,3]oxazetidin-3-yl, and $R^1$, $R^2$, $R^3$, $R^6$ and $R^7$ for a compound corresponds in each case to one row of Table A Table 669
Compounds of the formula I.1 in which $R^8$ and $R^9$, together with the nitrogen atom they are bound to, form (or in other words: $NR^8R^9$ is) [1,3]diazetidin-1-yl, and $R^1$, $R^2$, $R^3$, $R^6$ and $R^7$ for a compound corresponds in each case to one row of Table A Table 670
Compounds of the formula I.1 in which $R^8$ and $R^9$, together with the nitrogen atom they are bound to, form (or in other words: $NR^8R^9$ is) 2-oxa-6-aza-spiro[3.3]hept-6-yl, and $R^1$, $R^2$, $R^3$, $R^6$ and $R^7$ for a compound corresponds in each case to one row of Table A Table 671

Compounds of the formula I.1 in which $R^8$ and $R^9$, together with the nitrogen atom they are bound to, form (or in other words: $NR^8R^9$ is) 2,6-diaza-spiro[3.3]hept-2-yl, and $R^1$, $R^2$, $R^3$, $R^6$ and $R^7$ for a compound corresponds in each case to one row of Table A Table 672

Compounds of the formula I.1 in which $R^8$ and $R^9$, together with the nitrogen atom they are bound to, form (or in other words: $NR^8R^9$ is) 2-fluoropyrrolidin-1-yl, and $R^1$, $R^2$, $R^3$, $R^6$ and $R^7$ for a compound corresponds in each case to one row of Table A Table 673

Compounds of the formula I.1 in which $R^8$ and $R^9$, together with the nitrogen atom they are bound to, form (or in other words: $NR^8R^9$ is) 2,2-difluoropyrrolidin-1-yl, and $R^1$, $R^2$, $R^3$, $R^6$ and $R^7$ for a compound corresponds in each case to one row of Table A Table 674

Compounds of the formula I.1 in which $R^8$ and $R^9$, together with the nitrogen atom they are bound to, form (or in other words: $NR^8R^9$ is) 3-fluoropyrrolidin-1-yl, and $R^1$, $R^2$, $R^3$, $R^6$ and $R^7$ for a compound corresponds in each case to one row of Table A Table 675

Compounds of the formula I.1 in which $R^8$ and $R^9$, together with the nitrogen atom they are bound to, form (or in other words: $NR^8R^9$ is) 3,3-difluoropyrrolidin-1-yl, and $R^1$, $R^2$, $R^3$, $R^6$ and $R^7$ for a compound corresponds in each case to one row of Table A Table 676

Compounds of the formula I.1 in which $R^8$ and $R^9$, together with the nitrogen atom they are bound to, form (or in other words: $NR^8R^9$ is) 2-hydroxypyrrolidin-1-yl, and $R^1$, $R^2$, $R^3$, $R^6$ and $R^7$ for a compound corresponds in each case to one row of Table A Table 677

Compounds of the formula I.1 in which $R^8$ and $R^9$, together with the nitrogen atom they are bound to, form (or in other words: $NR^8R^9$ is) 3-hydroxypyrrolidin-1-yl, and $R^1$, $R^2$, $R^3$, $R^6$ and $R^7$ for a compound corresponds in each case to one row of Table A Table 678

Compounds of the formula I.1 in which $R^8$ and $R^9$, together with the nitrogen atom they are bound to, form (or in other words: $NR^8R^9$ is) 2-methoxypyrrolidin-1-yl, and $R^1$, $R^2$, $R^3$, $R^6$ and $R^7$ for a compound corresponds in each case to one row of Table A Table 679

Compounds of the formula I.1 in which $R^8$ and $R^9$, together with the nitrogen atom they are bound to, form (or in other words: $NR^8R^9$ is) 3-methoxypyrrolidin-1-yl, and $R^1$, $R^2$, $R^3$, $R^6$ and $R^7$ for a compound corresponds in each case to one row of Table A Table 680

Compounds of the formula I.1 in which $R^8$ and $R^9$, together with the nitrogen atom they are bound to, form (or in other words: $NR^8R^9$ is) 2-ethoxypyrrolidin-1-yl, and $R^1$, $R^2$, $R^3$, $R^6$ and $R^7$ for a compound corresponds in each case to one row of Table A Table 681

Compounds of the formula I.1 in which $R^8$ and $R^9$, together with the nitrogen atom they are bound to, form (or in other words: $NR^8R^9$ is) 3-ethoxypyrrolidin-1-yl, and $R^1$, $R^2$, $R^3$, $R^6$ and $R^7$ for a compound corresponds in each case to one row of Table A Table 682

Compounds of the formula I.1 in which $R^8$ and $R^9$, together with the nitrogen atom they are bound to, form (or in other words: $NR^8R^9$ is) 2-trifluoromethoxypyrrolidin-1-yl, and $R^1$, $R^2$, $R^3$, $R^6$ and $R^7$ for a compound corresponds in each case to one row of Table A Table 683

Compounds of the formula I.1 in which $R^8$ and $R^9$, together with the nitrogen atom they are bound to, form (or in other words: $NR^8R^9$ is) 3-trifluoromethoxypyrrolidin-1-yl, and $R^1$, $R^2$, $R^3$, $R^6$ and $R^7$ for a compound corresponds in each case to one row of Table A Table 684

Compounds of the formula I.1 in which $R^8$ and $R^9$, together with the nitrogen atom they are bound to, form (or in other words: $NR^8R^9$ is) 2-(oxetan-3-yl)-pyrrolidin-1-yl, and $R^1$, $R^2$, $R^3$, $R^6$ and $R^7$ for a compound corresponds in each case to one row of Table A Table 685

Compounds of the formula I.1 in which $R^8$ and $R^9$, together with the nitrogen atom they are bound to, form (or in other words: $NR^8R^9$ is) 3-(oxetan-3-yl)-pyrrolidin-1-yl, and $R^1$, $R^2$, $R^3$, $R^6$ and $R^7$ for a compound corresponds in each case to one row of Table A Table 686

Compounds of the formula I.1 in which $R^8$ and $R^9$, together with the nitrogen atom they are bound to, form (or in other words: $NR^8R^9$ is) tetrahydroisoxazolidin-2-yl, and $R^1$, $R^2$, $R^3$, $R^6$ and $R^7$ for a compound corresponds in each case to one row of Table A Table 687

Compounds of the formula I.1 in which $R^8$ and $R^9$, together with the nitrogen atom they are bound to, form (or in other words: $NR^8R^9$ is) tetrahydroxazolidin-3-yl, and $R^1$, $R^2$, $R^3$, $R^6$ and $R^7$ for a compound corresponds in each case to one row of Table A Table 688

Compounds of the formula I.1 in which $R^8$ and $R^9$, together with the nitrogen atom they are bound to, form (or in other words: $NR^8R^9$ is) tetrahydropyrazolidin-1-yl, and $R^1$, $R^2$, $R^3$, $R^6$ and $R^7$ for a compound corresponds in each case to one row of Table A Table 689

Compounds of the formula I.1 in which $R^8$ and $R^9$, together with the nitrogen atom they are bound to, form (or in other words: $NR^8R^9$ is) tetrahydroimidazolidin-1-yl, and $R^1$, $R^2$, $R^3$, $R^6$ and $R^7$ for a compound corresponds in each case to one row of Table A Table 690

Compounds of the formula I.1 in which $R^8$ and $R^9$, together with the nitrogen atom they are bound to, form (or in other words: $NR^8R^9$ is) 2-fluoropiperidin-1-yl, and $R^1$, $R^2$, $R^3$, $R^6$ and $R^7$ for a compound corresponds in each case to one row of Table A Table 691

Compounds of the formula I.1 in which $R^8$ and $R^9$, together with the nitrogen atom they are bound to, form (or in other words: $NR^8R^9$ is) 2,2-difluoropiperidin-1-yl, and $R^1$, $R^2$, $R^3$, $R^6$ and $R^7$ for a compound corresponds in each case to one row of Table A Table 692

Compounds of the formula I.1 in which $R^8$ and $R^9$, together with the nitrogen atom they are bound to, form (or in other words: $NR^8R^9$ is) 3-fluoropiperidin-1-yl, and $R^1$, $R^2$, $R^3$, $R^6$ and $R^7$ for a compound corresponds in each case to one row of Table A Table 693

Compounds of the formula I.1 in which $R^8$ and $R^9$, together with the nitrogen atom they are bound to, form (or in other words: $NR^8R^9$ is) 3,3-difluoropiperidin-1-yl, and $R^1$, $R^2$, $R^3$, $R^6$ and $R^7$ for a compound corresponds in each case to one row of Table A Table 694

Compounds of the formula I.1 in which $R^8$ and $R^9$, together with the nitrogen atom they are bound to, form (or in other words: $NR^8R^9$ is) 4-fluoropiperidin-1-yl, and $R^1$, $R^2$, $R^3$, $R^6$ and $R^7$ for a compound corresponds in each case to one row of Table A Table 695

Compounds of the formula I.1 in which $R^8$ and $R^9$, together with the nitrogen atom they are bound to, form (or in other words: $NR^8R^9$ is) 4,4-difluoropiperidin-1-yl, and $R^1$, $R^2$, $R^3$, $R^6$ and $R^7$ for a compound corresponds in each case to one row of Table A Table 696

Compounds of the formula I.1 in which $R^8$ and $R^9$, together with the nitrogen atom they are bound to, form (or in other words: $NR^8R^9$ is) 2-hydroxypiperidin-1-yl, and $R^1$, $R^2$, $R^3$, $R^6$ and $R^7$ for a compound corresponds in each case to one row of Table A Table 697

Compounds of the formula I.1 in which $R^8$ and $R^9$, together with the nitrogen atom they are bound to, form (or in other words: $NR^8R^9$ is) 3-hydroxypiperidin-1-yl, and $R^1$, $R^2$, $R^3$, $R^6$ and $R^7$ for a compound corresponds in each case to one row of Table A Table 698

Compounds of the formula I.1 in which $R^8$ and $R^9$, together with the nitrogen atom they are bound to, form (or in other words: $NR^8R^9$ is) 4-hydroxypiperidin-1-yl, and $R^1$, $R^2$, $R^3$, $R^6$ and $R^7$ for a compound corresponds in each case to one row of Table A Table 699

Compounds of the formula I.1 in which $R^8$ and $R^9$, together with the nitrogen atom they are bound to, form (or in other words: $NR^8R^9$ is) 2-methoxypiperidin-1-yl, and $R^1$, $R^2$, $R^3$, $R^6$ and $R^7$ for a compound corresponds in each case to one row of Table A Table 700

Compounds of the formula I.1 in which $R^8$ and $R^9$, together with the nitrogen atom they are bound to, form (or in other words: $NR^8R^9$ is) 3-methoxypiperidin-1-yl, and $R^1$, $R^2$, $R^3$, $R^6$ and $R^7$ for a compound corresponds in each case to one row of Table A Table 701

Compounds of the formula I.1 in which $R^8$ and $R^9$, together with the nitrogen atom they are bound to, form (or in other words: $NR^8R^9$ is) 4-methoxypiperidin-1-yl, and $R^1$, $R^2$, $R^3$, $R^6$ and $R^7$ for a compound corresponds in each case to one row of Table A Table 702

Compounds of the formula I.1 in which $R^8$ and $R^9$, together with the nitrogen atom they are bound to, form (or in other words: $NR^8R^9$ is) 2-ethoxypiperidin-1-yl, and $R^1$, $R^2$, $R^3$, $R^6$ and $R^7$ for a compound corresponds in each case to one row of Table A Table 703

Compounds of the formula I.1 in which $R^8$ and $R^9$, together with the nitrogen atom they are bound to, form (or in other words: $NR^8R^9$ is) 3-ethoxypiperidin-1-yl, and $R^1$, $R^2$, $R^3$, $R^6$ and $R^7$ for a compound corresponds in each case to one row of Table A Table 704

Compounds of the formula I.1 in which $R^8$ and $R^9$, together with the nitrogen atom they are bound to, form (or in other words: $NR^8R^9$ is) 4-ethoxypiperidin-1-yl, and $R^1$, $R^2$, $R^3$, $R^6$ and $R^7$ for a compound corresponds in each case to one row of Table A Table 705

Compounds of the formula I.1 in which $R^8$ and $R^9$, together with the nitrogen atom they are bound to, form (or in other words: $NR^8R^9$ is) 2-trifluoromethoxypiperidin-1-yl, and $R^1$, $R^2$, $R^3$, $R^6$ and $R^7$ for a compound corresponds in each case to one row of Table A Table 706

Compounds of the formula I.1 in which $R^8$ and $R^9$, together with the nitrogen atom they are bound to, form (or in other words: $NR^8R^9$ is) 3-trifluoromethoxypiperidin-1-yl, and $R^1$, $R^2$, $R^3$, $R^6$ and $R^7$ for a compound corresponds in each case to one row of Table A Table 707

Compounds of the formula I.1 in which $R^8$ and $R^9$, together with the nitrogen atom they are bound to, form (or in other words: $NR^8R^9$ is) 4-trifluoromethoxypiperidin-1-yl, and $R^1$, $R^2$, $R^3$, $R^6$ and $R^7$ for a compound corresponds in each case to one row of Table A Table 708

Compounds of the formula I.1 in which $R^8$ and $R^9$, together with the nitrogen atom they are bound to, form (or in other words: $NR^8R^9$ is) 2-(oxetan-3-yl)-piperidin-1-yl, and $R^1$, $R^2$, $R^3$, $R^6$ and $R^7$ for a compound corresponds in each case to one row of Table A Table 709

Compounds of the formula I.1 in which $R^8$ and $R^9$, together with the nitrogen atom they are bound to, form (or in other words: $NR^8R^9$ is) 3-(oxetan-3-yl)-piperidin-1-yl, and $R^1$, $R^2$, $R^3$, $R^6$ and $R^7$ for a compound corresponds in each case to one row of Table A Table 710

Compounds of the formula I.1 in which $R^8$ and $R^9$, together with the nitrogen atom they are bound to, form (or in other words: $NR^8R^9$ is) 4-(oxetan-3-yl)-piperidin-1-yl, and $R^1$, $R^2$, $R^3$, $R^6$ and $R^7$ for a compound corresponds in each case to one row of Table A Table 711

Compounds of the formula I.1 in which $R^8$ and $R^9$, together with the nitrogen atom they are bound to, form (or in other words: $NR^8R^9$ is) morpholin-4-yl, and $R^1$, $R^2$, $R^3$, $R^6$ and $R^7$ for a compound corresponds in each case to one row of Table A Table 712

Compounds of the formula I.1 in which $R^8$ and $R^9$, together with the nitrogen atom they are bound to, form (or in other words: $NR^8R^9$ is) piperazin-1-yl, and $R^1$, $R^2$, $R^3$, $R^6$ and $R^7$ for a compound corresponds in each case to one row of Table A Table 713

Compounds of the formula I.1 in which $R^8$ and $R^9$, together with the nitrogen atom they are bound to, form (or in other words: $NR^8R^9$ is) 2-oxa-7-aza-spiro[3.5]non-7-yl, and $R^1$, $R^2$, $R^3$, $R^6$ and $R^7$ for a compound corresponds in each case to one row of Table A Table 714

Compounds of the formula I.1 in which $R^8$ and $R^9$, together with the nitrogen atom they are bound to, form (or in other words: NR⁸R⁹ is) 2,7-diaza-spiro[3.5]non-7-yl, and R¹, R², R³, R⁶ and R⁷ for a compound corresponds in each case to one row of Table A
Table 715

Compounds of the formula I.1 in which R⁸ and R⁹, together with the nitrogen atom they are bound to, form (or in other words: NR⁸R⁹ is) 2,7-diaza-spiro[3.5]non-2-yl, and R¹, R², R³, R⁶ and R⁷ for a compound corresponds in each case to one row of Table A
Tables 716 to 1430

Compounds of the formula I.2, in which the combination of R⁸ and R⁹ is as defined in any one of Tables 1 to 715 and R¹, R², R³, R⁶ and R⁷ for a compound corresponds in each case to one row of Table A
Tables 1431 to 2145

Compounds of the formula I.3, in which the combination of R⁸ and R⁹ is as defined in any one of Tables 1 to 715 and R¹, R², R³, R⁶ and R⁷ for a compound corresponds in each case to one row of Table A
Tables 2146 to 2860

Compounds of the formula I.4, in which the combination of R⁸ and R⁹ is as defined in any one of Tables 1 to 715 and R¹, R², R³, R⁶ and R⁷ for a compound corresponds in each case to one row of Table A
Tables 2861 to 3575

Compounds of the formula I.5, in which the combination of R⁸ and R⁹ is as defined in any one of Tables 1 to 715 and R¹, R², R³, R⁶ and R⁷ for a compound corresponds in each case to one row of Table A
Tables 3576 to 4290

Compounds of the formula I.6, in which the combination of R⁸ and R⁹ is as defined in any one of Tables 1 to 715 and R¹, R², R³, R⁶ and R⁷ for a compound corresponds in each case to one row of Table A
Tables 4291 to 5005

Compounds of the formula I.7, in which the combination of R⁸ and R⁹ is as defined in any one of Tables 1 to 715 and R¹, R², R³, R⁶ and R⁷ for a compound corresponds in each case to one row of Table A
Tables 5006 to 5720

Compounds of the formula I.8, in which the combination of R⁸ and R⁹ is as defined in any one of Tables 1 to 715 and R¹, R², R³, R⁶ and R⁷ for a compound corresponds in each case to one row of Table A
Tables 5721 to 6435

Compounds of the formula I.9, in which the combination of R⁸ and R⁹ is as defined in any one of Tables 1 to 715 and R¹, R², R³, R⁶ and R⁷ for a compound corresponds in each case to one row of Table A
Tables 6436 to 7150

Compounds of the formula I.10, in which the combination of R⁸ and R⁹ is as defined in any one of Tables 1 to 715 and R¹, R², R³, R⁶ and R⁷ for a compound corresponds in each case to one row of Table A
Tables 7151 to 7865

Compounds of the formula I.11, in which the combination of R⁸ and R⁹ is as defined in any one of Tables 1 to 715 and R¹, R², R³, R⁶ and R⁷ for a compound corresponds in each case to one row of Table A
Tables 7866 to 8580

Compounds of the formula I.12, in which the combination of R⁸ and R⁹ is as defined in any one of Tables 1 to 715 and R¹, R², R³, R⁶ and R⁷ for a compound corresponds in each case to one row of Table A
Tables 8581 to 9295

Compounds of the formula I.13, in which the combination of R⁸ and R⁹ is as defined in any one of Tables 1 to 715 and R¹, R², R³, R⁶ and R⁷ for a compound corresponds in each case to one row of Table A
Tables 9296 to 10010

Compounds of the formula I.14, in which the combination of R⁸ and R⁹ is as defined in any one of Tables 1 to 715 and R¹, R², R³, R⁶ and R⁷ for a compound corresponds in each case to one row of Table A
Tables 10011 to 10725

Compounds of the formula I.15, in which the combination of R⁸ and R⁹ is as defined in any one of Tables 1 to 715 and R¹, R², R³, R⁶ and R⁷ for a compound corresponds in each case to one row of Table A
Tables 10726 to 11440

Compounds of the formula I.16, in which the combination of R⁸ and R⁹ is as defined in any one of Tables 1 to 715 and R¹, R², R³, R⁶ and R⁷ for a compound corresponds in each case to one row of Table A
Tables 11441 to 12155

Compounds of the formula I.17, in which the combination of R⁸ and R⁹ is as defined in any one of Tables 1 to 715 and R¹, R², R³, R⁶ and R⁷ for a compound corresponds in each case to one row of Table A
Tables 12156 to 12870

Compounds of the formula I.18, in which the combination of R⁸ and R⁹ is as defined in any one of Tables 1 to 715 and R¹, R², R³, R⁶ and R⁷ for a compound corresponds in each case to one row of Table A
Tables 12871 to 13585

Compounds of the formula I.19, in which the combination of R⁸ and R⁹ is as defined in any one of Tables 1 to 715 and R¹, R², R³, R⁶ and R⁷ for a compound corresponds in each case to one row of Table A
Tables 13586 to 14300

Compounds of the formula I.20, in which the combination of R⁸ and R⁹ is as defined in any one of Tables 1 to 715 and R¹, R², R³, R⁶ and R⁷ for a compound corresponds in each case to one row of Table A
Tables 14301 to 15015

Compounds of the formula I.21, in which the combination of R⁸ and R⁹ is as defined in any one of Tables 1 to 715 and R², R³, R⁶ and R⁷ for a compound corresponds in each case to one row of Table B
Tables 15016 to 15730

Compounds of the formula I.22, in which the combination of R⁸ and R⁹ is as defined in any one of Tables 1 to 715 and R², R³, R⁶ and R⁷ for a compound corresponds in each case to one row of Table B
Tables 15731 to 16445

Compounds of the formula I.23, in which the combination of R⁸ and R⁹ is as defined in any one of Tables 1 to 715 and R², R³, R⁶ and R⁷ for a compound corresponds in each case to one row of Table B
Tables 16646 to 17160

Compounds of the formula I.24, in which the combination of R⁸ and R⁹ is as defined in any one of Tables 1 to 715 and R², R³, R⁶ and R⁷ for a compound corresponds in each case to one row of Table B
Tables 17161 to 17875

Compounds of the formula I.25, in which the combination of R⁸ and R⁹ is as defined in any one of Tables 1 to 715 and R², R³, R⁶ and R⁷ for a compound corresponds in each case to one row of Table B Tables 17876 to 18590

Compounds of the formula I.26, in which the combination of $R^8$ and $R^9$ is as defined in any one of Tables 1 to 715 and $R^2$, $R^3$, $R^6$ and $R^7$ for a compound corresponds in each case to one row of Table B Tables 18591 to 19305

Compounds of the formula I.27, in which the combination of $R^8$ and $R^9$ is as defined in any one of Tables 1 to 715 and $R^2$, $R^3$, $R^6$ and $R^7$ for a compound corresponds in each case to one row of Table B Tables 19306 to 20020

Compounds of the formula I.28, in which the combination of $R^8$ and $R^9$ is as defined in any one of Tables 1 to 715 and $R^2$, $R^3$, $R^6$ and $R^7$ for a compound corresponds in each case to one row of Table B Tables 20021 to 20735

Compounds of the formula I.29, in which the combination of $R^8$ and $R^9$ is as defined in any one of Tables 1 to 715 and $R^2$, $R^3$, $R^6$ and $R^7$ for a compound corresponds in each case to one row of Table B Tables 20736 to 21450

Compounds of the formula I.30, in which the combination of $R^8$ and $R^9$ is as defined in any one of Tables 1 to 715 and $R^2$, $R^3$, $R^6$ and $R^7$ for a compound corresponds in each case to one row of Table B Tables 21451 to 22165

Compounds of the formula I.31, in which the combination of $R^8$ and $R^9$ is as defined in any one of Tables 1 to 715 and $R^2$, $R^3$, $R^6$ and $R^7$ for a compound corresponds in each case to one row of Table B Tables 22166 to 22880

Compounds of the formula I.32, in which the combination of $R^8$ and $R^9$ is as defined in any one of Tables 1 to 715 and $R^2$, $R^3$, $R^6$ and $R^7$ for a compound corresponds in each case to one row of Table B Tables 22881 to 23595

Compounds of the formula I.33, in which the combination of $R^8$ and $R^9$ is as defined in any one of Tables 1 to 715 and $R^2$, $R^3$, $R^6$ and $R^7$ for a compound corresponds in each case to one row of Table B Tables 23596 to 24310

Compounds of the formula I.34, in which the combination of $R^8$ and $R^9$ is as defined in any one of Tables 1 to 715 and $R^2$, $R^3$, $R^6$ and $R^7$ for a compound corresponds in each case to one row of Table B Tables 24311 to 25025

Compounds of the formula I.35, in which the combination of $R^8$ and $R^9$ is as defined in any one of Tables 1 to 715 and $R^2$, $R^3$, $R^6$ and $R^7$ for a compound corresponds in each case to one row of Table B Tables 25026 to 25740

Compounds of the formula I.36, in which the combination of $R^8$ and $R^9$ is as defined in any one of Tables 1 to 715 and $R^2$, $R^3$, $R^6$ and $R^7$ for a compound corresponds in each case to one row of Table B Tables 25741 to 26455

Compounds of the formula I.37, in which the combination of $R^8$ and $R^9$ is as defined in any one of Tables 1 to 715 and $R^2$, $R^3$, $R^6$ and $R^7$ for a compound corresponds in each case to one row of Table B Tables 26456 to 27170

Compounds of the formula I.38, in which the combination of $R^8$ and $R^9$ is as defined in any one of Tables 1 to 715 and $R^2$, $R^3$, $R^6$ and $R^7$ for a compound corresponds in each case to one row of Table B Tables 27171 to 27885

Compounds of the formula I.39, in which the combination of $R^8$ and $R^9$ is as defined in any one of Tables 1 to 715 and $R^2$, $R^3$, $R^6$ and $R^7$ for a compound corresponds in each case to one row of Table B Tables 27886 to 28600

Compounds of the formula I.40, in which the combination of $R^8$ and $R^9$ is as defined in any one of Tables 1 to 715 and $R^2$, $R^3$, $R^6$ and $R^7$ for a compound corresponds in each case to one row of Table B

TABLE A

| Example No. | $R^1$ | $R^2$ | $R^3$ | $R^6$ | $R^7$ |
|---|---|---|---|---|---|
| A-1. | H | H | H | CN | H |
| A-2. | F | H | H | CN | H |
| A-3. | $CH_3$ | H | H | CN | H |
| A-4. | $OCH_3$ | H | H | CN | H |
| A-5. | $CH_2F$ | H | H | CN | H |
| A-6. | $CHF_2$ | H | H | CN | H |
| A-7. | $CF_3$ | H | H | CN | H |
| A-8. | $OCH_2F$ | H | H | CN | H |
| A-9. | $OCHF_2$ | H | H | CN | H |
| A-10. | $OCF_3$ | H | H | CN | H |
| A-11. | H | F | H | CN | H |
| A-12. | H | $CH_3$ | H | CN | H |
| A-13. | H | $OCH_3$ | H | CN | H |
| A-14. | H | CN | H | CN | H |
| A-15. | H | $CH_2F$ | H | CN | H |
| A-16. | H | $CHF_2$ | H | CN | H |
| A-17. | H | $CF_3$ | H | CN | H |
| A-18. | H | $OCH_2F$ | H | CN | H |
| A-19. | H | $OCHF_2$ | H | CN | H |
| A-20. | H | $OCF_3$ | H | CN | H |
| A-21. | H | H | 3-F | CN | H |
| A-22. | H | H | 3-$CH_3$ | CN | H |
| A-23. | H | H | 3-$OCH_3$ | CN | H |
| A-24. | H | H | 5-F | CN | H |
| A-25. | H | H | 5-$CH_3$ | CN | H |
| A-26. | H | H | 5-$OCH_3$ | CN | H |
| A-27. | F | F | H | CN | H |
| A-28. | F | $CH_3$ | H | CN | H |
| A-29. | F | $OCH_3$ | H | CN | H |
| A-30. | F | CN | H | CN | H |
| A-31. | F | $CH_2F$ | H | CN | H |
| A-32. | F | $CHF_2$ | H | CN | H |
| A-33. | F | $CF_3$ | H | CN | H |
| A-34. | F | $OCH_2F$ | H | CN | H |
| A-35. | F | $OCHF_2$ | H | CN | H |
| A-36. | F | $OCF_3$ | H | CN | H |
| A-37. | F | H | 3-F | CN | H |
| A-38. | F | H | 3-$CH_3$ | CN | H |
| A-39. | F | H | 3-$OCH_3$ | CN | H |
| A-40. | F | H | 5-F | CN | H |
| A-41. | F | H | 5-$CH_3$ | CN | H |
| A-42. | F | H | 5-$OCH_3$ | CN | H |
| A-43. | $CH_3$ | F | H | CN | H |
| A-44. | $CH_3$ | $CH_3$ | H | CN | H |
| A-45. | $CH_3$ | $OCH_3$ | H | CN | H |
| A-46. | $CH_3$ | CN | H | CN | H |
| A-47. | $CH_3$ | $CH_2F$ | H | CN | H |
| A-48. | $CH_3$ | $CHF_2$ | H | CN | H |
| A-49. | $CH_3$ | $CF_3$ | H | CN | H |
| A-50. | $CH_3$ | $OCH_2F$ | H | CN | H |
| A-51. | $CH_3$ | $OCHF_2$ | H | CN | H |
| A-52. | $CH_3$ | $OCF_3$ | H | CN | H |
| A-53. | $CH_3$ | H | 3-F | CN | H |
| A-54. | $CH_3$ | H | 3-$CH_3$ | CN | H |
| A-55. | $CH_3$ | H | 3-$OCH_3$ | CN | H |
| A-56. | $CH_3$ | H | 5-F | CN | H |
| A-57. | $CH_3$ | H | 5-$CH_3$ | CN | H |
| A-58. | $CH_3$ | H | 5-$OCH_3$ | CN | H |
| A-59. | $OCH_3$ | F | H | CN | H |
| A-60. | $OCH_3$ | $CH_3$ | H | CN | H |
| A-61. | $OCH_3$ | $OCH_3$ | H | CN | H |
| A-62. | $OCH_3$ | CN | H | CN | H |
| A-63. | $OCH_3$ | $CH_2F$ | H | CN | H |
| A-64. | $OCH_3$ | $CHF_2$ | H | CN | H |

TABLE A-continued

| Example No. | R¹ | R² | R³ | R⁶ | R⁷ |
|---|---|---|---|---|---|
| A-65. | OCH₃ | CF₃ | H | CN | H |
| A-66. | OCH₃ | OCH₂F | H | CN | H |
| A-67. | OCH₃ | OCHF₂ | H | CN | H |
| A-68. | OCH₃ | OCF₃ | H | CN | H |
| A-69. | OCH₃ | H | 3-F | CN | H |
| A-70. | OCH₃ | H | 3-CH₃ | CN | H |
| A-71. | OCH₃ | H | 3-OCH₃ | CN | H |
| A-72. | OCH₃ | H | 5-F | CN | H |
| A-73. | OCH₃ | H | 5-CH₃ | CN | H |
| A-74. | OCH₃ | H | 5-OCH₃ | CN | H |
| A-75. | H | F | 3-F | CN | H |
| A-76. | H | F | 3-CH₃ | CN | H |
| A-77. | H | F | 3-OCH₃ | CN | H |
| A-78. | H | F | 5-F | CN | H |
| A-79. | H | F | 5-CH₃ | CN | H |
| A-80. | H | F | 5-OCH₃ | CN | H |
| A-81. | H | CH₃ | 3-F | CN | H |
| A-82. | H | CH₃ | 3-CH₃ | CN | H |
| A-83. | H | CH₃ | 3-OCH₃ | CN | H |
| A-84. | H | CH₃ | 5-F | CN | H |
| A-85. | H | CH₃ | 5-CH₃ | CN | H |
| A-86. | H | CH₃ | 5-OCH₃ | CN | H |
| A-87. | H | OCH₃ | 3-F | CN | H |
| A-88. | H | OCH₃ | 3-CH₃ | CN | H |
| A-89. | H | OCH₃ | 3-OCH₃ | CN | H |
| A-90. | H | OCH₃ | 5-F | CN | H |
| A-91. | H | OCH₃ | 5-CH₃ | CN | H |
| A-92. | H | OCH₃ | 5-OCH₃ | CN | H |
| A-93. | H | CN | 3-F | CN | H |
| A-94. | H | CN | 3-CH₃ | CN | H |
| A-95. | H | CN | 3-OCH₃ | CN | H |
| A-96. | H | CN | 5-F | CN | H |
| A-97. | H | CN | 5-CH₃ | CN | H |
| A-98. | H | CN | 5-OCH₃ | CN | H |
| A-99. | H | CH₂F | 3-F | CN | H |
| A-100. | H | CH₂F | 3-CH₃ | CN | H |
| A-101. | H | CH₂F | 3-OCH₃ | CN | H |
| A-102. | H | CH₂F | 5-F | CN | H |
| A-103. | H | CH₂F | 5-CH₃ | CN | H |
| A-104. | H | CH₂F | 5-OCH₃ | CN | H |
| A-105. | H | CHF₂ | 3-F | CN | H |
| A-106. | H | CHF₂ | 3-CH₃ | CN | H |
| A-107. | H | CHF₂ | 3-OCH₃ | CN | H |
| A-108. | H | CHF₂ | 5-F | CN | H |
| A-109. | H | CHF₂ | 5-CH₃ | CN | H |
| A-110. | H | CHF₂ | 5-OCH₃ | CN | H |
| A-111. | H | CF₃ | 3-F | CN | H |
| A-112. | H | CF₃ | 3-CH₃ | CN | H |
| A-113. | H | CF₃ | 3-OCH₃ | CN | H |
| A-114. | H | CF₃ | 5-F | CN | H |
| A-115. | H | CF₃ | 5-CH₃ | CN | H |
| A-116. | H | CF₃ | 5-OCH₃ | CN | H |
| A-117. | H | OCH₂F | 3-F | CN | H |
| A-118. | H | OCH₂F | 3-CH₃ | CN | H |
| A-119. | H | OCH₂F | 3-OCH₃ | CN | H |
| A-120. | H | OCH₂F | 5-F | CN | H |
| A-121. | H | OCH₂F | 5-CH₃ | CN | H |
| A-122. | H | OCH₂F | 5-OCH₃ | CN | H |
| A-123. | H | OCHF₂ | 3-F | CN | H |
| A-124. | H | OCHF₂ | 3-CH₃ | CN | H |
| A-125. | H | OCHF₂ | 3-OCH₃ | CN | H |
| A-126. | H | OCHF₂ | 5-F | CN | H |
| A-127. | H | OCHF₂ | 5-CH₃ | CN | H |
| A-128. | H | OCHF₂ | 5-OCH₃ | CN | H |
| A-129. | H | OCF₃ | 3-F | CN | H |
| A-130. | H | OCF₃ | 3-CH₃ | CN | H |
| A-131. | H | OCF₃ | 3-OCH₃ | CN | H |
| A-132. | H | OCF₃ | 5-F | CN | H |
| A-133. | H | OCF₃ | 5-CH₃ | CN | H |
| A-134. | H | OCF₃ | 5-OCH₃ | CN | H |
| A-135. | F | F | 3-F | CN | H |
| A-136. | F | F | 3-CH₃ | CN | H |
| A-137. | F | F | 3-OCH₃ | CN | H |
| A-138. | F | F | 5-F | CN | H |
| A-139. | F | F | 5-CH₃ | CN | H |
| A-140. | F | F | 5-OCH₃ | CN | H |
| A-141. | F | CH₃ | 3-F | CN | H |
| A-142. | F | CH₃ | 3-CH₃ | CN | H |
| A-143. | F | CH₃ | 3-OCH₃ | CN | H |
| A-144. | F | CH₃ | 5-F | CN | H |
| A-145. | F | CH₃ | 5-CH₃ | CN | H |
| A-146. | F | CH₃ | 5-OCH₃ | CN | H |
| A-147. | F | OCH₃ | 3-F | CN | H |
| A-148. | F | OCH₃ | 3-CH₃ | CN | H |
| A-149. | F | OCH₃ | 3-OCH₃ | CN | H |
| A-150. | F | OCH₃ | 5-F | CN | H |
| A-151. | F | OCH₃ | 5-CH₃ | CN | H |
| A-152. | F | OCH₃ | 5-OCH₃ | CN | H |
| A-153. | F | CN | 3-F | CN | H |
| A-154. | F | CN | 3-CH₃ | CN | H |
| A-155. | F | CN | 3-OCH₃ | CN | H |
| A-156. | F | CN | 5-F | CN | H |
| A-157. | F | CN | 5-CH₃ | CN | H |
| A-158. | F | CN | 5-OCH₃ | CN | H |
| A-159. | F | CH₂F | 3-F | CN | H |
| A-160. | F | CH₂F | 3-CH₃ | CN | H |
| A-161. | F | CH₂F | 3-OCH₃ | CN | H |
| A-162. | F | CH₂F | 5-F | CN | H |
| A-163. | F | CH₂F | 5-CH₃ | CN | H |
| A-164. | F | CH₂F | 5-OCH₃ | CN | H |
| A-165. | F | CHF₂ | 3-F | CN | H |
| A-166. | F | CHF₂ | 3-CH₃ | CN | H |
| A-167. | F | CHF₂ | 3-OCH₃ | CN | H |
| A-168. | F | CHF₂ | 5-F | CN | H |
| A-169. | F | CHF₂ | 5-CH₃ | CN | H |
| A-170. | F | CHF₂ | 5-OCH₃ | CN | H |
| A-171. | F | CF₃ | 3-F | CN | H |
| A-172. | F | CF₃ | 3-CH₃ | CN | H |
| A-173. | F | CF₃ | 3-OCH₃ | CN | H |
| A-174. | F | CF₃ | 5-F | CN | H |
| A-175. | F | CF₃ | 5-CH₃ | CN | H |
| A-176. | F | CF₃ | 5-OCH₃ | CN | H |
| A-177. | F | OCH₂F | 3-F | CN | H |
| A-178. | F | OCH₂F | 3-CH₃ | CN | H |
| A-179. | F | OCH₂F | 3-OCH₃ | CN | H |
| A-180. | F | OCH₂F | 5-F | CN | H |
| A-181. | F | OCH₂F | 5-CH₃ | CN | H |
| A-182. | F | OCH₂F | 5-OCH₃ | CN | H |
| A-183. | F | OCHF₂ | 3-F | CN | H |
| A-184. | F | OCHF₂ | 3-CH₃ | CN | H |
| A-185. | F | OCHF₂ | 3-OCH₃ | CN | H |
| A-186. | F | OCHF₂ | 5-F | CN | H |
| A-187. | F | OCHF₂ | 5-CH₃ | CN | H |
| A-188. | F | OCHF₂ | 5-OCH₃ | CN | H |
| A-189. | F | OCF₃ | 3-F | CN | H |
| A-190. | F | OCF₃ | 3-CH₃ | CN | H |
| A-191. | F | OCF₃ | 3-OCH₃ | CN | H |
| A-192. | F | OCF₃ | 5-F | CN | H |
| A-193. | F | OCF₃ | 5-CH₃ | CN | H |
| A-194. | F | OCF₃ | 5-OCH₃ | CN | H |
| A-195. | CH₃ | F | 3-F | CN | H |
| A-196. | CH₃ | F | 3-CH₃ | CN | H |
| A-197. | CH₃ | F | 3-OCH₃ | CN | H |
| A-198. | CH₃ | F | 5-F | CN | H |
| A-199. | CH₃ | F | 5-CH₃ | CN | H |
| A-200. | CH₃ | F | 5-OCH₃ | CN | H |
| A-201. | CH₃ | CH₃ | 3-F | CN | H |
| A-202. | CH₃ | CH₃ | 3-CH₃ | CN | H |
| A-203. | CH₃ | CH₃ | 3-OCH₃ | CN | H |
| A-204. | CH₃ | CH₃ | 5-F | CN | H |
| A-205. | CH₃ | CH₃ | 5-CH₃ | CN | H |
| A-206. | CH₃ | CH₃ | 5-OCH₃ | CN | H |
| A-207. | CH₃ | OCH₃ | 3-F | CN | H |
| A-208. | CH₃ | OCH₃ | 3-CH₃ | CN | H |
| A-209. | CH₃ | OCH₃ | 3-OCH₃ | CN | H |
| A-210. | CH₃ | OCH₃ | 5-F | CN | H |
| A-211. | CH₃ | OCH₃ | 5-CH₃ | CN | H |
| A-212. | CH₃ | OCH₃ | 5-OCH₃ | CN | H |
| A-213. | CH₃ | CN | 3-F | CN | H |
| A-214. | CH₃ | CN | 3-CH₃ | CN | H |
| A-215. | CH₃ | CN | 3-OCH₃ | CN | H |
| A-216. | CH₃ | CN | 5-F | CN | H |
| A-217. | CH₃ | CN | 5-CH₃ | CN | H |
| A-218. | CH₃ | CN | 5-OCH₃ | CN | H |
| A-219. | CH₃ | CH₂F | 3-F | CN | H |
| A-220. | CH₃ | CH₂F | 3-CH₃ | CN | H |

TABLE A-continued

| Example No. | R¹ | R² | R³ | R⁶ | R⁷ |
|---|---|---|---|---|---|
| A-221. | CH₃ | CH₂F | 3-OCH₃ | CN | H |
| A-222. | CH₃ | CH₂F | 5-F | CN | H |
| A-223. | CH₃ | CH₂F | 5-CH₃ | CN | H |
| A-224. | CH₃ | CH₂F | 5-OCH₃ | CN | H |
| A-225. | CH₃ | CHF₂ | 3-F | CN | H |
| A-226. | CH₃ | CHF₂ | 3-CH₃ | CN | H |
| A-227. | CH₃ | CHF₂ | 3-OCH₃ | CN | H |
| A-228. | CH₃ | CHF₂ | 5-F | CN | H |
| A-229. | CH₃ | CHF₂ | 5-CH₃ | CN | H |
| A-230. | CH₃ | CHF₂ | 5-OCH₃ | CN | H |
| A-231. | CH₃ | CF₃ | 3-F | CN | H |
| A-232. | CH₃ | CF₃ | 3-CH₃ | CN | H |
| A-233. | CH₃ | CF₃ | 3-OCH₃ | CN | H |
| A-234. | CH₃ | CF₃ | 5-F | CN | H |
| A-235. | CH₃ | CF₃ | 5-CH₃ | CN | H |
| A-236. | CH₃ | CF₃ | 5-OCH₃ | CN | H |
| A-237. | CH₃ | OCH₂F | 3-F | CN | H |
| A-238. | CH₃ | OCH₂F | 3-CH₃ | CN | H |
| A-239. | CH₃ | OCH₂F | 3-OCH₃ | CN | H |
| A-240. | CH₃ | OCH₂F | 5-F | CN | H |
| A-241. | CH₃ | OCH₂F | 5-CH₃ | CN | H |
| A-242. | CH₃ | OCH₂F | 5-OCH₃ | CN | H |
| A-243. | CH₃ | OCHF₂ | 3-F | CN | H |
| A-244. | CH₃ | OCHF₂ | 3-CH₃ | CN | H |
| A-245. | CH₃ | OCHF₂ | 3-OCH₃ | CN | H |
| A-246. | CH₃ | OCHF₂ | 5-F | CN | H |
| A-247. | CH₃ | OCHF₂ | 5-CH₃ | CN | H |
| A-248. | CH₃ | OCHF₂ | 5-OCH₃ | CN | H |
| A-249. | CH₃ | OCF₃ | 3-F | CN | H |
| A-250. | CH₃ | OCF₃ | 3-CH₃ | CN | H |
| A-251. | CH₃ | OCF₃ | 3-OCH₃ | CN | H |
| A-252. | CH₃ | OCF₃ | 5-F | CN | H |
| A-253. | CH₃ | OCF₃ | 5-CH₃ | CN | H |
| A-254. | CH₃ | OCF₃ | 5-OCH₃ | CN | H |
| A-255. | OCH₃ | F | 3-F | CN | H |
| A-256. | OCH₃ | F | 3-CH₃ | CN | H |
| A-257. | OCH₃ | F | 3-OCH₃ | CN | H |
| A-258. | OCH₃ | F | 5-F | CN | H |
| A-259. | OCH₃ | F | 5-CH₃ | CN | H |
| A-260. | OCH₃ | F | 5-OCH₃ | CN | H |
| A-261. | OCH₃ | CH₃ | 3-F | CN | H |
| A-262. | OCH₃ | CH₃ | 3-CH₃ | CN | H |
| A-263. | OCH₃ | CH₃ | 3-OCH₃ | CN | H |
| A-264. | OCH₃ | CH₃ | 5-F | CN | H |
| A-265. | OCH₃ | CH₃ | 5-CH₃ | CN | H |
| A-266. | OCH₃ | CH₃ | 5-OCH₃ | CN | H |
| A-267. | OCH₃ | OCH₃ | 3-F | CN | H |
| A-268. | OCH₃ | OCH₃ | 3-CH₃ | CN | H |
| A-269. | OCH₃ | OCH₃ | 3-OCH₃ | CN | H |
| A-270. | OCH₃ | OCH₃ | 5-F | CN | H |
| A-271. | OCH₃ | OCH₃ | 5-CH₃ | CN | H |
| A-272. | OCH₃ | OCH₃ | 5-OCH₃ | CN | H |
| A-273. | OCH₃ | CN | 3-F | CN | H |
| A-274. | OCH₃ | CN | 3-CH₃ | CN | H |
| A-275. | OCH₃ | CN | 3-OCH₃ | CN | H |
| A-276. | OCH₃ | CN | 5-F | CN | H |
| A-277. | OCH₃ | CN | 5-CH₃ | CN | H |
| A-278. | OCH₃ | CN | 5-OCH₃ | CN | H |
| A-279. | OCH₃ | CH₂F | 3-F | CN | H |
| A-280. | OCH₃ | CH₂F | 3-CH₃ | CN | H |
| A-281. | OCH₃ | CH₂F | 3-OCH₃ | CN | H |
| A-282. | OCH₃ | CH₂F | 5-F | CN | H |
| A-283. | OCH₃ | CH₂F | 5-CH₃ | CN | H |
| A-284. | OCH₃ | CH₂F | 5-OCH₃ | CN | H |
| A-285. | OCH₃ | CHF₂ | 3-F | CN | H |
| A-286. | OCH₃ | CHF₂ | 3-CH₃ | CN | H |
| A-287. | OCH₃ | CHF₂ | 3-OCH₃ | CN | H |
| A-288. | OCH₃ | CHF₂ | 5-F | CN | H |
| A-289. | OCH₃ | CHF₂ | 5-CH₃ | CN | H |
| A-290. | OCH₃ | CHF₂ | 5-OCH₃ | CN | H |
| A-291. | OCH₃ | CF₃ | 3-F | CN | H |
| A-292. | OCH₃ | CF₃ | 3-CH₃ | CN | H |
| A-293. | OCH₃ | CF₃ | 3-OCH₃ | CN | H |
| A-294. | OCH₃ | CF₃ | 5-F | CN | H |
| A-295. | OCH₃ | CF₃ | 5-CH₃ | CN | H |
| A-296. | OCH₃ | CF₃ | 5-OCH₃ | CN | H |
| A-297. | OCH₃ | OCH₂F | 3-F | CN | H |
| A-298. | OCH₃ | OCH₂F | 3-CH₃ | CN | H |
| A-299. | OCH₃ | OCH₂F | 3-OCH₃ | CN | H |
| A-300. | OCH₃ | OCH₂F | 5-F | CN | H |
| A-301. | OCH₃ | OCH₂F | 5-CH₃ | CN | H |
| A-302. | OCH₃ | OCH₂F | 5-OCH₃ | CN | H |
| A-303. | OCH₃ | OCHF₂ | 3-F | CN | H |
| A-304. | OCH₃ | OCHF₂ | 3-CH₃ | CN | H |
| A-305. | OCH₃ | OCHF₂ | 3-OCH₃ | CN | H |
| A-306. | OCH₃ | OCHF₂ | 5-F | CN | H |
| A-307. | OCH₃ | OCHF₂ | 5-CH₃ | CN | H |
| A-308. | OCH₃ | OCHF₂ | 5-OCH₃ | CN | H |
| A-309. | OCH₃ | OCF₃ | 3-F | CN | H |
| A-310. | OCH₃ | OCF₃ | 3-CH₃ | CN | H |
| A-311. | OCH₃ | OCF₃ | 3-OCH₃ | CN | H |
| A-312. | OCH₃ | OCF₃ | 5-F | CN | H |
| A-313. | OCH₃ | OCF₃ | 5-CH₃ | CN | H |
| A-314. | OCH₃ | OCF₃ | 5-OCH₃ | CN | H |
| A-315. | CH₂F | F | 3-F | CN | H |
| A-316. | CH₂F | F | 3-CH₃ | CN | H |
| A-317. | CH₂F | F | 3-OCH₃ | CN | H |
| A-318. | CH₂F | F | 5-F | CN | H |
| A-319. | CH₂F | F | 5-CH₃ | CN | H |
| A-320. | CH₂F | F | 5-OCH₃ | CN | H |
| A-321. | CH₂F | CH₃ | 3-F | CN | H |
| A-322. | CH₂F | CH₃ | 3-CH₃ | CN | H |
| A-323. | CH₂F | CH₃ | 3-OCH₃ | CN | H |
| A-324. | CH₂F | CH₃ | 5-F | CN | H |
| A-325. | CH₂F | CH₃ | 5-CH₃ | CN | H |
| A-326. | CH₂F | CH₃ | 5-OCH₃ | CN | H |
| A-327. | CH₂F | OCH₃ | 3-F | CN | H |
| A-328. | CH₂F | OCH₃ | 3-CH₃ | CN | H |
| A-329. | CH₂F | OCH₃ | 3-OCH₃ | CN | H |
| A-330. | CH₂F | OCH₃ | 5-F | CN | H |
| A-331. | CH₂F | OCH₃ | 5-CH₃ | CN | H |
| A-332. | CH₂F | OCH₃ | 5-OCH₃ | CN | H |
| A-333. | CH₂F | CN | 3-F | CN | H |
| A-334. | CH₂F | CN | 3-CH₃ | CN | H |
| A-335. | CH₂F | CN | 3-OCH₃ | CN | H |
| A-336. | CH₂F | CN | 5-F | CN | H |
| A-337. | CH₂F | CN | 5-CH₃ | CN | H |
| A-338. | CH₂F | CN | 5-OCH₃ | CN | H |
| A-339. | CH₂F | CH₂F | 3-F | CN | H |
| A-340. | CH₂F | CH₂F | 3-CH₃ | CN | H |
| A-341. | CH₂F | CH₂F | 3-OCH₃ | CN | H |
| A-342. | CH₂F | CH₂F | 5-F | CN | H |
| A-343. | CH₂F | CH₂F | 5-CH₃ | CN | H |
| A-344. | CH₂F | CH₂F | 5-OCH₃ | CN | H |
| A-345. | CH₂F | CHF₂ | 3-F | CN | H |
| A-346. | CH₂F | CHF₂ | 3-CH₃ | CN | H |
| A-347. | CH₂F | CHF₂ | 3-OCH₃ | CN | H |
| A-348. | CH₂F | CHF₂ | 5-F | CN | H |
| A-349. | CH₂F | CHF₂ | 5-CH₃ | CN | H |
| A-350. | CH₂F | CHF₂ | 5-OCH₃ | CN | H |
| A-351. | CH₂F | CF₃ | 3-F | CN | H |
| A-352. | CH₂F | CF₃ | 3-CH₃ | CN | H |
| A-353. | CH₂F | CF₃ | 3-OCH₃ | CN | H |
| A-354. | CH₂F | CF₃ | 5-F | CN | H |
| A-355. | CH₂F | CF₃ | 5-CH₃ | CN | H |
| A-356. | CH₂F | CF₃ | 5-OCH₃ | CN | H |
| A-357. | CH₂F | OCH₂F | 3-F | CN | H |
| A-358. | CH₂F | OCH₂F | 3-CH₃ | CN | H |
| A-359. | CH₂F | OCH₂F | 3-OCH₃ | CN | H |
| A-360. | CH₂F | OCH₂F | 5-F | CN | H |
| A-361. | CH₂F | OCH₂F | 5-CH₃ | CN | H |
| A-362. | CH₂F | OCH₂F | 5-OCH₃ | CN | H |
| A-363. | CH₂F | OCHF₂ | 3-F | CN | H |
| A-364. | CH₂F | OCHF₂ | 3-CH₃ | CN | H |
| A-365. | CH₂F | OCHF₂ | 3-OCH₃ | CN | H |
| A-366. | CH₂F | OCHF₂ | 5-F | CN | H |
| A-367. | CH₂F | OCHF₂ | 5-CH₃ | CN | H |
| A-368. | CH₂F | OCHF₂ | 5-OCH₃ | CN | H |
| A-369. | CH₂F | OCF₃ | 3-F | CN | H |
| A-370. | CH₂F | OCF₃ | 3-CH₃ | CN | H |
| A-371. | CH₂F | OCF₃ | 3-OCH₃ | CN | H |
| A-372. | CH₂F | OCF₃ | 5-F | CN | H |
| A-373. | CH₂F | OCF₃ | 5-CH₃ | CN | H |
| A-374. | CH₂F | OCF₃ | 5-OCH₃ | CN | H |
| A-375. | CHF₂ | F | 3-F | CN | H |
| A-376. | CHF₂ | F | 3-CH₃ | CN | H |

TABLE A-continued

| Example No. | R¹ | R² | R³ | R⁶ | R⁷ |
|---|---|---|---|---|---|
| A-377. | CHF₂ | F | 3-OCH₃ | CN | H |
| A-378. | CHF₂ | F | 5-F | CN | H |
| A-379. | CHF₂ | F | 5-CH₃ | CN | H |
| A-380. | CHF₂ | F | 5-OCH₃ | CN | H |
| A-381. | CHF₂ | CH₃ | 3-F | CN | H |
| A-382. | CHF₂ | CH₃ | 3-CH₃ | CN | H |
| A-383. | CHF₂ | CH₃ | 3-OCH₃ | CN | H |
| A-384. | CHF₂ | CH₃ | 5-F | CN | H |
| A-385. | CHF₂ | CH₃ | 5-CH₃ | CN | H |
| A-386. | CHF₂ | CH₃ | 5-OCH₃ | CN | H |
| A-387. | CHF₂ | OCH₃ | 3-F | CN | H |
| A-388. | CHF₂ | OCH₃ | 3-CH₃ | CN | H |
| A-389. | CHF₂ | OCH₃ | 3-OCH₃ | CN | H |
| A-390. | CHF₂ | OCH₃ | 5-F | CN | H |
| A-391. | CHF₂ | OCH₃ | 5-CH₃ | CN | H |
| A-392. | CHF₂ | OCH₃ | 5-OCH₃ | CN | H |
| A-393. | CHF₂ | CN | 3-F | CN | H |
| A-394. | CHF₂ | CN | 3-CH₃ | CN | H |
| A-395. | CHF₂ | CN | 3-OCH₃ | CN | H |
| A-396. | CHF₂ | CN | 5-F | CN | H |
| A-397. | CHF₂ | CN | 5-CH₃ | CN | H |
| A-398. | CHF₂ | CN | 5-OCH₃ | CN | H |
| A-399. | CHF₂ | CH₂F | 3-F | CN | H |
| A-400. | CHF₂ | CH₂F | 3-CH₃ | CN | H |
| A-401. | CHF₂ | CH₂F | 3-OCH₃ | CN | H |
| A-402. | CHF₂ | CH₂F | 5-F | CN | H |
| A-403. | CHF₂ | CH₂F | 5-CH₃ | CN | H |
| A-404. | CHF₂ | CH₂F | 5-OCH₃ | CN | H |
| A-405. | CHF₂ | CHF₂ | 3-F | CN | H |
| A-406. | CHF₂ | CHF₂ | 3-CH₃ | CN | H |
| A-407. | CHF₂ | CHF₂ | 3-OCH₃ | CN | H |
| A-408. | CHF₂ | CHF₂ | 5-F | CN | H |
| A-409. | CHF₂ | CHF₂ | 5-CH₃ | CN | H |
| A-410. | CHF₂ | CHF₂ | 5-OCH₃ | CN | H |
| A-411. | CHF₂ | CF₃ | 3-F | CN | H |
| A-412. | CHF₂ | CF₃ | 3-CH₃ | CN | H |
| A-413. | CHF₂ | CF₃ | 3-OCH₃ | CN | H |
| A-414. | CHF₂ | CF₃ | 5-F | CN | H |
| A-415. | CHF₂ | CF₃ | 5-CH₃ | CN | H |
| A-416. | CHF₂ | CF₃ | 5-OCH₃ | CN | H |
| A-417. | CHF₂ | OCH₂F | 3-F | CN | H |
| A-418. | CHF₂ | OCH₂F | 3-CH₃ | CN | H |
| A-419. | CHF₂ | OCH₂F | 3-OCH₃ | CN | H |
| A-420. | CHF₂ | OCH₂F | 5-F | CN | H |
| A-421. | CHF₂ | OCH₂F | 5-CH₃ | CN | H |
| A-422. | CHF₂ | OCH₂F | 5-OCH₃ | CN | H |
| A-423. | CHF₂ | OCHF₂ | 3-F | CN | H |
| A-424. | CHF₂ | OCHF₂ | 3-CH₃ | CN | H |
| A-425. | CHF₂ | OCHF₂ | 3-OCH₃ | CN | H |
| A-426. | CHF₂ | OCHF₂ | 5-F | CN | H |
| A-427. | CHF₂ | OCHF₂ | 5-CH₃ | CN | H |
| A-428. | CHF₂ | OCHF₂ | 5-OCH₃ | CN | H |
| A-429. | CHF₂ | OCF₃ | 3-F | CN | H |
| A-430. | CHF₂ | OCF₃ | 3-CH₃ | CN | H |
| A-431. | CHF₂ | OCF₃ | 3-OCH₃ | CN | H |
| A-432. | CHF₂ | OCF₃ | 5-F | CN | H |
| A-433. | CHF₂ | OCF₃ | 5-CH₃ | CN | H |
| A-434. | CHF₂ | OCF₃ | 5-OCH₃ | CN | H |
| A-435. | CF₃ | F | 3-F | CN | H |
| A-436. | CF₃ | F | 3-CH₃ | CN | H |
| A-437. | CF₃ | F | 3-OCH₃ | CN | H |
| A-438. | CF₃ | F | 5-F | CN | H |
| A-439. | CF₃ | F | 5-CH₃ | CN | H |
| A-440. | CF₃ | F | 5-OCH₃ | CN | H |
| A-441. | CF₃ | CH₃ | 3-F | CN | H |
| A-442. | CF₃ | CH₃ | 3-CH₃ | CN | H |
| A-443. | CF₃ | CH₃ | 3-OCH₃ | CN | H |
| A-444. | CF₃ | CH₃ | 5-F | CN | H |
| A-445. | CF₃ | CH₃ | 5-CH₃ | CN | H |
| A-446. | CF₃ | CH₃ | 5-OCH₃ | CN | H |
| A-447. | CF₃ | OCH₃ | 3-F | CN | H |
| A-448. | CF₃ | OCH₃ | 3-CH₃ | CN | H |
| A-449. | CF₃ | OCH₃ | 3-OCH₃ | CN | H |
| A-450. | CF₃ | OCH₃ | 5-F | CN | H |
| A-451. | CF₃ | OCH₃ | 5-CH₃ | CN | H |
| A-452. | CF₃ | OCH₃ | 5-OCH₃ | CN | H |
| A-453. | CF₃ | CN | 3-F | CN | H |
| A-454. | CF₃ | CN | 3-CH₃ | CN | H |
| A-455. | CF₃ | CN | 3-OCH₃ | CN | H |
| A-456. | CF₃ | CN | 5-F | CN | H |
| A-457. | CF₃ | CN | 5-CH₃ | CN | H |
| A-458. | CF₃ | CN | 5-OCH₃ | CN | H |
| A-459. | CF₃ | CH₂F | 3-F | CN | H |
| A-460. | CF₃ | CH₂F | 3-CH₃ | CN | H |
| A-461. | CF₃ | CH₂F | 3-OCH₃ | CN | H |
| A-462. | CF₃ | CH₂F | 5-F | CN | H |
| A-463. | CF₃ | CH₂F | 5-CH₃ | CN | H |
| A-464. | CF₃ | CH₂F | 5-OCH₃ | CN | H |
| A-465. | CF₃ | CHF₂ | 3-F | CN | H |
| A-466. | CF₃ | CHF₂ | 3-CH₃ | CN | H |
| A-467. | CF₃ | CHF₂ | 3-OCH₃ | CN | H |
| A-468. | CF₃ | CHF₂ | 5-F | CN | H |
| A-469. | CF₃ | CHF₂ | 5-CH₃ | CN | H |
| A-470. | CF₃ | CHF₂ | 5-OCH₃ | CN | H |
| A-471. | CF₃ | CF₃ | 3-F | CN | H |
| A-472. | CF₃ | CF₃ | 3-CH₃ | CN | H |
| A-473. | CF₃ | CF₃ | 3-OCH₃ | CN | H |
| A-474. | CF₃ | CF₃ | 5-F | CN | H |
| A-475. | CF₃ | CF₃ | 5-CH₃ | CN | H |
| A-476. | CF₃ | CF₃ | 5-OCH₃ | CN | H |
| A-477. | CF₃ | OCH₂F | 3-F | CN | H |
| A-478. | CF₃ | OCH₂F | 3-CH₃ | CN | H |
| A-479. | CF₃ | OCH₂F | 3-OCH₃ | CN | H |
| A-480. | CF₃ | OCH₂F | 5-F | CN | H |
| A-481. | CF₃ | OCH₂F | 5-CH₃ | CN | H |
| A-482. | CF₃ | OCH₂F | 5-OCH₃ | CN | H |
| A-483. | CF₃ | OCHF₂ | 3-F | CN | H |
| A-484. | CF₃ | OCHF₂ | 3-CH₃ | CN | H |
| A-485. | CF₃ | OCHF₂ | 3-OCH₃ | CN | H |
| A-486. | CF₃ | OCHF₂ | 5-F | CN | H |
| A-487. | CF₃ | OCHF₂ | 5-CH₃ | CN | H |
| A-488. | CF₃ | OCHF₂ | 5-OCH₃ | CN | H |
| A-489. | CF₃ | OCF₃ | 3-F | CN | H |
| A-490. | CF₃ | OCF₃ | 3-CH₃ | CN | H |
| A-491. | CF₃ | OCF₃ | 3-OCH₃ | CN | H |
| A-492. | CF₃ | OCF₃ | 5-F | CN | H |
| A-493. | CF₃ | OCF₃ | 5-CH₃ | CN | H |
| A-494. | CF₃ | OCF₃ | 5-OCH₃ | CN | H |
| A-495. | OCH₂F | F | 3-F | CN | H |
| A-496. | OCH₂F | F | 3-CH₃ | CN | H |
| A-497. | OCH₂F | F | 3-OCH₃ | CN | H |
| A-498. | OCH₂F | F | 5-F | CN | H |
| A-499. | OCH₂F | F | 5-CH₃ | CN | H |
| A-500. | OCH₂F | F | 5-OCH₃ | CN | H |
| A-501. | OCH₂F | CH₃ | 3-F | CN | H |
| A-502. | OCH₂F | CH₃ | 3-CH₃ | CN | H |
| A-503. | OCH₂F | CH₃ | 3-OCH₃ | CN | H |
| A-504. | OCH₂F | CH₃ | 5-F | CN | H |
| A-505. | OCH₂F | CH₃ | 5-CH₃ | CN | H |
| A-506. | OCH₂F | CH₃ | 5-OCH₃ | CN | H |
| A-507. | OCH₂F | OCH₃ | 3-F | CN | H |
| A-508. | OCH₂F | OCH₃ | 3-CH₃ | CN | H |
| A-509. | OCH₂F | OCH₃ | 3-OCH₃ | CN | H |
| A-510. | OCH₂F | OCH₃ | 5-F | CN | H |
| A-511. | OCH₂F | OCH₃ | 5-CH₃ | CN | H |
| A-512. | OCH₂F | OCH₃ | 5-OCH₃ | CN | H |
| A-513. | OCH₂F | CN | 3-F | CN | H |
| A-514. | OCH₂F | CN | 3-CH₃ | CN | H |
| A-515. | OCH₂F | CN | 3-OCH₃ | CN | H |
| A-516. | OCH₂F | CN | 5-F | CN | H |
| A-517. | OCH₂F | CN | 5-CH₃ | CN | H |
| A-518. | OCH₂F | CN | 5-OCH₃ | CN | H |
| A-519. | OCH₂F | CH₂F | 3-F | CN | H |
| A-520. | OCH₂F | CH₂F | 3-CH₃ | CN | H |
| A-521. | OCH₂F | CH₂F | 3-OCH₃ | CN | H |
| A-522. | OCH₂F | CH₂F | 5-F | CN | H |
| A-523. | OCH₂F | CH₂F | 5-CH₃ | CN | H |
| A-524. | OCH₂F | CH₂F | 5-OCH₃ | CN | H |
| A-525. | OCH₂F | CHF₂ | 3-F | CN | H |
| A-526. | OCH₂F | CHF₂ | 3-CH₃ | CN | H |
| A-527. | OCH₂F | CHF₂ | 3-OCH₃ | CN | H |
| A-528. | OCH₂F | CHF₂ | 5-F | CN | H |
| A-529. | OCH₂F | CHF₂ | 5-CH₃ | CN | H |
| A-530. | OCH₂F | CHF₂ | 5-OCH₃ | CN | H |
| A-531. | OCH₂F | CF₃ | 3-F | CN | H |
| A-532. | OCH₂F | CF₃ | 3-CH₃ | CN | H |

TABLE A-continued

| Example No. | R¹ | R² | R³ | R⁶ | R⁷ |
|---|---|---|---|---|---|
| A-533. | OCH$_2$F | CF$_3$ | 3-OCH$_3$ | CN | H |
| A-534. | OCH$_2$F | CF$_3$ | 5-F | CN | H |
| A-535. | OCH$_2$F | CF$_3$ | 5-CH$_3$ | CN | H |
| A-536. | OCH$_2$F | CF$_3$ | 5-OCH$_3$ | CN | H |
| A-537. | OCH$_2$F | OCH$_2$F | 3-F | CN | H |
| A-538. | OCH$_2$F | OCH$_2$F | 3-CH$_3$ | CN | H |
| A-539. | OCH$_2$F | OCH$_2$F | 3-OCH$_3$ | CN | H |
| A-540. | OCH$_2$F | OCH$_2$F | 5-F | CN | H |
| A-541. | OCH$_2$F | OCH$_2$F | 5-CH$_3$ | CN | H |
| A-542. | OCH$_2$F | OCH$_2$F | 5-OCH$_3$ | CN | H |
| A-543. | OCH$_2$F | OCHF$_2$ | 3-F | CN | H |
| A-544. | OCH$_2$F | OCHF$_2$ | 3-CH$_3$ | CN | H |
| A-545. | OCH$_2$F | OCHF$_2$ | 3-OCH$_3$ | CN | H |
| A-546. | OCH$_2$F | OCHF$_2$ | 5-F | CN | H |
| A-547. | OCH$_2$F | OCHF$_2$ | 5-CH$_3$ | CN | H |
| A-548. | OCH$_2$F | OCHF$_2$ | 5-OCH$_3$ | CN | H |
| A-549. | OCH$_2$F | OCF$_3$ | 3-F | CN | H |
| A-550. | OCH$_2$F | OCF$_3$ | 3-CH$_3$ | CN | H |
| A-551. | OCH$_2$F | OCF$_3$ | 3-OCH$_3$ | CN | H |
| A-552. | OCH$_2$F | OCF$_3$ | 5-F | CN | H |
| A-553. | OCH$_2$F | OCF$_3$ | 5-CH$_3$ | CN | H |
| A-554. | OCH$_2$F | OCF$_3$ | 5-OCH$_3$ | CN | H |
| A-555. | OCHF$_2$ | F | 3-F | CN | H |
| A-556. | OCHF$_2$ | F | 3-CH$_3$ | CN | H |
| A-557. | OCHF$_2$ | F | 3-OCH$_3$ | CN | H |
| A-558. | OCHF$_2$ | F | 5-F | CN | H |
| A-559. | OCHF$_2$ | F | 5-CH$_3$ | CN | H |
| A-560. | OCHF$_2$ | F | 5-OCH$_3$ | CN | H |
| A-561. | OCHF$_2$ | CH$_3$ | 3-F | CN | H |
| A-562. | OCHF$_2$ | CH$_3$ | 3-CH$_3$ | CN | H |
| A-563. | OCHF$_2$ | CH$_3$ | 3-OCH$_3$ | CN | H |
| A-564. | OCHF$_2$ | CH$_3$ | 5-F | CN | H |
| A-565. | OCHF$_2$ | CH$_3$ | 5-CH$_3$ | CN | H |
| A-566. | OCHF$_2$ | CH$_3$ | 5-OCH$_3$ | CN | H |
| A-567. | OCHF$_2$ | OCH$_3$ | 3-F | CN | H |
| A-568. | OCHF$_2$ | OCH$_3$ | 3-CH$_3$ | CN | H |
| A-569. | OCHF$_2$ | OCH$_3$ | 3-OCH$_3$ | CN | H |
| A-570. | OCHF$_2$ | OCH$_3$ | 5-F | CN | H |
| A-571. | OCHF$_2$ | OCH$_3$ | 5-CH$_3$ | CN | H |
| A-572. | OCHF$_2$ | OCH$_3$ | 5-OCH$_3$ | CN | H |
| A-573. | OCHF$_2$ | CN | 3-F | CN | H |
| A-574. | OCHF$_2$ | CN | 3-CH$_3$ | CN | H |
| A-575. | OCHF$_2$ | CN | 3-OCH$_3$ | CN | H |
| A-576. | OCHF$_2$ | CN | 5-F | CN | H |
| A-577. | OCHF$_2$ | CN | 5-CH$_3$ | CN | H |
| A-578. | OCHF$_2$ | CN | 5-OCH$_3$ | CN | H |
| A-579. | OCHF$_2$ | CH$_2$F | 3-F | CN | H |
| A-580. | OCHF$_2$ | CH$_2$F | 3-CH$_3$ | CN | H |
| A-581. | OCHF$_2$ | CH$_2$F | 3-OCH$_3$ | CN | H |
| A-582. | OCHF$_2$ | CH$_2$F | 5-F | CN | H |
| A-583. | OCHF$_2$ | CH$_2$F | 5-CH$_3$ | CN | H |
| A-584. | OCHF$_2$ | CH$_2$F | 5-OCH$_3$ | CN | H |
| A-585. | OCHF$_2$ | CHF$_2$ | 3-F | CN | H |
| A-586. | OCHF$_2$ | CHF$_2$ | 3-CH$_3$ | CN | H |
| A-587. | OCHF$_2$ | CHF$_2$ | 3-OCH$_3$ | CN | H |
| A-588. | OCHF$_2$ | CHF$_2$ | 5-F | CN | H |
| A-589. | OCHF$_2$ | CHF$_2$ | 5-CH$_3$ | CN | H |
| A-590. | OCHF$_2$ | CHF$_2$ | 5-OCH$_3$ | CN | H |
| A-591. | OCHF$_2$ | CF$_3$ | 3-F | CN | H |
| A-592. | OCHF$_2$ | CF$_3$ | 3-CH$_3$ | CN | H |
| A-593. | OCHF$_2$ | CF$_3$ | 3-OCH$_3$ | CN | H |
| A-594. | OCHF$_2$ | CF$_3$ | 5-F | CN | H |
| A-595. | OCHF$_2$ | CF$_3$ | 5-CH$_3$ | CN | H |
| A-596. | OCHF$_2$ | CF$_3$ | 5-OCH$_3$ | CN | H |
| A-597. | OCHF$_2$ | OCH$_2$F | 3-F | CN | H |
| A-598. | OCHF$_2$ | OCH$_2$F | 3-CH$_3$ | CN | H |
| A-599. | OCHF$_2$ | OCH$_2$F | 3-OCH$_3$ | CN | H |
| A-600. | OCHF$_2$ | OCH$_2$F | 5-F | CN | H |
| A-601. | OCHF$_2$ | OCH$_2$F | 5-CH$_3$ | CN | H |
| A-602. | OCHF$_2$ | OCH$_2$F | 5-OCH$_3$ | CN | H |
| A-603. | OCHF$_2$ | OCHF$_2$ | 3-F | CN | H |
| A-604. | OCHF$_2$ | OCHF$_2$ | 3-CH$_3$ | CN | H |
| A-605. | OCHF$_2$ | OCHF$_2$ | 3-OCH$_3$ | CN | H |
| A-606. | OCHF$_2$ | OCHF$_2$ | 5-F | CN | H |
| A-607. | OCHF$_2$ | OCHF$_2$ | 5-CH$_3$ | CN | H |
| A-608. | OCHF$_2$ | OCHF$_2$ | 5-OCH$_3$ | CN | H |
| A-609. | OCHF$_2$ | OCF$_3$ | 3-F | CN | H |
| A-610. | OCHF$_2$ | OCF$_3$ | 3-CH$_3$ | CN | H |
| A-611. | OCHF$_2$ | OCF$_3$ | 3-OCH$_3$ | CN | H |
| A-612. | OCHF$_2$ | OCF$_3$ | 5-F | CN | H |
| A-613. | OCHF$_2$ | OCF$_3$ | 5-CH$_3$ | CN | H |
| A-614. | OCHF$_2$ | OCF$_3$ | 5-OCH$_3$ | CN | H |
| A-615. | OCF$_3$ | F | 3-F | CN | H |
| A-616. | OCF$_3$ | F | 3-CH$_3$ | CN | H |
| A-617. | OCF$_3$ | F | 3-OCH$_3$ | CN | H |
| A-618. | OCF$_3$ | F | 5-F | CN | H |
| A-619. | OCF$_3$ | F | 5-CH$_3$ | CN | H |
| A-620. | OCF$_3$ | F | 5-OCH$_3$ | CN | H |
| A-621. | OCF$_3$ | CH$_3$ | 3-F | CN | H |
| A-622. | OCF$_3$ | CH$_3$ | 3-CH$_3$ | CN | H |
| A-623. | OCF$_3$ | CH$_3$ | 3-OCH$_3$ | CN | H |
| A-624. | OCF$_3$ | CH$_3$ | 5-F | CN | H |
| A-625. | OCF$_3$ | CH$_3$ | 5-CH$_3$ | CN | H |
| A-626. | OCF$_3$ | CH$_3$ | 5-OCH$_3$ | CN | H |
| A-627. | OCF$_3$ | OCH$_3$ | 3-F | CN | H |
| A-628. | OCF$_3$ | OCH$_3$ | 3-CH$_3$ | CN | H |
| A-629. | OCF$_3$ | OCH$_3$ | 3-OCH$_3$ | CN | H |
| A-630. | OCF$_3$ | OCH$_3$ | 5-F | CN | H |
| A-631. | OCF$_3$ | OCH$_3$ | 5-CH$_3$ | CN | H |
| A-632. | OCF$_3$ | OCH$_3$ | 5-OCH$_3$ | CN | H |
| A-633. | OCF$_3$ | CN | 3-F | CN | H |
| A-634. | OCF$_3$ | CN | 3-CH$_3$ | CN | H |
| A-635. | OCF$_3$ | CN | 3-OCH$_3$ | CN | H |
| A-636. | OCF$_3$ | CN | 5-F | CN | H |
| A-637. | OCF$_3$ | CN | 5-CH$_3$ | CN | H |
| A-638. | OCF$_3$ | CN | 5-OCH$_3$ | CN | H |
| A-639. | OCF$_3$ | CH$_2$F | 3-F | CN | H |
| A-640. | OCF$_3$ | CH$_2$F | 3-CH$_3$ | CN | H |
| A-641. | OCF$_3$ | CH$_2$F | 3-OCH$_3$ | CN | H |
| A-642. | OCF$_3$ | CH$_2$F | 5-F | CN | H |
| A-643. | OCF$_3$ | CH$_2$F | 5-CH$_3$ | CN | H |
| A-644. | OCF$_3$ | CH$_2$F | 5-OCH$_3$ | CN | H |
| A-645. | OCF$_3$ | CHF$_2$ | 3-F | CN | H |
| A-646. | OCF$_3$ | CHF$_2$ | 3-CH$_3$ | CN | H |
| A-647. | OCF$_3$ | CHF$_2$ | 3-OCH$_3$ | CN | H |
| A-648. | OCF$_3$ | CHF$_2$ | 5-F | CN | H |
| A-649. | OCF$_3$ | CHF$_2$ | 5-CH$_3$ | CN | H |
| A-650. | OCF$_3$ | CHF$_2$ | 5-OCH$_3$ | CN | H |
| A-651. | OCF$_3$ | CF$_3$ | 3-F | CN | H |
| A-652. | OCF$_3$ | CF$_3$ | 3-CH$_3$ | CN | H |
| A-653. | OCF$_3$ | CF$_3$ | 3-OCH$_3$ | CN | H |
| A-654. | OCF$_3$ | CF$_3$ | 5-F | CN | H |
| A-655. | OCF$_3$ | CF$_3$ | 5-CH$_3$ | CN | H |
| A-656. | OCF$_3$ | CF$_3$ | 5-OCH$_3$ | CN | H |
| A-657. | OCF$_3$ | OCH$_2$F | 3-F | CN | H |
| A-658. | OCF$_3$ | OCH$_2$F | 3-CH$_3$ | CN | H |
| A-659. | OCF$_3$ | OCH$_2$F | 3-OCH$_3$ | CN | H |
| A-660. | OCF$_3$ | OCH$_2$F | 5-F | CN | H |
| A-661. | OCF$_3$ | OCH$_2$F | 5-CH$_3$ | CN | H |
| A-662. | OCF$_3$ | OCH$_2$F | 5-OCH$_3$ | CN | H |
| A-663. | OCF$_3$ | OCHF$_2$ | 3-F | CN | H |
| A-664. | OCF$_3$ | OCHF$_2$ | 3-CH$_3$ | CN | H |
| A-665. | OCF$_3$ | OCHF$_2$ | 3-OCH$_3$ | CN | H |
| A-666. | OCF$_3$ | OCHF$_2$ | 5-F | CN | H |
| A-667. | OCF$_3$ | OCHF$_2$ | 5-CH$_3$ | CN | H |
| A-668. | OCF$_3$ | OCHF$_2$ | 5-OCH$_3$ | CN | H |
| A-669. | OCF$_3$ | OCF$_3$ | 3-F | CN | H |
| A-670. | OCF$_3$ | OCF$_3$ | 3-CH$_3$ | CN | H |
| A-671. | OCF$_3$ | OCF$_3$ | 3-OCH$_3$ | CN | H |
| A-672. | OCF$_3$ | OCF$_3$ | 5-F | CN | H |
| A-673. | OCF$_3$ | OCF$_3$ | 5-CH$_3$ | CN | H |
| A-674. | OCF$_3$ | OCF$_3$ | 5-OCH$_3$ | CN | H |
| A-675. | H | H | H | F | H |
| A-676. | F | H | H | F | H |
| A-677. | CH$_3$ | H | H | F | H |
| A-678. | OCH$_3$ | H | H | F | H |
| A-679. | CH$_2$F | H | H | F | H |
| A-680. | CHF$_2$ | H | H | F | H |
| A-681. | CF$_3$ | H | H | F | H |
| A-682. | OCH$_2$F | H | H | F | H |
| A-683. | OCHF$_2$ | H | H | F | H |
| A-684. | OCF$_3$ | H | H | F | H |
| A-685. | H | F | H | F | H |
| A-686. | H | CH$_3$ | H | F | H |
| A-687. | H | OCH$_3$ | H | F | H |
| A-688. | H | CN | H | F | H |

TABLE A-continued

| Example No. | R¹ | R² | R³ | R⁶ | R⁷ |
|---|---|---|---|---|---|
| A-689. | H | CH₂F | H | F | H |
| A-690. | H | CHF₂ | H | F | H |
| A-691. | H | CF₃ | H | F | H |
| A-692. | H | OCH₂F | H | F | H |
| A-693. | H | OCHF₂ | H | F | H |
| A-694. | H | OCF₃ | H | F | H |
| A-695. | H | H | 3-F | F | H |
| A-696. | H | H | 3-CH₃ | F | H |
| A-697. | H | H | 3-OCH₃ | F | H |
| A-698. | H | H | 5-F | F | H |
| A-699. | H | H | 5-CH₃ | F | H |
| A-700. | H | H | 5-OCH₃ | F | H |
| A-701. | F | F | H | F | H |
| A-702. | F | CH₃ | H | F | H |
| A-703. | F | OCH₃ | H | F | H |
| A-704. | F | CN | H | F | H |
| A-705. | F | CH₂F | H | F | H |
| A-706. | F | CHF₂ | H | F | H |
| A-707. | F | CF₃ | H | F | H |
| A-708. | F | OCH₂F | H | F | H |
| A-709. | F | OCHF₂ | H | F | H |
| A-710. | F | OCF₃ | H | F | H |
| A-711. | F | H | 3-F | F | H |
| A-712. | F | H | 3-CH₃ | F | H |
| A-713. | F | H | 3-OCH₃ | F | H |
| A-714. | F | H | 5-F | F | H |
| A-715. | F | H | 5-CH₃ | F | H |
| A-716. | F | H | 5-OCH₃ | F | H |
| A-717. | CH₃ | F | H | F | H |
| A-718. | CH₃ | CH₃ | H | F | H |
| A-719. | CH₃ | OCH₃ | H | F | H |
| A-720. | CH₃ | CN | H | F | H |
| A-721. | CH₃ | CH₂F | H | F | H |
| A-722. | CH₃ | CHF₂ | H | F | H |
| A-723. | CH₃ | CF₃ | H | F | H |
| A-724. | CH₃ | OCH₂F | H | F | H |
| A-725. | CH₃ | OCHF₂ | H | F | H |
| A-726. | CH₃ | OCF₃ | H | F | H |
| A-727. | CH₃ | H | 3-F | F | H |
| A-728. | CH₃ | H | 3-CH₃ | F | H |
| A-729. | CH₃ | H | 3-OCH₃ | F | H |
| A-730. | CH₃ | H | 5-F | F | H |
| A-731. | CH₃ | H | 5-CH₃ | F | H |
| A-732. | CH₃ | H | 5-OCH₃ | F | H |
| A-733. | OCH₃ | F | H | F | H |
| A-734. | OCH₃ | CH₃ | H | F | H |
| A-735. | OCH₃ | OCH₃ | H | F | H |
| A-736. | OCH₃ | CN | H | F | H |
| A-737. | OCH₃ | CH₂F | H | F | H |
| A-738. | OCH₃ | CHF₂ | H | F | H |
| A-739. | OCH₃ | CF₃ | H | F | H |
| A-740. | OCH₃ | OCH₂F | H | F | H |
| A-741. | OCH₃ | OCHF₂ | H | F | H |
| A-742. | OCH₃ | OCF₃ | H | F | H |
| A-743. | OCH₃ | H | 3-F | F | H |
| A-744. | OCH₃ | H | 3-CH₃ | F | H |
| A-745. | OCH₃ | H | 3-OCH₃ | F | H |
| A-746. | OCH₃ | H | 5-F | F | H |
| A-747. | OCH₃ | H | 5-CH₃ | F | H |
| A-748. | OCH₃ | H | 5-OCH₃ | F | H |
| A-749. | H | F | 3-F | F | H |
| A-750. | H | F | 3-CH₃ | F | H |
| A-751. | H | F | 3-OCH₃ | F | H |
| A-752. | H | F | 5-F | F | H |
| A-753. | H | F | 5-CH₃ | F | H |
| A-754. | H | F | 5-OCH₃ | F | H |
| A-755. | H | CH₃ | 3-F | F | H |
| A-756. | H | CH₃ | 3-CH₃ | F | H |
| A-757. | H | CH₃ | 3-OCH₃ | F | H |
| A-758. | H | CH₃ | 5-F | F | H |
| A-759. | H | CH₃ | 5-CH₃ | F | H |
| A-760. | H | CH₃ | 5-OCH₃ | F | H |
| A-761. | H | OCH₃ | 3-F | F | H |
| A-762. | H | OCH₃ | 3-CH₃ | F | H |
| A-763. | H | OCH₃ | 3-OCH₃ | F | H |
| A-764. | H | OCH₃ | 5-F | F | H |
| A-765. | H | OCH₃ | 5-CH₃ | F | H |
| A-766. | H | OCH₃ | 5-OCH₃ | F | H |
| A-767. | H | CN | 3-F | F | H |
| A-768. | H | CN | 3-CH₃ | F | H |
| A-769. | H | CN | 3-OCH₃ | F | H |
| A-770. | H | CN | 5-F | F | H |
| A-771. | H | CN | 5-CH₃ | F | H |
| A-772. | H | CN | 5-OCH₃ | F | H |
| A-773. | H | CH₂F | 3-F | F | H |
| A-774. | H | CH₂F | 3-CH₃ | F | H |
| A-775. | H | CH₂F | 3-OCH₃ | F | H |
| A-776. | H | CH₂F | 5-F | F | H |
| A-777. | H | CH₂F | 5-CH₃ | F | H |
| A-778. | H | CH₂F | 5-OCH₃ | F | H |
| A-779. | H | CHF₂ | 3-F | F | H |
| A-780. | H | CHF₂ | 3-CH₃ | F | H |
| A-781. | H | CHF₂ | 3-OCH₃ | F | H |
| A-782. | H | CHF₂ | 5-F | F | H |
| A-783. | H | CHF₂ | 5-CH₃ | F | H |
| A-784. | H | CHF₂ | 5-OCH₃ | F | H |
| A-785. | H | CF₃ | 3-F | F | H |
| A-786. | H | CF₃ | 3-CH₃ | F | H |
| A-787. | H | CF₃ | 3-OCH₃ | F | H |
| A-788. | H | CF₃ | 5-F | F | H |
| A-789. | H | CF₃ | 5-CH₃ | F | H |
| A-790. | H | CF₃ | 5-OCH₃ | F | H |
| A-791. | H | OCH₂F | 3-F | F | H |
| A-792. | H | OCH₂F | 3-CH₃ | F | H |
| A-793. | H | OCH₂F | 3-OCH₃ | F | H |
| A-794. | H | OCH₂F | 5-F | F | H |
| A-795. | H | OCH₂F | 5-CH₃ | F | H |
| A-796. | H | OCH₂F | 5-OCH₃ | F | H |
| A-797. | H | OCHF₂ | 3-F | F | H |
| A-798. | H | OCHF₂ | 3-CH₃ | F | H |
| A-799. | H | OCHF₂ | 3-OCH₃ | F | H |
| A-800. | H | OCHF₂ | 5-F | F | H |
| A-801. | H | OCHF₂ | 5-CH₃ | F | H |
| A-802. | H | OCHF₂ | 5-OCH₃ | F | H |
| A-803. | H | OCF₃ | 3-F | F | H |
| A-804. | H | OCF₃ | 3-CH₃ | F | H |
| A-805. | H | OCF₃ | 3-OCH₃ | F | H |
| A-806. | H | OCF₃ | 5-F | F | H |
| A-807. | H | OCF₃ | 5-CH₃ | F | H |
| A-808. | H | OCF₃ | 5-OCH₃ | F | H |
| A-809. | F | F | 3-F | F | H |
| A-810. | F | F | 3-CH₃ | F | H |
| A-811. | F | F | 3-OCH₃ | F | H |
| A-812. | F | F | 5-F | F | H |
| A-813. | F | F | 5-CH₃ | F | H |
| A-814. | F | F | 5-OCH₃ | F | H |
| A-815. | F | CH₃ | 3-F | F | H |
| A-816. | F | CH₃ | 3-CH₃ | F | H |
| A-817. | F | CH₃ | 3-OCH₃ | F | H |
| A-818. | F | CH₃ | 5-F | F | H |
| A-819. | F | CH₃ | 5-CH₃ | F | H |
| A-820. | F | CH₃ | 5-OCH₃ | F | H |
| A-821. | F | OCH₃ | 3-F | F | H |
| A-822. | F | OCH₃ | 3-CH₃ | F | H |
| A-823. | F | OCH₃ | 3-OCH₃ | F | H |
| A-824. | F | OCH₃ | 5-F | F | H |
| A-825. | F | OCH₃ | 5-CH₃ | F | H |
| A-826. | F | OCH₃ | 5-OCH₃ | F | H |
| A-827. | F | CN | 3-F | F | H |
| A-828. | F | CN | 3-CH₃ | F | H |
| A-829. | F | CN | 3-OCH₃ | F | H |
| A-830. | F | CN | 5-F | F | H |
| A-831. | F | CN | 5-CH₃ | F | H |
| A-832. | F | CN | 5-OCH₃ | F | H |
| A-833. | F | CH₂F | 3-F | F | H |
| A-834. | F | CH₂F | 3-CH₃ | F | H |
| A-835. | F | CH₂F | 3-OCH₃ | F | H |
| A-836. | F | CH₂F | 5-F | F | H |
| A-837. | F | CH₂F | 5-CH₃ | F | H |
| A-838. | F | CH₂F | 5-OCH₃ | F | H |
| A-839. | F | CHF₂ | 3-F | F | H |
| A-840. | F | CHF₂ | 3-CH₃ | F | H |
| A-841. | F | CHF₂ | 3-OCH₃ | F | H |
| A-842. | F | CHF₂ | 5-F | F | H |
| A-843. | F | CHF₂ | 5-CH₃ | F | H |
| A-844. | F | CHF₂ | 5-OCH₃ | F | H |

TABLE A-continued

| Example No. | R¹ | R² | R³ | R⁶ | R⁷ |
|---|---|---|---|---|---|
| A-845. | F | CF$_3$ | 3-F | F | H |
| A-846. | F | CF$_3$ | 3-CH$_3$ | F | H |
| A-847. | F | CF$_3$ | 3-OCH$_3$ | F | H |
| A-848. | F | CF$_3$ | 5-F | F | H |
| A-849. | F | CF$_3$ | 5-CH$_3$ | F | H |
| A-850. | F | CF$_3$ | 5-OCH$_3$ | F | H |
| A-851. | F | OCH$_2$F | 3-F | F | H |
| A-852. | F | OCH$_2$F | 3-CH$_3$ | F | H |
| A-853. | F | OCH$_2$F | 3-OCH$_3$ | F | H |
| A-854. | F | OCH$_2$F | 5-F | F | H |
| A-855. | F | OCH$_2$F | 5-CH$_3$ | F | H |
| A-856. | F | OCH$_2$F | 5-OCH$_3$ | F | H |
| A-857. | F | OCHF$_2$ | 3-F | F | H |
| A-858. | F | OCHF$_2$ | 3-CH$_3$ | F | H |
| A-859. | F | OCHF$_2$ | 3-OCH$_3$ | F | H |
| A-860. | F | OCHF$_2$ | 5-F | F | H |
| A-861. | F | OCHF$_2$ | 5-CH$_3$ | F | H |
| A-862. | F | OCHF$_2$ | 5-OCH$_3$ | F | H |
| A-863. | F | OCF$_3$ | 3-F | F | H |
| A-864. | F | OCF$_3$ | 3-CH$_3$ | F | H |
| A-865. | F | OCF$_3$ | 3-OCH$_3$ | F | H |
| A-866. | F | OCF$_3$ | 5-F | F | H |
| A-867. | F | OCF$_3$ | 5-CH$_3$ | F | H |
| A-868. | F | OCF$_3$ | 5-OCH$_3$ | F | H |
| A-869. | CH$_3$ | F | 3-F | F | H |
| A-870. | CH$_3$ | F | 3-CH$_3$ | F | H |
| A-871. | CH$_3$ | F | 3-OCH$_3$ | F | H |
| A-872. | CH$_3$ | F | 5-F | F | H |
| A-873. | CH$_3$ | F | 5-CH$_3$ | F | H |
| A-874. | CH$_3$ | F | 5-OCH$_3$ | F | H |
| A-875. | CH$_3$ | CH$_3$ | 3-F | F | H |
| A-876. | CH$_3$ | CH$_3$ | 3-CH$_3$ | F | H |
| A-877. | CH$_3$ | CH$_3$ | 3-OCH$_3$ | F | H |
| A-878. | CH$_3$ | CH$_3$ | 5-F | F | H |
| A-879. | CH$_3$ | CH$_3$ | 5-CH$_3$ | F | H |
| A-880. | CH$_3$ | CH$_3$ | 5-OCH$_3$ | F | H |
| A-881. | CH$_3$ | OCH$_3$ | 3-F | F | H |
| A-882. | CH$_3$ | OCH$_3$ | 3-CH$_3$ | F | H |
| A-883. | CH$_3$ | OCH$_3$ | 3-OCH$_3$ | F | H |
| A-884. | CH$_3$ | OCH$_3$ | 5-F | F | H |
| A-885. | CH$_3$ | OCH$_3$ | 5-CH$_3$ | F | H |
| A-886. | CH$_3$ | OCH$_3$ | 5-OCH$_3$ | F | H |
| A-887. | CH$_3$ | CN | 3-F | F | H |
| A-888. | CH$_3$ | CN | 3-CH$_3$ | F | H |
| A-889. | CH$_3$ | CN | 3-OCH$_3$ | F | H |
| A-890. | CH$_3$ | CN | 5-F | F | H |
| A-891. | CH$_3$ | CN | 5-CH$_3$ | F | H |
| A-892. | CH$_3$ | CN | 5-OCH$_3$ | F | H |
| A-893. | CH$_3$ | CH$_2$F | 3-F | F | H |
| A-894. | CH$_3$ | CH$_2$F | 3-CH$_3$ | F | H |
| A-895. | CH$_3$ | CH$_2$F | 3-OCH$_3$ | F | H |
| A-896. | CH$_3$ | CH$_2$F | 5-F | F | H |
| A-897. | CH$_3$ | CH$_2$F | 5-CH$_3$ | F | H |
| A-898. | CH$_3$ | CH$_2$F | 5-OCH$_3$ | F | H |
| A-899. | CH$_3$ | CHF$_2$ | 3-F | F | H |
| A-900. | CH$_3$ | CHF$_2$ | 3-CH$_3$ | F | H |
| A-901. | CH$_3$ | CHF$_2$ | 3-OCH$_3$ | F | H |
| A-902. | CH$_3$ | CHF$_2$ | 5-F | F | H |
| A-903. | CH$_3$ | CHF$_2$ | 5-CH$_3$ | F | H |
| A-904. | CH$_3$ | CHF$_2$ | 5-OCH$_3$ | F | H |
| A-905. | CH$_3$ | CF$_3$ | 3-F | F | H |
| A-906. | CH$_3$ | CF$_3$ | 3-CH$_3$ | F | H |
| A-907. | CH$_3$ | CF$_3$ | 3-OCH$_3$ | F | H |
| A-908. | CH$_3$ | CF$_3$ | 5-F | F | H |
| A-909. | CH$_3$ | CF$_3$ | 5-CH$_3$ | F | H |
| A-910. | CH$_3$ | CF$_3$ | 5-OCH$_3$ | F | H |
| A-911. | CH$_3$ | OCH$_2$F | 3-F | F | H |
| A-912. | CH$_3$ | OCH$_2$F | 3-CH$_3$ | F | H |
| A-913. | CH$_3$ | OCH$_2$F | 3-OCH$_3$ | F | H |
| A-914. | CH$_3$ | OCH$_2$F | 5-F | F | H |
| A-915. | CH$_3$ | OCH$_2$F | 5-CH$_3$ | F | H |
| A-916. | CH$_3$ | OCH$_2$F | 5-OCH$_3$ | F | H |
| A-917. | CH$_3$ | OCHF$_2$ | 3-F | F | H |
| A-918. | CH$_3$ | OCHF$_2$ | 3-CH$_3$ | F | H |
| A-919. | CH$_3$ | OCHF$_2$ | 3-OCH$_3$ | F | H |
| A-920. | CH$_3$ | OCHF$_2$ | 5-F | F | H |
| A-921. | CH$_3$ | OCHF$_2$ | 5-CH$_3$ | F | H |
| A-922. | CH$_3$ | OCHF$_2$ | 5-OCH$_3$ | F | H |
| A-923. | CH$_3$ | OCF$_3$ | 3-F | F | H |
| A-924. | CH$_3$ | OCF$_3$ | 3-CH$_3$ | F | H |
| A-925. | CH$_3$ | OCF$_3$ | 3-OCH$_3$ | F | H |
| A-926. | CH$_3$ | OCF$_3$ | 5-F | F | H |
| A-927. | CH$_3$ | OCF$_3$ | 5-CH$_3$ | F | H |
| A-928. | CH$_3$ | OCF$_3$ | 5-OCH$_3$ | F | H |
| A-929. | OCH$_3$ | F | 3-F | F | H |
| A-930. | OCH$_3$ | F | 3-CH$_3$ | F | H |
| A-931. | OCH$_3$ | F | 3-OCH$_3$ | F | H |
| A-932. | OCH$_3$ | F | 5-F | F | H |
| A-933. | OCH$_3$ | F | 5-CH$_3$ | F | H |
| A-934. | OCH$_3$ | F | 5-OCH$_3$ | F | H |
| A-935. | OCH$_3$ | CH$_3$ | 3-F | F | H |
| A-936. | OCH$_3$ | CH$_3$ | 3-CH$_3$ | F | H |
| A-937. | OCH$_3$ | CH$_3$ | 3-OCH$_3$ | F | H |
| A-938. | OCH$_3$ | CH$_3$ | 5-F | F | H |
| A-939. | OCH$_3$ | CH$_3$ | 5-CH$_3$ | F | H |
| A-940. | OCH$_3$ | CH$_3$ | 5-OCH$_3$ | F | H |
| A-941. | OCH$_3$ | OCH$_3$ | 3-F | F | H |
| A-942. | OCH$_3$ | OCH$_3$ | 3-CH$_3$ | F | H |
| A-943. | OCH$_3$ | OCH$_3$ | 3-OCH$_3$ | F | H |
| A-944. | OCH$_3$ | OCH$_3$ | 5-F | F | H |
| A-945. | OCH$_3$ | OCH$_3$ | 5-CH$_3$ | F | H |
| A-946. | OCH$_3$ | OCH$_3$ | 5-OCH$_3$ | F | H |
| A-947. | OCH$_3$ | CN | 3-F | F | H |
| A-948. | OCH$_3$ | CN | 3-CH$_3$ | F | H |
| A-949. | OCH$_3$ | CN | 3-OCH$_3$ | F | H |
| A-950. | OCH$_3$ | CN | 5-F | F | H |
| A-951. | OCH$_3$ | CN | 5-CH$_3$ | F | H |
| A-952. | OCH$_3$ | CN | 5-OCH$_3$ | F | H |
| A-953. | OCH$_3$ | CH$_2$F | 3-F | F | H |
| A-954. | OCH$_3$ | CH$_2$F | 3-CH$_3$ | F | H |
| A-955. | OCH$_3$ | CH$_2$F | 3-OCH$_3$ | F | H |
| A-956. | OCH$_3$ | CH$_2$F | 5-F | F | H |
| A-957. | OCH$_3$ | CH$_2$F | 5-CH$_3$ | F | H |
| A-958. | OCH$_3$ | CH$_2$F | 5-OCH$_3$ | F | H |
| A-959. | OCH$_3$ | CHF$_2$ | 3-F | F | H |
| A-960. | OCH$_3$ | CHF$_2$ | 3-CH$_3$ | F | H |
| A-961. | OCH$_3$ | CHF$_2$ | 3-OCH$_3$ | F | H |
| A-962. | OCH$_3$ | CHF$_2$ | 5-F | F | H |
| A-963. | OCH$_3$ | CHF$_2$ | 5-CH$_3$ | F | H |
| A-964. | OCH$_3$ | CHF$_2$ | 5-OCH$_3$ | F | H |
| A-965. | OCH$_3$ | CF$_3$ | 3-F | F | H |
| A-966. | OCH$_3$ | CF$_3$ | 3-CH$_3$ | F | H |
| A-967. | OCH$_3$ | CF$_3$ | 3-OCH$_3$ | F | H |
| A-968. | OCH$_3$ | CF$_3$ | 5-F | F | H |
| A-969. | OCH$_3$ | CF$_3$ | 5-CH$_3$ | F | H |
| A-970. | OCH$_3$ | CF$_3$ | 5-OCH$_3$ | F | H |
| A-971. | OCH$_3$ | OCH$_2$F | 3-F | F | H |
| A-972. | OCH$_3$ | OCH$_2$F | 3-CH$_3$ | F | H |
| A-973. | OCH$_3$ | OCH$_2$F | 3-OCH$_3$ | F | H |
| A-974. | OCH$_3$ | OCH$_2$F | 5-F | F | H |
| A-975. | OCH$_3$ | OCH$_2$F | 5-CH$_3$ | F | H |
| A-976. | OCH$_3$ | OCH$_2$F | 5-OCH$_3$ | F | H |
| A-977. | OCH$_3$ | OCHF$_2$ | 3-F | F | H |
| A-978. | OCH$_3$ | OCHF$_2$ | 3-CH$_3$ | F | H |
| A-979. | OCH$_3$ | OCHF$_2$ | 3-OCH$_3$ | F | H |
| A-980. | OCH$_3$ | OCHF$_2$ | 5-F | F | H |
| A-981. | OCH$_3$ | OCHF$_2$ | 5-CH$_3$ | F | H |
| A-982. | OCH$_3$ | OCHF$_2$ | 5-OCH$_3$ | F | H |
| A-983. | OCH$_3$ | OCF$_3$ | 3-F | F | H |
| A-984. | OCH$_3$ | OCF$_3$ | 3-CH$_3$ | F | H |
| A-985. | OCH$_3$ | OCF$_3$ | 3-OCH$_3$ | F | H |
| A-986. | OCH$_3$ | OCF$_3$ | 5-F | F | H |
| A-987. | OCH$_3$ | OCF$_3$ | 5-CH$_3$ | F | H |
| A-988. | OCH$_3$ | OCF$_3$ | 5-OCH$_3$ | F | H |
| A-989. | CH$_2$F | F | 3-F | F | H |
| A-990. | CH$_2$F | F | 3-CH$_3$ | F | H |
| A-991. | CH$_2$F | F | 3-OCH$_3$ | F | H |
| A-992. | CH$_2$F | F | 5-F | F | H |
| A-993. | CH$_2$F | F | 5-CH$_3$ | F | H |
| A-994. | CH$_2$F | F | 5-OCH$_3$ | F | H |
| A-995. | CH$_2$F | CH$_3$ | 3-F | F | H |
| A-996. | CH$_2$F | CH$_3$ | 3-CH$_3$ | F | H |
| A-997. | CH$_2$F | CH$_3$ | 3-OCH$_3$ | F | H |
| A-998. | CH$_2$F | CH$_3$ | 5-F | F | H |
| A-999. | CH$_2$F | CH$_3$ | 5-CH$_3$ | F | H |
| A-1000. | CH$_2$F | CH$_3$ | 5-OCH$_3$ | F | H |

TABLE A-continued

| Example No. | R$^1$ | R$^2$ | R$^3$ | R$^6$ | R$^7$ |
|---|---|---|---|---|---|
| A-1001. | CH$_2$F | OCH$_3$ | 3-F | F | H |
| A-1002. | CH$_2$F | OCH$_3$ | 3-CH$_3$ | F | H |
| A-1003. | CH$_2$F | OCH$_3$ | 3-OCH$_3$ | F | H |
| A-1004. | CH$_2$F | OCH$_3$ | 5-F | F | H |
| A-1005. | CH$_2$F | OCH$_3$ | 5-CH$_3$ | F | H |
| A-1006. | CH$_2$F | OCH$_3$ | 5-OCH$_3$ | F | H |
| A-1007. | CH$_2$F | CN | 3-F | F | H |
| A-1008. | CH$_2$F | CN | 3-CH$_3$ | F | H |
| A-1009. | CH$_2$F | CN | 3-OCH$_3$ | F | H |
| A-1010. | CH$_2$F | CN | 5-F | F | H |
| A-1011. | CH$_2$F | CN | 5-CH$_3$ | F | H |
| A-1012. | CH$_2$F | CN | 5-OCH$_3$ | F | H |
| A-1013. | CH$_2$F | CH$_2$F | 3-F | F | H |
| A-1014. | CH$_2$F | CH$_2$F | 3-CH$_3$ | F | H |
| A-1015. | CH$_2$F | CH$_2$F | 3-OCH$_3$ | F | H |
| A-1016. | CH$_2$F | CH$_2$F | 5-F | F | H |
| A-1017. | CH$_2$F | CH$_2$F | 5-CH$_3$ | F | H |
| A-1018. | CH$_2$F | CH$_2$F | 5-OCH$_3$ | F | H |
| A-1019. | CH$_2$F | CHF$_2$ | 3-F | F | H |
| A-1020. | CH$_2$F | CHF$_2$ | 3-CH$_3$ | F | H |
| A-1021. | CH$_2$F | CHF$_2$ | 3-OCH$_3$ | F | H |
| A-1022. | CH$_2$F | CHF$_2$ | 5-F | F | H |
| A-1023. | CH$_2$F | CHF$_2$ | 5-CH$_3$ | F | H |
| A-1024. | CH$_2$F | CHF$_2$ | 5-OCH$_3$ | F | H |
| A-1025. | CH$_2$F | CF$_3$ | 3-F | F | H |
| A-1026. | CH$_2$F | CF$_3$ | 3-CH$_3$ | F | H |
| A-1027. | CH$_2$F | CF$_3$ | 3-OCH$_3$ | F | H |
| A-1028. | CH$_2$F | CF$_3$ | 5-F | F | H |
| A-1029. | CH$_2$F | CF$_3$ | 5-CH$_3$ | F | H |
| A-1030. | CH$_2$F | CF$_3$ | 5-OCH$_3$ | F | H |
| A-1031. | CH$_2$F | OCH$_2$F | 3-F | F | H |
| A-1032. | CH$_2$F | OCH$_2$F | 3-CH$_3$ | F | H |
| A-1033. | CH$_2$F | OCH$_2$F | 3-OCH$_3$ | F | H |
| A-1034. | CH$_2$F | OCH$_2$F | 5-F | F | H |
| A-1035. | CH$_2$F | OCH$_2$F | 5-CH$_3$ | F | H |
| A-1036. | CH$_2$F | OCH$_2$F | 5-OCH$_3$ | F | H |
| A-1037. | CH$_2$F | OCHF$_2$ | 3-F | F | H |
| A-1038. | CH$_2$F | OCHF$_2$ | 3-CH$_3$ | F | H |
| A-1039. | CH$_2$F | OCHF$_2$ | 3-OCH$_3$ | F | H |
| A-1040. | CH$_2$F | OCHF$_2$ | 5-F | F | H |
| A-1041. | CH$_2$F | OCHF$_2$ | 5-CH$_3$ | F | H |
| A-1042. | CH$_2$F | OCHF$_2$ | 5-OCH$_3$ | F | H |
| A-1043. | CH$_2$F | OCF$_3$ | 3-F | F | H |
| A-1044. | CH$_2$F | OCF$_3$ | 3-CH$_3$ | F | H |
| A-1045. | CH$_2$F | OCF$_3$ | 3-OCH$_3$ | F | H |
| A-1046. | CH$_2$F | OCF$_3$ | 5-F | F | H |
| A-1047. | CH$_2$F | OCF$_3$ | 5-CH$_3$ | F | H |
| A-1048. | CH$_2$F | OCF$_3$ | 5-OCH$_3$ | F | H |
| A-1049. | CHF$_2$ | F | 3-F | F | H |
| A-1050. | CHF$_2$ | F | 3-CH$_3$ | F | H |
| A-1051. | CHF$_2$ | F | 3-OCH$_3$ | F | H |
| A-1052. | CHF$_2$ | F | 5-F | F | H |
| A-1053. | CHF$_2$ | F | 5-CH$_3$ | F | H |
| A-1054. | CHF$_2$ | F | 5-OCH$_3$ | F | H |
| A-1055. | CHF$_2$ | CH$_3$ | 3-F | F | H |
| A-1056. | CHF$_2$ | CH$_3$ | 3-CH$_3$ | F | H |
| A-1057. | CHF$_2$ | CH$_3$ | 3-OCH$_3$ | F | H |
| A-1058. | CHF$_2$ | CH$_3$ | 5-F | F | H |
| A-1059. | CHF$_2$ | CH$_3$ | 5-CH$_3$ | F | H |
| A-1060. | CHF$_2$ | CH$_3$ | 5-OCH$_3$ | F | H |
| A-1061. | CHF$_2$ | OCH$_3$ | 3-F | F | H |
| A-1062. | CHF$_2$ | OCH$_3$ | 3-CH$_3$ | F | H |
| A-1063. | CHF$_2$ | OCH$_3$ | 3-OCH$_3$ | F | H |
| A-1064. | CHF$_2$ | OCH$_3$ | 5-F | F | H |
| A-1065. | CHF$_2$ | OCH$_3$ | 5-CH$_3$ | F | H |
| A-1066. | CHF$_2$ | OCH$_3$ | 5-OCH$_3$ | F | H |
| A-1067. | CHF$_2$ | CN | 3-F | F | H |
| A-1068. | CHF$_2$ | CN | 3-CH$_3$ | F | H |
| A-1069. | CHF$_2$ | CN | 3-OCH$_3$ | F | H |
| A-1070. | CHF$_2$ | CN | 5-F | F | H |
| A-1071. | CHF$_2$ | CN | 5-CH$_3$ | F | H |
| A-1072. | CHF$_2$ | CN | 5-OCH$_3$ | F | H |
| A-1073. | CHF$_2$ | CH$_2$F | 3-F | F | H |
| A-1074. | CHF$_2$ | CH$_2$F | 3-CH$_3$ | F | H |
| A-1075. | CHF$_2$ | CH$_2$F | 3-OCH$_3$ | F | H |
| A-1076. | CHF$_2$ | CH$_2$F | 5-F | F | H |
| A-1077. | CHF$_2$ | CH$_2$F | 5-CH$_3$ | F | H |
| A-1078. | CHF$_2$ | CH$_2$F | 5-OCH$_3$ | F | H |
| A-1079. | CHF$_2$ | CHF$_2$ | 3-F | F | H |
| A-1080. | CHF$_2$ | CHF$_2$ | 3-CH$_3$ | F | H |
| A-1081. | CHF$_2$ | CHF$_2$ | 3-OCH$_3$ | F | H |
| A-1082. | CHF$_2$ | CHF$_2$ | 5-F | F | H |
| A-1083. | CHF$_2$ | CHF$_2$ | 5-CH$_3$ | F | H |
| A-1084. | CHF$_2$ | CHF$_2$ | 5-OCH$_3$ | F | H |
| A-1085. | CHF$_2$ | CF$_3$ | 3-F | F | H |
| A-1086. | CHF$_2$ | CF$_3$ | 3-CH$_3$ | F | H |
| A-1087. | CHF$_2$ | CF$_3$ | 3-OCH$_3$ | F | H |
| A-1088. | CHF$_2$ | CF$_3$ | 5-F | F | H |
| A-1089. | CHF$_2$ | CF$_3$ | 5-CH$_3$ | F | H |
| A-1090. | CHF$_2$ | CF$_3$ | 5-OCH$_3$ | F | H |
| A-1091. | CHF$_2$ | OCH$_2$F | 3-F | F | H |
| A-1092. | CHF$_2$ | OCH$_2$F | 3-CH$_3$ | F | H |
| A-1093. | CHF$_2$ | OCH$_2$F | 3-OCH$_3$ | F | H |
| A-1094. | CHF$_2$ | OCH$_2$F | 5-F | F | H |
| A-1095. | CHF$_2$ | OCH$_2$F | 5-CH$_3$ | F | H |
| A-1096. | CHF$_2$ | OCH$_2$F | 5-OCH$_3$ | F | H |
| A-1097. | CHF$_2$ | OCHF$_2$ | 3-F | F | H |
| A-1098. | CHF$_2$ | OCHF$_2$ | 3-CH$_3$ | F | H |
| A-1099. | CHF$_2$ | OCHF$_2$ | 3-OCH$_3$ | F | H |
| A-1100. | CHF$_2$ | OCHF$_2$ | 5-F | F | H |
| A-1101. | CHF$_2$ | OCHF$_2$ | 5-CH$_3$ | F | H |
| A-1102. | CHF$_2$ | OCHF$_2$ | 5-OCH$_3$ | F | H |
| A-1103. | CHF$_2$ | OCF$_3$ | 3-F | F | H |
| A-1104. | CHF$_2$ | OCF$_3$ | 3-CH$_3$ | F | H |
| A-1105. | CHF$_2$ | OCF$_3$ | 3-OCH$_3$ | F | H |
| A-1106. | CHF$_2$ | OCF$_3$ | 5-F | F | H |
| A-1107. | CHF$_2$ | OCF$_3$ | 5-CH$_3$ | F | H |
| A-1108. | CHF$_2$ | OCF$_3$ | 5-OCH$_3$ | F | H |
| A-1109. | CF$_3$ | F | 3-F | F | H |
| A-1110. | CF$_3$ | F | 3-CH$_3$ | F | H |
| A-1111. | CF$_3$ | F | 3-OCH$_3$ | F | H |
| A-1112. | CF$_3$ | F | 5-F | F | H |
| A-1113. | CF$_3$ | F | 5-CH$_3$ | F | H |
| A-1114. | CF$_3$ | F | 5-OCH$_3$ | F | H |
| A-1115. | CF$_3$ | CH$_3$ | 3-F | F | H |
| A-1116. | CF$_3$ | CH$_3$ | 3-CH$_3$ | F | H |
| A-1117. | CF$_3$ | CH$_3$ | 3-OCH$_3$ | F | H |
| A-1118. | CF$_3$ | CH$_3$ | 5-F | F | H |
| A-1119. | CF$_3$ | CH$_3$ | 5-CH$_3$ | F | H |
| A-1120. | CF$_3$ | CH$_3$ | 5-OCH$_3$ | F | H |
| A-1121. | CF$_3$ | OCH$_3$ | 3-F | F | H |
| A-1122. | CF$_3$ | OCH$_3$ | 3-CH$_3$ | F | H |
| A-1123. | CF$_3$ | OCH$_3$ | 3-OCH$_3$ | F | H |
| A-1124. | CF$_3$ | OCH$_3$ | 5-F | F | H |
| A-1125. | CF$_3$ | OCH$_3$ | 5-CH$_3$ | F | H |
| A-1126. | CF$_3$ | OCH$_3$ | 5-OCH$_3$ | F | H |
| A-1127. | CF$_3$ | CN | 3-F | F | H |
| A-1128. | CF$_3$ | CN | 3-CH$_3$ | F | H |
| A-1129. | CF$_3$ | CN | 3-OCH$_3$ | F | H |
| A-1130. | CF$_3$ | CN | 5-F | F | H |
| A-1131. | CF$_3$ | CN | 5-CH$_3$ | F | H |
| A-1132. | CF$_3$ | CN | 5-OCH$_3$ | F | H |
| A-1133. | CF$_3$ | CH$_2$F | 3-F | F | H |
| A-1134. | CF$_3$ | CH$_2$F | 3-CH$_3$ | F | H |
| A-1135. | CF$_3$ | CH$_2$F | 3-OCH$_3$ | F | H |
| A-1136. | CF$_3$ | CH$_2$F | 5-F | F | H |
| A-1137. | CF$_3$ | CH$_2$F | 5-CH$_3$ | F | H |
| A-1138. | CF$_3$ | CH$_2$F | 5-OCH$_3$ | F | H |
| A-1139. | CF$_3$ | CHF$_2$ | 3-F | F | H |
| A-1140. | CF$_3$ | CHF$_2$ | 3-CH$_3$ | F | H |
| A-1141. | CF$_3$ | CHF$_2$ | 3-OCH$_3$ | F | H |
| A-1142. | CF$_3$ | CHF$_2$ | 5-F | F | H |
| A-1143. | CF$_3$ | CHF$_2$ | 5-CH$_3$ | F | H |
| A-1144. | CF$_3$ | CHF$_2$ | 5-OCH$_3$ | F | H |
| A-1145. | CF$_3$ | CF$_3$ | 3-F | F | H |
| A-1146. | CF$_3$ | CF$_3$ | 3-CH$_3$ | F | H |
| A-1147. | CF$_3$ | CF$_3$ | 3-OCH$_3$ | F | H |
| A-1148. | CF$_3$ | CF$_3$ | 5-F | F | H |
| A-1149. | CF$_3$ | CF$_3$ | 5-CH$_3$ | F | H |
| A-1150. | CF$_3$ | CF$_3$ | 5-OCH$_3$ | F | H |
| A-1151. | CF$_3$ | OCH$_2$F | 3-F | F | H |
| A-1152. | CF$_3$ | OCH$_2$F | 3-CH$_3$ | F | H |
| A-1153. | CF$_3$ | OCH$_2$F | 3-OCH$_3$ | F | H |
| A-1154. | CF$_3$ | OCH$_2$F | 5-F | F | H |
| A-1155. | CF$_3$ | OCH$_2$F | 5-CH$_3$ | F | H |
| A-1156. | CF$_3$ | OCH$_2$F | 5-OCH$_3$ | F | H |

TABLE A-continued

| Example No. | R$^1$ | R$^2$ | R$^3$ | R$^6$ | R$^7$ |
|---|---|---|---|---|---|
| A-1157. | CF$_3$ | OCHF$_2$ | 3-F | F | H |
| A-1158. | CF$_3$ | OCHF$_2$ | 3-CH$_3$ | F | H |
| A-1159. | CF$_3$ | OCHF$_2$ | 3-OCH$_3$ | F | H |
| A-1160. | CF$_3$ | OCHF$_2$ | 5-F | F | H |
| A-1161. | CF$_3$ | OCHF$_2$ | 5-CH$_3$ | F | H |
| A-1162. | CF$_3$ | OCHF$_2$ | 5-OCH$_3$ | F | H |
| A-1163. | CF$_3$ | OCF$_3$ | 3-F | F | H |
| A-1164. | CF$_3$ | OCF$_3$ | 3-CH$_3$ | F | H |
| A-1165. | CF$_3$ | OCF$_3$ | 3-OCH$_3$ | F | H |
| A-1166. | CF$_3$ | OCF$_3$ | 5-F | F | H |
| A-1167. | CF$_3$ | OCF$_3$ | 5-CH$_3$ | F | H |
| A-1168. | CF$_3$ | OCF$_3$ | 5-OCH$_3$ | F | H |
| A-1169. | OCH$_2$F | F | 3-F | F | H |
| A-1170. | OCH$_2$F | F | 3-CH$_3$ | F | H |
| A-1171. | OCH$_2$F | F | 3-OCH$_3$ | F | H |
| A-1172. | OCH$_2$F | F | 5-F | F | H |
| A-1173. | OCH$_2$F | F | 5-CH$_3$ | F | H |
| A-1174. | OCH$_2$F | F | 5-OCH$_3$ | F | H |
| A-1175. | OCH$_2$F | CH$_3$ | 3-F | F | H |
| A-1176. | OCH$_2$F | CH$_3$ | 3-CH$_3$ | F | H |
| A-1177. | OCH$_2$F | CH$_3$ | 3-OCH$_3$ | F | H |
| A-1178. | OCH$_2$F | CH$_3$ | 5-F | F | H |
| A-1179. | OCH$_2$F | CH$_3$ | 5-CH$_3$ | F | H |
| A-1180. | OCH$_2$F | CH$_3$ | 5-OCH$_3$ | F | H |
| A-1181. | OCH$_2$F | OCH$_3$ | 3-F | F | H |
| A-1182. | OCH$_2$F | OCH$_3$ | 3-CH$_3$ | F | H |
| A-1183. | OCH$_2$F | OCH$_3$ | 3-OCH$_3$ | F | H |
| A-1184. | OCH$_2$F | OCH$_3$ | 5-F | F | H |
| A-1185. | OCH$_2$F | OCH$_3$ | 5-CH$_3$ | F | H |
| A-1186. | OCH$_2$F | OCH$_3$ | 5-OCH$_3$ | F | H |
| A-1187. | OCH$_2$F | CN | 3-F | F | H |
| A-1188. | OCH$_2$F | CN | 3-CH$_3$ | F | H |
| A-1189. | OCH$_2$F | CN | 3-OCH$_3$ | F | H |
| A-1190. | OCH$_2$F | CN | 5-F | F | H |
| A-1191. | OCH$_2$F | CN | 5-CH$_3$ | F | H |
| A-1192. | OCH$_2$F | CN | 5-OCH$_3$ | F | H |
| A-1193. | OCH$_2$F | CH$_2$F | 3-F | F | H |
| A-1194. | OCH$_2$F | CH$_2$F | 3-CH$_3$ | F | H |
| A-1195. | OCH$_2$F | CH$_2$F | 3-OCH$_3$ | F | H |
| A-1196. | OCH$_2$F | CH$_2$F | 5-F | F | H |
| A-1197. | OCH$_2$F | CH$_2$F | 5-CH$_3$ | F | H |
| A-1198. | OCH$_2$F | CH$_2$F | 5-OCH$_3$ | F | H |
| A-1199. | OCH$_2$F | CHF$_2$ | 3-F | F | H |
| A-1200. | OCH$_2$F | CHF$_2$ | 3-CH$_3$ | F | H |
| A-1201. | OCH$_2$F | CHF$_2$ | 3-OCH$_3$ | F | H |
| A-1202. | OCH$_2$F | CHF$_2$ | 5-F | F | H |
| A-1203. | OCH$_2$F | CHF$_2$ | 5-CH$_3$ | F | H |
| A-1204. | OCH$_2$F | CHF$_2$ | 5-OCH$_3$ | F | H |
| A-1205. | OCH$_2$F | CF$_3$ | 3-F | F | H |
| A-1206. | OCH$_2$F | CF$_3$ | 3-CH$_3$ | F | H |
| A-1207. | OCH$_2$F | CF$_3$ | 3-OCH$_3$ | F | H |
| A-1208. | OCH$_2$F | CF$_3$ | 5-F | F | H |
| A-1209. | OCH$_2$F | CF$_3$ | 5-CH$_3$ | F | H |
| A-1210. | OCH$_2$F | CF$_3$ | 5-OCH$_3$ | F | H |
| A-1211. | OCH$_2$F | OCH$_2$F | 3-F | F | H |
| A-1212. | OCH$_2$F | OCH$_2$F | 3-CH$_3$ | F | H |
| A-1213. | OCH$_2$F | OCH$_2$F | 3-OCH$_3$ | F | H |
| A-1214. | OCH$_2$F | OCH$_2$F | 5-F | F | H |
| A-1215. | OCH$_2$F | OCH$_2$F | 5-CH$_3$ | F | H |
| A-1216. | OCH$_2$F | OCH$_2$F | 5-OCH$_3$ | F | H |
| A-1217. | OCH$_2$F | OCHF$_2$ | 3-F | F | H |
| A-1218. | OCH$_2$F | OCHF$_2$ | 3-CH$_3$ | F | H |
| A-1219. | OCH$_2$F | OCHF$_2$ | 3-OCH$_3$ | F | H |
| A-1220. | OCH$_2$F | OCHF$_2$ | 5-F | F | H |
| A-1221. | OCH$_2$F | OCHF$_2$ | 5-CH$_3$ | F | H |
| A-1222. | OCH$_2$F | OCHF$_2$ | 5-OCH$_3$ | F | H |
| A-1223. | OCH$_2$F | OCF$_3$ | 3-F | F | H |
| A-1224. | OCH$_2$F | OCF$_3$ | 3-CH$_3$ | F | H |
| A-1225. | OCH$_2$F | OCF$_3$ | 3-OCH$_3$ | F | H |
| A-1226. | OCH$_2$F | OCF$_3$ | 5-F | F | H |
| A-1227. | OCH$_2$F | OCF$_3$ | 5-CH$_3$ | F | H |
| A-1228. | OCH$_2$F | OCF$_3$ | 5-OCH$_3$ | F | H |
| A-1229. | OCHF$_2$ | F | 3-F | F | H |
| A-1230. | OCHF$_2$ | F | 3-CH$_3$ | F | H |
| A-1231. | OCHF$_2$ | F | 3-OCH$_3$ | F | H |
| A-1232. | OCHF$_2$ | F | 5-F | F | H |
| A-1233. | OCHF$_2$ | F | 5-CH$_3$ | F | H |
| A-1234. | OCHF$_2$ | F | 5-OCH$_3$ | F | H |
| A-1235. | OCHF$_2$ | CH$_3$ | 3-F | F | H |
| A-1236. | OCHF$_2$ | CH$_3$ | 3-CH$_3$ | F | H |
| A-1237. | OCHF$_2$ | CH$_3$ | 3-OCH$_3$ | F | H |
| A-1238. | OCHF$_2$ | CH$_3$ | 5-F | F | H |
| A-1239. | OCHF$_2$ | CH$_3$ | 5-CH$_3$ | F | H |
| A-1240. | OCHF$_2$ | CH$_3$ | 5-OCH$_3$ | F | H |
| A-1241. | OCHF$_2$ | OCH$_3$ | 3-F | F | H |
| A-1242. | OCHF$_2$ | OCH$_3$ | 3-CH$_3$ | F | H |
| A-1243. | OCHF$_2$ | OCH$_3$ | 3-OCH$_3$ | F | H |
| A-1244. | OCHF$_2$ | OCH$_3$ | 5-F | F | H |
| A-1245. | OCHF$_2$ | OCH$_3$ | 5-CH$_3$ | F | H |
| A-1246. | OCHF$_2$ | OCH$_3$ | 5-OCH$_3$ | F | H |
| A-1247. | OCHF$_2$ | CN | 3-F | F | H |
| A-1248. | OCHF$_2$ | CN | 3-CH$_3$ | F | H |
| A-1249. | OCHF$_2$ | CN | 3-OCH$_3$ | F | H |
| A-1250. | OCHF$_2$ | CN | 5-F | F | H |
| A-1251. | OCHF$_2$ | CN | 5-CH$_3$ | F | H |
| A-1252. | OCHF$_2$ | CN | 5-OCH$_3$ | F | H |
| A-1253. | OCHF$_2$ | CH$_2$F | 3-F | F | H |
| A-1254. | OCHF$_2$ | CH$_2$F | 3-CH$_3$ | F | H |
| A-1255. | OCHF$_2$ | CH$_2$F | 3-OCH$_3$ | F | H |
| A-1256. | OCHF$_2$ | CH$_2$F | 5-F | F | H |
| A-1257. | OCHF$_2$ | CH$_2$F | 5-CH$_3$ | F | H |
| A-1258. | OCHF$_2$ | CH$_2$F | 5-OCH$_3$ | F | H |
| A-1259. | OCHF$_2$ | CHF$_2$ | 3-F | F | H |
| A-1260. | OCHF$_2$ | CHF$_2$ | 3-CH$_3$ | F | H |
| A-1261. | OCHF$_2$ | CHF$_2$ | 3-OCH$_3$ | F | H |
| A-1262. | OCHF$_2$ | CHF$_2$ | 5-F | F | H |
| A-1263. | OCHF$_2$ | CHF$_2$ | 5-CH$_3$ | F | H |
| A-1264. | OCHF$_2$ | CHF$_2$ | 5-OCH$_3$ | F | H |
| A-1265. | OCHF$_2$ | CF$_3$ | 3-F | F | H |
| A-1266. | OCHF$_2$ | CF$_3$ | 3-CH$_3$ | F | H |
| A-1267. | OCHF$_2$ | CF$_3$ | 3-OCH$_3$ | F | H |
| A-1268. | OCHF$_2$ | CF$_3$ | 5-F | F | H |
| A-1269. | OCHF$_2$ | CF$_3$ | 5-CH$_3$ | F | H |
| A-1270. | OCHF$_2$ | CF$_3$ | 5-OCH$_3$ | F | H |
| A-1271. | OCHF$_2$ | OCH$_2$F | 3-F | F | H |
| A-1272. | OCHF$_2$ | OCH$_2$F | 3-CH$_3$ | F | H |
| A-1273. | OCHF$_2$ | OCH$_2$F | 3-OCH$_3$ | F | H |
| A-1274. | OCHF$_2$ | OCH$_2$F | 5-F | F | H |
| A-1275. | OCHF$_2$ | OCH$_2$F | 5-CH$_3$ | F | H |
| A-1276. | OCHF$_2$ | OCH$_2$F | 5-OCH$_3$ | F | H |
| A-1277. | OCHF$_2$ | OCHF$_2$ | 3-F | F | H |
| A-1278. | OCHF$_2$ | OCHF$_2$ | 3-CH$_3$ | F | H |
| A-1279. | OCHF$_2$ | OCHF$_2$ | 3-OCH$_3$ | F | H |
| A-1280. | OCHF$_2$ | OCHF$_2$ | 5-F | F | H |
| A-1281. | OCHF$_2$ | OCHF$_2$ | 5-CH$_3$ | F | H |
| A-1282. | OCHF$_2$ | OCHF$_2$ | 5-OCH$_3$ | F | H |
| A-1283. | OCHF$_2$ | OCF$_3$ | 3-F | F | H |
| A-1284. | OCHF$_2$ | OCF$_3$ | 3-CH$_3$ | F | H |
| A-1285. | OCHF$_2$ | OCF$_3$ | 3-OCH$_3$ | F | H |
| A-1286. | OCHF$_2$ | OCF$_3$ | 5-F | F | H |
| A-1287. | OCHF$_2$ | OCF$_3$ | 5-CH$_3$ | F | H |
| A-1288. | OCHF$_2$ | OCF$_3$ | 5-OCH$_3$ | F | H |
| A-1289. | OCF$_3$ | F | 3-F | F | H |
| A-1290. | OCF$_3$ | F | 3-CH$_3$ | F | H |
| A-1291. | OCF$_3$ | F | 3-OCH$_3$ | F | H |
| A-1292. | OCF$_3$ | F | 5-F | F | H |
| A-1293. | OCF$_3$ | F | 5-CH$_3$ | F | H |
| A-1294. | OCF$_3$ | F | 5-OCH$_3$ | F | H |
| A-1295. | OCF$_3$ | CH$_3$ | 3-F | F | H |
| A-1296. | OCF$_3$ | CH$_3$ | 3-CH$_3$ | F | H |
| A-1297. | OCF$_3$ | CH$_3$ | 3-OCH$_3$ | F | H |
| A-1298. | OCF$_3$ | CH$_3$ | 5-F | F | H |
| A-1299. | OCF$_3$ | CH$_3$ | 5-CH$_3$ | F | H |
| A-1300. | OCF$_3$ | CH$_3$ | 5-OCH$_3$ | F | H |
| A-1301. | OCF$_3$ | OCH$_3$ | 3-F | F | H |
| A-1302. | OCF$_3$ | OCH$_3$ | 3-CH$_3$ | F | H |
| A-1303. | OCF$_3$ | OCH$_3$ | 3-OCH$_3$ | F | H |
| A-1304. | OCF$_3$ | OCH$_3$ | 5-F | F | H |
| A-1305. | OCF$_3$ | OCH$_3$ | 5-CH$_3$ | F | H |
| A-1306. | OCF$_3$ | OCH$_3$ | 5-OCH$_3$ | F | H |
| A-1307. | OCF$_3$ | CN | 3-F | F | H |
| A-1308. | OCF$_3$ | CN | 3-CH$_3$ | F | H |
| A-1309. | OCF$_3$ | CN | 3-OCH$_3$ | F | H |
| A-1310. | OCF$_3$ | CN | 5-F | F | H |
| A-1311. | OCF$_3$ | CN | 5-CH$_3$ | F | H |
| A-1312. | OCF$_3$ | CN | 5-OCH$_3$ | F | H |

TABLE A-continued

| Example No. | R¹ | R² | R³ | R⁶ | R⁷ |
|---|---|---|---|---|---|
| A-1313. | OCF₃ | CH₂F | 3-F | F | H |
| A-1314. | OCF₃ | CH₂F | 3-CH₃ | F | H |
| A-1315. | OCF₃ | CH₂F | 3-OCH₃ | F | H |
| A-1316. | OCF₃ | CH₂F | 5-F | F | H |
| A-1317. | OCF₃ | CH₂F | 5-CH₃ | F | H |
| A-1318. | OCF₃ | CH₂F | 5-OCH₃ | F | H |
| A-1319. | OCF₃ | CHF₂ | 3-F | F | H |
| A-1320. | OCF₃ | CHF₂ | 3-CH₃ | F | H |
| A-1321. | OCF₃ | CHF₂ | 3-OCH₃ | F | H |
| A-1322. | OCF₃ | CHF₂ | 5-F | F | H |
| A-1323. | OCF₃ | CHF₂ | 5-CH₃ | F | H |
| A-1324. | OCF₃ | CHF₂ | 5-OCH₃ | F | H |
| A-1325. | OCF₃ | CF₃ | 3-F | F | H |
| A-1326. | OCF₃ | CF₃ | 3-CH₃ | F | H |
| A-1327. | OCF₃ | CF₃ | 3-OCH₃ | F | H |
| A-1328. | OCF₃ | CF₃ | 5-F | F | H |
| A-1329. | OCF₃ | CF₃ | 5-CH₃ | F | H |
| A-1330. | OCF₃ | CF₃ | 5-OCH₃ | F | H |
| A-1331. | OCF₃ | OCH₂F | 3-F | F | H |
| A-1332. | OCF₃ | OCH₂F | 3-CH₃ | F | H |
| A-1333. | OCF₃ | OCH₂F | 3-OCH₃ | F | H |
| A-1334. | OCF₃ | OCH₂F | 5-F | F | H |
| A-1335. | OCF₃ | OCH₂F | 5-CH₃ | F | H |
| A-1336. | OCF₃ | OCH₂F | 5-OCH₃ | F | H |
| A-1337. | OCF₃ | OCHF₂ | 3-F | F | H |
| A-1338. | OCF₃ | OCHF₂ | 3-CH₃ | F | H |
| A-1339. | OCF₃ | OCHF₂ | 3-OCH₃ | F | H |
| A-1340. | OCF₃ | OCHF₂ | 5-F | F | H |
| A-1341. | OCF₃ | OCHF₂ | 5-CH₃ | F | H |
| A-1342. | OCF₃ | OCHF₂ | 5-OCH₃ | F | H |
| A-1343. | OCF₃ | OCF₃ | 3-F | F | H |
| A-1344. | OCF₃ | OCF₃ | 3-CH₃ | F | H |
| A-1345. | OCF₃ | OCF₃ | 3-OCH₃ | F | H |
| A-1346. | OCF₃ | OCF₃ | 5-F | F | H |
| A-1347. | OCF₃ | OCF₃ | 5-CH₃ | F | H |
| A-1348. | OCF₃ | OCF₃ | 5-OCH₃ | F | H |
| A-1349. | H | H | H | Cl | H |
| A-1350. | F | H | H | Cl | H |
| A-1351. | CH₃ | H | H | Cl | H |
| A-1352. | OCH₃ | H | H | Cl | H |
| A-1353. | CH₂F | H | H | Cl | H |
| A-1354. | CHF₂ | H | H | Cl | H |
| A-1355. | CF₃ | H | H | Cl | H |
| A-1356. | OCH₂F | H | H | Cl | H |
| A-1357. | OCHF₂ | H | H | Cl | H |
| A-1358. | OCF₃ | H | H | Cl | H |
| A-1359. | H | F | H | Cl | H |
| A-1360. | H | CH₃ | H | Cl | H |
| A-1361. | H | OCH₃ | H | Cl | H |
| A-1362. | H | CN | H | Cl | H |
| A-1363. | H | CH₂F | H | Cl | H |
| A-1364. | H | CHF₂ | H | Cl | H |
| A-1365. | H | CF₃ | H | Cl | H |
| A-1366. | H | OCH₂F | H | Cl | H |
| A-1367. | H | OCHF₂ | H | Cl | H |
| A-1368. | H | OCF₃ | H | Cl | H |
| A-1369. | H | H | 3-F | Cl | H |
| A-1370. | H | H | 3-CH₃ | Cl | H |
| A-1371. | H | H | 3-OCH₃ | Cl | H |
| A-1372. | H | H | 5-F | Cl | H |
| A-1373. | H | H | 5-CH₃ | Cl | H |
| A-1374. | H | H | 5-OCH₃ | Cl | H |
| A-1375. | F | F | H | Cl | H |
| A-1376. | F | CH₃ | H | Cl | H |
| A-1377. | F | OCH₃ | H | Cl | H |
| A-1378. | F | CN | H | Cl | H |
| A-1379. | F | CH₂F | H | Cl | H |
| A-1380. | F | CHF₂ | H | Cl | H |
| A-1381. | F | CF₃ | H | Cl | H |
| A-1382. | F | OCH₂F | H | Cl | H |
| A-1383. | F | OCHF₂ | H | Cl | H |
| A-1384. | F | OCF₃ | H | Cl | H |
| A-1385. | F | H | 3-F | Cl | H |
| A-1386. | F | H | 3-CH₃ | Cl | H |
| A-1387. | F | H | 3-OCH₃ | Cl | H |
| A-1388. | F | H | 5-F | Cl | H |
| A-1389. | F | H | 5-CH₃ | Cl | H |
| A-1390. | F | H | 5-OCH₃ | Cl | H |
| A-1391. | CH₃ | F | H | Cl | H |
| A-1392. | CH₃ | CH₃ | H | Cl | H |
| A-1393. | CH₃ | OCH₃ | H | Cl | H |
| A-1394. | CH₃ | CN | H | Cl | H |
| A-1395. | CH₃ | CH₂F | H | Cl | H |
| A-1396. | CH₃ | CHF₂ | H | Cl | H |
| A-1397. | CH₃ | CF₃ | H | Cl | H |
| A-1398. | CH₃ | OCH₂F | H | Cl | H |
| A-1399. | CH₃ | OCHF₂ | H | Cl | H |
| A-1400. | CH₃ | OCF₃ | H | Cl | H |
| A-1401. | CH₃ | H | 3-F | Cl | H |
| A-1402. | CH₃ | H | 3-CH₃ | Cl | H |
| A-1403. | CH₃ | H | 3-OCH₃ | Cl | H |
| A-1404. | CH₃ | H | 5-F | Cl | H |
| A-1405. | CH₃ | H | 5-CH₃ | Cl | H |
| A-1406. | CH₃ | H | 5-OCH₃ | Cl | H |
| A-1407. | OCH₃ | F | H | Cl | H |
| A-1408. | OCH₃ | CH₃ | H | Cl | H |
| A-1409. | OCH₃ | OCH₃ | H | Cl | H |
| A-1410. | OCH₃ | CN | H | Cl | H |
| A-1411. | OCH₃ | CH₂F | H | Cl | H |
| A-1412. | OCH₃ | CHF₂ | H | Cl | H |
| A-1413. | OCH₃ | CF₃ | H | Cl | H |
| A-1414. | OCH₃ | OCH₂F | H | Cl | H |
| A-1415. | OCH₃ | OCHF₂ | H | Cl | H |
| A-1416. | OCH₃ | OCF₃ | H | Cl | H |
| A-1417. | OCH₃ | H | 3-F | Cl | H |
| A-1418. | OCH₃ | H | 3-CH₃ | Cl | H |
| A-1419. | OCH₃ | H | 3-OCH₃ | Cl | H |
| A-1420. | OCH₃ | H | 5-F | Cl | H |
| A-1421. | OCH₃ | H | 5-CH₃ | Cl | H |
| A-1422. | OCH₃ | H | 5-OCH₃ | Cl | H |
| A-1423. | H | F | 3-F | Cl | H |
| A-1424. | H | F | 3-CH₃ | Cl | H |
| A-1425. | H | F | 3-OCH₃ | Cl | H |
| A-1426. | H | F | 5-F | Cl | H |
| A-1427. | H | F | 5-CH₃ | Cl | H |
| A-1428. | H | F | 5-OCH₃ | Cl | H |
| A-1429. | H | CH₃ | 3-F | Cl | H |
| A-1430. | H | CH₃ | 3-CH₃ | Cl | H |
| A-1431. | H | CH₃ | 3-OCH₃ | Cl | H |
| A-1432. | H | CH₃ | 5-F | Cl | H |
| A-1433. | H | CH₃ | 5-CH₃ | Cl | H |
| A-1434. | H | CH₃ | 5-OCH₃ | Cl | H |
| A-1435. | H | OCH₃ | 3-F | Cl | H |
| A-1436. | H | OCH₃ | 3-CH₃ | Cl | H |
| A-1437. | H | OCH₃ | 3-OCH₃ | Cl | H |
| A-1438. | H | OCH₃ | 5-F | Cl | H |
| A-1439. | H | OCH₃ | 5-CH₃ | Cl | H |
| A-1440. | H | OCH₃ | 5-OCH₃ | Cl | H |
| A-1441. | H | CN | 3-F | Cl | H |
| A-1442. | H | CN | 3-CH₃ | Cl | H |
| A-1443. | H | CN | 3-OCH₃ | Cl | H |
| A-1444. | H | CN | 5-F | Cl | H |
| A-1445. | H | CN | 5-CH₃ | Cl | H |
| A-1446. | H | CN | 5-OCH₃ | Cl | H |
| A-1447. | H | CH₂F | 3-F | Cl | H |
| A-1448. | H | CH₂F | 3-CH₃ | Cl | H |
| A-1449. | H | CH₂F | 3-OCH₃ | Cl | H |
| A-1450. | H | CH₂F | 5-F | Cl | H |
| A-1451. | H | CH₂F | 5-CH₃ | Cl | H |
| A-1452. | H | CH₂F | 5-OCH₃ | Cl | H |
| A-1453. | H | CHF₂ | 3-F | Cl | H |
| A-1454. | H | CHF₂ | 3-CH₃ | Cl | H |
| A-1455. | H | CHF₂ | 3-OCH₃ | Cl | H |
| A-1456. | H | CHF₂ | 5-F | Cl | H |
| A-1457. | H | CHF₂ | 5-CH₃ | Cl | H |
| A-1458. | H | CHF₂ | 5-OCH₃ | Cl | H |
| A-1459. | H | CF₃ | 3-F | Cl | H |
| A-1460. | H | CF₃ | 3-CH₃ | Cl | H |
| A-1461. | H | CF₃ | 3-OCH₃ | Cl | H |
| A-1462. | H | CF₃ | 5-F | Cl | H |
| A-1463. | H | CF₃ | 5-CH₃ | Cl | H |
| A-1464. | H | CF₃ | 5-OCH₃ | Cl | H |
| A-1465. | H | OCH₂F | 3-F | Cl | H |
| A-1466. | H | OCH₂F | 3-CH₃ | Cl | H |
| A-1467. | H | OCH₂F | 3-OCH₃ | Cl | H |
| A-1468. | H | OCH₂F | 5-F | Cl | H |

TABLE A-continued

| Example No. | R¹ | R² | R³ | R⁶ | R⁷ |
|---|---|---|---|---|---|
| A-1469. | H | OCH₂F | 5-CH₃ | Cl | H |
| A-1470. | H | OCH₂F | 5-OCH₃ | Cl | H |
| A-1471. | H | OCHF₂ | 3-F | Cl | H |
| A-1472. | H | OCHF₂ | 3-CH₃ | Cl | H |
| A-1473. | H | OCHF₂ | 3-OCH₃ | Cl | H |
| A-1474. | H | OCHF₂ | 5-F | Cl | H |
| A-1475. | H | OCHF₂ | 5-CH₃ | Cl | H |
| A-1476. | H | OCHF₂ | 5-OCH₃ | Cl | H |
| A-1477. | H | OCF₃ | 3-F | Cl | H |
| A-1478. | H | OCF₃ | 3-CH₃ | Cl | H |
| A-1479. | H | OCF₃ | 3-OCH₃ | Cl | H |
| A-1480. | H | OCF₃ | 5-F | Cl | H |
| A-1481. | H | OCF₃ | 5-CH₃ | Cl | H |
| A-1482. | H | OCF₃ | 5-OCH₃ | Cl | H |
| A-1483. | F | F | 3-F | Cl | H |
| A-1484. | F | F | 3-CH₃ | Cl | H |
| A-1485. | F | F | 3-OCH₃ | Cl | H |
| A-1486. | F | F | 5-F | Cl | H |
| A-1487. | F | F | 5-CH₃ | Cl | H |
| A-1488. | F | F | 5-OCH₃ | Cl | H |
| A-1489. | F | CH₃ | 3-F | Cl | H |
| A-1490. | F | CH₃ | 3-CH₃ | Cl | H |
| A-1491. | F | CH₃ | 3-OCH₃ | Cl | H |
| A-1492. | F | CH₃ | 5-F | Cl | H |
| A-1493. | F | CH₃ | 5-CH₃ | Cl | H |
| A-1494. | F | CH₃ | 5-OCH₃ | Cl | H |
| A-1495. | F | OCH₃ | 3-F | Cl | H |
| A-1496. | F | OCH₃ | 3-CH₃ | Cl | H |
| A-1497. | F | OCH₃ | 3-OCH₃ | Cl | H |
| A-1498. | F | OCH₃ | 5-F | Cl | H |
| A-1499. | F | OCH₃ | 5-CH₃ | Cl | H |
| A-1500. | F | OCH₃ | 5-OCH₃ | Cl | H |
| A-1501. | F | CN | 3-F | Cl | H |
| A-1502. | F | CN | 3-CH₃ | Cl | H |
| A-1503. | F | CN | 3-OCH₃ | Cl | H |
| A-1504. | F | CN | 5-F | Cl | H |
| A-1505. | F | CN | 5-CH₃ | Cl | H |
| A-1506. | F | CN | 5-OCH₃ | Cl | H |
| A-1507. | F | CH₂F | 3-F | Cl | H |
| A-1508. | F | CH₂F | 3-CH₃ | Cl | H |
| A-1509. | F | CH₂F | 3-OCH₃ | Cl | H |
| A-1510. | F | CH₂F | 5-F | Cl | H |
| A-1511. | F | CH₂F | 5-CH₃ | Cl | H |
| A-1512. | F | CH₂F | 5-OCH₃ | Cl | H |
| A-1513. | F | CHF₂ | 3-F | Cl | H |
| A-1514. | F | CHF₂ | 3-CH₃ | Cl | H |
| A-1515. | F | CHF₂ | 3-OCH₃ | Cl | H |
| A-1516. | F | CHF₂ | 5-F | Cl | H |
| A-1517. | F | CHF₂ | 5-CH₃ | Cl | H |
| A-1518. | F | CHF₂ | 5-OCH₃ | Cl | H |
| A-1519. | F | CF₃ | 3-F | Cl | H |
| A-1520. | F | CF₃ | 3-CH₃ | Cl | H |
| A-1521. | F | CF₃ | 3-OCH₃ | Cl | H |
| A-1522. | F | CF₃ | 5-F | Cl | H |
| A-1523. | F | CF₃ | 5-CH₃ | Cl | H |
| A-1524. | F | CF₃ | 5-OCH₃ | Cl | H |
| A-1525. | F | OCH₂F | 3-F | Cl | H |
| A-1526. | F | OCH₂F | 3-CH₃ | Cl | H |
| A-1527. | F | OCH₂F | 3-OCH₃ | Cl | H |
| A-1528. | F | OCH₂F | 5-F | Cl | H |
| A-1529. | F | OCH₂F | 5-CH₃ | Cl | H |
| A-1530. | F | OCH₂F | 5-OCH₃ | Cl | H |
| A-1531. | F | OCHF₂ | 3-F | Cl | H |
| A-1532. | F | OCHF₂ | 3-CH₃ | Cl | H |
| A-1533. | F | OCHF₂ | 3-OCH₃ | Cl | H |
| A-1534. | F | OCHF₂ | 5-F | Cl | H |
| A-1535. | F | OCHF₂ | 5-CH₃ | Cl | H |
| A-1536. | F | OCHF₂ | 5-OCH₃ | Cl | H |
| A-1537. | F | OCF₃ | 3-F | Cl | H |
| A-1538. | F | OCF₃ | 3-CH₃ | Cl | H |
| A-1539. | F | OCF₃ | 3-OCH₃ | Cl | H |
| A-1540. | F | OCF₃ | 5-F | Cl | H |
| A-1541. | F | OCF₃ | 5-CH₃ | Cl | H |
| A-1542. | F | OCF₃ | 5-OCH₃ | Cl | H |
| A-1543. | CH₃ | F | 3-F | Cl | H |
| A-1544. | CH₃ | F | 3-CH₃ | Cl | H |
| A-1545. | CH₃ | F | 3-OCH₃ | Cl | H |
| A-1546. | CH₃ | F | 5-F | Cl | H |
| A-1547. | CH₃ | F | 5-CH₃ | Cl | H |
| A-1548. | CH₃ | F | 5-OCH₃ | Cl | H |
| A-1549. | CH₃ | CH₃ | 3-F | Cl | H |
| A-1550. | CH₃ | CH₃ | 3-CH₃ | Cl | H |
| A-1551. | CH₃ | CH₃ | 3-OCH₃ | Cl | H |
| A-1552. | CH₃ | CH₃ | 5-F | Cl | H |
| A-1553. | CH₃ | CH₃ | 5-CH₃ | Cl | H |
| A-1554. | CH₃ | CH₃ | 5-OCH₃ | Cl | H |
| A-1555. | CH₃ | OCH₃ | 3-F | Cl | H |
| A-1556. | CH₃ | OCH₃ | 3-CH₃ | Cl | H |
| A-1557. | CH₃ | OCH₃ | 3-OCH₃ | Cl | H |
| A-1558. | CH₃ | OCH₃ | 5-F | Cl | H |
| A-1559. | CH₃ | OCH₃ | 5-CH₃ | Cl | H |
| A-1560. | CH₃ | OCH₃ | 5-OCH₃ | Cl | H |
| A-1561. | CH₃ | CN | 3-F | Cl | H |
| A-1562. | CH₃ | CN | 3-CH₃ | Cl | H |
| A-1563. | CH₃ | CN | 3-OCH₃ | Cl | H |
| A-1564. | CH₃ | CN | 5-F | Cl | H |
| A-1565. | CH₃ | CN | 5-CH₃ | Cl | H |
| A-1566. | CH₃ | CN | 5-OCH₃ | Cl | H |
| A-1567. | CH₃ | CH₂F | 3-F | Cl | H |
| A-1568. | CH₃ | CH₂F | 3-CH₃ | Cl | H |
| A-1569. | CH₃ | CH₂F | 3-OCH₃ | Cl | H |
| A-1570. | CH₃ | CH₂F | 5-F | Cl | H |
| A-1571. | CH₃ | CH₂F | 5-CH₃ | Cl | H |
| A-1572. | CH₃ | CH₂F | 5-OCH₃ | Cl | H |
| A-1573. | CH₃ | CHF₂ | 3-F | Cl | H |
| A-1574. | CH₃ | CHF₂ | 3-CH₃ | Cl | H |
| A-1575. | CH₃ | CHF₂ | 3-OCH₃ | Cl | H |
| A-1576. | CH₃ | CHF₂ | 5-F | Cl | H |
| A-1577. | CH₃ | CHF₂ | 5-CH₃ | Cl | H |
| A-1578. | CH₃ | CHF₂ | 5-OCH₃ | Cl | H |
| A-1579. | CH₃ | CF₃ | 3-F | Cl | H |
| A-1580. | CH₃ | CF₃ | 3-CH₃ | Cl | H |
| A-1581. | CH₃ | CF₃ | 3-OCH₃ | Cl | H |
| A-1582. | CH₃ | CF₃ | 5-F | Cl | H |
| A-1583. | CH₃ | CF₃ | 5-CH₃ | Cl | H |
| A-1584. | CH₃ | CF₃ | 5-OCH₃ | Cl | H |
| A-1585. | CH₃ | OCH₂F | 3-F | Cl | H |
| A-1586. | CH₃ | OCH₂F | 3-CH₃ | Cl | H |
| A-1587. | CH₃ | OCH₂F | 3-OCH₃ | Cl | H |
| A-1588. | CH₃ | OCH₂F | 5-F | Cl | H |
| A-1589. | CH₃ | OCH₂F | 5-CH₃ | Cl | H |
| A-1590. | CH₃ | OCH₂F | 5-OCH₃ | Cl | H |
| A-1591. | CH₃ | OCHF₂ | 3-F | Cl | H |
| A-1592. | CH₃ | OCHF₂ | 3-CH₃ | Cl | H |
| A-1593. | CH₃ | OCHF₂ | 3-OCH₃ | Cl | H |
| A-1594. | CH₃ | OCHF₂ | 5-F | Cl | H |
| A-1595. | CH₃ | OCHF₂ | 5-CH₃ | Cl | H |
| A-1596. | CH₃ | OCHF₂ | 5-OCH₃ | Cl | H |
| A-1597. | CH₃ | OCF₃ | 3-F | Cl | H |
| A-1598. | CH₃ | OCF₃ | 3-CH₃ | Cl | H |
| A-1599. | CH₃ | OCF₃ | 3-OCH₃ | Cl | H |
| A-1600. | CH₃ | OCF₃ | 5-F | Cl | H |
| A-1601. | CH₃ | OCF₃ | 5-CH₃ | Cl | H |
| A-1602. | CH₃ | OCF₃ | 5-OCH₃ | Cl | H |
| A-1603. | OCH₃ | F | 3-F | Cl | H |
| A-1604. | OCH₃ | F | 3-CH₃ | Cl | H |
| A-1605. | OCH₃ | F | 3-OCH₃ | Cl | H |
| A-1606. | OCH₃ | F | 5-F | Cl | H |
| A-1607. | OCH₃ | F | 5-CH₃ | Cl | H |
| A-1608. | OCH₃ | F | 5-OCH₃ | Cl | H |
| A-1609. | OCH₃ | CH₃ | 3-F | Cl | H |
| A-1610. | OCH₃ | CH₃ | 3-CH₃ | Cl | H |
| A-1611. | OCH₃ | CH₃ | 3-OCH₃ | Cl | H |
| A-1612. | OCH₃ | CH₃ | 5-F | Cl | H |
| A-1613. | OCH₃ | CH₃ | 5-CH₃ | Cl | H |
| A-1614. | OCH₃ | CH₃ | 5-OCH₃ | Cl | H |
| A-1615. | OCH₃ | OCH₃ | 3-F | Cl | H |
| A-1616. | OCH₃ | OCH₃ | 3-CH₃ | Cl | H |
| A-1617. | OCH₃ | OCH₃ | 3-OCH₃ | Cl | H |
| A-1618. | OCH₃ | OCH₃ | 5-F | Cl | H |
| A-1619. | OCH₃ | OCH₃ | 5-CH₃ | Cl | H |
| A-1620. | OCH₃ | OCH₃ | 5-OCH₃ | Cl | H |
| A-1621. | OCH₃ | CN | 3-F | Cl | H |
| A-1622. | OCH₃ | CN | 3-CH₃ | Cl | H |
| A-1623. | OCH₃ | CN | 3-OCH₃ | Cl | H |
| A-1624. | OCH₃ | CN | 5-F | Cl | H |

TABLE A-continued

| Example No. | R¹ | R² | R³ | R⁶ | R⁷ |
|---|---|---|---|---|---|
| A-1625. | OCH$_3$ | CN | 5-CH$_3$ | Cl | H |
| A-1626. | OCH$_3$ | CN | 5-OCH$_3$ | Cl | H |
| A-1627. | OCH$_3$ | CH$_2$F | 3-F | Cl | H |
| A-1628. | OCH$_3$ | CH$_2$F | 3-CH$_3$ | Cl | H |
| A-1629. | OCH$_3$ | CH$_2$F | 3-OCH$_3$ | Cl | H |
| A-1630. | OCH$_3$ | CH$_2$F | 5-F | Cl | H |
| A-1631. | OCH$_3$ | CH$_2$F | 5-CH$_3$ | Cl | H |
| A-1632. | OCH$_3$ | CH$_2$F | 5-OCH$_3$ | Cl | H |
| A-1633. | OCH$_3$ | CHF$_2$ | 3-F | Cl | H |
| A-1634. | OCH$_3$ | CHF$_2$ | 3-CH$_3$ | Cl | H |
| A-1635. | OCH$_3$ | CHF$_2$ | 3-OCH$_3$ | Cl | H |
| A-1636. | OCH$_3$ | CHF$_2$ | 5-F | Cl | H |
| A-1637. | OCH$_3$ | CHF$_2$ | 5-CH$_3$ | Cl | H |
| A-1638. | OCH$_3$ | CHF$_2$ | 5-OCH$_3$ | Cl | H |
| A-1639. | OCH$_3$ | CF$_3$ | 3-F | Cl | H |
| A-1640. | OCH$_3$ | CF$_3$ | 3-CH$_3$ | Cl | H |
| A-1641. | OCH$_3$ | CF$_3$ | 3-OCH$_3$ | Cl | H |
| A-1642. | OCH$_3$ | CF$_3$ | 5-F | Cl | H |
| A-1643. | OCH$_3$ | CF$_3$ | 5-CH$_3$ | Cl | H |
| A-1644. | OCH$_3$ | CF$_3$ | 5-OCH$_3$ | Cl | H |
| A-1645. | OCH$_3$ | OCH$_2$F | 3-F | Cl | H |
| A-1646. | OCH$_3$ | OCH$_2$F | 3-CH$_3$ | Cl | H |
| A-1647. | OCH$_3$ | OCH$_2$F | 3-OCH$_3$ | Cl | H |
| A-1648. | OCH$_3$ | OCH$_2$F | 5-F | Cl | H |
| A-1649. | OCH$_3$ | OCH$_2$F | 5-CH$_3$ | Cl | H |
| A-1650. | OCH$_3$ | OCH$_2$F | 5-OCH$_3$ | Cl | H |
| A-1651. | OCH$_3$ | OCHF$_2$ | 3-F | Cl | H |
| A-1652. | OCH$_3$ | OCHF$_2$ | 3-CH$_3$ | Cl | H |
| A-1653. | OCH$_3$ | OCHF$_2$ | 3-OCH$_3$ | Cl | H |
| A-1654. | OCH$_3$ | OCHF$_2$ | 5-F | Cl | H |
| A-1655. | OCH$_3$ | OCHF$_2$ | 5-CH$_3$ | Cl | H |
| A-1656. | OCH$_3$ | OCHF$_2$ | 5-OCH$_3$ | Cl | H |
| A-1657. | OCH$_3$ | OCF$_3$ | 3-F | Cl | H |
| A-1658. | OCH$_3$ | OCF$_3$ | 3-CH$_3$ | Cl | H |
| A-1659. | OCH$_3$ | OCF$_3$ | 3-OCH$_3$ | Cl | H |
| A-1660. | OCH$_3$ | OCF$_3$ | 5-F | Cl | H |
| A-1661. | OCH$_3$ | OCF$_3$ | 5-CH$_3$ | Cl | H |
| A-1662. | OCH$_3$ | OCF$_3$ | 5-OCH$_3$ | Cl | H |
| A-1663. | CH$_2$F | F | 3-F | Cl | H |
| A-1664. | CH$_2$F | F | 3-CH$_3$ | Cl | H |
| A-1665. | CH$_2$F | F | 3-OCH$_3$ | Cl | H |
| A-1666. | CH$_2$F | F | 5-F | Cl | H |
| A-1667. | CH$_2$F | F | 5-CH$_3$ | Cl | H |
| A-1668. | CH$_2$F | F | 5-OCH$_3$ | Cl | H |
| A-1669. | CH$_2$F | CH$_3$ | 3-F | Cl | H |
| A-1670. | CH$_2$F | CH$_3$ | 3-CH$_3$ | Cl | H |
| A-1671. | CH$_2$F | CH$_3$ | 3-OCH$_3$ | Cl | H |
| A-1672. | CH$_2$F | CH$_3$ | 5-F | Cl | H |
| A-1673. | CH$_2$F | CH$_3$ | 5-CH$_3$ | Cl | H |
| A-1674. | CH$_2$F | CH$_3$ | 5-OCH$_3$ | Cl | H |
| A-1675. | CH$_2$F | OCH$_3$ | 3-F | Cl | H |
| A-1676. | CH$_2$F | OCH$_3$ | 3-CH$_3$ | Cl | H |
| A-1677. | CH$_2$F | OCH$_3$ | 3-OCH$_3$ | Cl | H |
| A-1678. | CH$_2$F | OCH$_3$ | 5-F | Cl | H |
| A-1679. | CH$_2$F | OCH$_3$ | 5-CH$_3$ | Cl | H |
| A-1680. | CH$_2$F | OCH$_3$ | 5-OCH$_3$ | Cl | H |
| A-1681. | CH$_2$F | CN | 3-F | Cl | H |
| A-1682. | CH$_2$F | CN | 3-CH$_3$ | Cl | H |
| A-1683. | CH$_2$F | CN | 3-OCH$_3$ | Cl | H |
| A-1684. | CH$_2$F | CN | 5-F | Cl | H |
| A-1685. | CH$_2$F | CN | 5-CH$_3$ | Cl | H |
| A-1686. | CH$_2$F | CN | 5-OCH$_3$ | Cl | H |
| A-1687. | CH$_2$F | CH$_2$F | 3-F | Cl | H |
| A-1688. | CH$_2$F | CH$_2$F | 3-CH$_3$ | Cl | H |
| A-1689. | CH$_2$F | CH$_2$F | 3-OCH$_3$ | Cl | H |
| A-1690. | CH$_2$F | CH$_2$F | 5-F | Cl | H |
| A-1691. | CH$_2$F | CH$_2$F | 5-CH$_3$ | Cl | H |
| A-1692. | CH$_2$F | CH$_2$F | 5-OCH$_3$ | Cl | H |
| A-1693. | CH$_2$F | CHF$_2$ | 3-F | Cl | H |
| A-1694. | CH$_2$F | CHF$_2$ | 3-CH$_3$ | Cl | H |
| A-1695. | CH$_2$F | CHF$_2$ | 3-OCH$_3$ | Cl | H |
| A-1696. | CH$_2$F | CHF$_2$ | 5-F | Cl | H |
| A-1697. | CH$_2$F | CHF$_2$ | 5-CH$_3$ | Cl | H |
| A-1698. | CH$_2$F | CHF$_2$ | 5-OCH$_3$ | Cl | H |
| A-1699. | CH$_2$F | CF$_3$ | 3-F | Cl | H |
| A-1700. | CH$_2$F | CF$_3$ | 3-CH$_3$ | Cl | H |
| A-1701. | CH$_2$F | CF$_3$ | 3-OCH$_3$ | Cl | H |
| A-1702. | CH$_2$F | CF$_3$ | 5-F | Cl | H |
| A-1703. | CH$_2$F | CF$_3$ | 5-CH$_3$ | Cl | H |
| A-1704. | CH$_2$F | CF$_3$ | 5-OCH$_3$ | Cl | H |
| A-1705. | CH$_2$F | OCH$_2$F | 3-F | Cl | H |
| A-1706. | CH$_2$F | OCH$_2$F | 3-CH$_3$ | Cl | H |
| A-1707. | CH$_2$F | OCH$_2$F | 3-OCH$_3$ | Cl | H |
| A-1708. | CH$_2$F | OCH$_2$F | 5-F | Cl | H |
| A-1709. | CH$_2$F | OCH$_2$F | 5-CH$_3$ | Cl | H |
| A-1710. | CH$_2$F | OCH$_2$F | 5-OCH$_3$ | Cl | H |
| A-1711. | CH$_2$F | OCHF$_2$ | 3-F | Cl | H |
| A-1712. | CH$_2$F | OCHF$_2$ | 3-CH$_3$ | Cl | H |
| A-1713. | CH$_2$F | OCHF$_2$ | 3-OCH$_3$ | Cl | H |
| A-1714. | CH$_2$F | OCHF$_2$ | 5-F | Cl | H |
| A-1715. | CH$_2$F | OCHF$_2$ | 5-CH$_3$ | Cl | H |
| A-1716. | CH$_2$F | OCHF$_2$ | 5-OCH$_3$ | Cl | H |
| A-1717. | CH$_2$F | OCF$_3$ | 3-F | Cl | H |
| A-1718. | CH$_2$F | OCF$_3$ | 3-CH$_3$ | Cl | H |
| A-1719. | CH$_2$F | OCF$_3$ | 3-OCH$_3$ | Cl | H |
| A-1720. | CH$_2$F | OCF$_3$ | 5-F | Cl | H |
| A-1721. | CH$_2$F | OCF$_3$ | 5-CH$_3$ | Cl | H |
| A-1722. | CH$_2$F | OCF$_3$ | 5-OCH$_3$ | Cl | H |
| A-1723. | CHF$_2$ | F | 3-F | Cl | H |
| A-1724. | CHF$_2$ | F | 3-CH$_3$ | Cl | H |
| A-1725. | CHF$_2$ | F | 3-OCH$_3$ | Cl | H |
| A-1726. | CHF$_2$ | F | 5-F | Cl | H |
| A-1727. | CHF$_2$ | F | 5-CH$_3$ | Cl | H |
| A-1728. | CHF$_2$ | F | 5-OCH$_3$ | Cl | H |
| A-1729. | CHF$_2$ | CH$_3$ | 3-F | Cl | H |
| A-1730. | CHF$_2$ | CH$_3$ | 3-CH$_3$ | Cl | H |
| A-1731. | CHF$_2$ | CH$_3$ | 3-OCH$_3$ | Cl | H |
| A-1732. | CHF$_2$ | CH$_3$ | 5-F | Cl | H |
| A-1733. | CHF$_2$ | CH$_3$ | 5-CH$_3$ | Cl | H |
| A-1734. | CHF$_2$ | CH$_3$ | 5-OCH$_3$ | Cl | H |
| A-1735. | CHF$_2$ | OCH$_3$ | 3-F | Cl | H |
| A-1736. | CHF$_2$ | OCH$_3$ | 3-CH$_3$ | Cl | H |
| A-1737. | CHF$_2$ | OCH$_3$ | 3-OCH$_3$ | Cl | H |
| A-1738. | CHF$_2$ | OCH$_3$ | 5-F | Cl | H |
| A-1739. | CHF$_2$ | OCH$_3$ | 5-CH$_3$ | Cl | H |
| A-1740. | CHF$_2$ | OCH$_3$ | 5-OCH$_3$ | Cl | H |
| A-1741. | CHF$_2$ | CN | 3-F | Cl | H |
| A-1742. | CHF$_2$ | CN | 3-CH$_3$ | Cl | H |
| A-1743. | CHF$_2$ | CN | 3-OCH$_3$ | Cl | H |
| A-1744. | CHF$_2$ | CN | 5-F | Cl | H |
| A-1745. | CHF$_2$ | CN | 5-CH$_3$ | Cl | H |
| A-1746. | CHF$_2$ | CN | 5-OCH$_3$ | Cl | H |
| A-1747. | CHF$_2$ | CH$_2$F | 3-F | Cl | H |
| A-1748. | CHF$_2$ | CH$_2$F | 3-CH$_3$ | Cl | H |
| A-1749. | CHF$_2$ | CH$_2$F | 3-OCH$_3$ | Cl | H |
| A-1750. | CHF$_2$ | CH$_2$F | 5-F | Cl | H |
| A-1751. | CHF$_2$ | CH$_2$F | 5-CH$_3$ | Cl | H |
| A-1752. | CHF$_2$ | CH$_2$F | 5-OCH$_3$ | Cl | H |
| A-1753. | CHF$_2$ | CHF$_2$ | 3-F | Cl | H |
| A-1754. | CHF$_2$ | CHF$_2$ | 3-CH$_3$ | Cl | H |
| A-1755. | CHF$_2$ | CHF$_2$ | 3-OCH$_3$ | Cl | H |
| A-1756. | CHF$_2$ | CHF$_2$ | 5-F | Cl | H |
| A-1757. | CHF$_2$ | CHF$_2$ | 5-CH$_3$ | Cl | H |
| A-1758. | CHF$_2$ | CHF$_2$ | 5-OCH$_3$ | Cl | H |
| A-1759. | CHF$_2$ | CF$_3$ | 3-F | Cl | H |
| A-1760. | CHF$_2$ | CF$_3$ | 3-CH$_3$ | Cl | H |
| A-1761. | CHF$_2$ | CF$_3$ | 3-OCH$_3$ | Cl | H |
| A-1762. | CHF$_2$ | CF$_3$ | 5-F | Cl | H |
| A-1763. | CHF$_2$ | CF$_3$ | 5-CH$_3$ | Cl | H |
| A-1764. | CHF$_2$ | CF$_3$ | 5-OCH$_3$ | Cl | H |
| A-1765. | CHF$_2$ | OCH$_2$F | 3-F | Cl | H |
| A-1766. | CHF$_2$ | OCH$_2$F | 3-CH$_3$ | Cl | H |
| A-1767. | CHF$_2$ | OCH$_2$F | 3-OCH$_3$ | Cl | H |
| A-1768. | CHF$_2$ | OCH$_2$F | 5-F | Cl | H |
| A-1769. | CHF$_2$ | OCH$_2$F | 5-CH$_3$ | Cl | H |
| A-1770. | CHF$_2$ | OCH$_2$F | 5-OCH$_3$ | Cl | H |
| A-1771. | CHF$_2$ | OCHF$_2$ | 3-F | Cl | H |
| A-1772. | CHF$_2$ | OCHF$_2$ | 3-CH$_3$ | Cl | H |
| A-1773. | CHF$_2$ | OCHF$_2$ | 3-OCH$_3$ | Cl | H |
| A-1774. | CHF$_2$ | OCHF$_2$ | 5-F | Cl | H |
| A-1775. | CHF$_2$ | OCHF$_2$ | 5-CH$_3$ | Cl | H |
| A-1776. | CHF$_2$ | OCHF$_2$ | 5-OCH$_3$ | Cl | H |
| A-1777. | CHF$_2$ | OCF$_3$ | 3-F | Cl | H |
| A-1778. | CHF$_2$ | OCF$_3$ | 3-CH$_3$ | Cl | H |
| A-1779. | CHF$_2$ | OCF$_3$ | 3-OCH$_3$ | Cl | H |
| A-1780. | CHF$_2$ | OCF$_3$ | 5-F | Cl | H |

TABLE A-continued

| Example No. | R¹ | R² | R³ | R⁶ | R⁷ |
|---|---|---|---|---|---|
| A-1781. | CHF$_2$ | OCF$_3$ | 5-CH$_3$ | Cl | H |
| A-1782. | CHF$_2$ | OCF$_3$ | 5-OCH$_3$ | Cl | H |
| A-1783. | CF$_3$ | F | 3-F | Cl | H |
| A-1784. | CF$_3$ | F | 3-CH$_3$ | Cl | H |
| A-1785. | CF$_3$ | F | 3-OCH$_3$ | Cl | H |
| A-1786. | CF$_3$ | F | 5-F | Cl | H |
| A-1787. | CF$_3$ | F | 5-CH$_3$ | Cl | H |
| A-1788. | CF$_3$ | F | 5-OCH$_3$ | Cl | H |
| A-1789. | CF$_3$ | CH$_3$ | 3-F | Cl | H |
| A-1790. | CF$_3$ | CH$_3$ | 3-CH$_3$ | Cl | H |
| A-1791. | CF$_3$ | CH$_3$ | 3-OCH$_3$ | Cl | H |
| A-1792. | CF$_3$ | CH$_3$ | 5-F | Cl | H |
| A-1793. | CF$_3$ | CH$_3$ | 5-CH$_3$ | Cl | H |
| A-1794. | CF$_3$ | CH$_3$ | 5-OCH$_3$ | Cl | H |
| A-1795. | CF$_3$ | OCH$_3$ | 3-F | Cl | H |
| A-1796. | CF$_3$ | OCH$_3$ | 3-CH$_3$ | Cl | H |
| A-1797. | CF$_3$ | OCH$_3$ | 3-OCH$_3$ | Cl | H |
| A-1798. | CF$_3$ | OCH$_3$ | 5-F | Cl | H |
| A-1799. | CF$_3$ | OCH$_3$ | 5-CH$_3$ | Cl | H |
| A-1800. | CF$_3$ | OCH$_3$ | 5-OCH$_3$ | Cl | H |
| A-1801. | CF$_3$ | CN | 3-F | Cl | H |
| A-1802. | CF$_3$ | CN | 3-CH$_3$ | Cl | H |
| A-1803. | CF$_3$ | CN | 3-OCH$_3$ | Cl | H |
| A-1804. | CF$_3$ | CN | 5-F | Cl | H |
| A-1805. | CF$_3$ | CN | 5-CH$_3$ | Cl | H |
| A-1806. | CF$_3$ | CN | 5-OCH$_3$ | Cl | H |
| A-1807. | CF$_3$ | CH$_2$F | 3-F | Cl | H |
| A-1808. | CF$_3$ | CH$_2$F | 3-CH$_3$ | Cl | H |
| A-1809. | CF$_3$ | CH$_2$F | 3-OCH$_3$ | Cl | H |
| A-1810. | CF$_3$ | CH$_2$F | 5-F | Cl | H |
| A-1811. | CF$_3$ | CH$_2$F | 5-CH$_3$ | Cl | H |
| A-1812. | CF$_3$ | CH$_2$F | 5-OCH$_3$ | Cl | H |
| A-1813. | CF$_3$ | CHF$_2$ | 3-F | Cl | H |
| A-1814. | CF$_3$ | CHF$_2$ | 3-CH$_3$ | Cl | H |
| A-1815. | CF$_3$ | CHF$_2$ | 3-OCH$_3$ | Cl | H |
| A-1816. | CF$_3$ | CHF$_2$ | 5-F | Cl | H |
| A-1817. | CF$_3$ | CHF$_2$ | 5-CH$_3$ | Cl | H |
| A-1818. | CF$_3$ | CHF$_2$ | 5-OCH$_3$ | Cl | H |
| A-1819. | CF$_3$ | CF$_3$ | 3-F | Cl | H |
| A-1820. | CF$_3$ | CF$_3$ | 3-CH$_3$ | Cl | H |
| A-1821. | CF$_3$ | CF$_3$ | 3-OCH$_3$ | Cl | H |
| A-1822. | CF$_3$ | CF$_3$ | 5-F | Cl | H |
| A-1823. | CF$_3$ | CF$_3$ | 5-CH$_3$ | Cl | H |
| A-1824. | CF$_3$ | CF$_3$ | 5-OCH$_3$ | Cl | H |
| A-1825. | CF$_3$ | OCH$_2$F | 3-F | Cl | H |
| A-1826. | CF$_3$ | OCH$_2$F | 3-CH$_3$ | Cl | H |
| A-1827. | CF$_3$ | OCH$_2$F | 3-OCH$_3$ | Cl | H |
| A-1828. | CF$_3$ | OCH$_2$F | 5-F | Cl | H |
| A-1829. | CF$_3$ | OCH$_2$F | 5-CH$_3$ | Cl | H |
| A-1830. | CF$_3$ | OCH$_2$F | 5-OCH$_3$ | Cl | H |
| A-1831. | CF$_3$ | OCHF$_2$ | 3-F | Cl | H |
| A-1832. | CF$_3$ | OCHF$_2$ | 3-CH$_3$ | Cl | H |
| A-1833. | CF$_3$ | OCHF$_2$ | 3-OCH$_3$ | Cl | H |
| A-1834. | CF$_3$ | OCHF$_2$ | 5-F | Cl | H |
| A-1835. | CF$_3$ | OCHF$_2$ | 5-CH$_3$ | Cl | H |
| A-1836. | CF$_3$ | OCHF$_2$ | 5-OCH$_3$ | Cl | H |
| A-1837. | CF$_3$ | OCF$_3$ | 3-F | Cl | H |
| A-1838. | CF$_3$ | OCF$_3$ | 3-CH$_3$ | Cl | H |
| A-1839. | CF$_3$ | OCF$_3$ | 3-OCH$_3$ | Cl | H |
| A-1840. | CF$_3$ | OCF$_3$ | 5-F | Cl | H |
| A-1841. | CF$_3$ | OCF$_3$ | 5-CH$_3$ | Cl | H |
| A-1842. | CF$_3$ | OCF$_3$ | 5-OCH$_3$ | Cl | H |
| A-1843. | OCH$_2$F | F | 3-F | Cl | H |
| A-1844. | OCH$_2$F | F | 3-CH$_3$ | Cl | H |
| A-1845. | OCH$_2$F | F | 3-OCH$_3$ | Cl | H |
| A-1846. | OCH$_2$F | F | 5-F | Cl | H |
| A-1847. | OCH$_2$F | F | 5-CH$_3$ | Cl | H |
| A-1848. | OCH$_2$F | F | 5-OCH$_3$ | Cl | H |
| A-1849. | OCH$_2$F | CH$_3$ | 3-F | Cl | H |
| A-1850. | OCH$_2$F | CH$_3$ | 3-CH$_3$ | Cl | H |
| A-1851. | OCH$_2$F | CH$_3$ | 3-OCH$_3$ | Cl | H |
| A-1852. | OCH$_2$F | CH$_3$ | 5-F | Cl | H |
| A-1853. | OCH$_2$F | CH$_3$ | 5-CH$_3$ | Cl | H |
| A-1854. | OCH$_2$F | CH$_3$ | 5-OCH$_3$ | Cl | H |
| A-1855. | OCH$_2$F | OCH$_3$ | 3-F | Cl | H |
| A-1856. | OCH$_2$F | OCH$_3$ | 3-CH$_3$ | Cl | H |
| A-1857. | OCH$_2$F | OCH$_3$ | 3-OCH$_3$ | Cl | H |
| A-1858. | OCH$_2$F | OCH$_3$ | 5-F | Cl | H |
| A-1859. | OCH$_2$F | OCH$_3$ | 5-CH$_3$ | Cl | H |
| A-1860. | OCH$_2$F | OCH$_3$ | 5-OCH$_3$ | Cl | H |
| A-1861. | OCH$_2$F | CN | 3-F | Cl | H |
| A-1862. | OCH$_2$F | CN | 3-CH$_3$ | Cl | H |
| A-1863. | OCH$_2$F | CN | 3-OCH$_3$ | Cl | H |
| A-1864. | OCH$_2$F | CN | 5-F | Cl | H |
| A-1865. | OCH$_2$F | CN | 5-CH$_3$ | Cl | H |
| A-1866. | OCH$_2$F | CN | 5-OCH$_3$ | Cl | H |
| A-1867. | OCH$_2$F | CH$_2$F | 3-F | Cl | H |
| A-1868. | OCH$_2$F | CH$_2$F | 3-CH$_3$ | Cl | H |
| A-1869. | OCH$_2$F | CH$_2$F | 3-OCH$_3$ | Cl | H |
| A-1870. | OCH$_2$F | CH$_2$F | 5-F | Cl | H |
| A-1871. | OCH$_2$F | CH$_2$F | 5-CH$_3$ | Cl | H |
| A-1872. | OCH$_2$F | CH$_2$F | 5-OCH$_3$ | Cl | H |
| A-1873. | OCH$_2$F | CHF$_2$ | 3-F | Cl | H |
| A-1874. | OCH$_2$F | CHF$_2$ | 3-CH$_3$ | Cl | H |
| A-1875. | OCH$_2$F | CHF$_2$ | 3-OCH$_3$ | Cl | H |
| A-1876. | OCH$_2$F | CHF$_2$ | 5-F | Cl | H |
| A-1877. | OCH$_2$F | CHF$_2$ | 5-CH$_3$ | Cl | H |
| A-1878. | OCH$_2$F | CHF$_2$ | 5-OCH$_3$ | Cl | H |
| A-1879. | OCH$_2$F | CF$_3$ | 3-F | Cl | H |
| A-1880. | OCH$_2$F | CF$_3$ | 3-CH$_3$ | Cl | H |
| A-1881. | OCH$_2$F | CF$_3$ | 3-OCH$_3$ | Cl | H |
| A-1882. | OCH$_2$F | CF$_3$ | 5-F | Cl | H |
| A-1883. | OCH$_2$F | CF$_3$ | 5-CH$_3$ | Cl | H |
| A-1884. | OCH$_2$F | CF$_3$ | 5-OCH$_3$ | Cl | H |
| A-1885. | OCH$_2$F | OCH$_2$F | 3-F | Cl | H |
| A-1886. | OCH$_2$F | OCH$_2$F | 3-CH$_3$ | Cl | H |
| A-1887. | OCH$_2$F | OCH$_2$F | 3-OCH$_3$ | Cl | H |
| A-1888. | OCH$_2$F | OCH$_2$F | 5-F | Cl | H |
| A-1889. | OCH$_2$F | OCH$_2$F | 5-CH$_3$ | Cl | H |
| A-1890. | OCH$_2$F | OCH$_2$F | 5-OCH$_3$ | Cl | H |
| A-1891. | OCH$_2$F | OCHF$_2$ | 3-F | Cl | H |
| A-1892. | OCH$_2$F | OCHF$_2$ | 3-CH$_3$ | Cl | H |
| A-1893. | OCH$_2$F | OCHF$_2$ | 3-OCH$_3$ | Cl | H |
| A-1894. | OCH$_2$F | OCHF$_2$ | 5-F | Cl | H |
| A-1895. | OCH$_2$F | OCHF$_2$ | 5-CH$_3$ | Cl | H |
| A-1896. | OCH$_2$F | OCHF$_2$ | 5-OCH$_3$ | Cl | H |
| A-1897. | OCH$_2$F | OCF$_3$ | 3-F | Cl | H |
| A-1898. | OCH$_2$F | OCF$_3$ | 3-CH$_3$ | Cl | H |
| A-1899. | OCH$_2$F | OCF$_3$ | 3-OCH$_3$ | Cl | H |
| A-1900. | OCH$_2$F | OCF$_3$ | 5-F | Cl | H |
| A-1901. | OCH$_2$F | OCF$_3$ | 5-CH$_3$ | Cl | H |
| A-1902. | OCH$_2$F | OCF$_3$ | 5-OCH$_3$ | Cl | H |
| A-1903. | OCHF$_2$ | F | 3-F | Cl | H |
| A-1904. | OCHF$_2$ | F | 3-CH$_3$ | Cl | H |
| A-1905. | OCHF$_2$ | F | 3-OCH$_3$ | Cl | H |
| A-1906. | OCHF$_2$ | F | 5-F | Cl | H |
| A-1907. | OCHF$_2$ | F | 5-CH$_3$ | Cl | H |
| A-1908. | OCHF$_2$ | F | 5-OCH$_3$ | Cl | H |
| A-1909. | OCHF$_2$ | CH$_3$ | 3-F | Cl | H |
| A-1910. | OCHF$_2$ | CH$_3$ | 3-CH$_3$ | Cl | H |
| A-1911. | OCHF$_2$ | CH$_3$ | 3-OCH$_3$ | Cl | H |
| A-1912. | OCHF$_2$ | CH$_3$ | 5-F | Cl | H |
| A-1913. | OCHF$_2$ | CH$_3$ | 5-CH$_3$ | Cl | H |
| A-1914. | OCHF$_2$ | CH$_3$ | 5-OCH$_3$ | Cl | H |
| A-1915. | OCHF$_2$ | OCH$_3$ | 3-F | Cl | H |
| A-1916. | OCHF$_2$ | OCH$_3$ | 3-CH$_3$ | Cl | H |
| A-1917. | OCHF$_2$ | OCH$_3$ | 3-OCH$_3$ | Cl | H |
| A-1918. | OCHF$_2$ | OCH$_3$ | 5-F | Cl | H |
| A-1919. | OCHF$_2$ | OCH$_3$ | 5-CH$_3$ | Cl | H |
| A-1920. | OCHF$_2$ | OCH$_3$ | 5-OCH$_3$ | Cl | H |
| A-1921. | OCHF$_2$ | CN | 3-F | Cl | H |
| A-1922. | OCHF$_2$ | CN | 3-CH$_3$ | Cl | H |
| A-1923. | OCHF$_2$ | CN | 3-OCH$_3$ | Cl | H |
| A-1924. | OCHF$_2$ | CN | 5-F | Cl | H |
| A-1925. | OCHF$_2$ | CN | 5-CH$_3$ | Cl | H |
| A-1926. | OCHF$_2$ | CN | 5-OCH$_3$ | Cl | H |
| A-1927. | OCHF$_2$ | CH$_2$F | 3-F | Cl | H |
| A-1928. | OCHF$_2$ | CH$_2$F | 3-CH$_3$ | Cl | H |
| A-1929. | OCHF$_2$ | CH$_2$F | 3-OCH$_3$ | Cl | H |
| A-1930. | OCHF$_2$ | CH$_2$F | 5-F | Cl | H |
| A-1931. | OCHF$_2$ | CH$_2$F | 5-CH$_3$ | Cl | H |
| A-1932. | OCHF$_2$ | CH$_2$F | 5-OCH$_3$ | Cl | H |
| A-1933. | OCHF$_2$ | CHF$_2$ | 3-F | Cl | H |
| A-1934. | OCHF$_2$ | CHF$_2$ | 3-CH$_3$ | Cl | H |
| A-1935. | OCHF$_2$ | CHF$_2$ | 3-OCH$_3$ | Cl | H |
| A-1936. | OCHF$_2$ | CHF$_2$ | 5-F | Cl | H |

TABLE A-continued

| Example No. | R¹ | R² | R³ | R⁶ | R⁷ |
|---|---|---|---|---|---|
| A-1937. | OCHF₂ | CHF₂ | 5-CH₃ | Cl | H |
| A-1938. | OCHF₂ | CHF₂ | 5-OCH₃ | Cl | H |
| A-1939. | OCHF₂ | CF₃ | 3-F | Cl | H |
| A-1940. | OCHF₂ | CF₃ | 3-CH₃ | Cl | H |
| A-1941. | OCHF₂ | CF₃ | 3-OCH₃ | Cl | H |
| A-1942. | OCHF₂ | CF₃ | 5-F | Cl | H |
| A-1943. | OCHF₂ | CF₃ | 5-CH₃ | Cl | H |
| A-1944. | OCHF₂ | CF₃ | 5-OCH₃ | Cl | H |
| A-1945. | OCHF₂ | OCH₂F | 3-F | Cl | H |
| A-1946. | OCHF₂ | OCH₂F | 3-CH₃ | Cl | H |
| A-1947. | OCHF₂ | OCH₂F | 3-OCH₃ | Cl | H |
| A-1948. | OCHF₂ | OCH₂F | 5-F | Cl | H |
| A-1949. | OCHF₂ | OCH₂F | 5-CH₃ | Cl | H |
| A-1950. | OCHF₂ | OCH₂F | 5-OCH₃ | Cl | H |
| A-1951. | OCHF₂ | OCHF₂ | 3-F | Cl | H |
| A-1952. | OCHF₂ | OCHF₂ | 3-CH₃ | Cl | H |
| A-1953. | OCHF₂ | OCHF₂ | 3-OCH₃ | Cl | H |
| A-1954. | OCHF₂ | OCHF₂ | 5-F | Cl | H |
| A-1955. | OCHF₂ | OCHF₂ | 5-CH₃ | Cl | H |
| A-1956. | OCHF₂ | OCHF₂ | 5-OCH₃ | Cl | H |
| A-1957. | OCHF₂ | OCF₃ | 3-F | Cl | H |
| A-1958. | OCHF₂ | OCF₃ | 3-CH₃ | Cl | H |
| A-1959. | OCHF₂ | OCF₃ | 3-OCH₃ | Cl | H |
| A-1960. | OCHF₂ | OCF₃ | 5-F | Cl | H |
| A-1961. | OCHF₂ | OCF₃ | 5-CH₃ | Cl | H |
| A-1962. | OCHF₂ | OCF₃ | 5-OCH₃ | Cl | H |
| A-1963. | OCF₃ | F | 3-F | Cl | H |
| A-1964. | OCF₃ | F | 3-CH₃ | Cl | H |
| A-1965. | OCF₃ | F | 3-OCH₃ | Cl | H |
| A-1966. | OCF₃ | F | 5-F | Cl | H |
| A-1967. | OCF₃ | F | 5-CH₃ | Cl | H |
| A-1968. | OCF₃ | F | 5-OCH₃ | Cl | H |
| A-1969. | OCF₃ | CH₃ | 3-F | Cl | H |
| A-1970. | OCF₃ | CH₃ | 3-CH₃ | Cl | H |
| A-1971. | OCF₃ | CH₃ | 3-OCH₃ | Cl | H |
| A-1972. | OCF₃ | CH₃ | 5-F | Cl | H |
| A-1973. | OCF₃ | CH₃ | 5-CH₃ | Cl | H |
| A-1974. | OCF₃ | CH₃ | 5-OCH₃ | Cl | H |
| A-1975. | OCF₃ | OCH₃ | 3-F | Cl | H |
| A-1976. | OCF₃ | OCH₃ | 3-CH₃ | Cl | H |
| A-1977. | OCF₃ | OCH₃ | 3-OCH₃ | Cl | H |
| A-1978. | OCF₃ | OCH₃ | 5-F | Cl | H |
| A-1979. | OCF₃ | OCH₃ | 5-CH₃ | Cl | H |
| A-1980. | OCF₃ | OCH₃ | 5-OCH₃ | Cl | H |
| A-1981. | OCF₃ | CN | 3-F | Cl | H |
| A-1982. | OCF₃ | CN | 3-CH₃ | Cl | H |
| A-1983. | OCF₃ | CN | 3-OCH₃ | Cl | H |
| A-1984. | OCF₃ | CN | 5-F | Cl | H |
| A-1985. | OCF₃ | CN | 5-CH₃ | Cl | H |
| A-1986. | OCF₃ | CN | 5-OCH₃ | Cl | H |
| A-1987. | OCF₃ | CH₂F | 3-F | Cl | H |
| A-1988. | OCF₃ | CH₂F | 3-CH₃ | Cl | H |
| A-1989. | OCF₃ | CH₂F | 3-OCH₃ | Cl | H |
| A-1990. | OCF₃ | CH₂F | 5-F | Cl | H |
| A-1991. | OCF₃ | CH₂F | 5-CH₃ | Cl | H |
| A-1992. | OCF₃ | CH₂F | 5-OCH₃ | Cl | H |
| A-1993. | OCF₃ | CHF₂ | 3-F | Cl | H |
| A-1994. | OCF₃ | CHF₂ | 3-CH₃ | Cl | H |
| A-1995. | OCF₃ | CHF₂ | 3-OCH₃ | Cl | H |
| A-1996. | OCF₃ | CHF₂ | 5-F | Cl | H |
| A-1997. | OCF₃ | CHF₂ | 5-CH₃ | Cl | H |
| A-1998. | OCF₃ | CHF₂ | 5-OCH₃ | Cl | H |
| A-1999. | OCF₃ | CF₃ | 3-F | Cl | H |
| A-2000. | OCF₃ | CF₃ | 3-CH₃ | Cl | H |
| A-2001. | OCF₃ | CF₃ | 3-OCH₃ | Cl | H |
| A-2002. | OCF₃ | CF₃ | 5-F | Cl | H |
| A-2003. | OCF₃ | CF₃ | 5-CH₃ | Cl | H |
| A-2004. | OCF₃ | CF₃ | 5-OCH₃ | Cl | H |
| A-2005. | OCF₃ | OCH₂F | 3-F | Cl | H |
| A-2006. | OCF₃ | OCH₂F | 3-CH₃ | Cl | H |
| A-2007. | OCF₃ | OCH₂F | 3-OCH₃ | Cl | H |
| A-2008. | OCF₃ | OCH₂F | 5-F | Cl | H |
| A-2009. | OCF₃ | OCH₂F | 5-CH₃ | Cl | H |
| A-2010. | OCF₃ | OCH₂F | 5-OCH₃ | Cl | H |
| A-2011. | OCF₃ | OCHF₂ | 3-F | Cl | H |
| A-2012. | OCF₃ | OCHF₂ | 3-CH₃ | Cl | H |
| A-2013. | OCF₃ | OCHF₂ | 3-OCH₃ | Cl | H |
| A-2014. | OCF₃ | OCHF₂ | 5-F | Cl | H |
| A-2015. | OCF₃ | OCHF₂ | 5-CH₃ | Cl | H |
| A-2016. | OCF₃ | OCHF₂ | 5-OCH₃ | Cl | H |
| A-2017. | OCF₃ | OCF₃ | 3-F | Cl | H |
| A-2018. | OCF₃ | OCF₃ | 3-CH₃ | Cl | H |
| A-2019. | OCF₃ | OCF₃ | 3-OCH₃ | Cl | H |
| A-2020. | OCF₃ | OCF₃ | 5-F | Cl | H |
| A-2021. | OCF₃ | OCF₃ | 5-CH₃ | Cl | H |
| A-2022. | OCF₃ | OCF₃ | 5-OCH₃ | Cl | H |
| A-2023. | H | H | H | CN | F |
| A-2024. | F | H | H | CN | F |
| A-2025. | CH₃ | H | H | CN | F |
| A-2026. | OCH₃ | H | H | CN | F |
| A-2027. | CH₂F | H | H | CN | F |
| A-2028. | CHF₂ | H | H | CN | F |
| A-2029. | CF₃ | H | H | CN | F |
| A-2030. | OCH₂F | H | H | CN | F |
| A-2031. | OCHF₂ | H | H | CN | F |
| A-2032. | OCF₃ | H | H | CN | F |
| A-2033. | H | F | H | CN | F |
| A-2034. | H | CH₃ | H | CN | F |
| A-2035. | H | OCH₃ | H | CN | F |
| A-2036. | H | CN | H | CN | F |
| A-2037. | H | CH₂F | H | CN | F |
| A-2038. | H | CHF₂ | H | CN | F |
| A-2039. | H | CF₃ | H | CN | F |
| A-2040. | H | OCH₂F | H | CN | F |
| A-2041. | H | OCHF₂ | H | CN | F |
| A-2042. | H | OCF₃ | H | CN | F |
| A-2043. | H | H | 3-F | CN | F |
| A-2044. | H | H | 3-CH₃ | CN | F |
| A-2045. | H | H | 3-OCH₃ | CN | F |
| A-2046. | H | H | 5-F | CN | F |
| A-2047. | H | H | 5-CH₃ | CN | F |
| A-2048. | H | H | 5-OCH₃ | CN | F |
| A-2049. | F | F | H | CN | F |
| A-2050. | F | CH₃ | H | CN | F |
| A-2051. | F | OCH₃ | H | CN | F |
| A-2052. | F | CN | H | CN | F |
| A-2053. | F | CH₂F | H | CN | F |
| A-2054. | F | CHF₂ | H | CN | F |
| A-2055. | F | CF₃ | H | CN | F |
| A-2056. | F | OCH₂F | H | CN | F |
| A-2057. | F | OCHF₂ | H | CN | F |
| A-2058. | F | OCF₃ | H | CN | F |
| A-2059. | F | H | 3-F | CN | F |
| A-2060. | F | H | 3-CH₃ | CN | F |
| A-2061. | F | H | 3-OCH₃ | CN | F |
| A-2062. | F | H | 5-F | CN | F |
| A-2063. | F | H | 5-CH₃ | CN | F |
| A-2064. | F | H | 5-OCH₃ | CN | F |
| A-2065. | CH₃ | F | H | CN | F |
| A-2066. | CH₃ | CH₃ | H | CN | F |
| A-2067. | CH₃ | OCH₃ | H | CN | F |
| A-2068. | CH₃ | CN | H | CN | F |
| A-2069. | CH₃ | CH₂F | H | CN | F |
| A-2070. | CH₃ | CHF₂ | H | CN | F |
| A-2071. | CH₃ | CF₃ | H | CN | F |
| A-2072. | CH₃ | OCH₂F | H | CN | F |
| A-2073. | CH₃ | OCHF₂ | H | CN | F |
| A-2074. | CH₃ | OCF₃ | H | CN | F |
| A-2075. | CH₃ | H | 3-F | CN | F |
| A-2076. | CH₃ | H | 3-CH₃ | CN | F |
| A-2077. | CH₃ | H | 3-OCH₃ | CN | F |
| A-2078. | CH₃ | H | 5-F | CN | F |
| A-2079. | CH₃ | H | 5-CH₃ | CN | F |
| A-2080. | CH₃ | H | 5-OCH₃ | CN | F |
| A-2081. | OCH₃ | F | H | CN | F |
| A-2082. | OCH₃ | CH₃ | H | CN | F |
| A-2083. | OCH₃ | OCH₃ | H | CN | F |
| A-2084. | OCH₃ | CN | H | CN | F |
| A-2085. | OCH₃ | CH₂F | H | CN | F |
| A-2086. | OCH₃ | CHF₂ | H | CN | F |
| A-2087. | OCH₃ | CF₃ | H | CN | F |
| A-2088. | OCH₃ | OCH₂F | H | CN | F |
| A-2089. | OCH₃ | OCHF₂ | H | CN | F |
| A-2090. | OCH₃ | OCF₃ | H | CN | F |
| A-2091. | OCH₃ | H | 3-F | CN | F |
| A-2092. | OCH₃ | H | 3-CH₃ | CN | F |

TABLE A-continued

| Example No. | R¹ | R² | R³ | R⁶ | R⁷ |
|---|---|---|---|---|---|
| A-2093. | OCH₃ | H | 3-OCH₃ | CN | F |
| A-2094. | OCH₃ | H | 5-F | CN | F |
| A-2095. | OCH₃ | H | 5-CH₃ | CN | F |
| A-2096. | OCH₃ | H | 5-OCH₃ | CN | F |
| A-2097. | H | F | 3-F | CN | F |
| A-2098. | H | F | 3-CH₃ | CN | F |
| A-2099. | H | F | 3-OCH₃ | CN | F |
| A-2100. | H | F | 5-F | CN | F |
| A-2101. | H | F | 5-CH₃ | CN | F |
| A-2102. | H | F | 5-OCH₃ | CN | F |
| A-2103. | H | CH₃ | 3-F | CN | F |
| A-2104. | H | CH₃ | 3-CH₃ | CN | F |
| A-2105. | H | CH₃ | 3-OCH₃ | CN | F |
| A-2106. | H | CH₃ | 5-F | CN | F |
| A-2107. | H | CH₃ | 5-CH₃ | CN | F |
| A-2108. | H | CH₃ | 5-OCH₃ | CN | F |
| A-2109. | H | OCH₃ | 3-F | CN | F |
| A-2110. | H | OCH₃ | 3-CH₃ | CN | F |
| A-2111. | H | OCH₃ | 3-OCH₃ | CN | F |
| A-2112. | H | OCH₃ | 5-F | CN | F |
| A-2113. | H | OCH₃ | 5-CH₃ | CN | F |
| A-2114. | H | OCH₃ | 5-OCH₃ | CN | F |
| A-2115. | H | CN | 3-F | CN | F |
| A-2116. | H | CN | 3-CH₃ | CN | F |
| A-2117. | H | CN | 3-OCH₃ | CN | F |
| A-2118. | H | CN | 5-F | CN | F |
| A-2119. | H | CN | 5-CH₃ | CN | F |
| A-2120. | H | CN | 5-OCH₃ | CN | F |
| A-2121. | H | CH₂F | 3-F | CN | F |
| A-2122. | H | CH₂F | 3-CH₃ | CN | F |
| A-2123. | H | CH₂F | 3-OCH₃ | CN | F |
| A-2124. | H | CH₂F | 5-F | CN | F |
| A-2125. | H | CH₂F | 5-CH₃ | CN | F |
| A-2126. | H | CH₂F | 5-OCH₃ | CN | F |
| A-2127. | H | CHF₂ | 3-F | CN | F |
| A-2128. | H | CHF₂ | 3-CH₃ | CN | F |
| A-2129. | H | CHF₂ | 3-OCH₃ | CN | F |
| A-2130. | H | CHF₂ | 5-F | CN | F |
| A-2131. | H | CHF₂ | 5-CH₃ | CN | F |
| A-2132. | H | CHF₂ | 5-OCH₃ | CN | F |
| A-2133. | H | CF₃ | 3-F | CN | F |
| A-2134. | H | CF₃ | 3-CH₃ | CN | F |
| A-2135. | H | CF₃ | 3-OCH₃ | CN | F |
| A-2136. | H | CF₃ | 5-F | CN | F |
| A-2137. | H | CF₃ | 5-CH₃ | CN | F |
| A-2138. | H | CF₃ | 5-OCH₃ | CN | F |
| A-2139. | H | OCH₂F | 3-F | CN | F |
| A-2140. | H | OCH₂F | 3-CH₃ | CN | F |
| A-2141. | H | OCH₂F | 3-OCH₃ | CN | F |
| A-2142. | H | OCH₂F | 5-F | CN | F |
| A-2143. | H | OCH₂F | 5-CH₃ | CN | F |
| A-2144. | H | OCH₂F | 5-OCH₃ | CN | F |
| A-2145. | H | OCHF₂ | 3-F | CN | F |
| A-2146. | H | OCHF₂ | 3-CH₃ | CN | F |
| A-2147. | H | OCHF₂ | 3-OCH₃ | CN | F |
| A-2148. | H | OCHF₂ | 5-F | CN | F |
| A-2149. | H | OCHF₂ | 5-CH₃ | CN | F |
| A-2150. | H | OCHF₂ | 5-OCH₃ | CN | F |
| A-2151. | H | OCF₃ | 3-F | CN | F |
| A-2152. | H | OCF₃ | 3-CH₃ | CN | F |
| A-2153. | H | OCF₃ | 3-OCH₃ | CN | F |
| A-2154. | H | OCF₃ | 5-F | CN | F |
| A-2155. | H | OCF₃ | 5-CH₃ | CN | F |
| A-2156. | H | OCF₃ | 5-OCH₃ | CN | F |
| A-2157. | F | F | 3-F | CN | F |
| A-2158. | F | F | 3-CH₃ | CN | F |
| A-2159. | F | F | 3-OCH₃ | CN | F |
| A-2160. | F | F | 5-F | CN | F |
| A-2161. | F | F | 5-CH₃ | CN | F |
| A-2162. | F | F | 5-OCH₃ | CN | F |
| A-2163. | F | CH₃ | 3-F | CN | F |
| A-2164. | F | CH₃ | 3-CH₃ | CN | F |
| A-2165. | F | CH₃ | 3-OCH₃ | CN | F |
| A-2166. | F | CH₃ | 5-F | CN | F |
| A-2167. | F | CH₃ | 5-CH₃ | CN | F |
| A-2168. | F | CH₃ | 5-OCH₃ | CN | F |
| A-2169. | F | OCH₃ | 3-F | CN | F |
| A-2170. | F | OCH₃ | 3-CH₃ | CN | F |
| A-2171. | F | OCH₃ | 3-OCH₃ | CN | F |
| A-2172. | F | OCH₃ | 5-F | CN | F |
| A-2173. | F | OCH₃ | 5-CH₃ | CN | F |
| A-2174. | F | OCH₃ | 5-OCH₃ | CN | F |
| A-2175. | F | CN | 3-F | CN | F |
| A-2176. | F | CN | 3-CH₃ | CN | F |
| A-2177. | F | CN | 3-OCH₃ | CN | F |
| A-2178. | F | CN | 5-F | CN | F |
| A-2179. | F | CN | 5-CH₃ | CN | F |
| A-2180. | F | CN | 5-OCH₃ | CN | F |
| A-2181. | F | CH₂F | 3-F | CN | F |
| A-2182. | F | CH₂F | 3-CH₃ | CN | F |
| A-2183. | F | CH₂F | 3-OCH₃ | CN | F |
| A-2184. | F | CH₂F | 5-F | CN | F |
| A-2185. | F | CH₂F | 5-CH₃ | CN | F |
| A-2186. | F | CH₂F | 5-OCH₃ | CN | F |
| A-2187. | F | CHF₂ | 3-F | CN | F |
| A-2188. | F | CHF₂ | 3-CH₃ | CN | F |
| A-2189. | F | CHF₂ | 3-OCH₃ | CN | F |
| A-2190. | F | CHF₂ | 5-F | CN | F |
| A-2191. | F | CHF₂ | 5-CH₃ | CN | F |
| A-2192. | F | CHF₂ | 5-OCH₃ | CN | F |
| A-2193. | F | CF₃ | 3-F | CN | F |
| A-2194. | F | CF₃ | 3-CH₃ | CN | F |
| A-2195. | F | CF₃ | 3-OCH₃ | CN | F |
| A-2196. | F | CF₃ | 5-F | CN | F |
| A-2197. | F | CF₃ | 5-CH₃ | CN | F |
| A-2198. | F | CF₃ | 5-OCH₃ | CN | F |
| A-2199. | F | OCH₂F | 3-F | CN | F |
| A-2200. | F | OCH₂F | 3-CH₃ | CN | F |
| A-2201. | F | OCH₂F | 3-OCH₃ | CN | F |
| A-2202. | F | OCH₂F | 5-F | CN | F |
| A-2203. | F | OCH₂F | 5-CH₃ | CN | F |
| A-2204. | F | OCH₂F | 5-OCH₃ | CN | F |
| A-2205. | F | OCHF₂ | 3-F | CN | F |
| A-2206. | F | OCHF₂ | 3-CH₃ | CN | F |
| A-2207. | F | OCHF₂ | 3-OCH₃ | CN | F |
| A-2208. | F | OCHF₂ | 5-F | CN | F |
| A-2209. | F | OCHF₂ | 5-CH₃ | CN | F |
| A-2210. | F | OCHF₂ | 5-OCH₃ | CN | F |
| A-2211. | F | OCF₃ | 3-F | CN | F |
| A-2212. | F | OCF₃ | 3-CH₃ | CN | F |
| A-2213. | F | OCF₃ | 3-OCH₃ | CN | F |
| A-2214. | F | OCF₃ | 5-F | CN | F |
| A-2215. | F | OCF₃ | 5-CH₃ | CN | F |
| A-2216. | F | OCF₃ | 5-OCH₃ | CN | F |
| A-2217. | CH₃ | F | 3-F | CN | F |
| A-2218. | CH₃ | F | 3-CH₃ | CN | F |
| A-2219. | CH₃ | F | 3-OCH₃ | CN | F |
| A-2220. | CH₃ | F | 5-F | CN | F |
| A-2221. | CH₃ | F | 5-CH₃ | CN | F |
| A-2222. | CH₃ | F | 5-OCH₃ | CN | F |
| A-2223. | CH₃ | CH₃ | 3-F | CN | F |
| A-2224. | CH₃ | CH₃ | 3-CH₃ | CN | F |
| A-2225. | CH₃ | CH₃ | 3-OCH₃ | CN | F |
| A-2226. | CH₃ | CH₃ | 5-F | CN | F |
| A-2227. | CH₃ | CH₃ | 5-CH₃ | CN | F |
| A-2228. | CH₃ | CH₃ | 5-OCH₃ | CN | F |
| A-2229. | CH₃ | OCH₃ | 3-F | CN | F |
| A-2230. | CH₃ | OCH₃ | 3-CH₃ | CN | F |
| A-2231. | CH₃ | OCH₃ | 3-OCH₃ | CN | F |
| A-2232. | CH₃ | OCH₃ | 5-F | CN | F |
| A-2233. | CH₃ | OCH₃ | 5-CH₃ | CN | F |
| A-2234. | CH₃ | OCH₃ | 5-OCH₃ | CN | F |
| A-2235. | CH₃ | CN | 3-F | CN | F |
| A-2236. | CH₃ | CN | 3-CH₃ | CN | F |
| A-2237. | CH₃ | CN | 3-OCH₃ | CN | F |
| A-2238. | CH₃ | CN | 5-F | CN | F |
| A-2239. | CH₃ | CN | 5-CH₃ | CN | F |
| A-2240. | CH₃ | CN | 5-OCH₃ | CN | F |
| A-2241. | CH₃ | CH₂F | 3-F | CN | F |
| A-2242. | CH₃ | CH₂F | 3-CH₃ | CN | F |
| A-2243. | CH₃ | CH₂F | 3-OCH₃ | CN | F |
| A-2244. | CH₃ | CH₂F | 5-F | CN | F |
| A-2245. | CH₃ | CH₂F | 5-CH₃ | CN | F |
| A-2246. | CH₃ | CH₂F | 5-OCH₃ | CN | F |
| A-2247. | CH₃ | CHF₂ | 3-F | CN | F |
| A-2248. | CH₃ | CHF₂ | 3-CH₃ | CN | F |

TABLE A-continued

| Example No. | R¹ | R² | R³ | R⁶ | R⁷ |
|---|---|---|---|---|---|
| A-2249. | CH₃ | CHF₂ | 3-OCH₃ | CN | F |
| A-2250. | CH₃ | CHF₂ | 5-F | CN | F |
| A-2251. | CH₃ | CHF₂ | 5-CH₃ | CN | F |
| A-2252. | CH₃ | CHF₂ | 5-OCH₃ | CN | F |
| A-2253. | CH₃ | CF₃ | 3-F | CN | F |
| A-2254. | CH₃ | CF₃ | 3-CH₃ | CN | F |
| A-2255. | CH₃ | CF₃ | 3-OCH₃ | CN | F |
| A-2256. | CH₃ | CF₃ | 5-F | CN | F |
| A-2257. | CH₃ | CF₃ | 5-CH₃ | CN | F |
| A-2258. | CH₃ | CF₃ | 5-OCH₃ | CN | F |
| A-2259. | CH₃ | OCH₂F | 3-F | CN | F |
| A-2260. | CH₃ | OCH₂F | 3-CH₃ | CN | F |
| A-2261. | CH₃ | OCH₂F | 3-OCH₃ | CN | F |
| A-2262. | CH₃ | OCH₂F | 5-F | CN | F |
| A-2263. | CH₃ | OCH₂F | 5-CH₃ | CN | F |
| A-2264. | CH₃ | OCH₂F | 5-OCH₃ | CN | F |
| A-2265. | CH₃ | OCHF₂ | 3-F | CN | F |
| A-2266. | CH₃ | OCHF₂ | 3-CH₃ | CN | F |
| A-2267. | CH₃ | OCHF₂ | 3-OCH₃ | CN | F |
| A-2268. | CH₃ | OCHF₂ | 5-F | CN | F |
| A-2269. | CH₃ | OCHF₂ | 5-CH₃ | CN | F |
| A-2270. | CH₃ | OCHF₂ | 5-OCH₃ | CN | F |
| A-2271. | CH₃ | OCF₃ | 3-F | CN | F |
| A-2272. | CH₃ | OCF₃ | 3-CH₃ | CN | F |
| A-2273. | CH₃ | OCF₃ | 3-OCH₃ | CN | F |
| A-2274. | CH₃ | OCF₃ | 5-F | CN | F |
| A-2275. | CH₃ | OCF₃ | 5-CH₃ | CN | F |
| A-2276. | CH₃ | OCF₃ | 5-OCH₃ | CN | F |
| A-2277. | OCH₃ | F | 3-F | CN | F |
| A-2278. | OCH₃ | F | 3-CH₃ | CN | F |
| A-2279. | OCH₃ | F | 3-OCH₃ | CN | F |
| A-2280. | OCH₃ | F | 5-F | CN | F |
| A-2281. | OCH₃ | F | 5-CH₃ | CN | F |
| A-2282. | OCH₃ | F | 5-OCH₃ | CN | F |
| A-2283. | OCH₃ | CH₃ | 3-F | CN | F |
| A-2284. | OCH₃ | CH₃ | 3-CH₃ | CN | F |
| A-2285. | OCH₃ | CH₃ | 3-OCH₃ | CN | F |
| A-2286. | OCH₃ | CH₃ | 5-F | CN | F |
| A-2287. | OCH₃ | CH₃ | 5-CH₃ | CN | F |
| A-2288. | OCH₃ | CH₃ | 5-OCH₃ | CN | F |
| A-2289. | OCH₃ | OCH₃ | 3-F | CN | F |
| A-2290. | OCH₃ | OCH₃ | 3-CH₃ | CN | F |
| A-2291. | OCH₃ | OCH₃ | 3-OCH₃ | CN | F |
| A-2292. | OCH₃ | OCH₃ | 5-F | CN | F |
| A-2293. | OCH₃ | OCH₃ | 5-CH₃ | CN | F |
| A-2294. | OCH₃ | OCH₃ | 5-OCH₃ | CN | F |
| A-2295. | OCH₃ | CN | 3-F | CN | F |
| A-2296. | OCH₃ | CN | 3-CH₃ | CN | F |
| A-2297. | OCH₃ | CN | 3-OCH₃ | CN | F |
| A-2298. | OCH₃ | CN | 5-F | CN | F |
| A-2299. | OCH₃ | CN | 5-CH₃ | CN | F |
| A-2300. | OCH₃ | CN | 5-OCH₃ | CN | F |
| A-2301. | OCH₃ | CH₂F | 3-F | CN | F |
| A-2302. | OCH₃ | CH₂F | 3-CH₃ | CN | F |
| A-2303. | OCH₃ | CH₂F | 3-OCH₃ | CN | F |
| A-2304. | OCH₃ | CH₂F | 5-F | CN | F |
| A-2305. | OCH₃ | CH₂F | 5-CH₃ | CN | F |
| A-2306. | OCH₃ | CH₂F | 5-OCH₃ | CN | F |
| A-2307. | OCH₃ | CHF₂ | 3-F | CN | F |
| A-2308. | OCH₃ | CHF₂ | 3-CH₃ | CN | F |
| A-2309. | OCH₃ | CHF₂ | 3-OCH₃ | CN | F |
| A-2310. | OCH₃ | CHF₂ | 5-F | CN | F |
| A-2311. | OCH₃ | CHF₂ | 5-CH₃ | CN | F |
| A-2312. | OCH₃ | CHF₂ | 5-OCH₃ | CN | F |
| A-2313. | OCH₃ | CF₃ | 3-F | CN | F |
| A-2314. | OCH₃ | CF₃ | 3-CH₃ | CN | F |
| A-2315. | OCH₃ | CF₃ | 3-OCH₃ | CN | F |
| A-2316. | OCH₃ | CF₃ | 5-F | CN | F |
| A-2317. | OCH₃ | CF₃ | 5-CH₃ | CN | F |
| A-2318. | OCH₃ | CF₃ | 5-OCH₃ | CN | F |
| A-2319. | OCH₃ | OCH₂F | 3-F | CN | F |
| A-2320. | OCH₃ | OCH₂F | 3-CH₃ | CN | F |
| A-2321. | OCH₃ | OCH₂F | 3-OCH₃ | CN | F |
| A-2322. | OCH₃ | OCH₂F | 5-F | CN | F |
| A-2323. | OCH₃ | OCH₂F | 5-CH₃ | CN | F |
| A-2324. | OCH₃ | OCH₂F | 5-OCH₃ | CN | F |
| A-2325. | OCH₃ | OCHF₂ | 3-F | CN | F |
| A-2326. | OCH₃ | OCHF₂ | 3-CH₃ | CN | F |
| A-2327. | OCH₃ | OCHF₂ | 3-OCH₃ | CN | F |
| A-2328. | OCH₃ | OCHF₂ | 5-F | CN | F |
| A-2329. | OCH₃ | OCHF₂ | 5-CH₃ | CN | F |
| A-2330. | OCH₃ | OCHF₂ | 5-OCH₃ | CN | F |
| A-2331. | OCH₃ | OCF₃ | 3-F | CN | F |
| A-2332. | OCH₃ | OCF₃ | 3-CH₃ | CN | F |
| A-2333. | OCH₃ | OCF₃ | 3-OCH₃ | CN | F |
| A-2334. | OCH₃ | OCF₃ | 5-F | CN | F |
| A-2335. | OCH₃ | OCF₃ | 5-CH₃ | CN | F |
| A-2336. | OCH₃ | OCF₃ | 5-OCH₃ | CN | F |
| A-2337. | CH₂F | F | 3-F | CN | F |
| A-2338. | CH₂F | F | 3-CH₃ | CN | F |
| A-2339. | CH₂F | F | 3-OCH₃ | CN | F |
| A-2340. | CH₂F | F | 5-F | CN | F |
| A-2341. | CH₂F | F | 5-CH₃ | CN | F |
| A-2342. | CH₂F | F | 5-OCH₃ | CN | F |
| A-2343. | CH₂F | CH₃ | 3-F | CN | F |
| A-2344. | CH₂F | CH₃ | 3-CH₃ | CN | F |
| A-2345. | CH₂F | CH₃ | 3-OCH₃ | CN | F |
| A-2346. | CH₂F | CH₃ | 5-F | CN | F |
| A-2347. | CH₂F | CH₃ | 5-CH₃ | CN | F |
| A-2348. | CH₂F | CH₃ | 5-OCH₃ | CN | F |
| A-2349. | CH₂F | OCH₃ | 3-F | CN | F |
| A-2350. | CH₂F | OCH₃ | 3-CH₃ | CN | F |
| A-2351. | CH₂F | OCH₃ | 3-OCH₃ | CN | F |
| A-2352. | CH₂F | OCH₃ | 5-F | CN | F |
| A-2353. | CH₂F | OCH₃ | 5-CH₃ | CN | F |
| A-2354. | CH₂F | OCH₃ | 5-OCH₃ | CN | F |
| A-2355. | CH₂F | CN | 3-F | CN | F |
| A-2356. | CH₂F | CN | 3-CH₃ | CN | F |
| A-2357. | CH₂F | CN | 3-OCH₃ | CN | F |
| A-2358. | CH₂F | CN | 5-F | CN | F |
| A-2359. | CH₂F | CN | 5-CH₃ | CN | F |
| A-2360. | CH₂F | CN | 5-OCH₃ | CN | F |
| A-2361. | CH₂F | CH₂F | 3-F | CN | F |
| A-2362. | CH₂F | CH₂F | 3-CH₃ | CN | F |
| A-2363. | CH₂F | CH₂F | 3-OCH₃ | CN | F |
| A-2364. | CH₂F | CH₂F | 5-F | CN | F |
| A-2365. | CH₂F | CH₂F | 5-CH₃ | CN | F |
| A-2366. | CH₂F | CH₂F | 5-OCH₃ | CN | F |
| A-2367. | CH₂F | CHF₂ | 3-F | CN | F |
| A-2368. | CH₂F | CHF₂ | 3-CH₃ | CN | F |
| A-2369. | CH₂F | CHF₂ | 3-OCH₃ | CN | F |
| A-2370. | CH₂F | CHF₂ | 5-F | CN | F |
| A-2371. | CH₂F | CHF₂ | 5-CH₃ | CN | F |
| A-2372. | CH₂F | CHF₂ | 5-OCH₃ | CN | F |
| A-2373. | CH₂F | CF₃ | 3-F | CN | F |
| A-2374. | CH₂F | CF₃ | 3-CH₃ | CN | F |
| A-2375. | CH₂F | CF₃ | 3-OCH₃ | CN | F |
| A-2376. | CH₂F | CF₃ | 5-F | CN | F |
| A-2377. | CH₂F | CF₃ | 5-CH₃ | CN | F |
| A-2378. | CH₂F | CF₃ | 5-OCH₃ | CN | F |
| A-2379. | CH₂F | OCH₂F | 3-F | CN | F |
| A-2380. | CH₂F | OCH₂F | 3-CH₃ | CN | F |
| A-2381. | CH₂F | OCH₂F | 3-OCH₃ | CN | F |
| A-2382. | CH₂F | OCH₂F | 5-F | CN | F |
| A-2383. | CH₂F | OCH₂F | 5-CH₃ | CN | F |
| A-2384. | CH₂F | OCH₂F | 5-OCH₃ | CN | F |
| A-2385. | CH₂F | OCHF₂ | 3-F | CN | F |
| A-2386. | CH₂F | OCHF₂ | 3-CH₃ | CN | F |
| A-2387. | CH₂F | OCHF₂ | 3-OCH₃ | CN | F |
| A-2388. | CH₂F | OCHF₂ | 5-F | CN | F |
| A-2389. | CH₂F | OCHF₂ | 5-CH₃ | CN | F |
| A-2390. | CH₂F | OCHF₂ | 5-OCH₃ | CN | F |
| A-2391. | CH₂F | OCF₃ | 3-F | CN | F |
| A-2392. | CH₂F | OCF₃ | 3-CH₃ | CN | F |
| A-2393. | CH₂F | OCF₃ | 3-OCH₃ | CN | F |
| A-2394. | CH₂F | OCF₃ | 5-F | CN | F |
| A-2395. | CH₂F | OCF₃ | 5-CH₃ | CN | F |
| A-2396. | CH₂F | OCF₃ | 5-OCH₃ | CN | F |
| A-2397. | CHF₂ | F | 3-F | CN | F |
| A-2398. | CHF₂ | F | 3-CH₃ | CN | F |
| A-2399. | CHF₂ | F | 3-OCH₃ | CN | F |
| A-2400. | CHF₂ | F | 5-F | CN | F |
| A-2401. | CHF₂ | F | 5-CH₃ | CN | F |
| A-2402. | CHF₂ | F | 5-OCH₃ | CN | F |
| A-2403. | CHF₂ | CH₃ | 3-F | CN | F |
| A-2404. | CHF₂ | CH₃ | 3-CH₃ | CN | F |

TABLE A-continued

| Example No. | R¹ | R² | R³ | R⁶ | R⁷ |
| --- | --- | --- | --- | --- | --- |
| A-2405. | CHF₂ | CH₃ | 3-OCH₃ | CN | F |
| A-2406. | CHF₂ | CH₃ | 5-F | CN | F |
| A-2407. | CHF₂ | CH₃ | 5-CH₃ | CN | F |
| A-2408. | CHF₂ | CH₃ | 5-OCH₃ | CN | F |
| A-2409. | CHF₂ | OCH₃ | 3-F | CN | F |
| A-2410. | CHF₂ | OCH₃ | 3-CH₃ | CN | F |
| A-2411. | CHF₂ | OCH₃ | 3-OCH₃ | CN | F |
| A-2412. | CHF₂ | OCH₃ | 5-F | CN | F |
| A-2413. | CHF₂ | OCH₃ | 5-CH₃ | CN | F |
| A-2414. | CHF₂ | OCH₃ | 5-OCH₃ | CN | F |
| A-2415. | CHF₂ | CN | 3-F | CN | F |
| A-2416. | CHF₂ | CN | 3-CH₃ | CN | F |
| A-2417. | CHF₂ | CN | 3-OCH₃ | CN | F |
| A-2418. | CHF₂ | CN | 5-F | CN | F |
| A-2419. | CHF₂ | CN | 5-CH₃ | CN | F |
| A-2420. | CHF₂ | CN | 5-OCH₃ | CN | F |
| A-2421. | CHF₂ | CH₂F | 3-F | CN | F |
| A-2422. | CHF₂ | CH₂F | 3-CH₃ | CN | F |
| A-2423. | CHF₂ | CH₂F | 3-OCH₃ | CN | F |
| A-2424. | CHF₂ | CH₂F | 5-F | CN | F |
| A-2425. | CHF₂ | CH₂F | 5-CH₃ | CN | F |
| A-2426. | CHF₂ | CH₂F | 5-OCH₃ | CN | F |
| A-2427. | CHF₂ | CHF₂ | 3-F | CN | F |
| A-2428. | CHF₂ | CHF₂ | 3-CH₃ | CN | F |
| A-2429. | CHF₂ | CHF₂ | 3-OCH₃ | CN | F |
| A-2430. | CHF₂ | CHF₂ | 5-F | CN | F |
| A-2431. | CHF₂ | CHF₂ | 5-CH₃ | CN | F |
| A-2432. | CHF₂ | CHF₂ | 5-OCH₃ | CN | F |
| A-2433. | CHF₂ | CF₃ | 3-F | CN | F |
| A-2434. | CHF₂ | CF₃ | 3-CH₃ | CN | F |
| A-2435. | CHF₂ | CF₃ | 3-OCH₃ | CN | F |
| A-2436. | CHF₂ | CF₃ | 5-F | CN | F |
| A-2437. | CHF₂ | CF₃ | 5-CH₃ | CN | F |
| A-2438. | CHF₂ | CF₃ | 5-OCH₃ | CN | F |
| A-2439. | CHF₂ | OCH₂F | 3-F | CN | F |
| A-2440. | CHF₂ | OCH₂F | 3-CH₃ | CN | F |
| A-2441. | CHF₂ | OCH₂F | 3-OCH₃ | CN | F |
| A-2442. | CHF₂ | OCH₂F | 5-F | CN | F |
| A-2443. | CHF₂ | OCH₂F | 5-CH₃ | CN | F |
| A-2444. | CHF₂ | OCH₂F | 5-OCH₃ | CN | F |
| A-2445. | CHF₂ | OCHF₂ | 3-F | CN | F |
| A-2446. | CHF₂ | OCHF₂ | 3-CH₃ | CN | F |
| A-2447. | CHF₂ | OCHF₂ | 3-OCH₃ | CN | F |
| A-2448. | CHF₂ | OCHF₂ | 5-F | CN | F |
| A-2449. | CHF₂ | OCHF₂ | 5-CH₃ | CN | F |
| A-2450. | CHF₂ | OCHF₂ | 5-OCH₃ | CN | F |
| A-2451. | CHF₂ | OCF₃ | 3-F | CN | F |
| A-2452. | CHF₂ | OCF₃ | 3-CH₃ | CN | F |
| A-2453. | CHF₂ | OCF₃ | 3-OCH₃ | CN | F |
| A-2454. | CHF₂ | OCF₃ | 5-F | CN | F |
| A-2455. | CHF₂ | OCF₃ | 5-CH₃ | CN | F |
| A-2456. | CHF₂ | OCF₃ | 5-OCH₃ | CN | F |
| A-2457. | CF₃ | F | 3-F | CN | F |
| A-2458. | CF₃ | F | 3-CH₃ | CN | F |
| A-2459. | CF₃ | F | 3-OCH₃ | CN | F |
| A-2460. | CF₃ | F | 5-F | CN | F |
| A-2461. | CF₃ | F | 5-CH₃ | CN | F |
| A-2462. | CF₃ | F | 5-OCH₃ | CN | F |
| A-2463. | CF₃ | CH₃ | 3-F | CN | F |
| A-2464. | CF₃ | CH₃ | 3-CH₃ | CN | F |
| A-2465. | CF₃ | CH₃ | 3-OCH₃ | CN | F |
| A-2466. | CF₃ | CH₃ | 5-F | CN | F |
| A-2467. | CF₃ | CH₃ | 5-CH₃ | CN | F |
| A-2468. | CF₃ | CH₃ | 5-OCH₃ | CN | F |
| A-2469. | CF₃ | OCH₃ | 3-F | CN | F |
| A-2470. | CF₃ | OCH₃ | 3-CH₃ | CN | F |
| A-2471. | CF₃ | OCH₃ | 3-OCH₃ | CN | F |
| A-2472. | CF₃ | OCH₃ | 5-F | CN | F |
| A-2473. | CF₃ | OCH₃ | 5-CH₃ | CN | F |
| A-2474. | CF₃ | OCH₃ | 5-OCH₃ | CN | F |
| A-2475. | CF₃ | CN | 3-F | CN | F |
| A-2476. | CF₃ | CN | 3-CH₃ | CN | F |
| A-2477. | CF₃ | CN | 3-OCH₃ | CN | F |
| A-2478. | CF₃ | CN | 5-F | CN | F |
| A-2479. | CF₃ | CN | 5-CH₃ | CN | F |
| A-2480. | CF₃ | CN | 5-OCH₃ | CN | F |
| A-2481. | CF₃ | CH₂F | 3-F | CN | F |
| A-2482. | CF₃ | CH₂F | 3-CH₃ | CN | F |
| A-2483. | CF₃ | CH₂F | 3-OCH₃ | CN | F |
| A-2484. | CF₃ | CH₂F | 5-F | CN | F |
| A-2485. | CF₃ | CH₂F | 5-CH₃ | CN | F |
| A-2486. | CF₃ | CH₂F | 5-OCH₃ | CN | F |
| A-2487. | CF₃ | CHF₂ | 3-F | CN | F |
| A-2488. | CF₃ | CHF₂ | 3-CH₃ | CN | F |
| A-2489. | CF₃ | CHF₂ | 3-OCH₃ | CN | F |
| A-2490. | CF₃ | CHF₂ | 5-F | CN | F |
| A-2491. | CF₃ | CHF₂ | 5-CH₃ | CN | F |
| A-2492. | CF₃ | CHF₂ | 5-OCH₃ | CN | F |
| A-2493. | CF₃ | CF₃ | 3-F | CN | F |
| A-2494. | CF₃ | CF₃ | 3-CH₃ | CN | F |
| A-2495. | CF₃ | CF₃ | 3-OCH₃ | CN | F |
| A-2496. | CF₃ | CF₃ | 5-F | CN | F |
| A-2497. | CF₃ | CF₃ | 5-CH₃ | CN | F |
| A-2498. | CF₃ | CF₃ | 5-OCH₃ | CN | F |
| A-2499. | CF₃ | OCH₂F | 3-F | CN | F |
| A-2500. | CF₃ | OCH₂F | 3-CH₃ | CN | F |
| A-2501. | CF₃ | OCH₂F | 3-OCH₃ | CN | F |
| A-2502. | CF₃ | OCH₂F | 5-F | CN | F |
| A-2503. | CF₃ | OCH₂F | 5-CH₃ | CN | F |
| A-2504. | CF₃ | OCH₂F | 5-OCH₃ | CN | F |
| A-2505. | CF₃ | OCHF₂ | 3-F | CN | F |
| A-2506. | CF₃ | OCHF₂ | 3-CH₃ | CN | F |
| A-2507. | CF₃ | OCHF₂ | 3-OCH₃ | CN | F |
| A-2508. | CF₃ | OCHF₂ | 5-F | CN | F |
| A-2509. | CF₃ | OCHF₂ | 5-CH₃ | CN | F |
| A-2510. | CF₃ | OCHF₂ | 5-OCH₃ | CN | F |
| A-2511. | CF₃ | OCF₃ | 3-F | CN | F |
| A-2512. | CF₃ | OCF₃ | 3-CH₃ | CN | F |
| A-2513. | CF₃ | OCF₃ | 3-OCH₃ | CN | F |
| A-2514. | CF₃ | OCF₃ | 5-F | CN | F |
| A-2515. | CF₃ | OCF₃ | 5-CH₃ | CN | F |
| A-2516. | CF₃ | OCF₃ | 5-OCH₃ | CN | F |
| A-2517. | OCH₂F | F | 3-F | CN | F |
| A-2518. | OCH₂F | F | 3-CH₃ | CN | F |
| A-2519. | OCH₂F | F | 3-OCH₃ | CN | F |
| A-2520. | OCH₂F | F | 5-F | CN | F |
| A-2521. | OCH₂F | F | 5-CH₃ | CN | F |
| A-2522. | OCH₂F | F | 5-OCH₃ | CN | F |
| A-2523. | OCH₂F | CH₃ | 3-F | CN | F |
| A-2524. | OCH₂F | CH₃ | 3-CH₃ | CN | F |
| A-2525. | OCH₂F | CH₃ | 3-OCH₃ | CN | F |
| A-2526. | OCH₂F | CH₃ | 5-F | CN | F |
| A-2527. | OCH₂F | CH₃ | 5-CH₃ | CN | F |
| A-2528. | OCH₂F | CH₃ | 5-OCH₃ | CN | F |
| A-2529. | OCH₂F | OCH₃ | 3-F | CN | F |
| A-2530. | OCH₂F | OCH₃ | 3-CH₃ | CN | F |
| A-2531. | OCH₂F | OCH₃ | 3-OCH₃ | CN | F |
| A-2532. | OCH₂F | OCH₃ | 5-F | CN | F |
| A-2533. | OCH₂F | OCH₃ | 5-CH₃ | CN | F |
| A-2534. | OCH₂F | OCH₃ | 5-OCH₃ | CN | F |
| A-2535. | OCH₂F | CN | 3-F | CN | F |
| A-2536. | OCH₂F | CN | 3-CH₃ | CN | F |
| A-2537. | OCH₂F | CN | 3-OCH₃ | CN | F |
| A-2538. | OCH₂F | CN | 5-F | CN | F |
| A-2539. | OCH₂F | CN | 5-CH₃ | CN | F |
| A-2540. | OCH₂F | CN | 5-OCH₃ | CN | F |
| A-2541. | OCH₂F | CH₂F | 3-F | CN | F |
| A-2542. | OCH₂F | CH₂F | 3-CH₃ | CN | F |
| A-2543. | OCH₂F | CH₂F | 3-OCH₃ | CN | F |
| A-2544. | OCH₂F | CH₂F | 5-F | CN | F |
| A-2545. | OCH₂F | CH₂F | 5-CH₃ | CN | F |
| A-2546. | OCH₂F | CH₂F | 5-OCH₃ | CN | F |
| A-2547. | OCH₂F | CHF₂ | 3-F | CN | F |
| A-2548. | OCH₂F | CHF₂ | 3-CH₃ | CN | F |
| A-2549. | OCH₂F | CHF₂ | 3-OCH₃ | CN | F |
| A-2550. | OCH₂F | CHF₂ | 5-F | CN | F |
| A-2551. | OCH₂F | CHF₂ | 5-CH₃ | CN | F |
| A-2552. | OCH₂F | CHF₂ | 5-OCH₃ | CN | F |
| A-2553. | OCH₂F | CF₃ | 3-F | CN | F |
| A-2554. | OCH₂F | CF₃ | 3-CH₃ | CN | F |
| A-2555. | OCH₂F | CF₃ | 3-OCH₃ | CN | F |
| A-2556. | OCH₂F | CF₃ | 5-F | CN | F |
| A-2557. | OCH₂F | CF₃ | 5-CH₃ | CN | F |
| A-2558. | OCH₂F | CF₃ | 5-OCH₃ | CN | F |
| A-2559. | OCH₂F | OCH₂F | 3-F | CN | F |
| A-2560. | OCH₂F | OCH₂F | 3-CH₃ | CN | F |

TABLE A-continued

| Example No. | R¹ | R² | R³ | R⁶ | R⁷ |
|---|---|---|---|---|---|
| A-2561. | OCH$_2$F | OCH$_2$F | 3-OCH$_3$ | CN | F |
| A-2562. | OCH$_2$F | OCH$_2$F | 5-F | CN | F |
| A-2563. | OCH$_2$F | OCH$_2$F | 5-CH$_3$ | CN | F |
| A-2564. | OCH$_2$F | OCH$_2$F | 5-OCH$_3$ | CN | F |
| A-2565. | OCH$_2$F | OCHF$_2$ | 3-F | CN | F |
| A-2566. | OCH$_2$F | OCHF$_2$ | 3-CH$_3$ | CN | F |
| A-2567. | OCH$_2$F | OCHF$_2$ | 3-OCH$_3$ | CN | F |
| A-2568. | OCH$_2$F | OCHF$_2$ | 5-F | CN | F |
| A-2569. | OCH$_2$F | OCHF$_2$ | 5-CH$_3$ | CN | F |
| A-2570. | OCH$_2$F | OCHF$_2$ | 5-OCH$_3$ | CN | F |
| A-2571. | OCH$_2$F | OCF$_3$ | 3-F | CN | F |
| A-2572. | OCH$_2$F | OCF$_3$ | 3-CH$_3$ | CN | F |
| A-2573. | OCH$_2$F | OCF$_3$ | 3-OCH$_3$ | CN | F |
| A-2574. | OCH$_2$F | OCF$_3$ | 5-F | CN | F |
| A-2575. | OCH$_2$F | OCF$_3$ | 5-CH$_3$ | CN | F |
| A-2576. | OCH$_2$F | OCF$_3$ | 5-OCH$_3$ | CN | F |
| A-2577. | OCHF$_2$ | F | 3-F | CN | F |
| A-2578. | OCHF$_2$ | F | 3-CH$_3$ | CN | F |
| A-2579. | OCHF$_2$ | F | 3-OCH$_3$ | CN | F |
| A-2580. | OCHF$_2$ | F | 5-F | CN | F |
| A-2581. | OCHF$_2$ | F | 5-CH$_3$ | CN | F |
| A-2582. | OCHF$_2$ | F | 5-OCH$_3$ | CN | F |
| A-2583. | OCHF$_2$ | CH$_3$ | 3-F | CN | F |
| A-2584. | OCHF$_2$ | CH$_3$ | 3-CH$_3$ | CN | F |
| A-2585. | OCHF$_2$ | CH$_3$ | 3-OCH$_3$ | CN | F |
| A-2586. | OCHF$_2$ | CH$_3$ | 5-F | CN | F |
| A-2587. | OCHF$_2$ | CH$_3$ | 5-CH$_3$ | CN | F |
| A-2588. | OCHF$_2$ | CH$_3$ | 5-OCH$_3$ | CN | F |
| A-2589. | OCHF$_2$ | OCH$_3$ | 3-F | CN | F |
| A-2590. | OCHF$_2$ | OCH$_3$ | 3-CH$_3$ | CN | F |
| A-2591. | OCHF$_2$ | OCH$_3$ | 3-OCH$_3$ | CN | F |
| A-2592. | OCHF$_2$ | OCH$_3$ | 5-F | CN | F |
| A-2593. | OCHF$_2$ | OCH$_3$ | 5-CH$_3$ | CN | F |
| A-2594. | OCHF$_2$ | OCH$_3$ | 5-OCH$_3$ | CN | F |
| A-2595. | OCHF$_2$ | CN | 3-F | CN | F |
| A-2596. | OCHF$_2$ | CN | 3-CH$_3$ | CN | F |
| A-2597. | OCHF$_2$ | CN | 3-OCH$_3$ | CN | F |
| A-2598. | OCHF$_2$ | CN | 5-F | CN | F |
| A-2599. | OCHF$_2$ | CN | 5-CH$_3$ | CN | F |
| A-2600. | OCHF$_2$ | CN | 5-OCH$_3$ | CN | F |
| A-2601. | OCHF$_2$ | CH$_2$F | 3-F | CN | F |
| A-2602. | OCHF$_2$ | CH$_2$F | 3-CH$_3$ | CN | F |
| A-2603. | OCHF$_2$ | CH$_2$F | 3-OCH$_3$ | CN | F |
| A-2604. | OCHF$_2$ | CH$_2$F | 5-F | CN | F |
| A-2605. | OCHF$_2$ | CH$_2$F | 5-CH$_3$ | CN | F |
| A-2606. | OCHF$_2$ | CH$_2$F | 5-OCH$_3$ | CN | F |
| A-2607. | OCHF$_2$ | CHF$_2$ | 3-F | CN | F |
| A-2608. | OCHF$_2$ | CHF$_2$ | 3-CH$_3$ | CN | F |
| A-2609. | OCHF$_2$ | CHF$_2$ | 3-OCH$_3$ | CN | F |
| A-2610. | OCHF$_2$ | CHF$_2$ | 5-F | CN | F |
| A-2611. | OCHF$_2$ | CHF$_2$ | 5-CH$_3$ | CN | F |
| A-2612. | OCHF$_2$ | CHF$_2$ | 5-OCH$_3$ | CN | F |
| A-2613. | OCHF$_2$ | CF$_3$ | 3-F | CN | F |
| A-2614. | OCHF$_2$ | CF$_3$ | 3-CH$_3$ | CN | F |
| A-2615. | OCHF$_2$ | CF$_3$ | 3-OCH$_3$ | CN | F |
| A-2616. | OCHF$_2$ | CF$_3$ | 5-F | CN | F |
| A-2617. | OCHF$_2$ | CF$_3$ | 5-CH$_3$ | CN | F |
| A-2618. | OCHF$_2$ | CF$_3$ | 5-OCH$_3$ | CN | F |
| A-2619. | OCHF$_2$ | OCH$_2$F | 3-F | CN | F |
| A-2620. | OCHF$_2$ | OCH$_2$F | 3-CH$_3$ | CN | F |
| A-2621. | OCHF$_2$ | OCH$_2$F | 3-OCH$_3$ | CN | F |
| A-2622. | OCHF$_2$ | OCH$_2$F | 5-F | CN | F |
| A-2623. | OCHF$_2$ | OCH$_2$F | 5-CH$_3$ | CN | F |
| A-2624. | OCHF$_2$ | OCH$_2$F | 5-OCH$_3$ | CN | F |
| A-2625. | OCHF$_2$ | OCHF$_2$ | 3-F | CN | F |
| A-2626. | OCHF$_2$ | OCHF$_2$ | 3-CH$_3$ | CN | F |
| A-2627. | OCHF$_2$ | OCHF$_2$ | 3-OCH$_3$ | CN | F |
| A-2628. | OCHF$_2$ | OCHF$_2$ | 5-F | CN | F |
| A-2629. | OCHF$_2$ | OCHF$_2$ | 5-CH$_3$ | CN | F |
| A-2630. | OCHF$_2$ | OCHF$_2$ | 5-OCH$_3$ | CN | F |
| A-2631. | OCHF$_2$ | OCF$_3$ | 3-F | CN | F |
| A-2632. | OCHF$_2$ | OCF$_3$ | 3-CH$_3$ | CN | F |
| A-2633. | OCHF$_2$ | OCF$_3$ | 3-OCH$_3$ | CN | F |
| A-2634. | OCHF$_2$ | OCF$_3$ | 5-F | CN | F |
| A-2635. | OCHF$_2$ | OCF$_3$ | 5-CH$_3$ | CN | F |
| A-2636. | OCHF$_2$ | OCF$_3$ | 5-OCH$_3$ | CN | F |
| A-2637. | OCF$_3$ | F | 3-F | CN | F |
| A-2638. | OCF$_3$ | F | 3-CH$_3$ | CN | F |
| A-2639. | OCF$_3$ | F | 3-OCH$_3$ | CN | F |
| A-2640. | OCF$_3$ | F | 5-F | CN | F |
| A-2641. | OCF$_3$ | F | 5-CH$_3$ | CN | F |
| A-2642. | OCF$_3$ | F | 5-OCH$_3$ | CN | F |
| A-2643. | OCF$_3$ | CH$_3$ | 3-F | CN | F |
| A-2644. | OCF$_3$ | CH$_3$ | 3-CH$_3$ | CN | F |
| A-2645. | OCF$_3$ | CH$_3$ | 3-OCH$_3$ | CN | F |
| A-2646. | OCF$_3$ | CH$_3$ | 5-F | CN | F |
| A-2647. | OCF$_3$ | CH$_3$ | 5-CH$_3$ | CN | F |
| A-2648. | OCF$_3$ | CH$_3$ | 5-OCH$_3$ | CN | F |
| A-2649. | OCF$_3$ | OCH$_3$ | 3-F | CN | F |
| A-2650. | OCF$_3$ | OCH$_3$ | 3-CH$_3$ | CN | F |
| A-2651. | OCF$_3$ | OCH$_3$ | 3-OCH$_3$ | CN | F |
| A-2652. | OCF$_3$ | OCH$_3$ | 5-F | CN | F |
| A-2653. | OCF$_3$ | OCH$_3$ | 5-CH$_3$ | CN | F |
| A-2654. | OCF$_3$ | OCH$_3$ | 5-OCH$_3$ | CN | F |
| A-2655. | OCF$_3$ | CN | 3-F | CN | F |
| A-2656. | OCF$_3$ | CN | 3-CH$_3$ | CN | F |
| A-2657. | OCF$_3$ | CN | 3-OCH$_3$ | CN | F |
| A-2658. | OCF$_3$ | CN | 5-F | CN | F |
| A-2659. | OCF$_3$ | CN | 5-CH$_3$ | CN | F |
| A-2660. | OCF$_3$ | CN | 5-OCH$_3$ | CN | F |
| A-2661. | OCF$_3$ | CH$_2$F | 3-F | CN | F |
| A-2662. | OCF$_3$ | CH$_2$F | 3-CH$_3$ | CN | F |
| A-2663. | OCF$_3$ | CH$_2$F | 3-OCH$_3$ | CN | F |
| A-2664. | OCF$_3$ | CH$_2$F | 5-F | CN | F |
| A-2665. | OCF$_3$ | CH$_2$F | 5-CH$_3$ | CN | F |
| A-2666. | OCF$_3$ | CH$_2$F | 5-OCH$_3$ | CN | F |
| A-2667. | OCF$_3$ | CHF$_2$ | 3-F | CN | F |
| A-2668. | OCF$_3$ | CHF$_2$ | 3-CH$_3$ | CN | F |
| A-2669. | OCF$_3$ | CHF$_2$ | 3-OCH$_3$ | CN | F |
| A-2670. | OCF$_3$ | CHF$_2$ | 5-F | CN | F |
| A-2671. | OCF$_3$ | CHF$_2$ | 5-CH$_3$ | CN | F |
| A-2672. | OCF$_3$ | CHF$_2$ | 5-OCH$_3$ | CN | F |
| A-2673. | OCF$_3$ | CF$_3$ | 3-F | CN | F |
| A-2674. | OCF$_3$ | CF$_3$ | 3-CH$_3$ | CN | F |
| A-2675. | OCF$_3$ | CF$_3$ | 3-OCH$_3$ | CN | F |
| A-2676. | OCF$_3$ | CF$_3$ | 5-F | CN | F |
| A-2677. | OCF$_3$ | CF$_3$ | 5-CH$_3$ | CN | F |
| A-2678. | OCF$_3$ | CF$_3$ | 5-OCH$_3$ | CN | F |
| A-2679. | OCF$_3$ | OCH$_2$F | 3-F | CN | F |
| A-2680. | OCF$_3$ | OCH$_2$F | 3-CH$_3$ | CN | F |
| A-2681. | OCF$_3$ | OCH$_2$F | 3-OCH$_3$ | CN | F |
| A-2682. | OCF$_3$ | OCH$_2$F | 5-F | CN | F |
| A-2683. | OCF$_3$ | OCH$_2$F | 5-CH$_3$ | CN | F |
| A-2684. | OCF$_3$ | OCH$_2$F | 5-OCH$_3$ | CN | F |
| A-2685. | OCF$_3$ | OCHF$_2$ | 3-F | CN | F |
| A-2686. | OCF$_3$ | OCHF$_2$ | 3-CH$_3$ | CN | F |
| A-2687. | OCF$_3$ | OCHF$_2$ | 3-OCH$_3$ | CN | F |
| A-2688. | OCF$_3$ | OCHF$_2$ | 5-F | CN | F |
| A-2689. | OCF$_3$ | OCHF$_2$ | 5-CH$_3$ | CN | F |
| A-2690. | OCF$_3$ | OCHF$_2$ | 5-OCH$_3$ | CN | F |
| A-2691. | OCF$_3$ | OCF$_3$ | 3-F | CN | F |
| A-2692. | OCF$_3$ | OCF$_3$ | 3-CH$_3$ | CN | F |
| A-2693. | OCF$_3$ | OCF$_3$ | 3-OCH$_3$ | CN | F |
| A-2694. | OCF$_3$ | OCF$_3$ | 5-F | CN | F |
| A-2695. | OCF$_3$ | OCF$_3$ | 5-CH$_3$ | CN | F |
| A-2696. | OCF$_3$ | OCF$_3$ | 5-OCH$_3$ | CN | F |
| A-2697. | H | H | H | F | F |
| A-2698. | F | H | H | F | F |
| A-2699. | CH$_3$ | H | H | F | F |
| A-2700. | OCH$_3$ | H | H | F | F |
| A-2701. | CH$_2$F | H | H | F | F |
| A-2702. | CHF$_2$ | H | H | F | F |
| A-2703. | CF$_3$ | H | H | F | F |
| A-2704. | OCH$_2$F | H | H | F | F |
| A-2705. | OCHF$_2$ | H | H | F | F |
| A-2706. | OCF$_3$ | H | H | F | F |
| A-2707. | H | F | H | F | F |
| A-2708. | H | CH$_3$ | H | F | F |
| A-2709. | H | OCH$_3$ | H | F | F |
| A-2710. | H | CN | H | F | F |
| A-2711. | H | CH$_2$F | H | F | F |
| A-2712. | H | CHF$_2$ | H | F | F |
| A-2713. | H | CF$_3$ | H | F | F |
| A-2714. | H | OCH$_2$F | H | F | F |
| A-2715. | H | OCHF$_2$ | H | F | F |
| A-2716. | H | OCF$_3$ | H | F | F |

TABLE A-continued

| Example No. | R¹ | R² | R³ | R⁶ | R⁷ |
|---|---|---|---|---|---|
| A-2717. | H | H | 3-F | F | F |
| A-2718. | H | H | 3-CH₃ | F | F |
| A-2719. | H | H | 3-OCH₃ | F | F |
| A-2720. | H | H | 5-F | F | F |
| A-2721. | H | H | 5-CH₃ | F | F |
| A-2722. | H | H | 5-OCH₃ | F | F |
| A-2723. | F | F | H | F | F |
| A-2724. | F | CH₃ | H | F | F |
| A-2725. | F | OCH₃ | H | F | F |
| A-2726. | F | CN | H | F | F |
| A-2727. | F | CH₂F | H | F | F |
| A-2728. | F | CHF₂ | H | F | F |
| A-2729. | F | CF₃ | H | F | F |
| A-2730. | F | OCH₂F | H | F | F |
| A-2731. | F | OCHF₂ | H | F | F |
| A-2732. | F | OCF₃ | H | F | F |
| A-2733. | F | H | 3-F | F | F |
| A-2734. | F | H | 3-CH₃ | F | F |
| A-2735. | F | H | 3-OCH₃ | F | F |
| A-2736. | F | H | 5-F | F | F |
| A-2737. | F | H | 5-CH₃ | F | F |
| A-2738. | F | H | 5-OCH₃ | F | F |
| A-2739. | CH₃ | F | H | F | F |
| A-2740. | CH₃ | CH₃ | H | F | F |
| A-2741. | CH₃ | OCH₃ | H | F | F |
| A-2742. | CH₃ | CN | H | F | F |
| A-2743. | CH₃ | CH₂F | H | F | F |
| A-2744. | CH₃ | CHF₂ | H | F | F |
| A-2745. | CH₃ | CF₃ | H | F | F |
| A-2746. | CH₃ | OCH₂F | H | F | F |
| A-2747. | CH₃ | OCHF₂ | H | F | F |
| A-2748. | CH₃ | OCF₃ | H | F | F |
| A-2749. | CH₃ | H | 3-F | F | F |
| A-2750. | CH₃ | H | 3-CH₃ | F | F |
| A-2751. | CH₃ | H | 3-OCH₃ | F | F |
| A-2752. | CH₃ | H | 5-F | F | F |
| A-2753. | CH₃ | H | 5-CH₃ | F | F |
| A-2754. | CH₃ | H | 5-OCH₃ | F | F |
| A-2755. | OCH₃ | F | H | F | F |
| A-2756. | OCH₃ | CH₃ | H | F | F |
| A-2757. | OCH₃ | OCH₃ | H | F | F |
| A-2758. | OCH₃ | CN | H | F | F |
| A-2759. | OCH₃ | CH₂F | H | F | F |
| A-2760. | OCH₃ | CHF₂ | H | F | F |
| A-2761. | OCH₃ | CF₃ | H | F | F |
| A-2762. | OCH₃ | OCH₂F | H | F | F |
| A-2763. | OCH₃ | OCHF₂ | H | F | F |
| A-2764. | OCH₃ | OCF₃ | H | F | F |
| A-2765. | OCH₃ | H | 3-F | F | F |
| A-2766. | OCH₃ | H | 3-CH₃ | F | F |
| A-2767. | OCH₃ | H | 3-OCH₃ | F | F |
| A-2768. | OCH₃ | H | 5-F | F | F |
| A-2769. | OCH₃ | H | 5-CH₃ | F | F |
| A-2770. | OCH₃ | H | 5-OCH₃ | F | F |
| A-2771. | H | F | 3-F | F | F |
| A-2772. | H | F | 3-CH₃ | F | F |
| A-2773. | H | F | 3-OCH₃ | F | F |
| A-2774. | H | F | 5-F | F | F |
| A-2775. | H | F | 5-CH₃ | F | F |
| A-2776. | H | F | 5-OCH₃ | F | F |
| A-2777. | H | CH₃ | 3-F | F | F |
| A-2778. | H | CH₃ | 3-CH₃ | F | F |
| A-2779. | H | CH₃ | 3-OCH₃ | F | F |
| A-2780. | H | CH₃ | 5-F | F | F |
| A-2781. | H | CH₃ | 5-CH₃ | F | F |
| A-2782. | H | CH₃ | 5-OCH₃ | F | F |
| A-2783. | H | OCH₃ | 3-F | F | F |
| A-2784. | H | OCH₃ | 3-CH₃ | F | F |
| A-2785. | H | OCH₃ | 3-OCH₃ | F | F |
| A-2786. | H | OCH₃ | 5-F | F | F |
| A-2787. | H | OCH₃ | 5-CH₃ | F | F |
| A-2788. | H | OCH₃ | 5-OCH₃ | F | F |
| A-2789. | H | CN | 3-F | F | F |
| A-2790. | H | CN | 3-CH₃ | F | F |
| A-2791. | H | CN | 3-OCH₃ | F | F |
| A-2792. | H | CN | 5-F | F | F |
| A-2793. | H | CN | 5-CH₃ | F | F |
| A-2794. | H | CN | 5-OCH₃ | F | F |
| A-2795. | H | CH₂F | 3-F | F | F |
| A-2796. | H | CH₂F | 3-CH₃ | F | F |
| A-2797. | H | CH₂F | 3-OCH₃ | F | F |
| A-2798. | H | CH₂F | 5-F | F | F |
| A-2799. | H | CH₂F | 5-CH₃ | F | F |
| A-2800. | H | CH₂F | 5-OCH₃ | F | F |
| A-2801. | H | CHF₂ | 3-F | F | F |
| A-2802. | H | CHF₂ | 3-CH₃ | F | F |
| A-2803. | H | CHF₂ | 3-OCH₃ | F | F |
| A-2804. | H | CHF₂ | 5-F | F | F |
| A-2805. | H | CHF₂ | 5-CH₃ | F | F |
| A-2806. | H | CHF₂ | 5-OCH₃ | F | F |
| A-2807. | H | CF₃ | 3-F | F | F |
| A-2808. | H | CF₃ | 3-CH₃ | F | F |
| A-2809. | H | CF₃ | 3-OCH₃ | F | F |
| A-2810. | H | CF₃ | 5-F | F | F |
| A-2811. | H | CF₃ | 5-CH₃ | F | F |
| A-2812. | H | CF₃ | 5-OCH₃ | F | F |
| A-2813. | H | OCH₂F | 3-F | F | F |
| A-2814. | H | OCH₂F | 3-CH₃ | F | F |
| A-2815. | H | OCH₂F | 3-OCH₃ | F | F |
| A-2816. | H | OCH₂F | 5-F | F | F |
| A-2817. | H | OCH₂F | 5-CH₃ | F | F |
| A-2818. | H | OCH₂F | 5-OCH₃ | F | F |
| A-2819. | H | OCHF₂ | 3-F | F | F |
| A-2820. | H | OCHF₂ | 3-CH₃ | F | F |
| A-2821. | H | OCHF₂ | 3-OCH₃ | F | F |
| A-2822. | H | OCHF₂ | 5-F | F | F |
| A-2823. | H | OCHF₂ | 5-CH₃ | F | F |
| A-2824. | H | OCHF₂ | 5-OCH₃ | F | F |
| A-2825. | H | OCF₃ | 3-F | F | F |
| A-2826. | H | OCF₃ | 3-CH₃ | F | F |
| A-2827. | H | OCF₃ | 3-OCH₃ | F | F |
| A-2828. | H | OCF₃ | 5-F | F | F |
| A-2829. | H | OCF₃ | 5-CH₃ | F | F |
| A-2830. | H | OCF₃ | 5-OCH₃ | F | F |
| A-2831. | F | F | 3-F | F | F |
| A-2832. | F | F | 3-CH₃ | F | F |
| A-2833. | F | F | 3-OCH₃ | F | F |
| A-2834. | F | F | 5-F | F | F |
| A-2835. | F | F | 5-CH₃ | F | F |
| A-2836. | F | F | 5-OCH₃ | F | F |
| A-2837. | F | CH₃ | 3-F | F | F |
| A-2838. | F | CH₃ | 3-CH₃ | F | F |
| A-2839. | F | CH₃ | 3-OCH₃ | F | F |
| A-2840. | F | CH₃ | 5-F | F | F |
| A-2841. | F | CH₃ | 5-CH₃ | F | F |
| A-2842. | F | CH₃ | 5-OCH₃ | F | F |
| A-2843. | F | OCH₃ | 3-F | F | F |
| A-2844. | F | OCH₃ | 3-CH₃ | F | F |
| A-2845. | F | OCH₃ | 3-OCH₃ | F | F |
| A-2846. | F | OCH₃ | 5-F | F | F |
| A-2847. | F | OCH₃ | 5-CH₃ | F | F |
| A-2848. | F | OCH₃ | 5-OCH₃ | F | F |
| A-2849. | F | CN | 3-F | F | F |
| A-2850. | F | CN | 3-CH₃ | F | F |
| A-2851. | F | CN | 3-OCH₃ | F | F |
| A-2852. | F | CN | 5-F | F | F |
| A-2853. | F | CN | 5-CH₃ | F | F |
| A-2854. | F | CN | 5-OCH₃ | F | F |
| A-2855. | F | CH₂F | 3-F | F | F |
| A-2856. | F | CH₂F | 3-CH₃ | F | F |
| A-2857. | F | CH₂F | 3-OCH₃ | F | F |
| A-2858. | F | CH₂F | 5-F | F | F |
| A-2859. | F | CH₂F | 5-CH₃ | F | F |
| A-2860. | F | CH₂F | 5-OCH₃ | F | F |
| A-2861. | F | CHF₂ | 3-F | F | F |
| A-2862. | F | CHF₂ | 3-CH₃ | F | F |
| A-2863. | F | CHF₂ | 3-OCH₃ | F | F |
| A-2864. | F | CHF₂ | 5-F | F | F |
| A-2865. | F | CHF₂ | 5-CH₃ | F | F |
| A-2866. | F | CHF₂ | 5-OCH₃ | F | F |
| A-2867. | F | CF₃ | 3-F | F | F |
| A-2868. | F | CF₃ | 3-CH₃ | F | F |
| A-2869. | F | CF₃ | 3-OCH₃ | F | F |
| A-2870. | F | CF₃ | 5-F | F | F |
| A-2871. | F | CF₃ | 5-CH₃ | F | F |
| A-2872. | F | CF₃ | 5-OCH₃ | F | F |

TABLE A-continued

| Example No. | R¹ | R² | R³ | R⁶ | R⁷ |
|---|---|---|---|---|---|
| A-2873. | F | OCH₂F | 3-F | F | F |
| A-2874. | F | OCH₂F | 3-CH₃ | F | F |
| A-2875. | F | OCH₂F | 3-OCH₃ | F | F |
| A-2876. | F | OCH₂F | 5-F | F | F |
| A-2877. | F | OCH₂F | 5-CH₃ | F | F |
| A-2878. | F | OCH₂F | 5-OCH₃ | F | F |
| A-2879. | F | OCHF₂ | 3-F | F | F |
| A-2880. | F | OCHF₂ | 3-CH₃ | F | F |
| A-2881. | F | OCHF₂ | 3-OCH₃ | F | F |
| A-2882. | F | OCHF₂ | 5-F | F | F |
| A-2883. | F | OCHF₂ | 5-CH₃ | F | F |
| A-2884. | F | OCHF₂ | 5-OCH₃ | F | F |
| A-2885. | F | OCF₃ | 3-F | F | F |
| A-2886. | F | OCF₃ | 3-CH₃ | F | F |
| A-2887. | F | OCF₃ | 3-OCH₃ | F | F |
| A-2888. | F | OCF₃ | 5-F | F | F |
| A-2889. | F | OCF₃ | 5-CH₃ | F | F |
| A-2890. | F | OCF₃ | 5-OCH₃ | F | F |
| A-2891. | CH₃ | F | 3-F | F | F |
| A-2892. | CH₃ | F | 3-CH₃ | F | F |
| A-2893. | CH₃ | F | 3-OCH₃ | F | F |
| A-2894. | CH₃ | F | 5-F | F | F |
| A-2895. | CH₃ | F | 5-CH₃ | F | F |
| A-2896. | CH₃ | F | 5-OCH₃ | F | F |
| A-2897. | CH₃ | CH₃ | 3-F | F | F |
| A-2898. | CH₃ | CH₃ | 3-CH₃ | F | F |
| A-2899. | CH₃ | CH₃ | 3-OCH₃ | F | F |
| A-2900. | CH₃ | CH₃ | 5-F | F | F |
| A-2901. | CH₃ | CH₃ | 5-CH₃ | F | F |
| A-2902. | CH₃ | CH₃ | 5-OCH₃ | F | F |
| A-2903. | CH₃ | OCH₃ | 3-F | F | F |
| A-2904. | CH₃ | OCH₃ | 3-CH₃ | F | F |
| A-2905. | CH₃ | OCH₃ | 3-OCH₃ | F | F |
| A-2906. | CH₃ | OCH₃ | 5-F | F | F |
| A-2907. | CH₃ | OCH₃ | 5-CH₃ | F | F |
| A-2908. | CH₃ | OCH₃ | 5-OCH₃ | F | F |
| A-2909. | CH₃ | CN | 3-F | F | F |
| A-2910. | CH₃ | CN | 3-CH₃ | F | F |
| A-2911. | CH₃ | CN | 3-OCH₃ | F | F |
| A-2912. | CH₃ | CN | 5-F | F | F |
| A-2913. | CH₃ | CN | 5-CH₃ | F | F |
| A-2914. | CH₃ | CN | 5-OCH₃ | F | F |
| A-2915. | CH₃ | CH₂F | 3-F | F | F |
| A-2916. | CH₃ | CH₂F | 3-CH₃ | F | F |
| A-2917. | CH₃ | CH₂F | 3-OCH₃ | F | F |
| A-2918. | CH₃ | CH₂F | 5-F | F | F |
| A-2919. | CH₃ | CH₂F | 5-CH₃ | F | F |
| A-2920. | CH₃ | CH₂F | 5-OCH₃ | F | F |
| A-2921. | CH₃ | CHF₂ | 3-F | F | F |
| A-2922. | CH₃ | CHF₂ | 3-CH₃ | F | F |
| A-2923. | CH₃ | CHF₂ | 3-OCH₃ | F | F |
| A-2924. | CH₃ | CHF₂ | 5-F | F | F |
| A-2925. | CH₃ | CHF₂ | 5-CH₃ | F | F |
| A-2926. | CH₃ | CHF₂ | 5-OCH₃ | F | F |
| A-2927. | CH₃ | CF₃ | 3-F | F | F |
| A-2928. | CH₃ | CF₃ | 3-CH₃ | F | F |
| A-2929. | CH₃ | CF₃ | 3-OCH₃ | F | F |
| A-2930. | CH₃ | CF₃ | 5-F | F | F |
| A-2931. | CH₃ | CF₃ | 5-CH₃ | F | F |
| A-2932. | CH₃ | CF₃ | 5-OCH₃ | F | F |
| A-2933. | CH₃ | OCH₂F | 3-F | F | F |
| A-2934. | CH₃ | OCH₂F | 3-CH₃ | F | F |
| A-2935. | CH₃ | OCH₂F | 3-OCH₃ | F | F |
| A-2936. | CH₃ | OCH₂F | 5-F | F | F |
| A-2937. | CH₃ | OCH₂F | 5-CH₃ | F | F |
| A-2938. | CH₃ | OCH₂F | 5-OCH₃ | F | F |
| A-2939. | CH₃ | OCHF₂ | 3-F | F | F |
| A-2940. | CH₃ | OCHF₂ | 3-CH₃ | F | F |
| A-2941. | CH₃ | OCHF₂ | 3-OCH₃ | F | F |
| A-2942. | CH₃ | OCHF₂ | 5-F | F | F |
| A-2943. | CH₃ | OCHF₂ | 5-CH₃ | F | F |
| A-2944. | CH₃ | OCHF₂ | 5-OCH₃ | F | F |
| A-2945. | CH₃ | OCF₃ | 3-F | F | F |
| A-2946. | CH₃ | OCF₃ | 3-CH₃ | F | F |
| A-2947. | CH₃ | OCF₃ | 3-OCH₃ | F | F |
| A-2948. | CH₃ | OCF₃ | 5-F | F | F |
| A-2949. | CH₃ | OCF₃ | 5-CH₃ | F | F |
| A-2950. | CH₃ | OCF₃ | 5-OCH₃ | F | F |
| A-2951. | OCH₃ | F | 3-F | F | F |
| A-2952. | OCH₃ | F | 3-CH₃ | F | F |
| A-2953. | OCH₃ | F | 3-OCH₃ | F | F |
| A-2954. | OCH₃ | F | 5-F | F | F |
| A-2955. | OCH₃ | F | 5-CH₃ | F | F |
| A-2956. | OCH₃ | F | 5-OCH₃ | F | F |
| A-2957. | OCH₃ | CH₃ | 3-F | F | F |
| A-2958. | OCH₃ | CH₃ | 3-CH₃ | F | F |
| A-2959. | OCH₃ | CH₃ | 3-OCH₃ | F | F |
| A-2960. | OCH₃ | CH₃ | 5-F | F | F |
| A-2961. | OCH₃ | CH₃ | 5-CH₃ | F | F |
| A-2962. | OCH₃ | CH₃ | 5-OCH₃ | F | F |
| A-2963. | OCH₃ | OCH₃ | 3-F | F | F |
| A-2964. | OCH₃ | OCH₃ | 3-CH₃ | F | F |
| A-2965. | OCH₃ | OCH₃ | 3-OCH₃ | F | F |
| A-2966. | OCH₃ | OCH₃ | 5-F | F | F |
| A-2967. | OCH₃ | OCH₃ | 5-CH₃ | F | F |
| A-2968. | OCH₃ | OCH₃ | 5-OCH₃ | F | F |
| A-2969. | OCH₃ | CN | 3-F | F | F |
| A-2970. | OCH₃ | CN | 3-CH₃ | F | F |
| A-2971. | OCH₃ | CN | 3-OCH₃ | F | F |
| A-2972. | OCH₃ | CN | 5-F | F | F |
| A-2973. | OCH₃ | CN | 5-CH₃ | F | F |
| A-2974. | OCH₃ | CN | 5-OCH₃ | F | F |
| A-2975. | OCH₃ | CH₂F | 3-F | F | F |
| A-2976. | OCH₃ | CH₂F | 3-CH₃ | F | F |
| A-2977. | OCH₃ | CH₂F | 3-OCH₃ | F | F |
| A-2978. | OCH₃ | CH₂F | 5-F | F | F |
| A-2979. | OCH₃ | CH₂F | 5-CH₃ | F | F |
| A-2980. | OCH₃ | CH₂F | 5-OCH₃ | F | F |
| A-2981. | OCH₃ | CHF₂ | 3-F | F | F |
| A-2982. | OCH₃ | CHF₂ | 3-CH₃ | F | F |
| A-2983. | OCH₃ | CHF₂ | 3-OCH₃ | F | F |
| A-2984. | OCH₃ | CHF₂ | 5-F | F | F |
| A-2985. | OCH₃ | CHF₂ | 5-CH₃ | F | F |
| A-2986. | OCH₃ | CHF₂ | 5-OCH₃ | F | F |
| A-2987. | OCH₃ | CF₃ | 3-F | F | F |
| A-2988. | OCH₃ | CF₃ | 3-CH₃ | F | F |
| A-2989. | OCH₃ | CF₃ | 3-OCH₃ | F | F |
| A-2990. | OCH₃ | CF₃ | 5-F | F | F |
| A-2991. | OCH₃ | CF₃ | 5-CH₃ | F | F |
| A-2992. | OCH₃ | CF₃ | 5-OCH₃ | F | F |
| A-2993. | OCH₃ | OCH₂F | 3-F | F | F |
| A-2994. | OCH₃ | OCH₂F | 3-CH₃ | F | F |
| A-2995. | OCH₃ | OCH₂F | 3-OCH₃ | F | F |
| A-2996. | OCH₃ | OCH₂F | 5-F | F | F |
| A-2997. | OCH₃ | OCH₂F | 5-CH₃ | F | F |
| A-2998. | OCH₃ | OCH₂F | 5-OCH₃ | F | F |
| A-2999. | OCH₃ | OCHF₂ | 3-F | F | F |
| A-3000. | OCH₃ | OCHF₂ | 3-CH₃ | F | F |
| A-3001. | OCH₃ | OCHF₂ | 3-OCH₃ | F | F |
| A-3002. | OCH₃ | OCHF₂ | 5-F | F | F |
| A-3003. | OCH₃ | OCHF₂ | 5-CH₃ | F | F |
| A-3004. | OCH₃ | OCHF₂ | 5-OCH₃ | F | F |
| A-3005. | OCH₃ | OCF₃ | 3-F | F | F |
| A-3006. | OCH₃ | OCF₃ | 3-CH₃ | F | F |
| A-3007. | OCH₃ | OCF₃ | 3-OCH₃ | F | F |
| A-3008. | OCH₃ | OCF₃ | 5-F | F | F |
| A-3009. | OCH₃ | OCF₃ | 5-CH₃ | F | F |
| A-3010. | OCH₃ | OCF₃ | 5-OCH₃ | F | F |
| A-3011. | CH₂F | F | 3-F | F | F |
| A-3012. | CH₂F | F | 3-CH₃ | F | F |
| A-3013. | CH₂F | F | 3-OCH₃ | F | F |
| A-3014. | CH₂F | F | 5-F | F | F |
| A-3015. | CH₂F | F | 5-CH₃ | F | F |
| A-3016. | CH₂F | F | 5-OCH₃ | F | F |
| A-3017. | CH₂F | CH₃ | 3-F | F | F |
| A-3018. | CH₂F | CH₃ | 3-CH₃ | F | F |
| A-3019. | CH₂F | CH₃ | 3-OCH₃ | F | F |
| A-3020. | CH₂F | CH₃ | 5-F | F | F |
| A-3021. | CH₂F | CH₃ | 5-CH₃ | F | F |
| A-3022. | CH₂F | CH₃ | 5-OCH₃ | F | F |
| A-3023. | CH₂F | OCH₃ | 3-F | F | F |
| A-3024. | CH₂F | OCH₃ | 3-CH₃ | F | F |
| A-3025. | CH₂F | OCH₃ | 3-OCH₃ | F | F |
| A-3026. | CH₂F | OCH₃ | 5-F | F | F |
| A-3027. | CH₂F | OCH₃ | 5-CH₃ | F | F |
| A-3028. | CH₂F | OCH₃ | 5-OCH₃ | F | F |

TABLE A-continued

| Example No. | $R^1$ | $R^2$ | $R^3$ | $R^6$ | $R^7$ |
|---|---|---|---|---|---|
| A-3029. | $CH_2F$ | CN | 3-F | F | F |
| A-3030. | $CH_2F$ | CN | 3-$CH_3$ | F | F |
| A-3031. | $CH_2F$ | CN | 3-$OCH_3$ | F | F |
| A-3032. | $CH_2F$ | CN | 5-F | F | F |
| A-3033. | $CH_2F$ | CN | 5-$CH_3$ | F | F |
| A-3034. | $CH_2F$ | CN | 5-$OCH_3$ | F | F |
| A-3035. | $CH_2F$ | $CH_2F$ | 3-F | F | F |
| A-3036. | $CH_2F$ | $CH_2F$ | 3-$CH_3$ | F | F |
| A-3037. | $CH_2F$ | $CH_2F$ | 3-$OCH_3$ | F | F |
| A-3038. | $CH_2F$ | $CH_2F$ | 5-F | F | F |
| A-3039. | $CH_2F$ | $CH_2F$ | 5-$CH_3$ | F | F |
| A-3040. | $CH_2F$ | $CH_2F$ | 5-$OCH_3$ | F | F |
| A-3041. | $CH_2F$ | $CHF_2$ | 3-F | F | F |
| A-3042. | $CH_2F$ | $CHF_2$ | 3-$CH_3$ | F | F |
| A-3043. | $CH_2F$ | $CHF_2$ | 3-$OCH_3$ | F | F |
| A-3044. | $CH_2F$ | $CHF_2$ | 5-F | F | F |
| A-3045. | $CH_2F$ | $CHF_2$ | 5-$CH_3$ | F | F |
| A-3046. | $CH_2F$ | $CHF_2$ | 5-$OCH_3$ | F | F |
| A-3047. | $CH_2F$ | $CF_3$ | 3-F | F | F |
| A-3048. | $CH_2F$ | $CF_3$ | 3-$CH_3$ | F | F |
| A-3049. | $CH_2F$ | $CF_3$ | 3-$OCH_3$ | F | F |
| A-3050. | $CH_2F$ | $CF_3$ | 5-F | F | F |
| A-3051. | $CH_2F$ | $CF_3$ | 5-$CH_3$ | F | F |
| A-3052. | $CH_2F$ | $CF_3$ | 5-$OCH_3$ | F | F |
| A-3053. | $CH_2F$ | $OCH_2F$ | 3-F | F | F |
| A-3054. | $CH_2F$ | $OCH_2F$ | 3-$CH_3$ | F | F |
| A-3055. | $CH_2F$ | $OCH_2F$ | 3-$OCH_3$ | F | F |
| A-3056. | $CH_2F$ | $OCH_2F$ | 5-F | F | F |
| A-3057. | $CH_2F$ | $OCH_2F$ | 5-$CH_3$ | F | F |
| A-3058. | $CH_2F$ | $OCH_2F$ | 5-$OCH_3$ | F | F |
| A-3059. | $CH_2F$ | $OCHF_2$ | 3-F | F | F |
| A-3060. | $CH_2F$ | $OCHF_2$ | 3-$CH_3$ | F | F |
| A-3061. | $CH_2F$ | $OCHF_2$ | 3-$OCH_3$ | F | F |
| A-3062. | $CH_2F$ | $OCHF_2$ | 5-F | F | F |
| A-3063. | $CH_2F$ | $OCHF_2$ | 5-$CH_3$ | F | F |
| A-3064. | $CH_2F$ | $OCHF_2$ | 5-$OCH_3$ | F | F |
| A-3065. | $CH_2F$ | $OCF_3$ | 3-F | F | F |
| A-3066. | $CH_2F$ | $OCF_3$ | 3-$CH_3$ | F | F |
| A-3067. | $CH_2F$ | $OCF_3$ | 3-$OCH_3$ | F | F |
| A-3068. | $CH_2F$ | $OCF_3$ | 5-F | F | F |
| A-3069. | $CH_2F$ | $OCF_3$ | 5-$CH_3$ | F | F |
| A-3070. | $CH_2F$ | $OCF_3$ | 5-$OCH_3$ | F | F |
| A-3071. | $CHF_2$ | F | 3-F | F | F |
| A-3072. | $CHF_2$ | F | 3-$CH_3$ | F | F |
| A-3073. | $CHF_2$ | F | 3-$OCH_3$ | F | F |
| A-3074. | $CHF_2$ | F | 5-F | F | F |
| A-3075. | $CHF_2$ | F | 5-$CH_3$ | F | F |
| A-3076. | $CHF_2$ | F | 5-$OCH_3$ | F | F |
| A-3077. | $CHF_2$ | $CH_3$ | 3-F | F | F |
| A-3078. | $CHF_2$ | $CH_3$ | 3-$CH_3$ | F | F |
| A-3079. | $CHF_2$ | $CH_3$ | 3-$OCH_3$ | F | F |
| A-3080. | $CHF_2$ | $CH_3$ | 5-F | F | F |
| A-3081. | $CHF_2$ | $CH_3$ | 5-$CH_3$ | F | F |
| A-3082. | $CHF_2$ | $CH_3$ | 5-$OCH_3$ | F | F |
| A-3083. | $CHF_2$ | $OCH_3$ | 3-F | F | F |
| A-3084. | $CHF_2$ | $OCH_3$ | 3-$CH_3$ | F | F |
| A-3085. | $CHF_2$ | $OCH_3$ | 3-$OCH_3$ | F | F |
| A-3086. | $CHF_2$ | $OCH_3$ | 5-F | F | F |
| A-3087. | $CHF_2$ | $OCH_3$ | 5-$CH_3$ | F | F |
| A-3088. | $CHF_2$ | $OCH_3$ | 5-$OCH_3$ | F | F |
| A-3089. | $CHF_2$ | CN | 3-F | F | F |
| A-3090. | $CHF_2$ | CN | 3-$CH_3$ | F | F |
| A-3091. | $CHF_2$ | CN | 3-$OCH_3$ | F | F |
| A-3092. | $CHF_2$ | CN | 5-F | F | F |
| A-3093. | $CHF_2$ | CN | 5-$CH_3$ | F | F |
| A-3094. | $CHF_2$ | CN | 5-$OCH_3$ | F | F |
| A-3095. | $CHF_2$ | $CH_2F$ | 3-F | F | F |
| A-3096. | $CHF_2$ | $CH_2F$ | 3-$CH_3$ | F | F |
| A-3097. | $CHF_2$ | $CH_2F$ | 3-$OCH_3$ | F | F |
| A-3098. | $CHF_2$ | $CH_2F$ | 5-F | F | F |
| A-3099. | $CHF_2$ | $CH_2F$ | 5-$CH_3$ | F | F |
| A-3100. | $CHF_2$ | $CH_2F$ | 5-$OCH_3$ | F | F |
| A-3101. | $CHF_2$ | $CHF_2$ | 3-F | F | F |
| A-3102. | $CHF_2$ | $CHF_2$ | 3-$CH_3$ | F | F |
| A-3103. | $CHF_2$ | $CHF_2$ | 3-$OCH_3$ | F | F |
| A-3104. | $CHF_2$ | $CHF_2$ | 5-F | F | F |
| A-3105. | $CHF_2$ | $CHF_2$ | 5-$CH_3$ | F | F |
| A-3106. | $CHF_2$ | $CHF_2$ | 5-$OCH_3$ | F | F |
| A-3107. | $CHF_2$ | $CF_3$ | 3-F | F | F |
| A-3108. | $CHF_2$ | $CF_3$ | 3-$CH_3$ | F | F |
| A-3109. | $CHF_2$ | $CF_3$ | 3-$OCH_3$ | F | F |
| A-3110. | $CHF_2$ | $CF_3$ | 5-F | F | F |
| A-3111. | $CHF_2$ | $CF_3$ | 5-$CH_3$ | F | F |
| A-3112. | $CHF_2$ | $CF_3$ | 5-$OCH_3$ | F | F |
| A-3113. | $CHF_2$ | $OCH_2F$ | 3-F | F | F |
| A-3114. | $CHF_2$ | $OCH_2F$ | 3-$CH_3$ | F | F |
| A-3115. | $CHF_2$ | $OCH_2F$ | 3-$OCH_3$ | F | F |
| A-3116. | $CHF_2$ | $OCH_2F$ | 5-F | F | F |
| A-3117. | $CHF_2$ | $OCH_2F$ | 5-$CH_3$ | F | F |
| A-3118. | $CHF_2$ | $OCH_2F$ | 5-$OCH_3$ | F | F |
| A-3119. | $CHF_2$ | $OCHF_2$ | 3-F | F | F |
| A-3120. | $CHF_2$ | $OCHF_2$ | 3-$CH_3$ | F | F |
| A-3121. | $CHF_2$ | $OCHF_2$ | 3-$OCH_3$ | F | F |
| A-3122. | $CHF_2$ | $OCHF_2$ | 5-F | F | F |
| A-3123. | $CHF_2$ | $OCHF_2$ | 5-$CH_3$ | F | F |
| A-3124. | $CHF_2$ | $OCHF_2$ | 5-$OCH_3$ | F | F |
| A-3125. | $CHF_2$ | $OCF_3$ | 3-F | F | F |
| A-3126. | $CHF_2$ | $OCF_3$ | 3-$CH_3$ | F | F |
| A-3127. | $CHF_2$ | $OCF_3$ | 3-$OCH_3$ | F | F |
| A-3128. | $CHF_2$ | $OCF_3$ | 5-F | F | F |
| A-3129. | $CHF_2$ | $OCF_3$ | 5-$CH_3$ | F | F |
| A-3130. | $CHF_2$ | $OCF_3$ | 5-$OCH_3$ | F | F |
| A-3131. | $CF_3$ | F | 3-F | F | F |
| A-3132. | $CF_3$ | F | 3-$CH_3$ | F | F |
| A-3133. | $CF_3$ | F | 3-$OCH_3$ | F | F |
| A-3134. | $CF_3$ | F | 5-F | F | F |
| A-3135. | $CF_3$ | F | 5-$CH_3$ | F | F |
| A-3136. | $CF_3$ | F | 5-$OCH_3$ | F | F |
| A-3137. | $CF_3$ | $CH_3$ | 3-F | F | F |
| A-3138. | $CF_3$ | $CH_3$ | 3-$CH_3$ | F | F |
| A-3139. | $CF_3$ | $CH_3$ | 3-$OCH_3$ | F | F |
| A-3140. | $CF_3$ | $CH_3$ | 5-F | F | F |
| A-3141. | $CF_3$ | $CH_3$ | 5-$CH_3$ | F | F |
| A-3142. | $CF_3$ | $CH_3$ | 5-$OCH_3$ | F | F |
| A-3143. | $CF_3$ | $OCH_3$ | 3-F | F | F |
| A-3144. | $CF_3$ | $OCH_3$ | 3-$CH_3$ | F | F |
| A-3145. | $CF_3$ | $OCH_3$ | 3-$OCH_3$ | F | F |
| A-3146. | $CF_3$ | $OCH_3$ | 5-F | F | F |
| A-3147. | $CF_3$ | $OCH_3$ | 5-$CH_3$ | F | F |
| A-3148. | $CF_3$ | $OCH_3$ | 5-$OCH_3$ | F | F |
| A-3149. | $CF_3$ | CN | 3-F | F | F |
| A-3150. | $CF_3$ | CN | 3-$CH_3$ | F | F |
| A-3151. | $CF_3$ | CN | 3-$OCH_3$ | F | F |
| A-3152. | $CF_3$ | CN | 5-F | F | F |
| A-3153. | $CF_3$ | CN | 5-$CH_3$ | F | F |
| A-3154. | $CF_3$ | CN | 5-$OCH_3$ | F | F |
| A-3155. | $CF_3$ | $CH_2F$ | 3-F | F | F |
| A-3156. | $CF_3$ | $CH_2F$ | 3-$CH_3$ | F | F |
| A-3157. | $CF_3$ | $CH_2F$ | 3-$OCH_3$ | F | F |
| A-3158. | $CF_3$ | $CH_2F$ | 5-F | F | F |
| A-3159. | $CF_3$ | $CH_2F$ | 5-$CH_3$ | F | F |
| A-3160. | $CF_3$ | $CH_2F$ | 5-$OCH_3$ | F | F |
| A-3161. | $CF_3$ | $CHF_2$ | 3-F | F | F |
| A-3162. | $CF_3$ | $CHF_2$ | 3-$CH_3$ | F | F |
| A-3163. | $CF_3$ | $CHF_2$ | 3-$OCH_3$ | F | F |
| A-3164. | $CF_3$ | $CHF_2$ | 5-F | F | F |
| A-3165. | $CF_3$ | $CHF_2$ | 5-$CH_3$ | F | F |
| A-3166. | $CF_3$ | $CHF_2$ | 5-$OCH_3$ | F | F |
| A-3167. | $CF_3$ | $CF_3$ | 3-F | F | F |
| A-3168. | $CF_3$ | $CF_3$ | 3-$CH_3$ | F | F |
| A-3169. | $CF_3$ | $CF_3$ | 3-$OCH_3$ | F | F |
| A-3170. | $CF_3$ | $CF_3$ | 5-F | F | F |
| A-3171. | $CF_3$ | $CF_3$ | 5-$CH_3$ | F | F |
| A-3172. | $CF_3$ | $CF_3$ | 5-$OCH_3$ | F | F |
| A-3173. | $CF_3$ | $OCH_2F$ | 3-F | F | F |
| A-3174. | $CF_3$ | $OCH_2F$ | 3-$CH_3$ | F | F |
| A-3175. | $CF_3$ | $OCH_2F$ | 3-$OCH_3$ | F | F |
| A-3176. | $CF_3$ | $OCH_2F$ | 5-F | F | F |
| A-3177. | $CF_3$ | $OCH_2F$ | 5-$CH_3$ | F | F |
| A-3178. | $CF_3$ | $OCH_2F$ | 5-$OCH_3$ | F | F |
| A-3179. | $CF_3$ | $OCHF_2$ | 3-F | F | F |
| A-3180. | $CF_3$ | $OCHF_2$ | 3-$CH_3$ | F | F |
| A-3181. | $CF_3$ | $OCHF_2$ | 3-$OCH_3$ | F | F |
| A-3182. | $CF_3$ | $OCHF_2$ | 5-F | F | F |
| A-3183. | $CF_3$ | $OCHF_2$ | 5-$CH_3$ | F | F |
| A-3184. | $CF_3$ | $OCHF_2$ | 5-$OCH_3$ | F | F |

TABLE A-continued

| Example No. | R¹ | R² | R³ | R⁶ | R⁷ |
|---|---|---|---|---|---|
| A-3185. | CF₃ | OCF₃ | 3-F | F | F |
| A-3186. | CF₃ | OCF₃ | 3-CH₃ | F | F |
| A-3187. | CF₃ | OCF₃ | 3-OCH₃ | F | F |
| A-3188. | CF₃ | OCF₃ | 5-F | F | F |
| A-3189. | CF₃ | OCF₃ | 5-CH₃ | F | F |
| A-3190. | CF₃ | OCF₃ | 5-OCH₃ | F | F |
| A-3191. | OCH₂F | F | 3-F | F | F |
| A-3192. | OCH₂F | F | 3-CH₃ | F | F |
| A-3193. | OCH₂F | F | 3-OCH₃ | F | F |
| A-3194. | OCH₂F | F | 5-F | F | F |
| A-3195. | OCH₂F | F | 5-CH₃ | F | F |
| A-3196. | OCH₂F | F | 5-OCH₃ | F | F |
| A-3197. | OCH₂F | CH₃ | 3-F | F | F |
| A-3198. | OCH₂F | CH₃ | 3-CH₃ | F | F |
| A-3199. | OCH₂F | CH₃ | 3-OCH₃ | F | F |
| A-3200. | OCH₂F | CH₃ | 5-F | F | F |
| A-3201. | OCH₂F | CH₃ | 5-CH₃ | F | F |
| A-3202. | OCH₂F | CH₃ | 5-OCH₃ | F | F |
| A-3203. | OCH₂F | OCH₃ | 3-F | F | F |
| A-3204. | OCH₂F | OCH₃ | 3-CH₃ | F | F |
| A-3205. | OCH₂F | OCH₃ | 3-OCH₃ | F | F |
| A-3206. | OCH₂F | OCH₃ | 5-F | F | F |
| A-3207. | OCH₂F | OCH₃ | 5-CH₃ | F | F |
| A-3208. | OCH₂F | OCH₃ | 5-OCH₃ | F | F |
| A-3209. | OCH₂F | CN | 3-F | F | F |
| A-3210. | OCH₂F | CN | 3-CH₃ | F | F |
| A-3211. | OCH₂F | CN | 3-OCH₃ | F | F |
| A-3212. | OCH₂F | CN | 5-F | F | F |
| A-3213. | OCH₂F | CN | 5-CH₃ | F | F |
| A-3214. | OCH₂F | CN | 5-OCH₃ | F | F |
| A-3215. | OCH₂F | CH₂F | 3-F | F | F |
| A-3216. | OCH₂F | CH₂F | 3-CH₃ | F | F |
| A-3217. | OCH₂F | CH₂F | 3-OCH₃ | F | F |
| A-3218. | OCH₂F | CH₂F | 5-F | F | F |
| A-3219. | OCH₂F | CH₂F | 5-CH₃ | F | F |
| A-3220. | OCH₂F | CH₂F | 5-OCH₃ | F | F |
| A-3221. | OCH₂F | CHF₂ | 3-F | F | F |
| A-3222. | OCH₂F | CHF₂ | 3-CH₃ | F | F |
| A-3223. | OCH₂F | CHF₂ | 3-OCH₃ | F | F |
| A-3224. | OCH₂F | CHF₂ | 5-F | F | F |
| A-3225. | OCH₂F | CHF₂ | 5-CH₃ | F | F |
| A-3226. | OCH₂F | CHF₂ | 5-OCH₃ | F | F |
| A-3227. | OCH₂F | CF₃ | 3-F | F | F |
| A-3228. | OCH₂F | CF₃ | 3-CH₃ | F | F |
| A-3229. | OCH₂F | CF₃ | 3-OCH₃ | F | F |
| A-3230. | OCH₂F | CF₃ | 5-F | F | F |
| A-3231. | OCH₂F | CF₃ | 5-CH₃ | F | F |
| A-3232. | OCH₂F | CF₃ | 5-OCH₃ | F | F |
| A-3233. | OCH₂F | OCH₂F | 3-F | F | F |
| A-3234. | OCH₂F | OCH₂F | 3-CH₃ | F | F |
| A-3235. | OCH₂F | OCH₂F | 3-OCH₃ | F | F |
| A-3236. | OCH₂F | OCH₂F | 5-F | F | F |
| A-3237. | OCH₂F | OCH₂F | 5-CH₃ | F | F |
| A-3238. | OCH₂F | OCH₂F | 5-OCH₃ | F | F |
| A-3239. | OCH₂F | OCHF₂ | 3-F | F | F |
| A-3240. | OCH₂F | OCHF₂ | 3-CH₃ | F | F |
| A-3241. | OCH₂F | OCHF₂ | 3-OCH₃ | F | F |
| A-3242. | OCH₂F | OCHF₂ | 5-F | F | F |
| A-3243. | OCH₂F | OCHF₂ | 5-CH₃ | F | F |
| A-3244. | OCH₂F | OCHF₂ | 5-OCH₃ | F | F |
| A-3245. | OCH₂F | OCF₃ | 3-F | F | F |
| A-3246. | OCH₂F | OCF₃ | 3-CH₃ | F | F |
| A-3247. | OCH₂F | OCF₃ | 3-OCH₃ | F | F |
| A-3248. | OCH₂F | OCF₃ | 5-F | F | F |
| A-3249. | OCH₂F | OCF₃ | 5-CH₃ | F | F |
| A-3250. | OCH₂F | OCF₃ | 5-OCH₃ | F | F |
| A-3251. | OCHF₂ | F | 3-F | F | F |
| A-3252. | OCHF₂ | F | 3-CH₃ | F | F |
| A-3253. | OCHF₂ | F | 3-OCH₃ | F | F |
| A-3254. | OCHF₂ | F | 5-F | F | F |
| A-3255. | OCHF₂ | F | 5-CH₃ | F | F |
| A-3256. | OCHF₂ | F | 5-OCH₃ | F | F |
| A-3257. | OCHF₂ | CH₃ | 3-F | F | F |
| A-3258. | OCHF₂ | CH₃ | 3-CH₃ | F | F |
| A-3259. | OCHF₂ | CH₃ | 3-OCH₃ | F | F |
| A-3260. | OCHF₂ | CH₃ | 5-F | F | F |
| A-3261. | OCHF₂ | CH₃ | 5-CH₃ | F | F |
| A-3262. | OCHF₂ | CH₃ | 5-OCH₃ | F | F |
| A-3263. | OCHF₂ | OCH₃ | 3-F | F | F |
| A-3264. | OCHF₂ | OCH₃ | 3-CH₃ | F | F |
| A-3265. | OCHF₂ | OCH₃ | 3-OCH₃ | F | F |
| A-3266. | OCHF₂ | OCH₃ | 5-F | F | F |
| A-3267. | OCHF₂ | OCH₃ | 5-CH₃ | F | F |
| A-3268. | OCHF₂ | OCH₃ | 5-OCH₃ | F | F |
| A-3269. | OCHF₂ | CN | 3-F | F | F |
| A-3270. | OCHF₂ | CN | 3-CH₃ | F | F |
| A-3271. | OCHF₂ | CN | 3-OCH₃ | F | F |
| A-3272. | OCHF₂ | CN | 5-F | F | F |
| A-3273. | OCHF₂ | CN | 5-CH₃ | F | F |
| A-3274. | OCHF₂ | CN | 5-OCH₃ | F | F |
| A-3275. | OCHF₂ | CH₂F | 3-F | F | F |
| A-3276. | OCHF₂ | CH₂F | 3-CH₃ | F | F |
| A-3277. | OCHF₂ | CH₂F | 3-OCH₃ | F | F |
| A-3278. | OCHF₂ | CH₂F | 5-F | F | F |
| A-3279. | OCHF₂ | CH₂F | 5-CH₃ | F | F |
| A-3280. | OCHF₂ | CH₂F | 5-OCH₃ | F | F |
| A-3281. | OCHF₂ | CHF₂ | 3-F | F | F |
| A-3282. | OCHF₂ | CHF₂ | 3-CH₃ | F | F |
| A-3283. | OCHF₂ | CHF₂ | 3-OCH₃ | F | F |
| A-3284. | OCHF₂ | CHF₂ | 5-F | F | F |
| A-3285. | OCHF₂ | CHF₂ | 5-CH₃ | F | F |
| A-3286. | OCHF₂ | CHF₂ | 5-OCH₃ | F | F |
| A-3287. | OCHF₂ | CF₃ | 3-F | F | F |
| A-3288. | OCHF₂ | CF₃ | 3-CH₃ | F | F |
| A-3289. | OCHF₂ | CF₃ | 3-OCH₃ | F | F |
| A-3290. | OCHF₂ | CF₃ | 5-F | F | F |
| A-3291. | OCHF₂ | CF₃ | 5-CH₃ | F | F |
| A-3292. | OCHF₂ | CF₃ | 5-OCH₃ | F | F |
| A-3293. | OCHF₂ | OCH₂F | 3-F | F | F |
| A-3294. | OCHF₂ | OCH₂F | 3-CH₃ | F | F |
| A-3295. | OCHF₂ | OCH₂F | 3-OCH₃ | F | F |
| A-3296. | OCHF₂ | OCH₂F | 5-F | F | F |
| A-3297. | OCHF₂ | OCH₂F | 5-CH₃ | F | F |
| A-3298. | OCHF₂ | OCH₂F | 5-OCH₃ | F | F |
| A-3299. | OCHF₂ | OCHF₂ | 3-F | F | F |
| A-3300. | OCHF₂ | OCHF₂ | 3-CH₃ | F | F |
| A-3301. | OCHF₂ | OCHF₂ | 3-OCH₃ | F | F |
| A-3302. | OCHF₂ | OCHF₂ | 5-F | F | F |
| A-3303. | OCHF₂ | OCHF₂ | 5-CH₃ | F | F |
| A-3304. | OCHF₂ | OCHF₂ | 5-OCH₃ | F | F |
| A-3305. | OCHF₂ | OCF₃ | 3-F | F | F |
| A-3306. | OCHF₂ | OCF₃ | 3-CH₃ | F | F |
| A-3307. | OCHF₂ | OCF₃ | 3-OCH₃ | F | F |
| A-3308. | OCHF₂ | OCF₃ | 5-F | F | F |
| A-3309. | OCHF₂ | OCF₃ | 5-CH₃ | F | F |
| A-3310. | OCHF₂ | OCF₃ | 5-OCH₃ | F | F |
| A-3311. | OCF₃ | F | 3-F | F | F |
| A-3312. | OCF₃ | F | 3-CH₃ | F | F |
| A-3313. | OCF₃ | F | 3-OCH₃ | F | F |
| A-3314. | OCF₃ | F | 5-F | F | F |
| A-3315. | OCF₃ | F | 5-CH₃ | F | F |
| A-3316. | OCF₃ | F | 5-OCH₃ | F | F |
| A-3317. | OCF₃ | CH₃ | 3-F | F | F |
| A-3318. | OCF₃ | CH₃ | 3-CH₃ | F | F |
| A-3319. | OCF₃ | CH₃ | 3-OCH₃ | F | F |
| A-3320. | OCF₃ | CH₃ | 5-F | F | F |
| A-3321. | OCF₃ | CH₃ | 5-CH₃ | F | F |
| A-3322. | OCF₃ | CH₃ | 5-OCH₃ | F | F |
| A-3323. | OCF₃ | OCH₃ | 3-F | F | F |
| A-3324. | OCF₃ | OCH₃ | 3-CH₃ | F | F |
| A-3325. | OCF₃ | OCH₃ | 3-OCH₃ | F | F |
| A-3326. | OCF₃ | OCH₃ | 5-F | F | F |
| A-3327. | OCF₃ | OCH₃ | 5-CH₃ | F | F |
| A-3328. | OCF₃ | OCH₃ | 5-OCH₃ | F | F |
| A-3329. | OCF₃ | CN | 3-F | F | F |
| A-3330. | OCF₃ | CN | 3-CH₃ | F | F |
| A-3331. | OCF₃ | CN | 3-OCH₃ | F | F |
| A-3332. | OCF₃ | CN | 5-F | F | F |
| A-3333. | OCF₃ | CN | 5-CH₃ | F | F |
| A-3334. | OCF₃ | CN | 5-OCH₃ | F | F |
| A-3335. | OCF₃ | CH₂F | 3-F | F | F |
| A-3336. | OCF₃ | CH₂F | 3-CH₃ | F | F |
| A-3337. | OCF₃ | CH₂F | 3-OCH₃ | F | F |
| A-3338. | OCF₃ | CH₂F | 5-F | F | F |
| A-3339. | OCF₃ | CH₂F | 5-CH₃ | F | F |
| A-3340. | OCF₃ | CH₂F | 5-OCH₃ | F | F |

TABLE A-continued

| Example No. | R¹ | R² | R³ | R⁶ | R⁷ |
|---|---|---|---|---|---|
| A-3341. | OCF₃ | CHF₂ | 3-F | F | F |
| A-3342. | OCF₃ | CHF₂ | 3-CH₃ | F | F |
| A-3343. | OCF₃ | CHF₂ | 3-OCH₃ | F | F |
| A-3344. | OCF₃ | CHF₂ | 5-F | F | F |
| A-3345. | OCF₃ | CHF₂ | 5-CH₃ | F | F |
| A-3346. | OCF₃ | CHF₂ | 5-OCH₃ | F | F |
| A-3347. | OCF₃ | CF₃ | 3-F | F | F |
| A-3348. | OCF₃ | CF₃ | 3-CH₃ | F | F |
| A-3349. | OCF₃ | CF₃ | 3-OCH₃ | F | F |
| A-3350. | OCF₃ | CF₃ | 5-F | F | F |
| A-3351. | OCF₃ | CF₃ | 5-CH₃ | F | F |
| A-3352. | OCF₃ | CF₃ | 5-OCH₃ | F | F |
| A-3353. | OCF₃ | OCH₂F | 3-F | F | F |
| A-3354. | OCF₃ | OCH₂F | 3-CH₃ | F | F |
| A-3355. | OCF₃ | OCH₂F | 3-OCH₃ | F | F |
| A-3356. | OCF₃ | OCH₂F | 5-F | F | F |
| A-3357. | OCF₃ | OCH₂F | 5-CH₃ | F | F |
| A-3358. | OCF₃ | OCH₂F | 5-OCH₃ | F | F |
| A-3359. | OCF₃ | OCHF₂ | 3-F | F | F |
| A-3360. | OCF₃ | OCHF₂ | 3-CH₃ | F | F |
| A-3361. | OCF₃ | OCHF₂ | 3-OCH₃ | F | F |
| A-3362. | OCF₃ | OCHF₂ | 5-F | F | F |
| A-3363. | OCF₃ | OCHF₂ | 5-CH₃ | F | F |
| A-3364. | OCF₃ | OCHF₂ | 5-OCH₃ | F | F |
| A-3365. | OCF₃ | OCF₃ | 3-F | F | F |
| A-3366. | OCF₃ | OCF₃ | 3-CH₃ | F | F |
| A-3367. | OCF₃ | OCF₃ | 3-OCH₃ | F | F |
| A-3368. | OCF₃ | OCF₃ | 5-F | F | F |
| A-3369. | OCF₃ | OCF₃ | 5-CH₃ | F | F |
| A-3370. | OCF₃ | OCF₃ | 5-OCH₃ | F | F |
| A-3371. | H | H | H | Cl | F |
| A-3372. | F | H | H | Cl | F |
| A-3373. | CH₃ | H | H | Cl | F |
| A-3374. | OCH₃ | H | H | Cl | F |
| A-3375. | CH₂F | H | H | Cl | F |
| A-3376. | CHF₂ | H | H | Cl | F |
| A-3377. | CF₃ | H | H | Cl | F |
| A-3378. | OCH₂F | H | H | Cl | F |
| A-3379. | OCHF₂ | H | H | Cl | F |
| A-3380. | OCF₃ | H | H | Cl | F |
| A-3381. | H | F | H | Cl | F |
| A-3382. | H | CH₃ | H | Cl | F |
| A-3383. | H | OCH₃ | H | Cl | F |
| A-3384. | H | CN | H | Cl | F |
| A-3385. | H | CH₂F | H | Cl | F |
| A-3386. | H | CHF₂ | H | Cl | F |
| A-3387. | H | CF₃ | H | Cl | F |
| A-3388. | H | OCH₂F | H | Cl | F |
| A-3389. | H | OCHF₂ | H | Cl | F |
| A-3390. | H | OCF₃ | H | Cl | F |
| A-3391. | H | H | 3-F | Cl | F |
| A-3392. | H | H | 3-CH₃ | Cl | F |
| A-3393. | H | H | 3-OCH₃ | Cl | F |
| A-3394. | H | H | 5-F | Cl | F |
| A-3395. | H | H | 5-CH₃ | Cl | F |
| A-3396. | H | H | 5-OCH₃ | Cl | F |
| A-3397. | F | F | H | Cl | F |
| A-3398. | F | CH₃ | H | Cl | F |
| A-3399. | F | OCH₃ | H | Cl | F |
| A-3400. | F | CN | H | Cl | F |
| A-3401. | F | CH₂F | H | Cl | F |
| A-3402. | F | CHF₂ | H | Cl | F |
| A-3403. | F | CF₃ | H | Cl | F |
| A-3404. | F | OCH₂F | H | Cl | F |
| A-3405. | F | OCHF₂ | H | Cl | F |
| A-3406. | F | OCF₃ | H | Cl | F |
| A-3407. | F | H | 3-F | Cl | F |
| A-3408. | F | H | 3-CH₃ | Cl | F |
| A-3409. | F | H | 3-OCH₃ | Cl | F |
| A-3410. | F | H | 5-F | Cl | F |
| A-3411. | F | H | 5-CH₃ | Cl | F |
| A-3412. | F | H | 5-OCH₃ | Cl | F |
| A-3413. | CH₃ | F | H | Cl | F |
| A-3414. | CH₃ | CH₃ | H | Cl | F |
| A-3415. | CH₃ | OCH₃ | H | Cl | F |
| A-3416. | CH₃ | CN | H | Cl | F |
| A-3417. | CH₃ | CH₂F | H | Cl | F |
| A-3418. | CH₃ | CHF₂ | H | Cl | F |
| A-3419. | CH₃ | CF₃ | H | Cl | F |
| A-3420. | CH₃ | OCH₂F | H | Cl | F |
| A-3421. | CH₃ | OCHF₂ | H | Cl | F |
| A-3422. | CH₃ | OCF₃ | H | Cl | F |
| A-3423. | CH₃ | H | 3-F | Cl | F |
| A-3424. | CH₃ | H | 3-CH₃ | Cl | F |
| A-3425. | CH₃ | H | 3-OCH₃ | Cl | F |
| A-3426. | CH₃ | H | 5-F | Cl | F |
| A-3427. | CH₃ | H | 5-CH₃ | Cl | F |
| A-3428. | CH₃ | H | 5-OCH₃ | Cl | F |
| A-3429. | OCH₃ | F | H | Cl | F |
| A-3430. | OCH₃ | CH₃ | H | Cl | F |
| A-3431. | OCH₃ | OCH₃ | H | Cl | F |
| A-3432. | OCH₃ | CN | H | Cl | F |
| A-3433. | OCH₃ | CH₂F | H | Cl | F |
| A-3434. | OCH₃ | CHF₂ | H | Cl | F |
| A-3435. | OCH₃ | CF₃ | H | Cl | F |
| A-3436. | OCH₃ | OCH₂F | H | Cl | F |
| A-3437. | OCH₃ | OCHF₂ | H | Cl | F |
| A-3438. | OCH₃ | OCF₃ | H | Cl | F |
| A-3439. | OCH₃ | H | 3-F | Cl | F |
| A-3440. | OCH₃ | H | 3-CH₃ | Cl | F |
| A-3441. | OCH₃ | H | 3-OCH₃ | Cl | F |
| A-3442. | OCH₃ | H | 5-F | Cl | F |
| A-3443. | OCH₃ | H | 5-CH₃ | Cl | F |
| A-3444. | OCH₃ | H | 5-OCH₃ | Cl | F |
| A-3445. | H | F | 3-F | Cl | F |
| A-3446. | H | F | 3-CH₃ | Cl | F |
| A-3447. | H | F | 3-OCH₃ | Cl | F |
| A-3448. | H | F | 5-F | Cl | F |
| A-3449. | H | F | 5-CH₃ | Cl | F |
| A-3450. | H | F | 5-OCH₃ | Cl | F |
| A-3451. | H | CH₃ | 3-F | Cl | F |
| A-3452. | H | CH₃ | 3-CH₃ | Cl | F |
| A-3453. | H | CH₃ | 3-OCH₃ | Cl | F |
| A-3454. | H | CH₃ | 5-F | Cl | F |
| A-3455. | H | CH₃ | 5-CH₃ | Cl | F |
| A-3456. | H | CH₃ | 5-OCH₃ | Cl | F |
| A-3457. | H | OCH₃ | 3-F | Cl | F |
| A-3458. | H | OCH₃ | 3-CH₃ | Cl | F |
| A-3459. | H | OCH₃ | 3-OCH₃ | Cl | F |
| A-3460. | H | OCH₃ | 5-F | Cl | F |
| A-3461. | H | OCH₃ | 5-CH₃ | Cl | F |
| A-3462. | H | OCH₃ | 5-OCH₃ | Cl | F |
| A-3463. | H | CN | 3-F | Cl | F |
| A-3464. | H | CN | 3-CH₃ | Cl | F |
| A-3465. | H | CN | 3-OCH₃ | Cl | F |
| A-3466. | H | CN | 5-F | Cl | F |
| A-3467. | H | CN | 5-CH₃ | Cl | F |
| A-3468. | H | CN | 5-OCH₃ | Cl | F |
| A-3469. | H | CH₂F | 3-F | Cl | F |
| A-3470. | H | CH₂F | 3-CH₃ | Cl | F |
| A-3471. | H | CH₂F | 3-OCH₃ | Cl | F |
| A-3472. | H | CH₂F | 5-F | Cl | F |
| A-3473. | H | CH₂F | 5-CH₃ | Cl | F |
| A-3474. | H | CH₂F | 5-OCH₃ | Cl | F |
| A-3475. | H | CHF₂ | 3-F | Cl | F |
| A-3476. | H | CHF₂ | 3-CH₃ | Cl | F |
| A-3477. | H | CHF₂ | 3-OCH₃ | Cl | F |
| A-3478. | H | CHF₂ | 5-F | Cl | F |
| A-3479. | H | CHF₂ | 5-CH₃ | Cl | F |
| A-3480. | H | CHF₂ | 5-OCH₃ | Cl | F |
| A-3481. | H | CF₃ | 3-F | Cl | F |
| A-3482. | H | CF₃ | 3-CH₃ | Cl | F |
| A-3483. | H | CF₃ | 3-OCH₃ | Cl | F |
| A-3484. | H | CF₃ | 5-F | Cl | F |
| A-3485. | H | CF₃ | 5-CH₃ | Cl | F |
| A-3486. | H | CF₃ | 5-OCH₃ | Cl | F |
| A-3487. | H | OCH₂F | 3-F | Cl | F |
| A-3488. | H | OCH₂F | 3-CH₃ | Cl | F |
| A-3489. | H | OCH₂F | 3-OCH₃ | Cl | F |
| A-3490. | H | OCH₂F | 5-F | Cl | F |
| A-3491. | H | OCH₂F | 5-CH₃ | Cl | F |
| A-3492. | H | OCH₂F | 5-OCH₃ | Cl | F |
| A-3493. | H | OCHF₂ | 3-F | Cl | F |
| A-3494. | H | OCHF₂ | 3-CH₃ | Cl | F |
| A-3495. | H | OCHF₂ | 3-OCH₃ | Cl | F |
| A-3496. | H | OCHF₂ | 5-F | Cl | F |

TABLE A-continued

| Example No. | R¹ | R² | R³ | R⁶ | R⁷ |
|---|---|---|---|---|---|
| A-3497. | H | OCHF₂ | 5-CH₃ | Cl | F |
| A-3498. | H | OCHF₂ | 5-OCH₃ | Cl | F |
| A-3499. | H | OCF₃ | 3-F | Cl | F |
| A-3500. | H | OCF₃ | 3-CH₃ | Cl | F |
| A-3501. | H | OCF₃ | 3-OCH₃ | Cl | F |
| A-3502. | H | OCF₃ | 5-F | Cl | F |
| A-3503. | H | OCF₃ | 5-CH₃ | Cl | F |
| A-3504. | H | OCF₃ | 5-OCH₃ | Cl | F |
| A-3505. | F | F | 3-F | Cl | F |
| A-3506. | F | F | 3-CH₃ | Cl | F |
| A-3507. | F | F | 3-OCH₃ | Cl | F |
| A-3508. | F | F | 5-F | Cl | F |
| A-3509. | F | F | 5-CH₃ | Cl | F |
| A-3510. | F | F | 5-OCH₃ | Cl | F |
| A-3511. | F | CH₃ | 3-F | Cl | F |
| A-3512. | F | CH₃ | 3-CH₃ | Cl | F |
| A-3513. | F | CH₃ | 3-OCH₃ | Cl | F |
| A-3514. | F | CH₃ | 5-F | Cl | F |
| A-3515. | F | CH₃ | 5-CH₃ | Cl | F |
| A-3516. | F | CH₃ | 5-OCH₃ | Cl | F |
| A-3517. | F | OCH₃ | 3-F | Cl | F |
| A-3518. | F | OCH₃ | 3-CH₃ | Cl | F |
| A-3519. | F | OCH₃ | 3-OCH₃ | Cl | F |
| A-3520. | F | OCH₃ | 5-F | Cl | F |
| A-3521. | F | OCH₃ | 5-CH₃ | Cl | F |
| A-3522. | F | OCH₃ | 5-OCH₃ | Cl | F |
| A-3523. | F | CN | 3-F | Cl | F |
| A-3524. | F | CN | 3-CH₃ | Cl | F |
| A-3525. | F | CN | 3-OCH₃ | Cl | F |
| A-3526. | F | CN | 5-F | Cl | F |
| A-3527. | F | CN | 5-CH₃ | Cl | F |
| A-3528. | F | CN | 5-OCH₃ | Cl | F |
| A-3529. | F | CH₂F | 3-F | Cl | F |
| A-3530. | F | CH₂F | 3-CH₃ | Cl | F |
| A-3531. | F | CH₂F | 3-OCH₃ | Cl | F |
| A-3532. | F | CH₂F | 5-F | Cl | F |
| A-3533. | F | CH₂F | 5-CH₃ | Cl | F |
| A-3534. | F | CH₂F | 5-OCH₃ | Cl | F |
| A-3535. | F | CHF₂ | 3-F | Cl | F |
| A-3536. | F | CHF₂ | 3-CH₃ | Cl | F |
| A-3537. | F | CHF₂ | 3-OCH₃ | Cl | F |
| A-3538. | F | CHF₂ | 5-F | Cl | F |
| A-3539. | F | CHF₂ | 5-CH₃ | Cl | F |
| A-3540. | F | CHF₂ | 5-OCH₃ | Cl | F |
| A-3541. | F | CF₃ | 3-F | Cl | F |
| A-3542. | F | CF₃ | 3-CH₃ | Cl | F |
| A-3543. | F | CF₃ | 3-OCH₃ | Cl | F |
| A-3544. | F | CF₃ | 5-F | Cl | F |
| A-3545. | F | CF₃ | 5-CH₃ | Cl | F |
| A-3546. | F | CF₃ | 5-OCH₃ | Cl | F |
| A-3547. | F | OCH₂F | 3-F | Cl | F |
| A-3548. | F | OCH₂F | 3-CH₃ | Cl | F |
| A-3549. | F | OCH₂F | 3-OCH₃ | Cl | F |
| A-3550. | F | OCH₂F | 5-F | Cl | F |
| A-3551. | F | OCH₂F | 5-CH₃ | Cl | F |
| A-3552. | F | OCH₂F | 5-OCH₃ | Cl | F |
| A-3553. | F | OCHF₂ | 3-F | Cl | F |
| A-3554. | F | OCHF₂ | 3-CH₃ | Cl | F |
| A-3555. | F | OCHF₂ | 3-OCH₃ | Cl | F |
| A-3556. | F | OCHF₂ | 5-F | Cl | F |
| A-3557. | F | OCHF₂ | 5-CH₃ | Cl | F |
| A-3558. | F | OCHF₂ | 5-OCH₃ | Cl | F |
| A-3559. | F | OCF₃ | 3-F | Cl | F |
| A-3560. | F | OCF₃ | 3-CH₃ | Cl | F |
| A-3561. | F | OCF₃ | 3-OCH₃ | Cl | F |
| A-3562. | F | OCF₃ | 5-F | Cl | F |
| A-3563. | F | OCF₃ | 5-CH₃ | Cl | F |
| A-3564. | F | OCF₃ | 5-OCH₃ | Cl | F |
| A-3565. | CH₃ | F | 3-F | Cl | F |
| A-3566. | CH₃ | F | 3-CH₃ | Cl | F |
| A-3567. | CH₃ | F | 3-OCH₃ | Cl | F |
| A-3568. | CH₃ | F | 5-F | Cl | F |
| A-3569. | CH₃ | F | 5-CH₃ | Cl | F |
| A-3570. | CH₃ | F | 5-OCH₃ | Cl | F |
| A-3571. | CH₃ | CH₃ | 3-F | Cl | F |
| A-3572. | CH₃ | CH₃ | 3-CH₃ | Cl | F |
| A-3573. | CH₃ | CH₃ | 3-OCH₃ | Cl | F |
| A-3574. | CH₃ | CH₃ | 5-F | Cl | F |
| A-3575. | CH₃ | CH₃ | 5-CH₃ | Cl | F |
| A-3576. | CH₃ | CH₃ | 5-OCH₃ | Cl | F |
| A-3577. | CH₃ | OCH₃ | 3-F | Cl | F |
| A-3578. | CH₃ | OCH₃ | 3-CH₃ | Cl | F |
| A-3579. | CH₃ | OCH₃ | 3-OCH₃ | Cl | F |
| A-3580. | CH₃ | OCH₃ | 5-F | Cl | F |
| A-3581. | CH₃ | OCH₃ | 5-CH₃ | Cl | F |
| A-3582. | CH₃ | OCH₃ | 5-OCH₃ | Cl | F |
| A-3583. | CH₃ | CN | 3-F | Cl | F |
| A-3584. | CH₃ | CN | 3-CH₃ | Cl | F |
| A-3585. | CH₃ | CN | 3-OCH₃ | Cl | F |
| A-3586. | CH₃ | CN | 5-F | Cl | F |
| A-3587. | CH₃ | CN | 5-CH₃ | Cl | F |
| A-3588. | CH₃ | CN | 5-OCH₃ | Cl | F |
| A-3589. | CH₃ | CH₂F | 3-F | Cl | F |
| A-3590. | CH₃ | CH₂F | 3-CH₃ | Cl | F |
| A-3591. | CH₃ | CH₂F | 3-OCH₃ | Cl | F |
| A-3592. | CH₃ | CH₂F | 5-F | Cl | F |
| A-3593. | CH₃ | CH₂F | 5-CH₃ | Cl | F |
| A-3594. | CH₃ | CH₂F | 5-OCH₃ | Cl | F |
| A-3595. | CH₃ | CHF₂ | 3-F | Cl | F |
| A-3596. | CH₃ | CHF₂ | 3-CH₃ | Cl | F |
| A-3597. | CH₃ | CHF₂ | 3-OCH₃ | Cl | F |
| A-3598. | CH₃ | CHF₂ | 5-F | Cl | F |
| A-3599. | CH₃ | CHF₂ | 5-CH₃ | Cl | F |
| A-3600. | CH₃ | CHF₂ | 5-OCH₃ | Cl | F |
| A-3601. | CH₃ | CF₃ | 3-F | Cl | F |
| A-3602. | CH₃ | CF₃ | 3-CH₃ | Cl | F |
| A-3603. | CH₃ | CF₃ | 3-OCH₃ | Cl | F |
| A-3604. | CH₃ | CF₃ | 5-F | Cl | F |
| A-3605. | CH₃ | CF₃ | 5-CH₃ | Cl | F |
| A-3606. | CH₃ | CF₃ | 5-OCH₃ | Cl | F |
| A-3607. | CH₃ | OCH₂F | 3-F | Cl | F |
| A-3608. | CH₃ | OCH₂F | 3-CH₃ | Cl | F |
| A-3609. | CH₃ | OCH₂F | 3-OCH₃ | Cl | F |
| A-3610. | CH₃ | OCH₂F | 5-F | Cl | F |
| A-3611. | CH₃ | OCH₂F | 5-CH₃ | Cl | F |
| A-3612. | CH₃ | OCH₂F | 5-OCH₃ | Cl | F |
| A-3613. | CH₃ | OCHF₂ | 3-F | Cl | F |
| A-3614. | CH₃ | OCHF₂ | 3-CH₃ | Cl | F |
| A-3615. | CH₃ | OCHF₂ | 3-OCH₃ | Cl | F |
| A-3616. | CH₃ | OCHF₂ | 5-F | Cl | F |
| A-3617. | CH₃ | OCHF₂ | 5-CH₃ | Cl | F |
| A-3618. | CH₃ | OCHF₂ | 5-OCH₃ | Cl | F |
| A-3619. | CH₃ | OCF₃ | 3-F | Cl | F |
| A-3620. | CH₃ | OCF₃ | 3-CH₃ | Cl | F |
| A-3621. | CH₃ | OCF₃ | 3-OCH₃ | Cl | F |
| A-3622. | CH₃ | OCF₃ | 5-F | Cl | F |
| A-3623. | CH₃ | OCF₃ | 5-CH₃ | Cl | F |
| A-3624. | CH₃ | OCF₃ | 5-OCH₃ | Cl | F |
| A-3625. | OCH₃ | F | 3-F | Cl | F |
| A-3626. | OCH₃ | F | 3-CH₃ | Cl | F |
| A-3627. | OCH₃ | F | 3-OCH₃ | Cl | F |
| A-3628. | OCH₃ | F | 5-F | Cl | F |
| A-3629. | OCH₃ | F | 5-CH₃ | Cl | F |
| A-3630. | OCH₃ | F | 5-OCH₃ | Cl | F |
| A-3631. | OCH₃ | CH₃ | 3-F | Cl | F |
| A-3632. | OCH₃ | CH₃ | 3-CH₃ | Cl | F |
| A-3633. | OCH₃ | CH₃ | 3-OCH₃ | Cl | F |
| A-3634. | OCH₃ | CH₃ | 5-F | Cl | F |
| A-3635. | OCH₃ | CH₃ | 5-CH₃ | Cl | F |
| A-3636. | OCH₃ | CH₃ | 5-OCH₃ | Cl | F |
| A-3637. | OCH₃ | OCH₃ | 3-F | Cl | F |
| A-3638. | OCH₃ | OCH₃ | 3-CH₃ | Cl | F |
| A-3639. | OCH₃ | OCH₃ | 3-OCH₃ | Cl | F |
| A-3640. | OCH₃ | OCH₃ | 5-F | Cl | F |
| A-3641. | OCH₃ | OCH₃ | 5-CH₃ | Cl | F |
| A-3642. | OCH₃ | OCH₃ | 5-OCH₃ | Cl | F |
| A-3643. | OCH₃ | CN | 3-F | Cl | F |
| A-3644. | OCH₃ | CN | 3-CH₃ | Cl | F |
| A-3645. | OCH₃ | CN | 3-OCH₃ | Cl | F |
| A-3646. | OCH₃ | CN | 5-F | Cl | F |
| A-3647. | OCH₃ | CN | 5-CH₃ | Cl | F |
| A-3648. | OCH₃ | CN | 5-OCH₃ | Cl | F |
| A-3649. | OCH₃ | CH₂F | 3-F | Cl | F |
| A-3650. | OCH₃ | CH₂F | 3-CH₃ | Cl | F |
| A-3651. | OCH₃ | CH₂F | 3-OCH₃ | Cl | F |
| A-3652. | OCH₃ | CH₂F | 5-F | Cl | F |

TABLE A-continued

| Example No. | R¹ | R² | R³ | R⁶ | R⁷ |
|---|---|---|---|---|---|
| A-3653. | OCH₃ | CH₂F | 5-CH₃ | Cl | F |
| A-3654. | OCH₃ | CH₂F | 5-OCH₃ | Cl | F |
| A-3655. | OCH₃ | CHF₂ | 3-F | Cl | F |
| A-3656. | OCH₃ | CHF₂ | 3-CH₃ | Cl | F |
| A-3657. | OCH₃ | CHF₂ | 3-OCH₃ | Cl | F |
| A-3658. | OCH₃ | CHF₂ | 5-F | Cl | F |
| A-3659. | OCH₃ | CHF₂ | 5-CH₃ | Cl | F |
| A-3660. | OCH₃ | CHF₂ | 5-OCH₃ | Cl | F |
| A-3661. | OCH₃ | CF₃ | 3-F | Cl | F |
| A-3662. | OCH₃ | CF₃ | 3-CH₃ | Cl | F |
| A-3663. | OCH₃ | CF₃ | 3-OCH₃ | Cl | F |
| A-3664. | OCH₃ | CF₃ | 5-F | Cl | F |
| A-3665. | OCH₃ | CF₃ | 5-CH₃ | Cl | F |
| A-3666. | OCH₃ | CF₃ | 5-OCH₃ | Cl | F |
| A-3667. | OCH₃ | OCH₂F | 3-F | Cl | F |
| A-3668. | OCH₃ | OCH₂F | 3-CH₃ | Cl | F |
| A-3669. | OCH₃ | OCH₂F | 3-OCH₃ | Cl | F |
| A-3670. | OCH₃ | OCH₂F | 5-F | Cl | F |
| A-3671. | OCH₃ | OCH₂F | 5-CH₃ | Cl | F |
| A-3672. | OCH₃ | OCH₂F | 5-OCH₃ | Cl | F |
| A-3673. | OCH₃ | OCHF₂ | 3-F | Cl | F |
| A-3674. | OCH₃ | OCHF₂ | 3-CH₃ | Cl | F |
| A-3675. | OCH₃ | OCHF₂ | 3-OCH₃ | Cl | F |
| A-3676. | OCH₃ | OCHF₂ | 5-F | Cl | F |
| A-3677. | OCH₃ | OCHF₂ | 5-CH₃ | Cl | F |
| A-3678. | OCH₃ | OCHF₂ | 5-OCH₃ | Cl | F |
| A-3679. | OCH₃ | OCF₃ | 3-F | Cl | F |
| A-3680. | OCH₃ | OCF₃ | 3-CH₃ | Cl | F |
| A-3681. | OCH₃ | OCF₃ | 3-OCH₃ | Cl | F |
| A-3682. | OCH₃ | OCF₃ | 5-F | Cl | F |
| A-3683. | OCH₃ | OCF₃ | 5-CH₃ | Cl | F |
| A-3684. | OCH₃ | OCF₃ | 5-OCH₃ | Cl | F |
| A-3685. | CH₂F | F | 3-F | Cl | F |
| A-3686. | CH₂F | F | 3-CH₃ | Cl | F |
| A-3687. | CH₂F | F | 3-OCH₃ | Cl | F |
| A-3688. | CH₂F | F | 5-F | Cl | F |
| A-3689. | CH₂F | F | 5-CH₃ | Cl | F |
| A-3690. | CH₂F | F | 5-OCH₃ | Cl | F |
| A-3691. | CH₂F | CH₃ | 3-F | Cl | F |
| A-3692. | CH₂F | CH₃ | 3-CH₃ | Cl | F |
| A-3693. | CH₂F | CH₃ | 3-OCH₃ | Cl | F |
| A-3694. | CH₂F | CH₃ | 5-F | Cl | F |
| A-3695. | CH₂F | CH₃ | 5-CH₃ | Cl | F |
| A-3696. | CH₂F | CH₃ | 5-OCH₃ | Cl | F |
| A-3697. | CH₂F | OCH₃ | 3-F | Cl | F |
| A-3698. | CH₂F | OCH₃ | 3-CH₃ | Cl | F |
| A-3699. | CH₂F | OCH₃ | 3-OCH₃ | Cl | F |
| A-3700. | CH₂F | OCH₃ | 5-F | Cl | F |
| A-3701. | CH₂F | OCH₃ | 5-CH₃ | Cl | F |
| A-3702. | CH₂F | OCH₃ | 5-OCH₃ | Cl | F |
| A-3703. | CH₂F | CN | 3-F | Cl | F |
| A-3704. | CH₂F | CN | 3-CH₃ | Cl | F |
| A-3705. | CH₂F | CN | 3-OCH₃ | Cl | F |
| A-3706. | CH₂F | CN | 5-F | Cl | F |
| A-3707. | CH₂F | CN | 5-CH₃ | Cl | F |
| A-3708. | CH₂F | CN | 5-OCH₃ | Cl | F |
| A-3709. | CH₂F | CH₂F | 3-F | Cl | F |
| A-3710. | CH₂F | CH₂F | 3-CH₃ | Cl | F |
| A-3711. | CH₂F | CH₂F | 3-OCH₃ | Cl | F |
| A-3712. | CH₂F | CH₂F | 5-F | Cl | F |
| A-3713. | CH₂F | CH₂F | 5-CH₃ | Cl | F |
| A-3714. | CH₂F | CH₂F | 5-OCH₃ | Cl | F |
| A-3715. | CH₂F | CHF₂ | 3-F | Cl | F |
| A-3716. | CH₂F | CHF₂ | 3-CH₃ | Cl | F |
| A-3717. | CH₂F | CHF₂ | 3-OCH₃ | Cl | F |
| A-3718. | CH₂F | CHF₂ | 5-F | Cl | F |
| A-3719. | CH₂F | CHF₂ | 5-CH₃ | Cl | F |
| A-3720. | CH₂F | CHF₂ | 5-OCH₃ | Cl | F |
| A-3721. | CH₂F | CF₃ | 3-F | Cl | F |
| A-3722. | CH₂F | CF₃ | 3-CH₃ | Cl | F |
| A-3723. | CH₂F | CF₃ | 3-OCH₃ | Cl | F |
| A-3724. | CH₂F | CF₃ | 5-F | Cl | F |
| A-3725. | CH₂F | CF₃ | 5-CH₃ | Cl | F |
| A-3726. | CH₂F | CF₃ | 5-OCH₃ | Cl | F |
| A-3727. | CH₂F | OCH₂F | 3-F | Cl | F |
| A-3728. | CH₂F | OCH₂F | 3-CH₃ | Cl | F |
| A-3729. | CH₂F | OCH₂F | 3-OCH₃ | Cl | F |
| A-3730. | CH₂F | OCH₂F | 5-F | Cl | F |
| A-3731. | CH₂F | OCH₂F | 5-CH₃ | Cl | F |
| A-3732. | CH₂F | OCH₂F | 5-OCH₃ | Cl | F |
| A-3733. | CH₂F | OCHF₂ | 3-F | Cl | F |
| A-3734. | CH₂F | OCHF₂ | 3-CH₃ | Cl | F |
| A-3735. | CH₂F | OCHF₂ | 3-OCH₃ | Cl | F |
| A-3736. | CH₂F | OCHF₂ | 5-F | Cl | F |
| A-3737. | CH₂F | OCHF₂ | 5-CH₃ | Cl | F |
| A-3738. | CH₂F | OCHF₂ | 5-OCH₃ | Cl | F |
| A-3739. | CH₂F | OCF₃ | 3-F | Cl | F |
| A-3740. | CH₂F | OCF₃ | 3-CH₃ | Cl | F |
| A-3741. | CH₂F | OCF₃ | 3-OCH₃ | Cl | F |
| A-3742. | CH₂F | OCF₃ | 5-F | Cl | F |
| A-3743. | CH₂F | OCF₃ | 5-CH₃ | Cl | F |
| A-3744. | CH₂F | OCF₃ | 5-OCH₃ | Cl | F |
| A-3745. | CHF₂ | F | 3-F | Cl | F |
| A-3746. | CHF₂ | F | 3-CH₃ | Cl | F |
| A-3747. | CHF₂ | F | 3-OCH₃ | Cl | F |
| A-3748. | CHF₂ | F | 5-F | Cl | F |
| A-3749. | CHF₂ | F | 5-CH₃ | Cl | F |
| A-3750. | CHF₂ | F | 5-OCH₃ | Cl | F |
| A-3751. | CHF₂ | CH₃ | 3-F | Cl | F |
| A-3752. | CHF₂ | CH₃ | 3-CH₃ | Cl | F |
| A-3753. | CHF₂ | CH₃ | 3-OCH₃ | Cl | F |
| A-3754. | CHF₂ | CH₃ | 5-F | Cl | F |
| A-3755. | CHF₂ | CH₃ | 5-CH₃ | Cl | F |
| A-3756. | CHF₂ | CH₃ | 5-OCH₃ | Cl | F |
| A-3757. | CHF₂ | OCH₃ | 3-F | Cl | F |
| A-3758. | CHF₂ | OCH₃ | 3-CH₃ | Cl | F |
| A-3759. | CHF₂ | OCH₃ | 3-OCH₃ | Cl | F |
| A-3760. | CHF₂ | OCH₃ | 5-F | Cl | F |
| A-3761. | CHF₂ | OCH₃ | 5-CH₃ | Cl | F |
| A-3762. | CHF₂ | OCH₃ | 5-OCH₃ | Cl | F |
| A-3763. | CHF₂ | CN | 3-F | Cl | F |
| A-3764. | CHF₂ | CN | 3-CH₃ | Cl | F |
| A-3765. | CHF₂ | CN | 3-OCH₃ | Cl | F |
| A-3766. | CHF₂ | CN | 5-F | Cl | F |
| A-3767. | CHF₂ | CN | 5-CH₃ | Cl | F |
| A-3768. | CHF₂ | CN | 5-OCH₃ | Cl | F |
| A-3769. | CHF₂ | CH₂F | 3-F | Cl | F |
| A-3770. | CHF₂ | CH₂F | 3-CH₃ | Cl | F |
| A-3771. | CHF₂ | CH₂F | 3-OCH₃ | Cl | F |
| A-3772. | CHF₂ | CH₂F | 5-F | Cl | F |
| A-3773. | CHF₂ | CH₂F | 5-CH₃ | Cl | F |
| A-3774. | CHF₂ | CH₂F | 5-OCH₃ | Cl | F |
| A-3775. | CHF₂ | CHF₂ | 3-F | Cl | F |
| A-3776. | CHF₂ | CHF₂ | 3-CH₃ | Cl | F |
| A-3777. | CHF₂ | CHF₂ | 3-OCH₃ | Cl | F |
| A-3778. | CHF₂ | CHF₂ | 5-F | Cl | F |
| A-3779. | CHF₂ | CHF₂ | 5-CH₃ | Cl | F |
| A-3780. | CHF₂ | CHF₂ | 5-OCH₃ | Cl | F |
| A-3781. | CHF₂ | CF₃ | 3-F | Cl | F |
| A-3782. | CHF₂ | CF₃ | 3-CH₃ | Cl | F |
| A-3783. | CHF₂ | CF₃ | 3-OCH₃ | Cl | F |
| A-3784. | CHF₂ | CF₃ | 5-F | Cl | F |
| A-3785. | CHF₂ | CF₃ | 5-CH₃ | Cl | F |
| A-3786. | CHF₂ | CF₃ | 5-OCH₃ | Cl | F |
| A-3787. | CHF₂ | OCH₂F | 3-F | Cl | F |
| A-3788. | CHF₂ | OCH₂F | 3-CH₃ | Cl | F |
| A-3789. | CHF₂ | OCH₂F | 3-OCH₃ | Cl | F |
| A-3790. | CHF₂ | OCH₂F | 5-F | Cl | F |
| A-3791. | CHF₂ | OCH₂F | 5-CH₃ | Cl | F |
| A-3792. | CHF₂ | OCH₂F | 5-OCH₃ | Cl | F |
| A-3793. | CHF₂ | OCHF₂ | 3-F | Cl | F |
| A-3794. | CHF₂ | OCHF₂ | 3-CH₃ | Cl | F |
| A-3795. | CHF₂ | OCHF₂ | 3-OCH₃ | Cl | F |
| A-3796. | CHF₂ | OCHF₂ | 5-F | Cl | F |
| A-3797. | CHF₂ | OCHF₂ | 5-CH₃ | Cl | F |
| A-3798. | CHF₂ | OCHF₂ | 5-OCH₃ | Cl | F |
| A-3799. | CHF₂ | OCF₃ | 3-F | Cl | F |
| A-3800. | CHF₂ | OCF₃ | 3-CH₃ | Cl | F |
| A-3801. | CHF₂ | OCF₃ | 3-OCH₃ | Cl | F |
| A-3802. | CHF₂ | OCF₃ | 5-F | Cl | F |
| A-3803. | CHF₂ | OCF₃ | 5-CH₃ | Cl | F |
| A-3804. | CHF₂ | OCF₃ | 5-OCH₃ | Cl | F |
| A-3805. | CF₃ | F | 3-F | Cl | F |
| A-3806. | CF₃ | F | 3-CH₃ | Cl | F |
| A-3807. | CF₃ | F | 3-OCH₃ | Cl | F |
| A-3808. | CF₃ | F | 5-F | Cl | F |

TABLE A-continued

| Example No. | R¹ | R² | R³ | R⁶ | R⁷ |
|---|---|---|---|---|---|
| A-3809. | CF₃ | F | 5-CH₃ | Cl | F |
| A-3810. | CF₃ | F | 5-OCH₃ | Cl | F |
| A-3811. | CF₃ | CH₃ | 3-F | Cl | F |
| A-3812. | CF₃ | CH₃ | 3-CH₃ | Cl | F |
| A-3813. | CF₃ | CH₃ | 3-OCH₃ | Cl | F |
| A-3814. | CF₃ | CH₃ | 5-F | Cl | F |
| A-3815. | CF₃ | CH₃ | 5-CH₃ | Cl | F |
| A-3816. | CF₃ | CH₃ | 5-OCH₃ | Cl | F |
| A-3817. | CF₃ | OCH₃ | 3-F | Cl | F |
| A-3818. | CF₃ | OCH₃ | 3-CH₃ | Cl | F |
| A-3819. | CF₃ | OCH₃ | 3-OCH₃ | Cl | F |
| A-3820. | CF₃ | OCH₃ | 5-F | Cl | F |
| A-3821. | CF₃ | OCH₃ | 5-CH₃ | Cl | F |
| A-3822. | CF₃ | OCH₃ | 5-OCH₃ | Cl | F |
| A-3823. | CF₃ | CN | 3-F | Cl | F |
| A-3824. | CF₃ | CN | 3-CH₃ | Cl | F |
| A-3825. | CF₃ | CN | 3-OCH₃ | Cl | F |
| A-3826. | CF₃ | CN | 5-F | Cl | F |
| A-3827. | CF₃ | CN | 5-CH₃ | Cl | F |
| A-3828. | CF₃ | CN | 5-OCH₃ | Cl | F |
| A-3829. | CF₃ | CH₂F | 3-F | Cl | F |
| A-3830. | CF₃ | CH₂F | 3-CH₃ | Cl | F |
| A-3831. | CF₃ | CH₂F | 3-OCH₃ | Cl | F |
| A-3832. | CF₃ | CH₂F | 5-F | Cl | F |
| A-3833. | CF₃ | CH₂F | 5-CH₃ | Cl | F |
| A-3834. | CF₃ | CH₂F | 5-OCH₃ | Cl | F |
| A-3835. | CF₃ | CHF₂ | 3-F | Cl | F |
| A-3836. | CF₃ | CHF₂ | 3-CH₃ | Cl | F |
| A-3837. | CF₃ | CHF₂ | 3-OCH₃ | Cl | F |
| A-3838. | CF₃ | CHF₂ | 5-F | Cl | F |
| A-3839. | CF₃ | CHF₂ | 5-CH₃ | Cl | F |
| A-3840. | CF₃ | CHF₂ | 5-OCH₃ | Cl | F |
| A-3841. | CF₃ | CF₃ | 3-F | Cl | F |
| A-3842. | CF₃ | CF₃ | 3-CH₃ | Cl | F |
| A-3843. | CF₃ | CF₃ | 3-OCH₃ | Cl | F |
| A-3844. | CF₃ | CF₃ | 5-F | Cl | F |
| A-3845. | CF₃ | CF₃ | 5-CH₃ | Cl | F |
| A-3846. | CF₃ | CF₃ | 5-OCH₃ | Cl | F |
| A-3847. | CF₃ | OCH₂F | 3-F | Cl | F |
| A-3848. | CF₃ | OCH₂F | 3-CH₃ | Cl | F |
| A-3849. | CF₃ | OCH₂F | 3-OCH₃ | Cl | F |
| A-3850. | CF₃ | OCH₂F | 5-F | Cl | F |
| A-3851. | CF₃ | OCH₂F | 5-CH₃ | Cl | F |
| A-3852. | CF₃ | OCH₂F | 5-OCH₃ | Cl | F |
| A-3853. | CF₃ | OCHF₂ | 3-F | Cl | F |
| A-3854. | CF₃ | OCHF₂ | 3-CH₃ | Cl | F |
| A-3855. | CF₃ | OCHF₂ | 3-OCH₃ | Cl | F |
| A-3856. | CF₃ | OCHF₂ | 5-F | Cl | F |
| A-3857. | CF₃ | OCHF₂ | 5-CH₃ | Cl | F |
| A-3858. | CF₃ | OCHF₂ | 5-OCH₃ | Cl | F |
| A-3859. | CF₃ | OCF₃ | 3-F | Cl | F |
| A-3860. | CF₃ | OCF₃ | 3-CH₃ | Cl | F |
| A-3861. | CF₃ | OCF₃ | 3-OCH₃ | Cl | F |
| A-3862. | CF₃ | OCF₃ | 5-F | Cl | F |
| A-3863. | CF₃ | OCF₃ | 5-CH₃ | Cl | F |
| A-3864. | CF₃ | OCF₃ | 5-OCH₃ | Cl | F |
| A-3865. | OCH₂F | F | 3-F | Cl | F |
| A-3866. | OCH₂F | F | 3-CH₃ | Cl | F |
| A-3867. | OCH₂F | F | 3-OCH₃ | Cl | F |
| A-3868. | OCH₂F | F | 5-F | Cl | F |
| A-3869. | OCH₂F | F | 5-CH₃ | Cl | F |
| A-3870. | OCH₂F | F | 5-OCH₃ | Cl | F |
| A-3871. | OCH₂F | CH₃ | 3-F | Cl | F |
| A-3872. | OCH₂F | CH₃ | 3-CH₃ | Cl | F |
| A-3873. | OCH₂F | CH₃ | 3-OCH₃ | Cl | F |
| A-3874. | OCH₂F | CH₃ | 5-F | Cl | F |
| A-3875. | OCH₂F | CH₃ | 5-CH₃ | Cl | F |
| A-3876. | OCH₂F | CH₃ | 5-OCH₃ | Cl | F |
| A-3877. | OCH₂F | OCH₃ | 3-F | Cl | F |
| A-3878. | OCH₂F | OCH₃ | 3-CH₃ | Cl | F |
| A-3879. | OCH₂F | OCH₃ | 3-OCH₃ | Cl | F |
| A-3880. | OCH₂F | OCH₃ | 5-F | Cl | F |
| A-3881. | OCH₂F | OCH₃ | 5-CH₃ | Cl | F |
| A-3882. | OCH₂F | OCH₃ | 5-OCH₃ | Cl | F |
| A-3883. | OCH₂F | CN | 3-F | Cl | F |
| A-3884. | OCH₂F | CN | 3-CH₃ | Cl | F |
| A-3885. | OCH₂F | CN | 3-OCH₃ | Cl | F |
| A-3886. | OCH₂F | CN | 5-F | Cl | F |
| A-3887. | OCH₂F | CN | 5-CH₃ | Cl | F |
| A-3888. | OCH₂F | CN | 5-OCH₃ | Cl | F |
| A-3889. | OCH₂F | CH₂F | 3-F | Cl | F |
| A-3890. | OCH₂F | CH₂F | 3-CH₃ | Cl | F |
| A-3891. | OCH₂F | CH₂F | 3-OCH₃ | Cl | F |
| A-3892. | OCH₂F | CH₂F | 5-F | Cl | F |
| A-3893. | OCH₂F | CH₂F | 5-CH₃ | Cl | F |
| A-3894. | OCH₂F | CH₂F | 5-OCH₃ | Cl | F |
| A-3895. | OCH₂F | CHF₂ | 3-F | Cl | F |
| A-3896. | OCH₂F | CHF₂ | 3-CH₃ | Cl | F |
| A-3897. | OCH₂F | CHF₂ | 3-OCH₃ | Cl | F |
| A-3898. | OCH₂F | CHF₂ | 5-F | Cl | F |
| A-3899. | OCH₂F | CHF₂ | 5-CH₃ | Cl | F |
| A-3900. | OCH₂F | CHF₂ | 5-OCH₃ | Cl | F |
| A-3901. | OCH₂F | CF₃ | 3-F | Cl | F |
| A-3902. | OCH₂F | CF₃ | 3-CH₃ | Cl | F |
| A-3903. | OCH₂F | CF₃ | 3-OCH₃ | Cl | F |
| A-3904. | OCH₂F | CF₃ | 5-F | Cl | F |
| A-3905. | OCH₂F | CF₃ | 5-CH₃ | Cl | F |
| A-3906. | OCH₂F | CF₃ | 5-OCH₃ | Cl | F |
| A-3907. | OCH₂F | OCH₂F | 3-F | Cl | F |
| A-3908. | OCH₂F | OCH₂F | 3-CH₃ | Cl | F |
| A-3909. | OCH₂F | OCH₂F | 3-OCH₃ | Cl | F |
| A-3910. | OCH₂F | OCH₂F | 5-F | Cl | F |
| A-3911. | OCH₂F | OCH₂F | 5-CH₃ | Cl | F |
| A-3912. | OCH₂F | OCH₂F | 5-OCH₃ | Cl | F |
| A-3913. | OCH₂F | OCHF₂ | 3-F | Cl | F |
| A-3914. | OCH₂F | OCHF₂ | 3-CH₃ | Cl | F |
| A-3915. | OCH₂F | OCHF₂ | 3-OCH₃ | Cl | F |
| A-3916. | OCH₂F | OCHF₂ | 5-F | Cl | F |
| A-3917. | OCH₂F | OCHF₂ | 5-CH₃ | Cl | F |
| A-3918. | OCH₂F | OCHF₂ | 5-OCH₃ | Cl | F |
| A-3919. | OCH₂F | OCF₃ | 3-F | Cl | F |
| A-3920. | OCH₂F | OCF₃ | 3-CH₃ | Cl | F |
| A-3921. | OCH₂F | OCF₃ | 3-OCH₃ | Cl | F |
| A-3922. | OCH₂F | OCF₃ | 5-F | Cl | F |
| A-3923. | OCH₂F | OCF₃ | 5-CH₃ | Cl | F |
| A-3924. | OCH₂F | OCF₃ | 5-OCH₃ | Cl | F |
| A-3925. | OCHF₂ | F | 3-F | Cl | F |
| A-3926. | OCHF₂ | F | 3-CH₃ | Cl | F |
| A-3927. | OCHF₂ | F | 3-OCH₃ | Cl | F |
| A-3928. | OCHF₂ | F | 5-F | Cl | F |
| A-3929. | OCHF₂ | F | 5-CH₃ | Cl | F |
| A-3930. | OCHF₂ | F | 5-OCH₃ | Cl | F |
| A-3931. | OCHF₂ | CH₃ | 3-F | Cl | F |
| A-3932. | OCHF₂ | CH₃ | 3-CH₃ | Cl | F |
| A-3933. | OCHF₂ | CH₃ | 3-OCH₃ | Cl | F |
| A-3934. | OCHF₂ | CH₃ | 5-F | Cl | F |
| A-3935. | OCHF₂ | CH₃ | 5-CH₃ | Cl | F |
| A-3936. | OCHF₂ | CH₃ | 5-OCH₃ | Cl | F |
| A-3937. | OCHF₂ | OCH₃ | 3-F | Cl | F |
| A-3938. | OCHF₂ | OCH₃ | 3-CH₃ | Cl | F |
| A-3939. | OCHF₂ | OCH₃ | 3-OCH₃ | Cl | F |
| A-3940. | OCHF₂ | OCH₃ | 5-F | Cl | F |
| A-3941. | OCHF₂ | OCH₃ | 5-CH₃ | Cl | F |
| A-3942. | OCHF₂ | OCH₃ | 5-OCH₃ | Cl | F |
| A-3943. | OCHF₂ | CN | 3-F | Cl | F |
| A-3944. | OCHF₂ | CN | 3-CH₃ | Cl | F |
| A-3945. | OCHF₂ | CN | 3-OCH₃ | Cl | F |
| A-3946. | OCHF₂ | CN | 5-F | Cl | F |
| A-3947. | OCHF₂ | CN | 5-CH₃ | Cl | F |
| A-3948. | OCHF₂ | CN | 5-OCH₃ | Cl | F |
| A-3949. | OCHF₂ | CH₂F | 3-F | Cl | F |
| A-3950. | OCHF₂ | CH₂F | 3-CH₃ | Cl | F |
| A-3951. | OCHF₂ | CH₂F | 3-OCH₃ | Cl | F |
| A-3952. | OCHF₂ | CH₂F | 5-F | Cl | F |
| A-3953. | OCHF₂ | CH₂F | 5-CH₃ | Cl | F |
| A-3954. | OCHF₂ | CH₂F | 5-OCH₃ | Cl | F |
| A-3955. | OCHF₂ | CHF₂ | 3-F | Cl | F |
| A-3956. | OCHF₂ | CHF₂ | 3-CH₃ | Cl | F |
| A-3957. | OCHF₂ | CHF₂ | 3-OCH₃ | Cl | F |
| A-3958. | OCHF₂ | CHF₂ | 5-F | Cl | F |
| A-3959. | OCHF₂ | CHF₂ | 5-CH₃ | Cl | F |
| A-3960. | OCHF₂ | CHF₂ | 5-OCH₃ | Cl | F |
| A-3961. | OCHF₂ | CF₃ | 3-F | Cl | F |
| A-3962. | OCHF₂ | CF₃ | 3-CH₃ | Cl | F |
| A-3963. | OCHF₂ | CF₃ | 3-OCH₃ | Cl | F |
| A-3964. | OCHF₂ | CF₃ | 5-F | Cl | F |

TABLE A-continued

| Example No. | R¹ | R² | R³ | R⁶ | R⁷ |
|---|---|---|---|---|---|
| A-3965. | OCHF₂ | CF₃ | 5-CH₃ | Cl | F |
| A-3966. | OCHF₂ | CF₃ | 5-OCH₃ | Cl | F |
| A-3967. | OCHF₂ | OCH₂F | 3-F | Cl | F |
| A-3968. | OCHF₂ | OCH₂F | 3-CH₃ | Cl | F |
| A-3969. | OCHF₂ | OCH₂F | 3-OCH₃ | Cl | F |
| A-3970. | OCHF₂ | OCH₂F | 5-F | Cl | F |
| A-3971. | OCHF₂ | OCH₂F | 5-CH₃ | Cl | F |
| A-3972. | OCHF₂ | OCH₂F | 5-OCH₃ | Cl | F |
| A-3973. | OCHF₂ | OCHF₂ | 3-F | Cl | F |
| A-3974. | OCHF₂ | OCHF₂ | 3-CH₃ | Cl | F |
| A-3975. | OCHF₂ | OCHF₂ | 3-OCH₃ | Cl | F |
| A-3976. | OCHF₂ | OCHF₂ | 5-F | Cl | F |
| A-3977. | OCHF₂ | OCHF₂ | 5-CH₃ | Cl | F |
| A-3978. | OCHF₂ | OCHF₂ | 5-OCH₃ | Cl | F |
| A-3979. | OCHF₂ | OCF₃ | 3-F | Cl | F |
| A-3980. | OCHF₂ | OCF₃ | 3-CH₃ | Cl | F |
| A-3981. | OCHF₂ | OCF₃ | 3-OCH₃ | Cl | F |
| A-3982. | OCHF₂ | OCF₃ | 5-F | Cl | F |
| A-3983. | OCHF₂ | OCF₃ | 5-CH₃ | Cl | F |
| A-3984. | OCHF₂ | OCF₃ | 5-OCH₃ | Cl | F |
| A-3985. | OCF₃ | F | 3-F | Cl | F |
| A-3986. | OCF₃ | F | 3-CH₃ | Cl | F |
| A-3987. | OCF₃ | F | 3-OCH₃ | Cl | F |
| A-3988. | OCF₃ | F | 5-F | Cl | F |
| A-3989. | OCF₃ | F | 5-CH₃ | Cl | F |
| A-3990. | OCF₃ | F | 5-OCH₃ | Cl | F |
| A-3991. | OCF₃ | CH₃ | 3-F | Cl | F |
| A-3992. | OCF₃ | CH₃ | 3-CH₃ | Cl | F |
| A-3993. | OCF₃ | CH₃ | 3-OCH₃ | Cl | F |
| A-3994. | OCF₃ | CH₃ | 5-F | Cl | F |
| A-3995. | OCF₃ | CH₃ | 5-CH₃ | Cl | F |
| A-3996. | OCF₃ | CH₃ | 5-OCH₃ | Cl | F |
| A-3997. | OCF₃ | OCH₃ | 3-F | Cl | F |
| A-3998. | OCF₃ | OCH₃ | 3-CH₃ | Cl | F |
| A-3999. | OCF₃ | OCH₃ | 3-OCH₃ | Cl | F |
| A-4000. | OCF₃ | OCH₃ | 5-F | Cl | F |
| A-4001. | OCF₃ | OCH₃ | 5-CH₃ | Cl | F |
| A-4002. | OCF₃ | OCH₃ | 5-OCH₃ | Cl | F |
| A-4003. | OCF₃ | CN | 3-F | Cl | F |
| A-4004. | OCF₃ | CN | 3-CH₃ | Cl | F |
| A-4005. | OCF₃ | CN | 3-OCH₃ | Cl | F |
| A-4006. | OCF₃ | CN | 5-F | Cl | F |
| A-4007. | OCF₃ | CN | 5-CH₃ | Cl | F |
| A-4008. | OCF₃ | CN | 5-OCH₃ | Cl | F |
| A-4009. | OCF₃ | CH₂F | 3-F | Cl | F |
| A-4010. | OCF₃ | CH₂F | 3-CH₃ | Cl | F |
| A-4011. | OCF₃ | CH₂F | 3-OCH₃ | Cl | F |
| A-4012. | OCF₃ | CH₂F | 5-F | Cl | F |
| A-4013. | OCF₃ | CH₂F | 5-CH₃ | Cl | F |
| A-4014. | OCF₃ | CH₂F | 5-OCH₃ | Cl | F |
| A-4015. | OCF₃ | CHF₂ | 3-F | Cl | F |
| A-4016. | OCF₃ | CHF₂ | 3-CH₃ | Cl | F |
| A-4017. | OCF₃ | CHF₂ | 3-OCH₃ | Cl | F |
| A-4018. | OCF₃ | CHF₂ | 5-F | Cl | F |
| A-4019. | OCF₃ | CHF₂ | 5-CH₃ | Cl | F |
| A-4020. | OCF₃ | CHF₂ | 5-OCH₃ | Cl | F |
| A-4021. | OCF₃ | CF₃ | 3-F | Cl | F |
| A-4022. | OCF₃ | CF₃ | 3-CH₃ | Cl | F |
| A-4023. | OCF₃ | CF₃ | 3-OCH₃ | Cl | F |
| A-4024. | OCF₃ | CF₃ | 5-F | Cl | F |
| A-4025. | OCF₃ | CF₃ | 5-CH₃ | Cl | F |
| A-4026. | OCF₃ | CF₃ | 5-OCH₃ | Cl | F |
| A-4027. | OCF₃ | OCH₂F | 3-F | Cl | F |
| A-4028. | OCF₃ | OCH₂F | 3-CH₃ | Cl | F |
| A-4029. | OCF₃ | OCH₂F | 3-OCH₃ | Cl | F |
| A-4030. | OCF₃ | OCH₂F | 5-F | Cl | F |
| A-4031. | OCF₃ | OCH₂F | 5-CH₃ | Cl | F |
| A-4032. | OCF₃ | OCH₂F | 5-OCH₃ | Cl | F |
| A-4033. | OCF₃ | OCHF₂ | 3-F | Cl | F |
| A-4034. | OCF₃ | OCHF₂ | 3-CH₃ | Cl | F |
| A-4035. | OCF₃ | OCHF₂ | 3-OCH₃ | Cl | F |
| A-4036. | OCF₃ | OCHF₂ | 5-F | Cl | F |
| A-4037. | OCF₃ | OCHF₂ | 5-CH₃ | Cl | F |
| A-4038. | OCF₃ | OCHF₂ | 5-OCH₃ | Cl | F |
| A-4039. | OCF₃ | OCF₃ | 3-F | Cl | F |
| A-4040. | OCF₃ | OCF₃ | 3-CH₃ | Cl | F |
| A-4041. | OCF₃ | OCF₃ | 3-OCH₃ | Cl | F |
| A-4042. | OCF₃ | OCF₃ | 5-F | Cl | F |
| A-4043. | OCF₃ | OCF₃ | 5-CH₃ | Cl | F |
| A-4044. | OCF₃ | OCF₃ | 5-OCH₃ | Cl | F |

TABLE B

| Example No. | R² | R³ | R⁶ | R⁷ |
|---|---|---|---|---|
| B-1. | H | H | CN | H |
| B-2. | F | H | CN | H |
| B-3. | CH₃ | H | CN | H |
| B-4. | OCH₃ | H | CN | H |
| B-5. | CN | H | CN | H |
| B-6. | CH₂F | H | CN | H |
| B-7. | CHF₂ | H | CN | H |
| B-8. | CF₃ | H | CN | H |
| B-9. | OCH₂F | H | CN | H |
| B-10. | OCHF₂ | H | CN | H |
| B-11. | OCF₃ | H | CN | H |
| B-12. | H | 3-F | CN | H |
| B-13. | H | 3-CH₃ | CN | H |
| B-14. | H | 3-OCH₃ | CN | H |
| B-15. | H | 5-F | CN | H |
| B-16. | H | 5-CH₃ | CN | H |
| B-17. | H | 5-OCH₃ | CN | H |
| B-18. | H | 6-F | CN | H |
| B-19. | H | 6-CH₃ | CN | H |
| B-20. | H | 6-OCH₃ | CN | H |
| B-21. | F | 3-F | CN | H |
| B-22. | F | 3-CH₃ | CN | H |
| B-23. | F | 3-OCH₃ | CN | H |
| B-24. | F | 5-F | CN | H |
| B-25. | F | 5-CH₃ | CN | H |
| B-26. | F | 5-OCH₃ | CN | H |
| B-27. | F | 6-F | CN | H |
| B-28. | F | 6-CH₃ | CN | H |
| B-29. | F | 6-OCH₃ | CN | H |
| B-30. | CH₃ | 3-F | CN | H |
| B-31. | CH₃ | 3-CH₃ | CN | H |
| B-32. | CH₃ | 3-OCH₃ | CN | H |
| B-33. | CH₃ | 5-F | CN | H |
| B-34. | CH₃ | 5-CH₃ | CN | H |
| B-35. | CH₃ | 5-OCH₃ | CN | H |
| B-36. | CH₃ | 6-F | CN | H |
| B-37. | CH₃ | 6-CH₃ | CN | H |
| B-38. | CH₃ | 6-OCH₃ | CN | H |
| B-39. | OCH₃ | 3-F | CN | H |
| B-40. | OCH₃ | 3-CH₃ | CN | H |
| B-41. | OCH₃ | 3-OCH₃ | CN | H |
| B-42. | OCH₃ | 5-F | CN | H |
| B-43. | OCH₃ | 5-CH₃ | CN | H |
| B-44. | OCH₃ | 5-OCH₃ | CN | H |
| B-45. | OCH₃ | 6-F | CN | H |
| B-46. | OCH₃ | 6-CH₃ | CN | H |
| B-47. | OCH₃ | 6-OCH₃ | CN | H |
| B-48. | CN | 3-F | CN | H |
| B-49. | CN | 3-CH₃ | CN | H |
| B-50. | CN | 3-OCH₃ | CN | H |
| B-51. | CN | 5-F | CN | H |
| B-52. | CN | 5-CH₃ | CN | H |
| B-53. | CN | 5-OCH₃ | CN | H |
| B-54. | CN | 6-F | CN | H |
| B-55. | CN | 6-CH₃ | CN | H |
| B-56. | CN | 6-OCH₃ | CN | H |
| B-57. | CH₂F | 3-F | CN | H |
| B-58. | CH₂F | 3-CH₃ | CN | H |
| B-59. | CH₂F | 3-OCH₃ | CN | H |
| B-60. | CH₂F | 5-F | CN | H |
| B-61. | CH₂F | 5-CH₃ | CN | H |
| B-62. | CH₂F | 5-OCH₃ | CN | H |
| B-63. | CH₂F | 6-F | CN | H |
| B-64. | CH₂F | 6-CH₃ | CN | H |
| B-65. | CH₂F | 6-OCH₃ | CN | H |
| B-66. | CHF₂ | 3-F | CN | H |
| B-67. | CHF₂ | 3-CH₃ | CN | H |
| B-68. | CHF₂ | 3-OCH₃ | CN | H |

TABLE B-continued

| Example No. | $R^2$ | $R^3$ | $R^6$ | $R^7$ |
|---|---|---|---|---|
| B-69. | $CHF_2$ | 5-F | CN | H |
| B-70. | $CHF_2$ | 5-$CH_3$ | CN | H |
| B-71. | $CHF_2$ | 5-$OCH_3$ | CN | H |
| B-72. | $CHF_2$ | 6-F | CN | H |
| B-73. | $CHF_2$ | 6-$CH_3$ | CN | H |
| B-74. | $CHF_2$ | 6-$OCH_3$ | CN | H |
| B-75. | $CF_3$ | 3-F | CN | H |
| B-76. | $CF_3$ | 3-$CH_3$ | CN | H |
| B-77. | $CF_3$ | 3-$OCH_3$ | CN | H |
| B-78. | $CF_3$ | 5-F | CN | H |
| B-79. | $CF_3$ | 5-$CH_3$ | CN | H |
| B-80. | $CF_3$ | 5-$OCH_3$ | CN | H |
| B-81. | $CF_3$ | 6-F | CN | H |
| B-82. | $CF_3$ | 6-$CH_3$ | CN | H |
| B-83. | $CF_3$ | 6-$OCH_3$ | CN | H |
| B-84. | $OCH_2F$ | 3-F | CN | H |
| B-85. | $OCH_2F$ | 3-$CH_3$ | CN | H |
| B-86. | $OCH_2F$ | 3-$OCH_3$ | CN | H |
| B-87. | $OCH_2F$ | 5-F | CN | H |
| B-88. | $OCH_2F$ | 5-$CH_3$ | CN | H |
| B-89. | $OCH_2F$ | 5-$OCH_3$ | CN | H |
| B-90. | $OCH_2F$ | 6-F | CN | H |
| B-91. | $OCH_2F$ | 6-$CH_3$ | CN | H |
| B-92. | $OCH_2F$ | 6-$OCH_3$ | CN | H |
| B-93. | $OCHF_2$ | 3-F | CN | H |
| B-94. | $OCHF_2$ | 3-$CH_3$ | CN | H |
| B-95. | $OCHF_2$ | 3-$OCH_3$ | CN | H |
| B-96. | $OCHF_2$ | 5-F | CN | H |
| B-97. | $OCHF_2$ | 5-$CH_3$ | CN | H |
| B-98. | $OCHF_2$ | 5-$OCH_3$ | CN | H |
| B-99. | $OCHF_2$ | 6-F | CN | H |
| B-100. | $OCHF_2$ | 6-$CH_3$ | CN | H |
| B-101. | $OCHF_2$ | 6-$OCH_3$ | CN | H |
| B-102. | $OCF_3$ | 3-F | CN | H |
| B-103. | $OCF_3$ | 3-$CH_3$ | CN | H |
| B-104. | $OCF_3$ | 3-$OCH_3$ | CN | H |
| B-105. | $OCF_3$ | 5-F | CN | H |
| B-106. | $OCF_3$ | 5-$CH_3$ | CN | H |
| B-107. | $OCF_3$ | 5-$OCH_3$ | CN | H |
| B-108. | $OCF_3$ | 6-F | CN | H |
| B-109. | $OCF_3$ | 6-$CH_3$ | CN | H |
| B-110. | $OCF_3$ | 6-$OCH_3$ | CN | H |
| B-111. | H | H | F | H |
| B-112. | F | H | F | H |
| B-113. | $CH_3$ | H | F | H |
| B-114. | $OCH_3$ | H | F | H |
| B-115. | CN | H | F | H |
| B-116. | $CH_2F$ | H | F | H |
| B-117. | $CHF_2$ | H | F | H |
| B-118. | $CF_3$ | H | F | H |
| B-119. | $OCH_2F$ | H | F | H |
| B-120. | $OCHF_2$ | H | F | H |
| B-121. | $OCF_3$ | H | F | H |
| B-122. | H | 3-F | F | H |
| B-123. | H | 3-$CH_3$ | F | H |
| B-124. | H | 3-$OCH_3$ | F | H |
| B-125. | H | 5-F | F | H |
| B-126. | H | 5-$CH_3$ | F | H |
| B-127. | H | 5-$OCH_3$ | F | H |
| B-128. | H | 6-F | F | H |
| B-129. | H | 6-$CH_3$ | F | H |
| B-130. | H | 6-$OCH_3$ | F | H |
| B-131. | F | 3-F | F | H |
| B-132. | F | 3-$CH_3$ | F | H |
| B-133. | F | 3-$OCH_3$ | F | H |
| B-134. | F | 5-F | F | H |
| B-135. | F | 5-$CH_3$ | F | H |
| B-136. | F | 5-$OCH_3$ | F | H |
| B-137. | F | 6-F | F | H |
| B-138. | F | 6-$CH_3$ | F | H |
| B-139. | F | 6-$OCH_3$ | F | H |
| B-140. | $CH_3$ | 3-F | F | H |
| B-141. | $CH_3$ | 3-$CH_3$ | F | H |
| B-142. | $CH_3$ | 3-$OCH_3$ | F | H |
| B-143. | $CH_3$ | 5-F | F | H |
| B-144. | $CH_3$ | 5-$CH_3$ | F | H |
| B-145. | $CH_3$ | 5-$OCH_3$ | F | H |
| B-146. | $CH_3$ | 6-F | F | H |
| B-147. | $CH_3$ | 6-$CH_3$ | F | H |
| B-148. | $CH_3$ | 6-$OCH_3$ | F | H |
| B-149. | $OCH_3$ | 3-F | F | H |
| B-150. | $OCH_3$ | 3-$CH_3$ | F | H |
| B-151. | $OCH_3$ | 3-$OCH_3$ | F | H |
| B-152. | $OCH_3$ | 5-F | F | H |
| B-153. | $OCH_3$ | 5-$CH_3$ | F | H |
| B-154. | $OCH_3$ | 5-$OCH_3$ | F | H |
| B-155. | $OCH_3$ | 6-F | F | H |
| B-156. | $OCH_3$ | 6-$CH_3$ | F | H |
| B-157. | $OCH_3$ | 6-$OCH_3$ | F | H |
| B-158. | CN | 3-F | F | H |
| B-159. | CN | 3-$CH_3$ | F | H |
| B-160. | CN | 3-$OCH_3$ | F | H |
| B-161. | CN | 5-F | F | H |
| B-162. | CN | 5-$CH_3$ | F | H |
| B-163. | CN | 5-$OCH_3$ | F | H |
| B-164. | CN | 6-F | F | H |
| B-165. | CN | 6-$CH_3$ | F | H |
| B-166. | CN | 6-$OCH_3$ | F | H |
| B-167. | $CH_2F$ | 3-F | F | H |
| B-168. | $CH_2F$ | 3-$CH_3$ | F | H |
| B-169. | $CH_2F$ | 3-$OCH_3$ | F | H |
| B-170. | $CH_2F$ | 5-F | F | H |
| B-171. | $CH_2F$ | 5-$CH_3$ | F | H |
| B-172. | $CH_2F$ | 5-$OCH_3$ | F | H |
| B-173. | $CH_2F$ | 6-F | F | H |
| B-174. | $CH_2F$ | 6-$CH_3$ | F | H |
| B-175. | $CH_2F$ | 6-$OCH_3$ | F | H |
| B-176. | $CHF_2$ | 3-F | F | H |
| B-177. | $CHF_2$ | 3-$CH_3$ | F | H |
| B-178. | $CHF_2$ | 3-$OCH_3$ | F | H |
| B-179. | $CHF_2$ | 5-F | F | H |
| B-180. | $CHF_2$ | 5-$CH_3$ | F | H |
| B-181. | $CHF_2$ | 5-$OCH_3$ | F | H |
| B-182. | $CHF_2$ | 6-F | F | H |
| B-183. | $CHF_2$ | 6-$CH_3$ | F | H |
| B-184. | $CHF_2$ | 6-$OCH_3$ | F | H |
| B-185. | $CF_3$ | 3-F | F | H |
| B-186. | $CF_3$ | 3-$CH_3$ | F | H |
| B-187. | $CF_3$ | 3-$OCH_3$ | F | H |
| B-188. | $CF_3$ | 5-F | F | H |
| B-189. | $CF_3$ | 5-$CH_3$ | F | H |
| B-190. | $CF_3$ | 5-$OCH_3$ | F | H |
| B-191. | $CF_3$ | 6-F | F | H |
| B-192. | $CF_3$ | 6-$CH_3$ | F | H |
| B-193. | $CF_3$ | 6-$OCH_3$ | F | H |
| B-194. | $OCH_2F$ | 3-F | F | H |
| B-195. | $OCH_2F$ | 3-$CH_3$ | F | H |
| B-196. | $OCH_2F$ | 3-$OCH_3$ | F | H |
| B-197. | $OCH_2F$ | 5-F | F | H |
| B-198. | $OCH_2F$ | 5-$CH_3$ | F | H |
| B-199. | $OCH_2F$ | 5-$OCH_3$ | F | H |
| B-200. | $OCH_2F$ | 6-F | F | H |
| B-201. | $OCH_2F$ | 6-$CH_3$ | F | H |
| B-202. | $OCH_2F$ | 6-$OCH_3$ | F | H |
| B-203. | $OCHF_2$ | 3-F | F | H |
| B-204. | $OCHF_2$ | 3-$CH_3$ | F | H |
| B-205. | $OCHF_2$ | 3-$OCH_3$ | F | H |
| B-206. | $OCHF_2$ | 5-F | F | H |
| B-207. | $OCHF_2$ | 5-$CH_3$ | F | H |
| B-208. | $OCHF_2$ | 5-$OCH_3$ | F | H |
| B-209. | $OCHF_2$ | 6-F | F | H |
| B-210. | $OCHF_2$ | 6-$CH_3$ | F | H |
| B-211. | $OCHF_2$ | 6-$OCH_3$ | F | H |
| B-212. | $OCF_3$ | 3-F | F | H |
| B-213. | $OCF_3$ | 3-$CH_3$ | F | H |
| B-214. | $OCF_3$ | 3-$OCH_3$ | F | H |
| B-215. | $OCF_3$ | 5-F | F | H |
| B-216. | $OCF_3$ | 5-$CH_3$ | F | H |
| B-217. | $OCF_3$ | 5-$OCH_3$ | F | H |
| B-218. | $OCF_3$ | 6-F | F | H |
| B-219. | $OCF_3$ | 6-$CH_3$ | F | H |
| B-220. | $OCF_3$ | 6-$OCH_3$ | F | H |
| B-221. | H | H | Cl | H |
| B-222. | F | H | Cl | H |
| B-223. | $CH_3$ | H | Cl | H |
| B-224. | $OCH_3$ | H | Cl | H |

TABLE B-continued

| Example No. | R² | R³ | R⁶ | R⁷ |
|---|---|---|---|---|
| B-225. | CN | H | Cl | H |
| B-226. | CH₂F | H | Cl | H |
| B-227. | CHF₂ | H | Cl | H |
| B-228. | CF₃ | H | Cl | H |
| B-229. | OCH₂F | H | Cl | H |
| B-230. | OCHF₂ | H | Cl | H |
| B-231. | OCF₃ | H | Cl | H |
| B-232. | H | 3-F | Cl | H |
| B-233. | H | 3-CH₃ | Cl | H |
| B-234. | H | 3-OCH₃ | Cl | H |
| B-235. | H | 5-F | Cl | H |
| B-236. | H | 5-CH₃ | Cl | H |
| B-237. | H | 5-OCH₃ | Cl | H |
| B-238. | H | 6-F | Cl | H |
| B-239. | H | 6-CH₃ | Cl | H |
| B-240. | H | 6-OCH₃ | Cl | H |
| B-241. | F | 3-F | Cl | H |
| B-242. | F | 3-CH₃ | Cl | H |
| B-243. | F | 3-OCH₃ | Cl | H |
| B-244. | F | 5-F | Cl | H |
| B-245. | F | 5-CH₃ | Cl | H |
| B-246. | F | 5-OCH₃ | Cl | H |
| B-247. | F | 6-F | Cl | H |
| B-248. | F | 6-CH₃ | Cl | H |
| B-249. | F | 6-OCH₃ | Cl | H |
| B-250. | CH₃ | 3-F | Cl | H |
| B-251. | CH₃ | 3-CH₃ | Cl | H |
| B-252. | CH₃ | 3-OCH₃ | Cl | H |
| B-253. | CH₃ | 5-F | Cl | H |
| B-254. | CH₃ | 5-CH₃ | Cl | H |
| B-255. | CH₃ | 5-OCH₃ | Cl | H |
| B-256. | CH₃ | 6-F | Cl | H |
| B-257. | CH₃ | 6-CH₃ | Cl | H |
| B-258. | CH₃ | 6-OCH₃ | Cl | H |
| B-259. | OCH₃ | 3-F | Cl | H |
| B-260. | OCH₃ | 3-CH₃ | Cl | H |
| B-261. | OCH₃ | 3-OCH₃ | Cl | H |
| B-262. | OCH₃ | 5-F | Cl | H |
| B-263. | OCH₃ | 5-CH₃ | Cl | H |
| B-264. | OCH₃ | 5-OCH₃ | Cl | H |
| B-265. | OCH₃ | 6-F | Cl | H |
| B-266. | OCH₃ | 6-CH₃ | Cl | H |
| B-267. | OCH₃ | 6-OCH₃ | Cl | H |
| B-268. | CN | 3-F | Cl | H |
| B-269. | CN | 3-CH₃ | Cl | H |
| B-270. | CN | 3-OCH₃ | Cl | H |
| B-271. | CN | 5-F | Cl | H |
| B-272. | CN | 5-CH₃ | Cl | H |
| B-273. | CN | 5-OCH₃ | Cl | H |
| B-274. | CN | 6-F | Cl | H |
| B-275. | CN | 6-CH₃ | Cl | H |
| B-276. | CN | 6-OCH₃ | Cl | H |
| B-277. | CH₂F | 3-F | Cl | H |
| B-278. | CH₂F | 3-CH₃ | Cl | H |
| B-279. | CH₂F | 3-OCH₃ | Cl | H |
| B-280. | CH₂F | 5-F | Cl | H |
| B-281. | CH₂F | 5-CH₃ | Cl | H |
| B-282. | CH₂F | 5-OCH₃ | Cl | H |
| B-283. | CH₂F | 6-F | Cl | H |
| B-284. | CH₂F | 6-CH₃ | Cl | H |
| B-285. | CH₂F | 6-OCH₃ | Cl | H |
| B-286. | CHF₂ | 3-F | Cl | H |
| B-287. | CHF₂ | 3-CH₃ | Cl | H |
| B-288. | CHF₂ | 3-OCH₃ | Cl | H |
| B-289. | CHF₂ | 5-F | Cl | H |
| B-290. | CHF₂ | 5-CH₃ | Cl | H |
| B-291. | CHF₂ | 5-OCH₃ | Cl | H |
| B-292. | CHF₂ | 6-F | Cl | H |
| B-293. | CHF₂ | 6-CH₃ | Cl | H |
| B-294. | CHF₂ | 6-OCH₃ | Cl | H |
| B-295. | CF₃ | 3-F | Cl | H |
| B-296. | CF₃ | 3-CH₃ | Cl | H |
| B-297. | CF₃ | 3-OCH₃ | Cl | H |
| B-298. | CF₃ | 5-F | Cl | H |
| B-299. | CF₃ | 5-CH₃ | Cl | H |
| B-300. | CF₃ | 5-OCH₃ | Cl | H |
| B-301. | CF₃ | 6-F | Cl | H |
| B-302. | CF₃ | 6-CH₃ | Cl | H |
| B-303. | CF₃ | 6-OCH₃ | Cl | H |
| B-304. | OCH₂F | 3-F | Cl | H |
| B-305. | OCH₂F | 3-CH₃ | Cl | H |
| B-306. | OCH₂F | 3-OCH₃ | Cl | H |
| B-307. | OCH₂F | 5-F | Cl | H |
| B-308. | OCH₂F | 5-CH₃ | Cl | H |
| B-309. | OCH₂F | 5-OCH₃ | Cl | H |
| B-310. | OCH₂F | 6-F | Cl | H |
| B-311. | OCH₂F | 6-CH₃ | Cl | H |
| B-312. | OCH₂F | 6-OCH₃ | Cl | H |
| B-313. | OCHF₂ | 3-F | Cl | H |
| B-314. | OCHF₂ | 3-CH₃ | Cl | H |
| B-315. | OCHF₂ | 3-OCH₃ | Cl | H |
| B-316. | OCHF₂ | 5-F | Cl | H |
| B-317. | OCHF₂ | 5-CH₃ | Cl | H |
| B-318. | OCHF₂ | 5-OCH₃ | Cl | H |
| B-319. | OCHF₂ | 6-F | Cl | H |
| B-320. | OCHF₂ | 6-CH₃ | Cl | H |
| B-321. | OCHF₂ | 6-OCH₃ | Cl | H |
| B-322. | OCF₃ | 3-F | Cl | H |
| B-323. | OCF₃ | 3-CH₃ | Cl | H |
| B-324. | OCF₃ | 3-OCH₃ | Cl | H |
| B-325. | OCF₃ | 5-F | Cl | H |
| B-326. | OCF₃ | 5-CH₃ | Cl | H |
| B-327. | OCF₃ | 5-OCH₃ | Cl | H |
| B-328. | OCF₃ | 6-F | Cl | H |
| B-329. | OCF₃ | 6-CH₃ | Cl | H |
| B-330. | OCF₃ | 6-OCH₃ | Cl | H |
| B-331. | H | H | CN | F |
| B-332. | F | H | CN | F |
| B-333. | CH₃ | H | CN | F |
| B-334. | OCH₃ | H | CN | F |
| B-335. | CN | H | CN | F |
| B-336. | CH₂F | H | CN | F |
| B-337. | CHF₂ | H | CN | F |
| B-338. | CF₃ | H | CN | F |
| B-339. | OCH₂F | H | CN | F |
| B-340. | OCHF₂ | H | CN | F |
| B-341. | OCF₃ | H | CN | F |
| B-342. | H | 3-F | CN | F |
| B-343. | H | 3-CH₃ | CN | F |
| B-344. | H | 3-OCH₃ | CN | F |
| B-345. | H | 5-F | CN | F |
| B-346. | H | 5-CH₃ | CN | F |
| B-347. | H | 5-OCH₃ | CN | F |
| B-348. | H | 6-F | CN | F |
| B-349. | H | 6-CH₃ | CN | F |
| B-350. | H | 6-OCH₃ | CN | F |
| B-351. | F | 3-F | CN | F |
| B-352. | F | 3-CH₃ | CN | F |
| B-353. | F | 3-OCH₃ | CN | F |
| B-354. | F | 5-F | CN | F |
| B-355. | F | 5-CH₃ | CN | F |
| B-356. | F | 5-OCH₃ | CN | F |
| B-357. | F | 6-F | CN | F |
| B-358. | F | 6-CH₃ | CN | F |
| B-359. | F | 6-OCH₃ | CN | F |
| B-360. | CH₃ | 3-F | CN | F |
| B-361. | CH₃ | 3-CH₃ | CN | F |
| B-362. | CH₃ | 3-OCH₃ | CN | F |
| B-363. | CH₃ | 5-F | CN | F |
| B-364. | CH₃ | 5-CH₃ | CN | F |
| B-365. | CH₃ | 5-OCH₃ | CN | F |
| B-366. | CH₃ | 6-F | CN | F |
| B-367. | CH₃ | 6-CH₃ | CN | F |
| B-368. | CH₃ | 6-OCH₃ | CN | F |
| B-369. | OCH₃ | 3-F | CN | F |
| B-370. | OCH₃ | 3-CH₃ | CN | F |
| B-371. | OCH₃ | 3-OCH₃ | CN | F |
| B-372. | OCH₃ | 5-F | CN | F |
| B-373. | OCH₃ | 5-CH₃ | CN | F |
| B-374. | OCH₃ | 5-OCH₃ | CN | F |
| B-375. | OCH₃ | 6-F | CN | F |
| B-376. | OCH₃ | 6-CH₃ | CN | F |
| B-377. | OCH₃ | 6-OCH₃ | CN | F |
| B-378. | CN | 3-F | CN | F |
| B-379. | CN | 3-CH₃ | CN | F |
| B-380. | CN | 3-OCH₃ | CN | F |

TABLE B-continued

| Example No. | $R^2$ | $R^3$ | $R^6$ | $R^7$ |
|---|---|---|---|---|
| B-381. | CN | 5-F | CN | F |
| B-382. | CN | 5-CH$_3$ | CN | F |
| B-383. | CN | 5-OCH$_3$ | CN | F |
| B-384. | CN | 6-F | CN | F |
| B-385. | CN | 6-CH$_3$ | CN | F |
| B-386. | CN | 6-OCH$_3$ | CN | F |
| B-387. | CH$_2$F | 3-F | CN | F |
| B-388. | CH$_2$F | 3-CH$_3$ | CN | F |
| B-389. | CH$_2$F | 3-OCH$_3$ | CN | F |
| B-390. | CH$_2$F | 5-F | CN | F |
| B-391. | CH$_2$F | 5-CH$_3$ | CN | F |
| B-392. | CH$_2$F | 5-OCH$_3$ | CN | F |
| B-393. | CH$_2$F | 6-F | CN | F |
| B-394. | CH$_2$F | 6-CH$_3$ | CN | F |
| B-395. | CH$_2$F | 6-OCH$_3$ | CN | F |
| B-396. | CHF$_2$ | 3-F | CN | F |
| B-397. | CHF$_2$ | 3-CH$_3$ | CN | F |
| B-398. | CHF$_2$ | 3-OCH$_3$ | CN | F |
| B-399. | CHF$_2$ | 5-F | CN | F |
| B-400. | CHF$_2$ | 5-CH$_3$ | CN | F |
| B-401. | CHF$_2$ | 5-OCH$_3$ | CN | F |
| B-402. | CHF$_2$ | 6-F | CN | F |
| B-403. | CHF$_2$ | 6-CH$_3$ | CN | F |
| B-404. | CHF$_2$ | 6-OCH$_3$ | CN | F |
| B-405. | CF$_3$ | 3-F | CN | F |
| B-406. | CF$_3$ | 3-CH$_3$ | CN | F |
| B-407. | CF$_3$ | 3-OCH$_3$ | CN | F |
| B-408. | CF$_3$ | 5-F | CN | F |
| B-409. | CF$_3$ | 5-CH$_3$ | CN | F |
| B-410. | CF$_3$ | 5-OCH$_3$ | CN | F |
| B-411. | CF$_3$ | 6-F | CN | F |
| B-412. | CF$_3$ | 6-CH$_3$ | CN | F |
| B-413. | CF$_3$ | 6-OCH$_3$ | CN | F |
| B-414. | OCH$_2$F | 3-F | CN | F |
| B-415. | OCH$_2$F | 3-CH$_3$ | CN | F |
| B-416. | OCH$_2$F | 3-OCH$_3$ | CN | F |
| B-417. | OCH$_2$F | 5-F | CN | F |
| B-418. | OCH$_2$F | 5-CH$_3$ | CN | F |
| B-419. | OCH$_2$F | 5-OCH$_3$ | CN | F |
| B-420. | OCH$_2$F | 6-F | CN | F |
| B-421. | OCH$_2$F | 6-CH$_3$ | CN | F |
| B-422. | OCH$_2$F | 6-OCH$_3$ | CN | F |
| B-423. | OCHF$_2$ | 3-F | CN | F |
| B-424. | OCHF$_2$ | 3-CH$_3$ | CN | F |
| B-425. | OCHF$_2$ | 3-OCH$_3$ | CN | F |
| B-426. | OCHF$_2$ | 5-F | CN | F |
| B-427. | OCHF$_2$ | 5-CH$_3$ | CN | F |
| B-428. | OCHF$_2$ | 5-OCH$_3$ | CN | F |
| B-429. | OCHF$_2$ | 6-F | CN | F |
| B-430. | OCHF$_2$ | 6-CH$_3$ | CN | F |
| B-431. | OCHF$_2$ | 6-OCH$_3$ | CN | F |
| B-432. | OCF$_3$ | 3-F | CN | F |
| B-433. | OCF$_3$ | 3-CH$_3$ | CN | F |
| B-434. | OCF$_3$ | 3-OCH$_3$ | CN | F |
| B-435. | OCF$_3$ | 5-F | CN | F |
| B-436. | OCF$_3$ | 5-CH$_3$ | CN | F |
| B-437. | OCF$_3$ | 5-OCH$_3$ | CN | F |
| B-438. | OCF$_3$ | 6-F | CN | F |
| B-439. | OCF$_3$ | 6-CH$_3$ | CN | F |
| B-440. | OCF$_3$ | 6-OCH$_3$ | CN | F |
| B-441. | H | H | F | F |
| B-442. | F | H | F | F |
| B-443. | CH$_3$ | H | F | F |
| B-444. | OCH$_3$ | H | F | F |
| B-445. | CN | H | F | F |
| B-446. | CH$_2$F | H | F | F |
| B-447. | CHF$_2$ | H | F | F |
| B-448. | CF$_3$ | H | F | F |
| B-449. | OCH$_2$F | H | F | F |
| B-450. | OCHF$_2$ | H | F | F |
| B-451. | OCF$_3$ | H | F | F |
| B-452. | H | 3-F | F | F |
| B-453. | H | 3-CH$_3$ | F | F |
| B-454. | H | 3-OCH$_3$ | F | F |
| B-455. | H | 5-F | F | F |
| B-456. | H | 5-CH$_3$ | F | F |
| B-457. | H | 5-OCH$_3$ | F | F |
| B-458. | H | 6-F | F | F |
| B-459. | H | 6-CH$_3$ | F | F |
| B-460. | H | 6-OCH$_3$ | F | F |
| B-461. | F | 3-F | F | F |
| B-462. | F | 3-CH$_3$ | F | F |
| B-463. | F | 3-OCH$_3$ | F | F |
| B-464. | F | 5-F | F | F |
| B-465. | F | 5-CH$_3$ | F | F |
| B-466. | F | 5-OCH$_3$ | F | F |
| B-467. | F | 6-F | F | F |
| B-468. | F | 6-CH$_3$ | F | F |
| B-469. | F | 6-OCH$_3$ | F | F |
| B-470. | CH$_3$ | 3-F | F | F |
| B-471. | CH$_3$ | 3-CH$_3$ | F | F |
| B-472. | CH$_3$ | 3-OCH$_3$ | F | F |
| B-473. | CH$_3$ | 5-F | F | F |
| B-474. | CH$_3$ | 5-CH$_3$ | F | F |
| B-475. | CH$_3$ | 5-OCH$_3$ | F | F |
| B-476. | CH$_3$ | 6-F | F | F |
| B-477. | CH$_3$ | 6-CH$_3$ | F | F |
| B-478. | CH$_3$ | 6-OCH$_3$ | F | F |
| B-479. | OCH$_3$ | 3-F | F | F |
| B-480. | OCH$_3$ | 3-CH$_3$ | F | F |
| B-481. | OCH$_3$ | 3-OCH$_3$ | F | F |
| B-482. | OCH$_3$ | 5-F | F | F |
| B-483. | OCH$_3$ | 5-CH$_3$ | F | F |
| B-484. | OCH$_3$ | 5-OCH$_3$ | F | F |
| B-485. | OCH$_3$ | 6-F | F | F |
| B-486. | OCH$_3$ | 6-CH$_3$ | F | F |
| B-487. | OCH$_3$ | 6-OCH$_3$ | F | F |
| B-488. | CN | 3-F | F | F |
| B-489. | CN | 3-CH$_3$ | F | F |
| B-490. | CN | 3-OCH$_3$ | F | F |
| B-491. | CN | 5-F | F | F |
| B-492. | CN | 5-CH$_3$ | F | F |
| B-493. | CN | 5-OCH$_3$ | F | F |
| B-494. | CN | 6-F | F | F |
| B-495. | CN | 6-CH$_3$ | F | F |
| B-496. | CN | 6-OCH$_3$ | F | F |
| B-497. | CH$_2$F | 3-F | F | F |
| B-498. | CH$_2$F | 3-CH$_3$ | F | F |
| B-499. | CH$_2$F | 3-OCH$_3$ | F | F |
| B-500. | CH$_2$F | 5-F | F | F |
| B-501. | CH$_2$F | 5-CH$_3$ | F | F |
| B-502. | CH$_2$F | 5-OCH$_3$ | F | F |
| B-503. | CH$_2$F | 6-F | F | F |
| B-504. | CH$_2$F | 6-CH$_3$ | F | F |
| B-505. | CH$_2$F | 6-OCH$_3$ | F | F |
| B-506. | CHF$_2$ | 3-F | F | F |
| B-507. | CHF$_2$ | 3-CH$_3$ | F | F |
| B-508. | CHF$_2$ | 3-OCH$_3$ | F | F |
| B-509. | CHF$_2$ | 5-F | F | F |
| B-510. | CHF$_2$ | 5-CH$_3$ | F | F |
| B-511. | CHF$_2$ | 5-OCH$_3$ | F | F |
| B-512. | CHF$_2$ | 6-F | F | F |
| B-513. | CHF$_2$ | 6-CH$_3$ | F | F |
| B-514. | CHF$_2$ | 6-OCH$_3$ | F | F |
| B-515. | CF$_3$ | 3-F | F | F |
| B-516. | CF$_3$ | 3-CH$_3$ | F | F |
| B-517. | CF$_3$ | 3-OCH$_3$ | F | F |
| B-518. | CF$_3$ | 5-F | F | F |
| B-519. | CF$_3$ | 5-CH$_3$ | F | F |
| B-520. | CF$_3$ | 5-OCH$_3$ | F | F |
| B-521. | CF$_3$ | 6-F | F | F |
| B-522. | CF$_3$ | 6-CH$_3$ | F | F |
| B-523. | CF$_3$ | 6-OCH$_3$ | F | F |
| B-524. | OCH$_2$F | 3-F | F | F |
| B-525. | OCH$_2$F | 3-CH$_3$ | F | F |
| B-526. | OCH$_2$F | 3-OCH$_3$ | F | F |
| B-527. | OCH$_2$F | 5-F | F | F |
| B-528. | OCH$_2$F | 5-CH$_3$ | F | F |
| B-529. | OCH$_2$F | 5-OCH$_3$ | F | F |
| B-530. | OCH$_2$F | 6-F | F | F |
| B-531. | OCH$_2$F | 6-CH$_3$ | F | F |
| B-532. | OCH$_2$F | 6-OCH$_3$ | F | F |
| B-533. | OCHF$_2$ | 3-F | F | F |
| B-534. | OCHF$_2$ | 3-CH$_3$ | F | F |
| B-535. | OCHF$_2$ | 3-OCH$_3$ | F | F |
| B-536. | OCHF$_2$ | 5-F | F | F |

TABLE B-continued

| Example No. | R² | R³ | R⁶ | R⁷ |
|---|---|---|---|---|
| B-537. | OCHF₂ | 5-CH₃ | F | F |
| B-538. | OCHF₂ | 5-OCH₃ | F | F |
| B-539. | OCHF₂ | 6-F | F | F |
| B-540. | OCHF₂ | 6-CH₃ | F | F |
| B-541. | OCHF₂ | 6-OCH₃ | F | F |
| B-542. | OCF₃ | 3-F | F | F |
| B-543. | OCF₃ | 3-CH₃ | F | F |
| B-544. | OCF₃ | 3-OCH₃ | F | F |
| B-545. | OCF₃ | 5-F | F | F |
| B-546. | OCF₃ | 5-CH₃ | F | F |
| B-547. | OCF₃ | 5-OCH₃ | F | F |
| B-548. | OCF₃ | 6-F | F | F |
| B-549. | OCF₃ | 6-CH₃ | F | F |
| B-550. | OCF₃ | 6-OCH₃ | F | F |
| B-551. | H | H | Cl | F |
| B-552. | F | H | Cl | F |
| B-553. | CH₃ | H | Cl | F |
| B-554. | OCH₃ | H | Cl | F |
| B-555. | CN | H | Cl | F |
| B-556. | CH₂F | H | Cl | F |
| B-557. | CHF₂ | H | Cl | F |
| B-558. | CF₃ | H | Cl | F |
| B-559. | OCH₂F | H | Cl | F |
| B-560. | OCHF₂ | H | Cl | F |
| B-561. | OCF₃ | H | Cl | F |
| B-562. | H | 3-F | Cl | F |
| B-563. | H | 3-CH₃ | Cl | F |
| B-564. | H | 3-OCH₃ | Cl | F |
| B-565. | H | 5-F | Cl | F |
| B-566. | H | 5-CH₃ | Cl | F |
| B-567. | H | 5-OCH₃ | Cl | F |
| B-568. | H | 6-F | Cl | F |
| B-569. | H | 6-CH₃ | Cl | F |
| B-570. | H | 6-OCH₃ | Cl | F |
| B-571. | F | 3-F | Cl | F |
| B-572. | F | 3-CH₃ | Cl | F |
| B-573. | F | 3-OCH₃ | Cl | F |
| B-574. | F | 5-F | Cl | F |
| B-575. | F | 5-CH₃ | Cl | F |
| B-576. | F | 5-OCH₃ | Cl | F |
| B-577. | F | 6-F | Cl | F |
| B-578. | F | 6-CH₃ | Cl | F |
| B-579. | F | 6-OCH₃ | Cl | F |
| B-580. | CH₃ | 3-F | Cl | F |
| B-581. | CH₃ | 3-CH₃ | Cl | F |
| B-582. | CH₃ | 3-OCH₃ | Cl | F |
| B-583. | CH₃ | 5-F | Cl | F |
| B-584. | CH₃ | 5-CH₃ | Cl | F |
| B-585. | CH₃ | 5-OCH₃ | Cl | F |
| B-586. | CH₃ | 6-F | Cl | F |
| B-587. | CH₃ | 6-CH₃ | Cl | F |
| B-588. | CH₃ | 6-OCH₃ | Cl | F |
| B-589. | OCH₃ | 3-F | Cl | F |
| B-590. | OCH₃ | 3-CH₃ | Cl | F |
| B-591. | OCH₃ | 3-OCH₃ | Cl | F |
| B-592. | OCH₃ | 5-F | Cl | F |
| B-593. | OCH₃ | 5-CH₃ | Cl | F |
| B-594. | OCH₃ | 5-OCH₃ | Cl | F |
| B-595. | OCH₃ | 6-F | Cl | F |
| B-596. | OCH₃ | 6-CH₃ | Cl | F |
| B-597. | OCH₃ | 6-OCH₃ | Cl | F |
| B-598. | CN | 3-F | Cl | F |
| B-599. | CN | 3-CH₃ | Cl | F |
| B-600. | CN | 3-OCH₃ | Cl | F |
| B-601. | CN | 5-F | Cl | F |
| B-602. | CN | 5-CH₃ | Cl | F |
| B-603. | CN | 5-OCH₃ | Cl | F |
| B-604. | CN | 6-F | Cl | F |
| B-605. | CN | 6-CH₃ | Cl | F |
| B-606. | CN | 6-OCH₃ | Cl | F |
| B-607. | CH₂F | 3-F | Cl | F |
| B-608. | CH₂F | 3-CH₃ | Cl | F |
| B-609. | CH₂F | 3-OCH₃ | Cl | F |
| B-610. | CH₂F | 5-F | Cl | F |
| B-611. | CH₂F | 5-CH₃ | Cl | F |
| B-612. | CH₂F | 5-OCH₃ | Cl | F |
| B-613. | CH₂F | 6-F | Cl | F |
| B-614. | CH₂F | 6-CH₃ | Cl | F |
| B-615. | CH₂F | 6-OCH₃ | Cl | F |
| B-616. | CHF₂ | 3-F | Cl | F |
| B-617. | CHF₂ | 3-CH₃ | Cl | F |
| B-618. | CHF₂ | 3-OCH₃ | Cl | F |
| B-619. | CHF₂ | 5-F | Cl | F |
| B-620. | CHF₂ | 5-CH₃ | Cl | F |
| B-621. | CHF₂ | 5-OCH₃ | Cl | F |
| B-622. | CHF₂ | 6-F | Cl | F |
| B-623. | CHF₂ | 6-CH₃ | Cl | F |
| B-624. | CHF₂ | 6-OCH₃ | Cl | F |
| B-625. | CF₃ | 3-F | Cl | F |
| B-626. | CF₃ | 3-CH₃ | Cl | F |
| B-627. | CF₃ | 3-OCH₃ | Cl | F |
| B-628. | CF₃ | 5-F | Cl | F |
| B-629. | CF₃ | 5-CH₃ | Cl | F |
| B-630. | CF₃ | 5-OCH₃ | Cl | F |
| B-631. | CF₃ | 6-F | Cl | F |
| B-632. | CF₃ | 6-CH₃ | Cl | F |
| B-633. | CF₃ | 6-OCH₃ | Cl | F |
| B-634. | OCH₂F | 3-F | Cl | F |
| B-635. | OCH₂F | 3-CH₃ | Cl | F |
| B-636. | OCH₂F | 3-OCH₃ | Cl | F |
| B-637. | OCH₂F | 5-F | Cl | F |
| B-638. | OCH₂F | 5-CH₃ | Cl | F |
| B-639. | OCH₂F | 5-OCH₃ | Cl | F |
| B-640. | OCH₂F | 6-F | Cl | F |
| B-641. | OCH₂F | 6-CH₃ | Cl | F |
| B-642. | OCH₂F | 6-OCH₃ | Cl | F |
| B-643. | OCHF₂ | 3-F | Cl | F |
| B-644. | OCHF₂ | 3-CH₃ | Cl | F |
| B-645. | OCHF₂ | 3-OCH₃ | Cl | F |
| B-646. | OCHF₂ | 5-F | Cl | F |
| B-647. | OCHF₂ | 5-CH₃ | Cl | F |
| B-648. | OCHF₂ | 5-OCH₃ | Cl | F |
| B-649. | OCHF₂ | 6-F | Cl | F |
| B-650. | OCHF₂ | 6-CH₃ | Cl | F |
| B-651. | OCHF₂ | 6-OCH₃ | Cl | F |
| B-652. | OCF₃ | 3-F | Cl | F |
| B-653. | OCF₃ | 3-CH₃ | Cl | F |
| B-654. | OCF₃ | 3-OCH₃ | Cl | F |
| B-655. | OCF₃ | 5-F | Cl | F |
| B-656. | OCF₃ | 5-CH₃ | Cl | F |
| B-657. | OCF₃ | 5-OCH₃ | Cl | F |
| B-658. | OCF₃ | 6-F | Cl | F |
| B-659. | OCF₃ | 6-CH₃ | Cl | F |
| B-660. | OCF₃ | 6-OCH₃ | Cl | F |

The positions (e.g. 3-/5-/6-) of $R^3$ are relative to the 2- and 4-positions of radicals $R^1$ and $R^2$ and to the 1-position of the attachment point of the ring to the SO₂ group.

The preferred compounds among the compounds I.1 to I.40 mentioned above are those of the formulae I.1, I.6, I.11, I.16, I.21, I.26, I.31 and I.36, and especially compounds of the formulae I.1, I.6, I.16 and I.21. Particularly preferred are compounds of the formulae I.1 and I.6.

In a specific embodiment, the compounds I are selected from the compounds specified in the examples, either as a free base or in form of a pharmaceutically acceptable salt, an N-oxide or a stereoisomer thereof or as their racemate or any other mixture of their stereoisomers.

The compounds I of the invention have a center of chirality in position 3 of the 2-oxindole ring. The compounds of the invention may therefore be in the form of a 1:1 mixture of enantiomers (racemate) or of a nonracemic mixture of enantiomers in which one of the two enantiomers, either the enantiomer which rotates the plane of vibration of linearly polarized light to the left (i.e. minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer. Since the compounds of the invention have a single center of asymmetry and no axis/plane of chirality, a nonracemic mixture can also be defined as a mixture of enantiomers in which either the R or the S enantiomer predominates. Substantially enantiopure compounds can accordingly also be defined as substantially enantiopure R enantiomer or substantially enantiopure S enantiomer.

"Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

In one embodiment of the invention, the compounds of the invention are in the form of substantially enantiopure compounds. Particularly preferred compounds have an enantiomeric excess of at least 85% ee, more preferably of at least 90% ee, even more preferably of at least 95% ee and in particular at least 98% ee.

The invention thus relates both to the pure enantiomers and to mixtures thereof, e.g. mixtures in which one enantiomer is present in enriched form, but also to the racemates. The invention also relates to the pharmaceutically acceptable salts of the pure enantiomers of compounds I, and the mixtures of enantiomers in the form of the pharmaceutically acceptable salts of compounds I.

Preferred embodiments of the invention are compounds of the formula I as detailed above which are characterized in that they are in optically active form, and the enantiomer of the relevant compound of the formula I is the S-enantiomer, in the form of a free base, or a pharmaceutically acceptable salt thereof.

Particularly preference is given to compounds of the general formula I and their pharmaceutically acceptable salts as detailed above in which the corresponding S-enantiomer is present in an optical purity (enantiomeric excess, ee) of more than 50% ee, particularly preferably of at least 80% ee, more preferably of at least 90% ee and even more preferably of at least 95% ee and in particular at least 98% ee.

Likewise preferred embodiments of the invention are compounds of the general formula I as detailed above which are characterized in that they are in optically inactive form, i.e. in the form of the racemate, or in the form of a pharmaceutically acceptable salt of the racemate.

Examples of synthetic routes for preparing the oxindole derivatives of the invention are described below.

The compounds of the invention can be prepared by using methods described in WO 2005/030755, WO 2006/005609 and the other references mentioned in the outset for synthesizing analogous compounds, and the preparation is outlined by way of example in the below synthesis schemes. The variables in these synthetic schemes have the same meanings as in formula I.

As shown in scheme 1, 3-hydroxy-1,3-dihydroindol-2-ones IV can be obtained by addition of metallated heterocycles III onto the 3-keto group of the isatins II. The metallated heterocycles, such as, for example, the corresponding Grignard (Mg) or organyllithium compound III (M=MgX or Li; X=I or Br), can be obtained in any conventional way from halogen or hydrocarbon compounds by reaction with Mg or lithium-organic compounds. Exemplary methods are described in Houben-Weyl, Methoden der Organischen Chemie, vol. 13, 1-2, chapter on Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IV can be converted into the compounds V which have a leaving group LG' in position 3, where the leaving group LG' is a conventional leaving group such as, for example, chlorine or bromide. The intermediate V with for example LG'=Cl can be prepared by treating the alcohol IV with thionyl chloride in the pres-presence of a base such as, for example, pyridine, in a suitable solvent such as, for example, dichloromethane. The compounds V can subsequently be reacted with amines, such as, for example, ammonia, in a substitution reaction to give the amines VI.

In the first variant amines VI are converted into the sulfonylated product VIII by treatment with sulfonyl chlorides VII after deprotonation with a strong base such as, for example, potassium tert-butoxide or sodium hydride in DMF. Sulfonyl chlorides VII employed can either be purchased or be prepared by known processes (for example J. Med. Chem. 40, 1149 (1997)). Compounds VIII are then reacted with carbonic acid halide, such as phenyl chloroformate, in the presence of a base such as, for example, pyridine, to give the corresponding carbamate IX (LG=leaving group; in case of using phenyl chloroformate, LG=phenoxy).

As shown in scheme 2, intermediate IX can then be reacted with an appropriate amine X to give directly the compounds of the general formula I; this conversion can be done at room temperature or elevated temperature and with the addition of auxiliary bases such as, for example, triethylamine or diisopropylethylamine.

In a second variant compounds of the general formula I are prepared from intermediates IX in a two-step sequence: intermediate IX can be reacted with an appropriate azetidine-3-one XII or 1-(3-azetidinyl)-4-piperidinone XIII employing the same method and conditions as described above to give the corresponding oxo compounds XIV or XV. Reductive amination of compounds XIV or XV with the appropriate amines XVI or XVII then gives the compounds of the general formula I. The latter reaction is carried out in the presence of a suitable reduction agent, e.g. boron-based reduction agent, typically a boronic ester, such as sodium triacetoxyhydroborate, or cyanoborohydride; where appropriate a Lewis acid such as e.g. zinc chloride or titanium isopropoxide is added to the reaction. General examples for reductive amination are described in the literature, e.g. Comprehensive Organic Transformations 2$^{nd}$ ed, R. Larock, Wiley VCH, 835-846.

As shown in scheme 3, in a third variant amines VI are first reacted with a carbonic acid halide, such as phenyl chloroformate, in the presence of a base such as, for example, pyridine, to give the corresponding carbamate XVIII (LG=leaving group; in case of using phenyl chloroformate, LG=phenoxy), and then reacted further with an appropriate amine at room temperature or elevated temperature and with the addition of auxiliary bases such as, for example, pyridine, triethylamine or diisopropylethylamine. to give intermediate XIX. Sulfonylation of compounds XIX by treatment with sulfonyl chlorides VII after deprotonation with a strong base such as, for example, potassium tert-butoxide or sodium hydride in DMF, then gives the compounds of the general formula I.

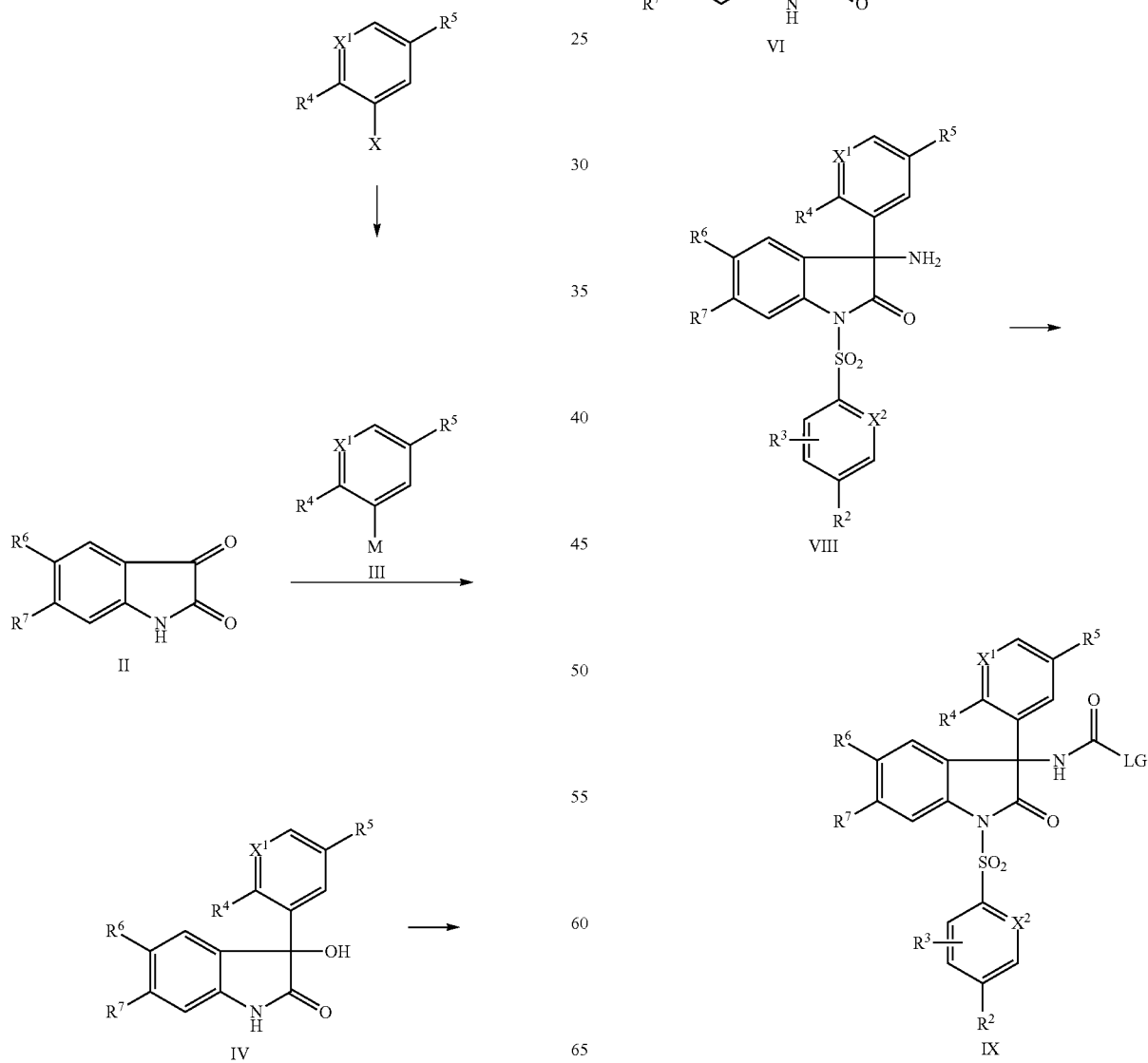

Scheme 2
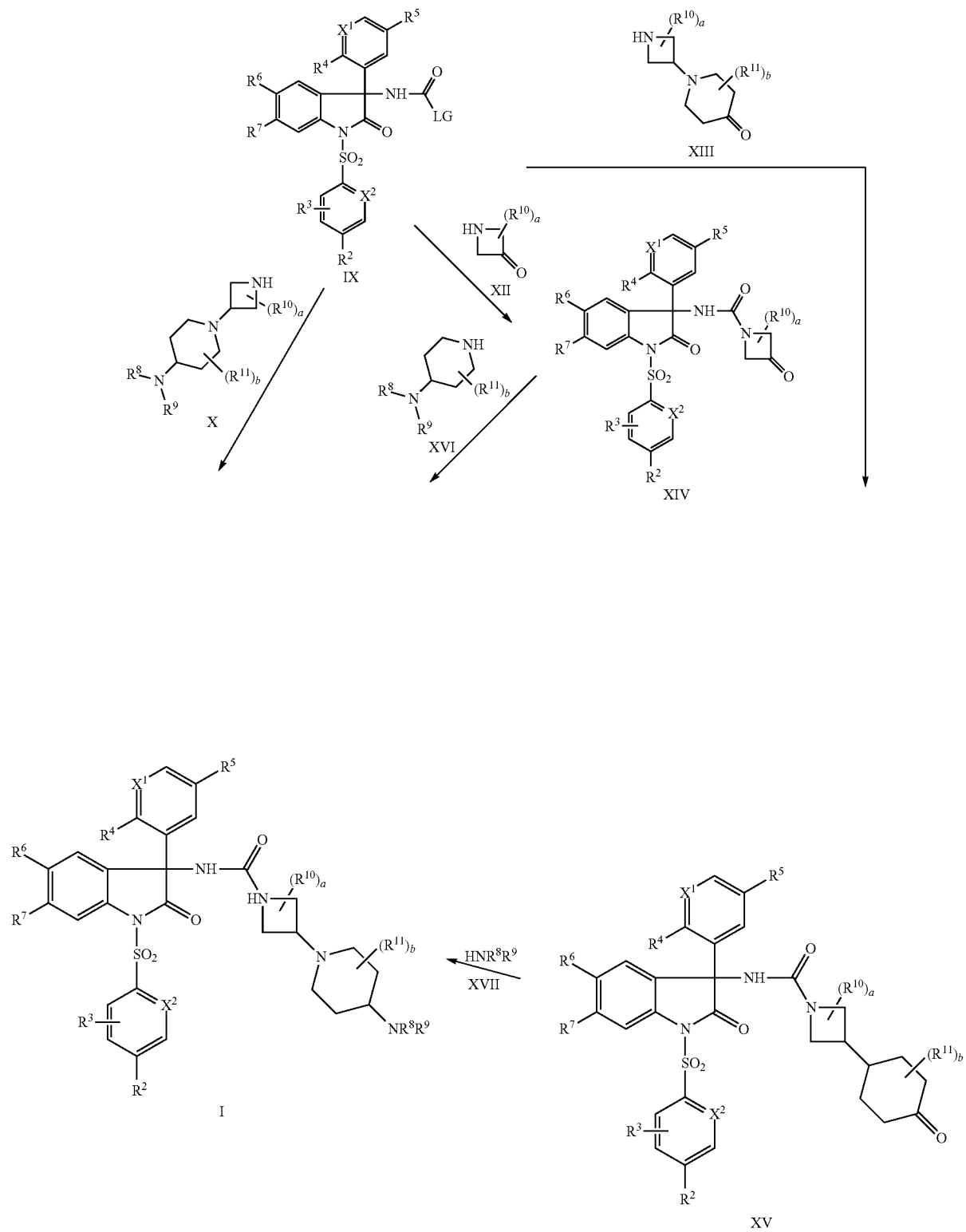

Scheme 3

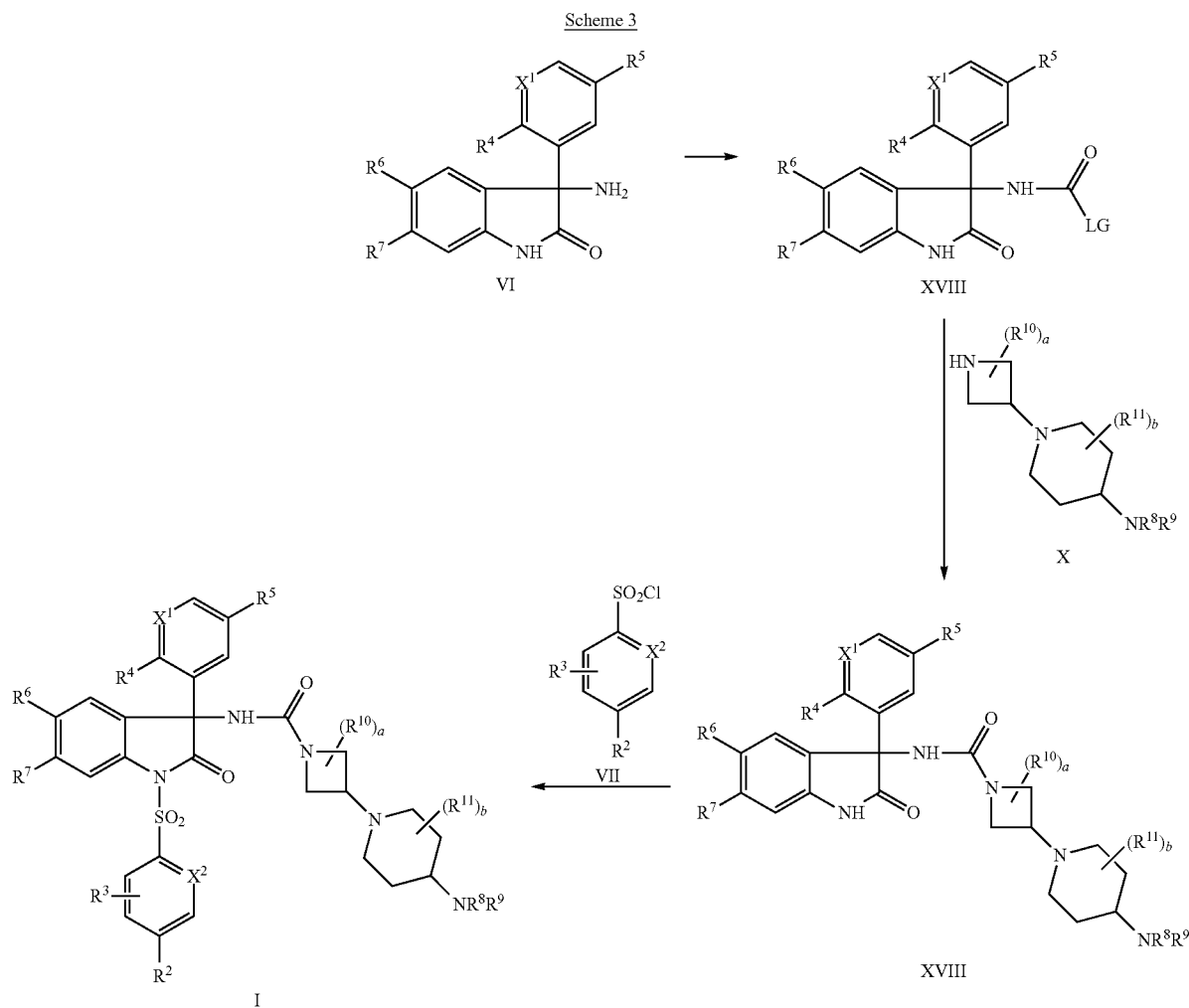

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis (3rd ed.), John Wiley & Sons, NY (1999), which is incorporated herein by reference in its entirety. Synthesis of the compounds of the invention may be accomplished by methods analogous to those described in the synthetic scheme described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the compounds according to the invention contain more of the respective isotope than this naturally occurs and thus is anyway present in the compounds I.

Stable isotopes (e.g., deuterium, $^{13}C$, $^{15}N$, $^{18}O$) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

Incorporation of a heavy atom, particularly substitution of deuterium for hydrogen, can give rise to an isotope effect that could alter the pharmacokinetics of the drug.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

A further aspect of the present invention relates to a pharmaceutical composition comprising at least one compound of the general formula I and/or an N-oxide, a stereoisomer or a pharmaceutically acceptable salt thereof as detailed above, and a pharmaceutically acceptable carrier; or comprising at least one compound I wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance. Suitable carriers depend inter alia on the dosage form of the composition and are known in principle to the skilled worker. Some suitable carriers are described hereinafter.

The present invention furthermore relates to a compound I as defined above or an N-oxide, a stereoisomer or a pharmaceutically acceptable salt thereof for use as a medicament. The present invention also relates to a compound I as defined above or an N-oxide, a stereoisomer or a pharmaceutically acceptable salt thereof for the treatment of vasopressin-related diseases, especially of disorders which respond to the modulation of the vasopressin receptor and in particular of the V1b receptor.

A further aspect of the present invention relates to the use of compounds of the formula I and/or of an N-oxide, a stereoisomer or of pharmaceutically acceptable salts thereof for the manufacture of a medicament for the treatment and/or prophylaxis of vasopressin-related diseases, especially of disorders which respond to the modulation of the vasopressin receptor and in particular of the V1b receptor.

Vasopressin-related diseases are those in which the progress of the disease is at least partly dependent on vasopressin, i.e. diseases which show an elevated vasopressin level which may contribute directly or indirectly to the pathological condition. In other words, vasopressin-related diseases are those which can be influenced by modulating the vasopressin receptor, for example by administration of a vasopressin receptor ligand (agonist, antagonist, partial antagonist/agonist, inverse agonist etc.).

In a preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from diabetes, insulin resistance, nocturnal enuresis, incontinence and diseases in which impairments of blood clotting occur, and/or for delaying micturition. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastritic vasospasm, hepatocirrhosis, gastric and intestinal ulcers, emesis, emesis occurring during chemotherapy, and travel sickness.

The compounds of the invention of the formula I or their N-oxides, stereoisomers or pharmaceutically acceptable salts or the pharmaceutical composition of the invention can also be used for the treatment of various vasopressin-related complaints which have central nervous causes or alterations in the HPA axis (hypothalamic pituitary adrenal axis), for example for affective disorders such as depressive disorders and anxiety disorders. Depressive disorders include for example dysthymic disorders, major depression, seasonal depression, treatment-resistant depression disorders, bipolar disorders, or childhood onset mood disorders. Anxiety disorders include for example phobias, post-traumatic stress disorders, general anxiety disorders, panic disorders, drug withdrawal-induced anxiety disorders, and obsessive-compulsive disorders.

Vasopressin-related complaints which have central nervous causes or alterations in the HPA axis are further cognitive disorders such as Alzheimer's disease, MCI (Mild Cognitive Impairment) and CIAS (Cognitive Impairment Associated with Schizophrenia).

The compounds of the invention of the formula I and their N-oxides, a stereoisomers or pharmaceutically acceptable salts or the pharmaceutical composition of the invention can likewise be employed for the treatment of anxiety disorders and stress-dependent anxiety disorders, such as, for example, generalized anxiety disorders, phobias, post-traumatic anxiety disorders, panic anxiety disorders, obsessive-compulsive anxiety disorders, acute stress-dependent anxiety disorders, drug withdrawal-induced anxiety disorders and social phobia.

The compounds of the invention of the formula I and their N-oxides, stereoisomers or pharmaceutically acceptable salts or the pharmaceutical composition of the invention can likewise be employed for the treatment and/or prophylaxis of social impairment, such as autism or social impairment related with schizophrenia.

The compounds of the invention of the formula I and their N-oxides, stereoisomers or pharmaceutically acceptable salts or the pharmaceutical composition of the invention can likewise be employed for the treatment and/or prophylaxis of increased aggression in conditions such as Alzheimer's disease and schizophrenia.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of an N-oxide, a stereoisomer or pharmaceutically acceptable salts thereof for the manufacture of a medicament for the treatment of affective disorders.

In a further preferred embodiment, the present invention relates to the use of compounds of the invention of the formula I or of an N-oxide, a stereoisomer or pharmaceutically acceptable salts thereof for the manufacture of a medicament for the treatment of anxiety disorders and/or stress-dependent anxiety disorders.

In a further preferred embodiment, the present invention relates to the use of compounds of the invention of the formula I or of an N-oxide, a stereoisomer or pharmaceutically acceptable salts thereof for the manufacture of a medicament for the treatment of memory impairments and/or Alzheimer's disease.

In a further preferred embodiment, the present invention relates to the use of compounds of the invention of the formula I or of an N-oxide, a stereoisomer or pharmaceutically acceptable salts thereof for the manufacture of a medicament for the treatment of psychoses and/or psychotic disorders.

In a further preferred embodiment, the present invention relates to the use of compounds of the invention of the formula I or of an N-oxide, a stereoisomer or pharmaceutically acceptable salts thereof for the manufacture of a medicament for the treatment of Cushing's syndrome or other stress-dependent diseases.

In a further preferred embodiment, the present invention relates to the use of compounds of the invention of the formula I or of an N-oxide, a stereoisomer or pharmaceutically acceptable salts thereof for the manufacture of a medicament for the treatment of sleep disorders.

In a further preferred embodiment, the present invention relates to the use of compounds of the invention of the formula I or of an N-oxide, a stereoisomer or pharmaceutically acceptable salts thereof for the manufacture of a medicament for the treatment of depressive disorders. In the case of depressive disorders, specific mention is to be made of childhood onset mood disorders, i.e. depressive moods having their onset in childhood, but also of major depression, seasonal depression, bipolar disorders and dysthymic disorders, and especially of major depression and seasonal depression as well as of the depressive phases of bipolar disorders. The invention also relates to compounds of the formula I or N-oxides, stereoisomers or pharmaceutically acceptable salts thereof for the manufacture of a medicament for the treatment of treatment-resistant depression disorders and for the use in an add-on therapy of depressive disorders.

In a further preferred embodiment, the present invention relates to the use of compounds of the invention of the formula I or of an N-oxide, a stereoisomer or pharmaceutically acceptable salts thereof for the manufacture of a medicament for the treatment of vasomotor symptoms and/or thermoregulatory dysfunctions such as, for example, the hot flush symptom.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors. To be more precise, the present invention relates to the use of compounds of the invention of the formula I or of an N-oxide, a stereoisomer or pharmaceutically acceptable salts thereof for the manufacture of a medicament for the treatment and/or prophylaxis of substance-related and addictive disorders such as substance use disorder, substance-induced disorder, alcohol use disorder, alcohol intoxication, alcohol withdrawal, unspecified alcohol-related disorder, caffeine intoxication, caffeine withdrawal, unspecified caffeine disorder, *cannabis* use disorder, *cannabis* withdrawal, unspecified *cannabis*-related disorder, phencyclidine use disorder, other hallucinogen use disorders, phencyclidine intoxication, other hallucinogen disorders, hallucinogen persisting perception disorder, unspecified phencyclidine disorder, inhalant use disorder, inhalant intoxication, opioid use disorder, opioid withdrawal, sedative, hypnotic or anxiolytic use disorder, sedative, hypnotic or anxiolytic withdrawal, stimu-stimulant use disorder, stimulant intoxication, stimulant withdrawal, tobacco use disorder, tobacco withdrawal, unspecified tobacco-related disorder, other (or unknown) substance use disorders, other (or unknown) substance intoxication, other (or unknown) substance withdrawal, other (or unknown) substance related disorder and gambling disorder; as well as to compounds of the invention of the formula I or of an N-oxide, a stereoisomer or of pharmaceutically acceptable salts thereof for the treatment and/or prophylaxis of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of schizophrenia and/or psychosis.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of pain, e.g. acute or chronic pain, preferably chronic pain, especially neuropathic pain. Chronic pain may be a complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

A further aspect of the invention relates to a compound I or pharmaceutically acceptable salts thereof for use as a medicament, and to a compound I or an N-oxide, a stereoisomer or pharmaceutically acceptable salts thereof for the manufacture of a medicament for the treatment and/or prophylaxis of the above-defined diseases.

A further aspect of the invention relates to a method for the treatment and/or prophylaxis of vasopressin-related diseases, in which an effective amount of at least one compound of the invention of the formula I or of an N-oxide, a stereoisomer or of at least one pharmaceutically acceptable salt thereof or of a pharmaceutical composition of the invention is administered to a patient.

Concerning the definition of vasopressin-related diseases, reference is made to the above statements.

In a preferred embodiment of the invention, the method of the invention serves for the treatment and/or prophylaxis of disorders selected from diabetes, insulin resistance, nocturnal enuresis, incontinence and diseases in which impairments of blood clotting occur, and/or for delaying micturition. Concerning the definition of diabetes, reference is made to the above statements.

In a further preferred embodiment, the method of the invention serves for the treatment and/or prophylaxis of disorders selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastritic vasospasm, hepatocirrhosis, gastric and intestinal ulcers, emesis, emesis occurring during chemotherapy, and travel sickness.

In a further preferred embodiment, the method of the invention serves for the treatment and/or prophylaxis of affective disorders.

In a further preferred embodiment, the method of the invention serves for the treatment and/or prophylaxis of anxiety disorders and/or stress-dependent anxiety disorders.

In a further preferred embodiment, the method of the invention serves for the treatment and/or prophylaxis of memory impairments and/or Alzheimer's disease.

In a further preferred embodiment, the method of the invention serves for the treatment and/or prophylaxis of psychoses and/or psychotic disorders.

In a further preferred embodiment, the method of the invention serves for the treatment and/or prophylaxis of Cushing's syndrome.

In a further preferred embodiment, the method of the invention serves for the treatment and/or prophylaxis of sleep disorders in a patient.

In a further preferred embodiment, the method of the invention serves for the treatment and/or prophylaxis of depressive disorders. In the case of depressive disorders, specific mention is to be made of major depression, seasonal depression, bipolar disorders, dysthymic disorders and childhood onset mood disorders, i.e. depressive moods having their onset in childhood, and especially of major depression and seasonal depression as well as of the depressive phases of bipolar disorders. The method of the invention also serves for the treatment of treatment-resistant depression disorders and as an add-on therapy of depressive disorders.

In a further preferred embodiment, the method of the invention serves for the treatment and/or prophylaxis of vasomotor symptoms and/or thermoregulatory dysfunctions, such as, for example, the hot flush symptom.

In a further preferred embodiment, the method of the invention serves for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence, and/or for the treatment and/or prophylaxis of stress-induced relapses into drug or pharmaceutical dependencies and/or dependencies mediated by other factors.

In a further preferred embodiment, the method of the invention serves for the treatment and/or prophylaxis of schizophrenia and/or psychosis.

In a further preferred embodiment, the method of the invention serves for the treatment and/or prophylaxis of pain, e.g. acute or chronic pain, preferably chronic pain, especially neuropathic pain.

The patient to be treated prophylactically or therapeutically with the method of the invention is preferably a mammal, for example a human or a nonhuman mammal or a nonhuman transgenic mammal. Specifically it is a human.

The compounds of the general formula I and their pharmaceutically acceptable salts as detailed above can be prepared by a skilled worker with knowledge of the technical teaching of the invention in implementing and/or in analogous implementation of process steps known per se.

The compounds I and/or their pharmaceutically acceptable salts, N-oxides and their stereoisomers are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I and/or their pharmaceutically acceptable salts, N-oxides and a stereoisomers are distinguished by having an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-related diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention and/or an N-oxide, a stereoisomer and/or a pharmaceutically acceptable salt thereof and suitable pharmaceutical carriers (drug carriers).

These drug carriers are chosen according to the pharmaceutical form and the desired mode of administration and are known in principle to the skilled worker.

The compounds of the invention of the formula I, their N-oxides, stereoisomers or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, or salt thereof.

The invention is explained in more detail below by means of examples, but the examples are not to be understood to be restrictive.

The compounds of the invention can be prepared by various synthetic routes. The methods mentioned, as described accordingly in synthesis schemes 1, 2 and 3, are explained in greater detail merely by way of example using the given examples without being exclusively restricted to synthesis route 1, 2 or 3 or analogous methods.

EXPERIMENTAL SECTION

Abbreviations Used:
Et$_3$N: Triethylamine
THF: Tetrahydrofuran
DMF: N,N-Dimethylformamide
DMSO: Dimethyl sulfoxide
TFA: Trifluoroacetic acid
RT room temperature
p: pseudo (for example pt pseudo triplet)
b: broad (for example bs broad singlet)
s: singlet
d: doublet
t: triplet
m: multiplet
dd: doublet of doublets
dt: doublet of triplets
tt: triplet of triplets
I. Preparation of the Starting Compounds 1.) (S)—N-(5-Cyano-1-((2,4-dimethoxyphenyl)sulfonyl)-3-(2-ethoxypyridin-3-yl)-2-oxoindolin-3-yl)-3-oxoazetidine-1-carboxamide To a solution of (S)-phenyl (5-cyano-1-((2,4-dimethoxyphenyl)sulfonyl)-3-(2-ethoxypyridin-3-yl)-2-oxoindolin-3-yl)carbamate (425 mg, 0,691 mmol) and azetidin-3-one hydrochloride (80 mg, 0,744 mmol) in DMF (6 ml) Et3N (1 ml, 7.17 mmol) was added and the mixture stirred over night at room temperature. Subsequently 40 ml of water and 10 ml NaHCO$_3$-solution were added and the mixture extracted twice with ethyl acetate. The combined organic layers were washed 3× with brine, dried over MgSO$_4$, filtered off and evaporated to give 430 mg of a yellow solid.
Flash chromatography (silica gel/gradient from 0 to 5% methanol in dichloromethane) yielded 330 mg of the title compound as white solid.
ESI-MS [M+H$^+$]=592.2

2.) (S)—N-(5-Cyano-1-((2,4-dimethoxyphenyl)sulfonyl)-3-(2-methoxypyridin-3-yl)-2-oxoindolin-3-yl)-3-oxoazetidine-1-carboxamide To a solution of (S)-phenyl (5-cyano-1-((2,4-dimethoxyphenyl)sulfonyl)-3-(2-methoxypyridin-3-yl)-2-oxoindolin-3-yl)carbamate (1 g, 1,665 mmol) and azetidin-3-one hydrochloride (220 mg, 2,046 mmol) in 10 ml of DMF Et$_3$N (1.5 ml, 10.76 mmol) was added and the mixture stirred over night at room temperature. 70 ml of water and 10 ml of 10% NaHCO$_3$-solution were added, the mixture extracted twice with ethyl acetate, the combined organic layers washed twice with brine, dried over MgSO$_4$, filtered and concentrated to leave 1.3 g of the crude product as yellow oil. Flash chromatography (silica gel/gradient from 0 to 5% methanol in dichloromethane) yielded 610 mg of the title compound as an off-white solid.
ESI-MS [M+H$^+$]=578.1

3.) (S)—N-(5-Cyano-1-((2,4-dimethoxyphenyl)sulfonyl)-3-(2-ethoxypyridin-3-yl)-2-oxoindolin-3-yl)-3-(4-oxopiperidin-1-yl)azetidine-1-carboxamide To a solution of (S)-phenyl (5-cyano-1-((2,4-dimethoxyphenyl)sulfonyl)-3-(2-ethoxypyridin-3-yl)-2-oxoindolin-3-yl)carbamate (1.3 g, 2,009 mmol) and 1-(3-azetidinyl)-4-piperidinone (0.37 g, 2,399 mmol) in DMF (9 ml) Et$_3$N (2 ml, 14.35 mmol) was added and the mixture stirred over night at room temperature. Water (80 ml) was added, stirring continued for 30 min, the precipitated solid filtered off, subsequently washed with water and n-pentane, and dried under vacuum to give 705 mg of a solid. The aqueous layers were re-extracted twice with ethyl acetate, the combined organic layers washed with brine, dried over MgSO$_4$, filtered and evaporated to leave 360 mg of yellow oil. Flash chromatography (silica gel/gradient from 0 to 5% methanol in dichloromethane) of the combined crude product yielded 500 mg of the title compound as white solid.

ESI-MS [M+H$^+$]=675.2.

Following the procedures as described for intermediates 1 and 2 and using the appropriate starting material were prepared:

4.) (S)—N-(1-((2,4-dimethoxyphenyl)sulfonyl)-3-(2-ethoxypyridin-3-yl)-5,6-difluoro-2-oxoindolin-3-yl)-3-oxoazetidine-1-carboxamide

ESI-MS [M+H$^+$]=603.1.

5.) (S)—N-(5-cyano-1-((2,4-dimethoxyphenyl)sulfonyl)-3-(2-ethoxypyridin-3-yl)-6-fluoro-2-oxoindolin-3-yl)-3-oxoazetidine-1-carboxamide

ESI-MS [M+H$^+$]=610.1.

6.) (S)—N-(5-chloro-1-((2,4-dimethoxyphenyl)sulfonyl)-3-(2-ethoxypyridin-3-yl)-2-oxoindolin-3-yl)-3-oxoazetidine-1-carboxamide

ESI-MS [M+H$^+$]=602.1.

7.) (S)—N-(5-cyano-1-((2,4-dimethoxyphenyl)sulfonyl)-3-(2-methoxypyridin-3-yl)-2-oxoindolin-3-yl)-3-(4-oxopiperidin-1-yl)azetidine-1-carboxamide

ESI-MS [M+H$^+$]=661.2.

8.) (S)—N-(5-cyano-3-(2-ethoxypyridin-3-yl)-2-oxoindolin-3-yl)-3-(4-morpholinopiperidin-1-yl)azetidine-1-carboxamide a) To a solution of (S)-3-amino-3-(2-ethoxypyridin-3-yl)-2-oxoindoline-5-carbonitrile (9 g, 30.6 mmol) in dichloromethane (150 ml) at 5° C. were added subsequently pyridine (20 ml) and then dropwise phenyl chloroformate (4.5 ml, 35.8 mmol), and stirring was continued for 1.5 hr. Dichloromethane (220 ml) and water (60 ml) were added, the mixture was stirred for 20 min, the organic layer washed subsequently with water and brine, dried over MgSO$_4$, filtered and concentrated to give 18.7 g of a brown oil. Flash chromatography of the crude product (silica gel/gradient from 0 to 30% methanol in dichloromethane) yielded 12.1 g of the title compound as amorphous solid; ESI-MS [M+H$^+$]=415.0.

b) To a solution of (S)-phenyl (5-cyano-3-(2-ethoxypyridin-3-yl)-2-oxoindolin-3-yl)carbamate (2.6 g, 5.65 mmol) and 4-(1-(azetidin-3-yl)piperidin-4-yl)morpholine×3TFA (3.3 g, 5.82 mmol) in acetonitrile (80 ml) at 5° C. Et$_3$N (5.5 ml, 39.5 mmol) was added and then stirred over night at room temperature. The mixture then was concentrated, treated with 100 ml of ice water, digested 3× with dichloromethane, the combined organic layers washed with brine, dried over MgSO$_4$, filtered and evaporated to give 3.0 g of a yellow oil. Flash chromatography of the crude product (silica gel/gradient from 0 to 50% methanol in dichloromethane) yielded 1.2 g of the title compound as amorphous solid; ESI-MS [M+H+]=546.2.

9.) (S)—N—(C-cyano-3-(2-methoxypyridin-3-yl)-2-oxoindolin-3-yl)-3-(4-(methyl(oxetan-3-yl)amino)piperidin-1-yl)azetidine-1-carboxamide Synthesis according to procedure as described for intermediate 8.

ESI-MS [M+H$^+$]=532.2.

10.) (S)-Phenyl (5-Cyano-3-(2,5-dimethoxyphenyl)-1-((2,4-dimethoxyphenyl)sulfonyl)-2-oxoindolin-3-yl)carbamate To a solution of (S)-3-amino-3-(2,5-dimethoxyphenyl)-2-oxoindoline-5-carbonitrile (425 mg, 1,374 mmol) DMF (10 ml) at 5° C. first sodium hydride (60%: 77 mg, 1,924 mmol) and after stirring for 20 min 2,4-dimethoxybenzenesulfonyl chloride (358 mg, 1,511 mmol) was added, and stirring continued for 30 min. Then 40 ml of water and 10 ml of 10% NaHCO$_3$-solution were added, extracted twice with ethyl acetate, the combined organic layers washed with brine, dried over MgSO$_4$, filtered and evaporated to give 730 mg of a yellow solid.

The crude product was dissolved in dichloromethane (20 ml), pyridine (0,834 ml, 10.32 mmol) and phenyl chloroformate (0,194 ml, 1,547 mmol) were added at 5° C. and stirred 1 for h at 5° C. The mixture was diluted with 120 ml of water, the organic layer washed 3× with water, dried over MgSO$_4$, filtered and evaporated to leave 966 mg of a yellow solid, which was treated with 50 ml of methyl-tert-butyle-ther/diisopropylether 1:5 to give 630 mg of the title compound as white solid.

ESI-MS [M+H+]=630.0

11) N-Methyl-N-(oxetan-3-yl)piperidin-4-amine×2TFA

To a solution of 1-Boc-4-methylaminopiperidine (500 mg, 2,333 mmol) in THF (10 ml) 3-oxetanone (235 mg, 3.27 mmol) was added and the mixture stirred over night at room temperature. Then subsequently sodium cyanoborohydride (176 mg, 2.80 mmol) and acetic acid (0.27 ml, 4.72 mmol) were added and stirring continued for 3 days at room temperature. The mixture was concentrated under vacuum, the obtained residue diluted with 20 ml of and 10 ml of 10% NaHCO$_3$-solution, extracted 2× with dichloromethane, the combined organic layers dried over MgSO$_4$, filtered off and evaporated to leave 700 mg of the crude product. Flash chromatography (silica gel/gradient from 0 to 10% methanol in dichloromethane) gave 230 mg of a clear oil, which was treated with TFA (2 ml, 26.0 mmol) for 1 hr. The mixture was concentrated, diluted with 20 ml of methyl-tert-butylether, the precipitate filtered off, washed with 10 ml of methyl-tert-butyl ether and dried to yield 340 mg of the title compound as white solid;

ESI-MS [M+H+]=171.2.

12) N-Ethyl-N-(oxetan-3-yl)piperidin-4-amine×2TFA

To a solution of 1-Boc-4-piperidinone (0.6 g, 3.01 mmol) and N-ethyloxetan-3-amine (0.38 g, 3.76 mmol) in methanol (5 ml) were added zinc chloride (1,231 g, 9.03 mmol), and then after 10 min stirring sodium cyanoborohydride (0,473 g, 7.53 mmol), and the mixture stirred over night at room temperature. For work-up 2 ml of 10% NaHCO$_3$-solution were added, the mixture concentrated, diluted with 80 ml of water, extracted 3× with ethyl acetate, the combined organic layers washed twice with brine, dried over MgSO$_4$, filtered and evaporated to give 730 mg of a clear oil. The Boc-protected amine was treated with 2 ml of TFA for 1 hr, concentrated, and the obtained residue digested with 20 ml methyl-tert-butylether. Filtering off the precipitate, washing and drying gave 690 mg of the title compound as white solid.
ESI-MS [M+H$^+$]=185.2.

13) N-Cyclopropyl-N-(oxetan-3-yl)piperidin-4-amine×2TFA

To a solution of 1-tert-butoxycarbonyl-4-(cyclopropylamino)piperidine (2 g, 8.32 mmol) and 3-oxetanone (0,840 g, 11.65 mmol) in methanol (25 ml) subsequently zinc chloride (2,155 g, 15.81 mmol)—and after stirring for 10 min—sodium cyanoborohydride (0,994 g, 15.81 mmol) were added and the mixture was stirred over night. 20 ml of a 10% NaHCO$_3$-solution were added to the reaction mixture and concentrated under vacuum. After addition of 60 ml of water, 10 ml of 10% NaHCO$_3$-solution and 30 ml of dichloromethane the formed solid was filtered off, washed with 10 ml of water and 10 ml of dichloromethane, the aqueous layer digested again with dichloromethane, and the combined organic layers then washed with water, dried over MgSO$_4$, filtered and evaporated to leave 2.29 g of a yellow oil. Hash chromatography (silica gel/gradient from 0 to 15% methanol in dichloromethane) yielded 1.57 g of a clear oil, which was dissolved in dichloromethane (1 ml) and treated with TFA (4 ml) for 15 min. The mixture was concentrated, 40 ml of methyl-tert-butylether added and stirred for 2 hr. The precipitate was filtered off, washed and dried to give 1.9 g of the title compound as white solid.
ESI-MS [M+H$^+$]=197.2

14) 1-(Azetidin-3-yl)-N-methyl-N-(oxetan-3-yl)piperidin-4-amine×3TFA a. To a solution of 1-Boc-4-methylaminopiperidine (5.5 g, 25.7 mmol) and 3-oxetanone (3 g, 41.6 mmol) in methanol (50 ml) and THF (40 ml) subsequently were added zinc chloride—and after stirring for 10 min—sodium cyanoborohydride (2.3 g, 36.6 mmol), and the mixture stirred over night at room temperature. The mixture was concentrated, 30 ml of 10% NaHCO$_3$-solution, 100 ml of water and 70 ml of dichloromethane added, filtered, and the aqueous layer digested with dichloromethane. The combined organic layers were washed with brine, dried over MgSO$_4$, filtered and evaporated to leave 6.78 g of a pale yellow oil. The crude product was treated with TFA (15 ml) in dichloromethane (40 ml) at 5° C. over night, the mixture concentrated, diluted with 150 ml of methyl-tert-butylether, stirred for 2 hr, the precipitated solid was filtered off, washed again with 50 ml methyl-tert-butylether and dried to give 9.63 g of the amine 2TFA salt as white solid.

c. Reductive amination tert-butyl 3-oxoazetidine-1-carboxylate (3 g, 17.52 mmol) with N-methyl-N-(oxetan-3-yl)piperidin-4-amine×2TFA (8 g, 20.09 mmol) following the procedure as described for step a and followed by BOC-cleavage using TFA gave 19.5 g of a yellow oil, which was treated with 150 ml of methyl-tert-butylether for 2 hr, the precipitated solid filtered off, washed and dried to give 8.5 g of the title compound as white solid.
ESI-MS [M+H+]=171.2

15) 4-(1-(Azetidin-3-yl)piperidin-4-yl)morpholine×3TFA

Reductive amination of 1-Boc-azetidinone (5 g, 29.2 mmol) and 4-(piperidin-4-yl)-morpholine (5.97 g, 35.0 mmol) as described for intermediate 13 and subsequent cleavage of Boc yielded 12.1 g of the title compound as white solid.
ESI-MS [M+H+]=226.2

II. Preparation of the Compounds of the Formula I
Enantiomers of the compounds I were prepared by using enantiomerically pure starting compounds.

Example 1

(S)—N-(5-cyano-1-((2,4-dimethoxyphenyl)sulfonyl)-3-(2-ethoxypyridin-3-yl)-2-oxoindolin-3-yl)-3-(4-morpholinopiperidin-1-yl)azetidine-1-carboxamide (compound of formula I.1, wherein R$^1$ is methoxy, R$^2$ is methoxy, R$^3$ is H, R$^6$ is CN, R$^7$ is H, and R$^8$ and R$^9$, together with the nitrogen atom they are bound to, form morpholin-4-yl)

(S)—N-(5-cyano-1-((2,4-dimethoxyphenyl)sulfonyl)-3-(2-ethoxypyridin-3-yl)-2-oxoindolin-3-yl)-3-oxoazetidine-1-carboxamide (400 mg, 0,676 mmol) and 4-(piperidin-4-yl)-morpholine (400 mg, 2.35 mmol) were stirred in THF (15 ml) over night at room temperature. Sodium cyanoborohydride (70 mg, 1,114 mmol) and acetic acid (250 µl, 4.37 mmol) were added and the mixture was stirred for 2 hr. Subsequently 40 ml of water and 10 ml of a 10% NaHCO$_3$-solution were added, extracted twice with ethyl acetate, the combined organic layers washed with brine, dried over MgSO$_4$, filtered off and evaporated to give 620 mg as white solid. Flash chromatography of the crude product (silica gel/gradient from 0 to 10% methanol in dichloromethane) yielded 336 mg of the title compound as white solid.
ESI-MS [M+H$^+$]=746.3
$^1$H-NMR (600 MHz DMSO), δ [ppm]: 8.14 (dd, 1H), 7.88 (dd, 1H), 7.83 (m, 3H), 7.66 (s, 1H), 7.55 (s, 1H), 7.05 (dd, 1H), 6.70 (dd, 1H), 6.65 (d, 1H), 4.08 (q, 2H), 3.86 (s, 3H), 3.79 (m broad, 2H), 3.65-3.50 (m, 6H), 3.46 (s, 3H), 2.95 (m, 1H), 2.71 (m, 2H), 2.39 (m, 4H), 2.08 (m, 1H), 1.71 (4H), 1.34 (m, 2H), 0.95 (t, 3H).

Example 2

(S)—N-(5-cyano-1-((2,4-dimethoxyphenyl)sulfonyl)-3-(2-ethoxypyridin-3-yl)-2-oxoindolin-3-yl)-3-(4-(methyl(oxetan-3-yl)amino)piperidin-1-yl)azetidine-1-carboxamide (compound of formula I.1, wherein R$^1$ is methoxy, R$^2$ is methoxy, R$^3$ is H, R$^6$ is CN, R$^7$ is H, R$^8$ is methyl, and R$^9$ is oxetan-3-yl)

To a solution of (S)—N-(5-cyano-1-((2,4-dimethoxyphenyl)sulfonyl)-3-(2-ethoxypyridin-3-yl)-2-oxoindolin-3-yl)-3-oxoazetidine-1-carboxamide (250 mg, 0,423 mmol) and N-methyl-N-(oxetan-3-yl)piperidin-4-amine TFA-salt (200 mg, 0,502 mmol) in methanol (5 ml) zinc chloride (115 mg, 0,844 mmol) was added and stirred for 10 min. Sodium cyanoborohydride (55 mg, 0,875 mmol) was added and the mixture stirred over night. Then 2 ml of 10% NaHCO$_3$-solution were added, the mixture was concentrated under vacuum, 60 ml of water and 20 ml of dichloromethane were added, and the solid was filtered off and washed with 10 ml of water and 10 ml of dichloromethane. The aqueous layer was separated and extracted with dichloromethane, and the combined organic layers were washed with water, dried over MgSO$_4$, filtered and concentrated to give 350 mg of a clear oil. Flash chromatography of the crude product (silica gel/ gradient from 0 to 10% methanol in dichloromethane) afforded 123 mg of the title compound as white solid.

ESI-MS [M+H⁺]=746.3.

¹H-NMR (600 MHz DMSO), δ [ppm]: 8.14 (dd, 1H), 7.88 (dd, 1H), 7.83 (m, 3H), 7.66 (s, 1H), 7.55 (s, 1H), 7.05 (dd, 1H), 6.70 (dd, 1H), 6.66 (d, 1H), 4.46 (m, 4H), 4.07 (q, 2H), 3.85 (s, 3H), 3.78 (m broad, 3H), 3.55 (m broad, 2H), 3.46 (s, 3H), 2.93 (m, 1H), 2.71 (m, 2H), 2.20 (m, 1H), 2.08 (s, 3H), 1.67 (m, 2H), 1.51 (m, 2H), 1.36 (m, 2H), 0.95 (t, 3H).

Example 3

(S)—N-(5-Cyano-1-((2,4-dimethoxyphenyl)sulfonyl)-3-(2-methoxypyridin-3-yl)-2-oxoindolin-3-yl)-3-(4-morpholinopiperidin-1-yl)azetidine-1-carboxamide (compound of formula I.6, wherein R¹ is methoxy, R² is methoxy, R³ is H, R⁶ is CN, R⁷ is H, and R⁸ and R⁹, together with the nitrogen atom they are bound to, form morpholin-4-yl)

To a solution of (S)—N-(5-cyano-1-((2,4-dimethoxyphenyl)sulfonyl)-3-(2-methoxypyridin-3-yl)-2-oxoindolin-3-yl)-3-oxoazetidine-1-carboxamide (80 mg, 0,139 mmol) and 4-(piperidin-4-yl)-morpholine (50 mg, 0,294 mmol) in ethanol (5 ml) and THF (5 ml) titanium isopropoxide (2000, 0,672 mmol) was added, the mixture then stirred over night at room temperature and then for 50 min. at 60° C. The mixture was then cooled to 25° C., sodium cyanoborohydride (25 mg, 0,398 mmol) was added and stirring continued for 30 min. For work-up 2 ml of water and 2 ml of 10% NaHCO₃-solution were added, the mixture concentrated under vacuum, the obtained residue di-diluted with 20 ml of water and 20 ml dichloromethane, filtered over celite, washed with 20 ml of dichloromethane, the organic layer separated and dried over MgSO₄, to leave 80 mg of a yellow solid. Flash chromatography of the crude product (silica gel/gradient from 0 to 10% methanol in dichloromethane) afforded 17.7 mg of the title compound as white solid.

ESI-MS [M+H⁺]=732.3.

¹H-NMR (600 MHz DMSO), δ [ppm]: 8.15 (dd, 1H), 7.91 (d, 1H), 7.86 (d, 1H), 7.80 (dd, 1H), 7.78 (dd, 1H), 7.70 (m, 1H), 7.64 (s broad, 1H), 7.06 (dd, 1H), 6.72 (dd, 1H), 6.68 (dd, 1H), 3.87 (s, 3H), 3.70 (s, 3H), 3.65-3.55 (m, 6H), 3.51 (s, 3H), 2.96 (m, 1H), 2.74 (m, 2H), 2.55-2.40 (m, overlapped with DMSO), 2.1 (m, 1H), 1.75 (m, 4H), 1.37 (m, 2H).

Example 4

(S)—N-(5-Cyano-1-((2,4-dimethoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein R¹ is methoxy, R² is methoxy, R³ is H, R⁶ is CN, R⁷ is H, R⁸ is methyl, and R⁹ is oxetan-3-yl)

To a solution of (S)—N-(5-cyano-1-((2,4-dimethoxyphenyl)sulfonyl)-3-(2-methoxypyridin-3-yl)-2-oxoindolin-3-yl)-3-oxoazetidine-1-carboxamide (225 mg, 0,390 mmol) and N-methyl-N-(oxetan-3-yl)piperidin-4-amine TFA-salt (220 mg, 0,552 mmol) in methanol (3 ml) and THF (6 ml) zinc chloride (200 mg, 1,468 mmol) was added and the mixture stirred for 10 min. The sodium cyanoborohydride (100 mg, 1,591 mmol) was added and stirring continued over night at room temperature. Then 6 ml of 10% NaHCO₃-solution were added, concentrated under vacuum, 50 ml of water and 20 ml of ethyl acetate, the aqueous layer extracted again with ethyl acetate, and the combined organic layers washed twice with brine, dried over MgSO₄, filtered and evaporated to leave 235 mg of a yellow solid. Flash chromatography of the crude product (silica gel/gradient from 0 to 10% methanol in dichloromethane) afforded 108 mg of the title compound as white solid.

ESI-MS [M+H⁺]=732.3.

¹H-NMR (600 MHz DMSO), δ [ppm]: 8.15 (dd, 1H), 7.90 (d, 1H), 7.82 (d, 1H), 7.81 (dd, 1H), 7.79 (dd, 1H), 7.70 (m, 1H), 7.58 (s broad, 1H), 7.06 (dd, 1H), 6.72 (dd, 1H), 6.68 (dd, 1H), 4.46 (m, 4H), 3.86 (s, 3H), 3.80-3.70 (m broad, 3H), 3.65 (s, 3H), 3.60-3.52 (m broad, 2H), 3.50 (s, 3H), 2.92 (m, 1H), 2.71 (d, 2H), 2.19 (m, 2H), 2.19 (m, 1H), 1.67 (m, 2H), 1.51 (m, 2H), 1.36 (m, 2H).

The following compounds were obtained according to the procedures described for examples 1-4 using the appropriate starting materials.

Example 5

(S)—N-(5-Cyano-1-((2,4-dimethoxyphenyl)sulfonyl)-3-(2-ethoxypyridin-3-yl)-2-oxoindolin-3-yl)-3-(4-(ethyl(oxetan-3-yl)amino)piperidin-1-yl)azetidine-1-carboxamide (compound of formula I.1, wherein R¹ is methoxy, R² is methoxy, R³ is H, R⁶ is CN, R⁷ is H, R⁸ is ethyl, and R⁹ is oxetan-3-yl)

ESI-MS [M+H+]=760.6.

¹H-NMR (600 MHz DMSO), δ [ppm]: 8.14 (dd, 1H), 7.88 (d, 1H), 7.86-7.80 (m, 3H), 7.66 (s, 1H), 7.55 (s, 1H), 7.05 (dd, 1H), 6.70 (dd, 1H), 6.66 (d, 1H), 4.47 (dt, 4H), 4.15-3.99 (m, 3H), 3.86 (s, 1H), 3.77 (m broad, 1H), 3.54 (m broad, 1H), 3.46 (s, 3H), 2.93 (m, 1H), 2.70 (t, 2H), 2.58 (m, 2H), 2.37 (m, 1H), 1.68 (m, 2H), 1.51 (m, 2H), 1.29 (m, 2H), 0.94 (dt, 6H).

Example 6

(S)-3-(4-(2-Oxa-7-Azaspiro[3.5]nonan-7-yl)piperidin-1-yl)-N-(5-cyano-1-((2,4-dimethoxyphenyl)sulfonyl)-3-(2-ethoxypyridin-3-yl)-2-oxoindolin-3-yl)azetidine-1-carboxamide (compound of formula I.1, wherein R¹ is methoxy, R² is methoxy, R³ is H, R⁶ is CN, R⁷ is H, and R⁸ and R⁹, together with the nitrogen atom they are bound to, form 2-oxa-7-aza-spiro[3.5]non-7-yl)

ESI-MS [M+H+]=786.30.

¹H-NMR (600 MHz DMSO), δ [ppm]: 8.13 (dd, 1H), 7.88 (d, 1H), 7.84-7.80 (m, 3H), 7.66 (s, 1H), 7.54 (s, 1H), 7.05 (dd, 1H), 6.70 (dd, 1H), 6.66 (d, 1H), 4.24 (s, 4H), 4.09 (q, 2H), 3.86 (s, 3H), 3.80 and 3.62 (each m broad, 2H), 3.46 (s, 3H), 2.93 (m, 1H), 2.71 (m, 2H), 2.40-2.30 (m, 4H), 2.15 (m, 1H), 1.85-1.65 (m, 8H), 1.38 (m, 2H), 0.95 (t, 3H).

Example 7

N-[(3S)-5-Cyano-1-(2,4-dimethoxyphenyl)sulfonyl-3-(2-ethoxy-3-pyridyl)-2-oxoindolin-3-yl]-3-[4-[cyclopropyl(oxetan-3-yl)amino]-1-piperidyl]azetidine-1-carboxamide (compound of formula I.1, wherein R¹ is methoxy, R² is methoxy, R³ is H, R⁶ is CN, R⁷ is H, R⁸ is cyclopropyl, and R⁹ is oxetan-3-yl)

ESI-MS [M+H+]=772.3.

¹H-NMR (600 MHz DMSO), δ [ppm]: 8.14 (dd, 1H), 7.89 (d, 1H), 7.83 (dd, 3H), 7.66 (s, 1H), 7.55 (s, 1H), 7.05 (dd, 1H), 6.71 (dd, 1H), 6.66 (d, 1H), 4.67 (m, 2H), 4.43 (m, 2H), 4.18 (m, 1H), 4.09 (q, 2H), 3.86 (s, 3H), 3.73 (m broad, 2H), 3.60 (m broad, 2H), 3.46 (s, 3H), 2.93 (m, 1H), 2.72 (t, 2H), 2.48 (m, overlapped with DMSO), 1.94 (m, 1H), 1.67 (m, 2H), 1.56 (m, 2H), 1.45 (m, 2H), 0.95 (t, 3H), 0.50 (m, 2H), 0.30 (m, 2H).

Example 8

(S)—N-(1-((2,4-Dimethoxyphenyl)sulfonyl)-3-(2-ethoxypyridin-3-yl)-5,6-difluoro-2-oxoindolin-3-yl)-3-(4-morpholinopiperidin-1-yl)azetidine-1-carboxamide (compound of formula I.1, wherein $R^1$ is methoxy, $R^2$ is methoxy, $R^3$ is H, $R^6$ is F, $R^7$ is F, and $R^8$ and $R^9$, together with the nitrogen atom they are bound to, form morpholin-4-yl)

ESI-MS [M+H+]=757.3.

$^1$H-NMR (600 MHz DMSO), δ [ppm]: 8.13 (dd, 1H), 7.89 (d, 1H), 7.74 (dd, 1H), 7.62 (dd, 1H), 7.48 (s, 1H), 7.34 (m, 1H), 7.02 (dd, 1H), 6.70 (dd, 1H), 6.67 (d, 1H), 4.11 (q, 2H), 3.86 (s, 3H), 3.80-3.70 (m broad, 2H), 3.67-3.52 (m, 6H), 3.50 (s, 3H), 2.94 (m, 1H), 2.70 (m, 2H), 2.42 (m, 4H), 2.08 (m, 1H), 1.71 (m, 4H), 1.35 (m, 2H), 1.01 (t, 3H).

Example 9

(S)—N-(5-Cyano-1-((2,4-dimethoxyphenyl)sulfonyl)-3-(2-ethoxypyridin-3-yl)-6-fluoro-2-oxoindolin-3-yl)-3-(4-morpholinopiperidin-1-yl)azetidine-1-carboxamide (compound of formula I.1, wherein $R^1$ is methoxy, $R^2$ is methoxy, $R^3$ is H, $R^6$ is CN, $R^7$ is F, and $R^8$ and $R^9$, together with the nitrogen atom they are bound to, form morpholin-4-yl)

ESI-MS [M+H+]=764.3.

$^1$H-NMR (600 MHz DMSO), δ [ppm]: 8.15 (dd, 1H), 7.89 (s, 1H), 7.88 (s, 1H), 7.71 (d, 1H), 7.68 (d, 1H), 7.56 (s, 1H), 7.07 (dd, 1H), 6.71 (dd, 1H), 6.67 (d, 1H), 4.10 (q, 2H), 3.86 (s, 3H), 3.84-3.70 (m broad, 2H), 3.68-3.53 (m, 6H), 3.52 (s, 3H), 2.94 (m, 1H), 2.71 (m, 2H), 2.42 (m, 4H), 2.08 (m, 1H), 1.72 (m, 4H), 1.34 (m, 2H), 0.99 (t, 3H).

Example 10

(S)—N-(5-Cyano-1-((2,4-dimethoxyphenyl)sulfonyl)-3-(2-ethoxypyridin-3-yl)-6-fluoro-2-oxoindolin-3-yl)-3-(4-(methyl(oxetan-3-yl)amino)piperidin-1-yl)azetidine-1-carboxamide (compound of formula I.1, wherein $R^1$ is methoxy, $R^2$ is methoxy, $R^3$ is H, $R^6$ is CN, $R^7$ is F, $R^8$ is methyl, and $R^9$ is oxetan-3-yl)

ESI-MS [M+H+]=764.3.

$^1$H-NMR (600 MHz DMSO), δ [ppm]: 8.15 (dd, 1H), 7.88 (m, 1H), 7.69 (dd, 1H), 7.56 (s, 1H), 7.07 (dd, 1H), 6.71 (dd, 1H), 6.67 (d, 1H), 4.53-4.38 (m, 4H), 4.09 (q, 2H), 3.84 (m broad, 2H), 3.58 (m broad, 2H), 3.51 (s, 3H), 2.93 (m, 1H), 2.71 (m, 2H), 2.19 (m, 1H), 1.67 (m, 2H), 1.51 (m, 2H), 1.36 (m, 2H), 0.99 (t, 3H).

Example 11

N-[(3S)-1-[(2,4-Dimethoxyphenyl)sulfonyl]-3-(2-ethoxypyridin-3-yl)-5,6-difluoro-2-oxo-2,3-dihydro-1H-indol-3-yl]-3-{4-[methyl(oxetan-3-yl)amino]piperidin-1-yl}azetidine-1-carboxamide (compound of formula I.1, wherein $R^1$ is methoxy, $R^2$ is methoxy, $R^3$ is H, $R^6$ is F, $R^7$ is F, $R^8$ is methyl, and $R^9$ is oxetan-3-yl)

ESI-MS [M+H+]=757.3.

$^1$H-NMR (600 MHz DMSO), δ [ppm]: 8.13 (dd, 1H), 7.89 (d, 1H), 7.73 (dd, 1H), 7.62 (dd, 1H), 7.48 (s, 1H), 7.34 (m, 1H), 7.02 (dd, 1H), 6.71 (dd 1H), 6.67 (d, 1H), 4.46 (m, 4H), 4.10 (q, 2H), 3.85 (s, 3H), 3.75 (m broad, 3H), 3.55 (m broad, 2H), 3.50 (s, 3H), 2.93 (m, 1H), 2.71 (m, 2H), 2.19 (m, 1H), 2.11 (s, 3H), 1.67 (m, 2H), 1.51 (m, 2H), 1.36 (m, 2H), 1.01 (t, 3H).

Example 12

(S)—N-(5-Cyano-1-((2,4-dimethoxyphenyl)sulfonyl)-3-(2-methoxypyridin-3-yl)-2-oxoindolin-3-yl)-3-(4-(cyclopropyl(oxetan-3-yl)amino)piperidin-1-yl)azetidine-1-carboxamide (compound of formula I.6, wherein $R^1$ is methoxy, $R^2$ is methoxy, $R^3$ is H, $R^6$ is CN, $R^7$ is H, $R^8$ is cyclopropyl, and $R^9$ is oxetan-3-yl)

ESI-MS [M+H+]=758.3.

$^1$H-NMR (600 MHz DMSO), δ [ppm]: 8.15 (dd, 1H), 7.90 (d, 1H), 7.86 (d, 1H), 7.81 (m, 2H), 7.70 (d, 1H), 7.59 (s, 1H), 7.06 (dd, 1H), 6.72 (dd, 1H), 6.68 (d, 1H), 4.67 (m 2H), 4.43 (m 2H), 4.18 (1H), 3.87 s, 3H), 3.77 (m broad, 2H), 3.65 (s, 3H), 3.58 (m broad, 2H), 3.52 (s, 3H), 2.94 (m, 1H), 2.71 (m, 2H), 2.61 (m, 2H), 2.39 (m, 1H), 1.68 (m, 2H), 1.52 (m, 2H), 1.29 (m, 2H), 0.93 (t, 3H).

Example 13

(S)—N-(5-Chloro-1-((2,4-dimethoxyphenyl)sulfonyl)-3-(2-ethoxypyridin-3-yl)-2-oxoindolin-3-yl)-3-(4-morpholinopiperidin-1-yl)azetidine-1-carboxamide (compound of formula I.1, wherein $R^1$ is methoxy, $R^2$ is methoxy, $R^3$ is H, $R^6$ is Cl, $R^7$ is H, and $R^8$ and $R^9$, together with the nitrogen atom they are bound to, form morpholin-4-yl)

ESI-MS [M+H+]=756.3.

$^1$H-NMR (600 MHz DMSO), δ [ppm]: 8.12 (dd, 1H), 7.88 (d, 1H), 7.69 (dd, 1H), 7.66 (d, 1H), 7.49 (s, 1H), 7.38 (dd, 1H), 7.33 (d, 1H), 7.01 (dd, 1H), 6.70 (dd, 1H), 6.66 (d, 1H), 4.11 (q, 2H), 3.86 (s, 3H), 3.79 (m broad, 2H), 3.68-3.50 (m, 6H), 3.47 (s, 3H), 2.95 (m, 1H), 2.73 (m, 2H), 2.09 (m, 1H), 1.72 (m, 4H), 1.35 (m, 2H), 1.0 (t, 3H).

Example 14

(S)—N-(5-Chloro-1-((2,4-dimethoxyphenyl)sulfonyl)-3-(2-ethoxypyridin-3-yl)-2-oxoindolin-3-yl)-3-(4-(methyl(oxetan-3-yl)amino)piperidin-1-yl)azetidine-1-carboxamide (compound of formula I.1, wherein $R^1$ is methoxy, $R^2$ is methoxy, $R^3$ is H, $R^6$ is Cl, $R^7$ is H, $R^8$ is methyl, and $R^9$ is oxetan-3-yl)

ESI-MS [M+H+]=756.3.

$^1$H-NMR (600 MHz DMSO), δ [ppm]: 8.12 (dd, 1H), 7.88 (d, 1H), 7.69 (d, 1H), 7.66 (d, 1H), 7.49 (s, 1H), 7.38 (dd, 1H), 7.33 (d, 1H), 7.01 (dd, 1H), 6.70 (dd, 1H), 6.66 (d, 1H), 4.45 (m, 4H), 4.11 (q, 2H), 3.88 (s, 3H), 3.80 (m broad, 2H), 3.57 (m broad, 3H), 3.46 (s, 3H), 2.92 (m, 1H), 2.71 (m, 2H), 2.20 (m, 1H), 2.08 (s, 3H), 1.67 (m, 2H), 1.51 (m, 2H), 1.36 (m, 2H), 1.00 (t, 3H).

Example 15

(S)—N-(5-Cyano-1-((2,4-dimethoxyphenyl)sulfonyl)-3-(2-ethoxypyridin-3-yl)-2-oxoindolin-3-yl)-3-(4-((2-methoxyethyl)(methyl)amino)piperidin-1-yl)azetidine-1-carboxamide (compound of formula I.1, wherein $R^1$ is methoxy, $R^2$ is methoxy, $R^3$ is H, $R^6$ is CN, $R^7$ is H, $R^8$ is methyl and $R^9$ is 2-methoxyethyl)

To a solution of (S)—N-(5-cyano-1-((2,4-dimethoxyphenyl)sulfonyl)-3-(2-ethoxypyridin-3-yl)-2-oxoindolin-3-yl)-3-(4-oxopiperidin-1-yl)azetidine-1-carboxamide (60 mg, 0,089 mmol) and N-(2-methoxyethyl)methylamine (10 mg, 0,112 mmol) in a 1:1 mixture of methanol and THF (3 ml) first zinc chloride (20 mg, 0,147 mmol), and after stirring for 10 min, sodium cyanoborohydride (15 mg, 0,239 mmol) was added and stirring continued over night. For work-up 5 ml of 10% NaHCO3-solution were added, the mixture concentrated, diluted with 50 ml of water and 20 ml of ethyl acetate, separated and the aqueous layer re-extracted with ethyl acetate. The combined organic layers then were washed with brine, dried over MgSO4, filtered and evaporated to leave 70 mg of a white solid. Flash chromatography of the crude product (silica gel/gradient from 0 to 10% methanol in dichloromethane) yielded 45 mg of the title compound as white solid.

ESI-MS [M+H+]=748.3.

$^1$H-NMR (600 MHz DMSO), δ [ppm]: 8.14 (dd, 1H), 7.88 (d, 1H), 7.83 (m, 3H), 7.66 (s, 1H), 7.55 (s, 1H), 7.05 (dd, 1H), 6.70 (dd, 1H), 6.66 (d, 1H), 4.09 (q, 2H), 3.86 (s, 3H), 3.77 (m broad, 2H), 3.58 (m broad, 2H), 3.46 (s, 3H), 3.22 (s, 3H), 2.94 (m, 1H), 2.72 (m, 2H), 2.52 (m overlapped with DMSO), 2.28 (m, 1H), 2.17 (s, 3H), 1.70 (m, 2H), 1.63 (m, 2H), 1.38 (m, 2H), 0.95 (t, 3H).

Example 16

(S)—N-(5-Cyano-1-((2,4-dimethoxyphenyl)sulfonyl)-3-(2-ethoxypyridin-3-yl)-2-oxoindolin-3-yl)-3-(4-(methoxy(methyl)amino)piperidin-1-yl)azetidine-1-carboxamide (compound of formula I.1, wherein $R^1$ is methoxy, $R^2$ is methoxy, $R^3$ is H, $R^6$ is CN, $R^7$ is H, $R^8$ is methyl, and $R^9$ is methoxy)

ESI-MS [M+H+]=720.3

Example 17

(S)—N-(5-Cyano-1-((2,4-dimethoxyphenyl)sulfonyl)-3-(2-ethoxypyridin-3-yl)-2-oxoindolin-3-yl)-3-(4-(isoxazolidin-2-yl)piperidin-1-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form isoxazolidin-2-yl)

ESI-MS [M+H+]=732.3

$^1$H-NMR (600 MHz DMSO), δ [ppm]: 8.14 (dd, 1H), 7.89 (d, 1H), 7.83 (m, 3H), 7.67 (s, 1H), 7.54 (s, 1H), 7.05 (dd, 1H), 6.70 (dd, 1H), 6.66 (d, 1H), 4.09 (q, 2H), 3.86 (s, 3H), 3.76 (m, 3H), 3.62 (m, 3H), 3.47 (s, 3H), 3.03 (m, 1H), 2.96 (m, 1H), 2.65 (m, 2H), 2.55 (m, 1H), 2.36 (m, 1H), 2.13 (m, 2H), 2.13 (m, 1H), 1.92 (m, 1H), 1.77 (m, 2H), 1.64 (m, 1H), 1.35 (m, 2H), 0.94 (t, 3H).

Example 18

(S)—N-(5-Cyano-1-((2,4-dimethoxyphenyl)sulfonyl)-3-(2-ethoxypyridin-3-yl)-2-oxoindolin-3-yl)-3-(4-(3-(oxetan-3-yl)azetidin-1-yl)piperidin-1-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 3-(oxetan-3-yl)-azetidin-1-yl)

ESI-MS [M+H+]=772.3

$^1$H-NMR (600 MHz DMSO), δ [ppm]: 8.13 (dd, 1H), 7.88 (d, 1H), 7.84 (m, 3H), 7.66 (s, 1H), 7.54 (s, 1H), 7.05 (dd, 1H), 6.70 (dd, 1H), 6.66 (d, 1H), 4.63 (dd, 2H), 4.27 (dd, 2H), 4.09 (q, 2H), 3.86 (s, 3H), 3.72 (m broad, 2H), 3.53 (m broad, 2H), 3.46 (s, 3H), 3.22 (m, 2H), 3.11 (m, 1H), 2.95 (m, 1H), 2.76 (m, 2H), 2.62 (m, 1H), 2.53 (m overlapped with DMSO), 1.96 (m, 1H), 1.79 (m, 2H), 1.57 (m, 2H), 1.10 (m, 2H), 0.95 (t, 3H).

Example 19

(S)-3-(4-(2-Oxa-6-azaspiro[3.3]heptan-6-yl)piperidin-1-yl)-N-(5-cyano-1-((2,4-dimethoxyphenyl)sulfonyl)-3-(2-ethoxypyridin-3-yl)-2-oxoindolin-3-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 2-oxa-6-aza-spiro[3.3]hept-6-yl)

ESI-MS [M+H+]=758.3

$^1$H-NMR (600 MHz DMSO), δ [ppm]: 8.13 (dd, 1H), 7.88 (d, 1H), 7.83 (m, 3H), 7.66 (s, 1H), 7.53 (s, 1H), 7.05 (dd, 1H), 6.70 (dd, 1H), 6.65 (d, 1H), 4.57 (s, 4H), 4.08 (q, 2H), 3.85 (s, 3H), 3.78 (m broad, 2H), 3.58 (m broad, 2H), 3.46 (s, 3H), 3.19 (s, 3H), 2.94 (m, 1H), 2.54 (overlapped with DMSO), 1.86 (m, 1H), 1.75 (m, 2H), 1.54 (m, 2H), 1.09 (m, 2H), 0.94 (t, 3H).

Example 20

(S)—N-(5-Cyano-1-((2,4-dimethoxyphenyl)sulfonyl)-3-(2-methoxypyridin-3-yl)-2-oxoindolin-3-yl)-3-(4-(oxetan-3-ylamino)piperidin-1-yl)azetidine-1-carboxamide (compound of formula I.6, wherein $R^1$ is methoxy, $R^2$ is methoxy, $R^3$ is H, $R^6$ is CN, $R^7$ is H, $R^8$ is hydrogen, and $R^9$ is oxetan-3-yl)

ESI-MS [M+H+]=718.3

$^1$H-NMR (600 MHz DMSO), δ [ppm]: 8.15 (dd, 1H), 7.91 (d, 1H), 7.86 (d, 1H), 7.82 (d, 1H), 7.80 (dd, 1H), 7.70 (d, 1H), 7.57 (s, 1H), 7.06 (dd, 1H), 6.71 (dd, 1H), 6.68 (d, 1H), 4.60 (m, 2H), 4.28 (m, 2H), 3.91 (m, 1H), 3.85 (s, 3H), 3.75 (m broad, 2H), 3.65 (s, 3H), 3.59 (m broad, 3H), 3.53 (s, 3H), 2.93 (m, 1H), 2.61 (m, 2H), 2.30 (m, 1H), 1.72 (m, 2H), 1.60 (m, 2H), 1.17 (m, 2H).

Example 21

(S)—N-(5-Cyano-1-((2,4-dimethoxyphenyl)sulfonyl)-3-(2-methoxypyridin-3-yl)-2-oxoindolin-3-yl)-3-(4-(methyl(tetrahydro-2H-pyran-4-yl)amino)piperidin-1-yl)azetidine-1-carboxamide (compound of formula I.6, wherein $R^1$ is methoxy, $R^2$ is methoxy, $R^3$ is H, $R^6$ is CN, $R^7$ is H, $R^8$ is methyl, and $R^9$ is tetrahydropyran-4-yl)

ESI-MS [M+H+]=760.3

$^1$H-NMR (600 MHz DMSO), δ [ppm]: 8.15 (dd, 1H), 7.91 (d, 1H), 7.86 (d, 1H), 7.82 (d, 1H), 7.80 (m, 2H), 7.70 (d, 1H), 7.58 (s, 1H), 7.06 (dd, 1H), 6.72 (dd, 1H), 6.68 (d, 1H), 3.85 (s, 3H), 3.80 (m, 3H), 3.75 (m, 2H), 3.65 (s, 3H), 3.60 (m, 2H), 3.51 (s, 3H), 3.27 (m, 2H), 2.93 (m, 1H), 2.74-2.64 (m, 3H), 1.72 (m, 2H), 1.58 (m, 4H), 1.43 (m, 4H).

Example 22

(S)—N-(5-Cyano-1-((2,4-dimethoxyphenyl)sulfonyl)-3-(2-methoxypyridin-3-yl)-2-oxoindolin-3-yl)-3-(4-(oxetan-3-yl(propyl)amino)piperidin-1-yl)azetidine-1-carboxamide (compound of formula I.6, wherein $R^1$ is methoxy, $R^2$ is methoxy, $R^3$ is H, $R^6$ is CN, $R^7$ is H, $R^8$ is propyl, and $R^9$ is oxetan-3-yl)

ESI-MS [M+H+]=760.3

$^1$H-NMR (600 MHz DMSO), δ [ppm]: 8.13 (dd, 1H), 7.89 (d, 1H), 7.73 (dd, 1H), 7.62 (dd, 1H), 7.48 (s, 1H), 7.34 (m, 1H), 7.02 (dd, 1H), 6.70 (dd, 1H), 6.67 (d, 1H), 4.46 (m, 4H), 4.11 (q, 2H), 3.86 (s, 3H), 3.78 (m broad, 2H), 3.57 (m broad, 2H), 3.50 (s, 3H), 2.93 (m, 1H), 2.71 (m, 2H), 2.54 (m, overlapped with DMSO), 2.19 (m, 1H), 2.08 (s, 3H), 1.67 (m, 2H), 1.51 (m, 2H), 1.36 (m, 2H), 1.01 (t, 3H).

Example 23

(S)—N-(5-Cyano-1-((2,4-dimethoxyphenyl)sulfonyl)-3-(2-methoxypyridin-3-yl)-2-oxoindolin-3-yl)-3-(4-(ethyl(oxetan-3-yl)amino)piperidin-1-yl)azetidine-1-carboxamide (compound of formula I.6, wherein $R^1$ is methoxy, $R^2$ is methoxy, $R^3$ is H, $R^6$ is CN, $R^7$ is H, $R^8$ is ethyl, and $R^9$ is oxetan-3-yl)

ESI-MS [M+H+]=746.3

$^1$H NMR (600 MHz, DMSO) δ 8.15 (dd, 1H), 7.90 (d, 1H), 7.86 (d, 1H), 7.80 (m, 2H), 7.69 (d, 1H), 7.58 (s, 1H), 7.06 (dd, 1H), 6.72 (dd, 1H), 6.68 (d, 1H), 4.47 (dt, 4H), 4.04 (m, 1H), 3.87 (s, 3H), 3.85 (m broad, 2H), 3.65 (m, 3H), 3.56 (m broad, 2H), 3.53 (s, 3H), 2.94 (m, 1H), 2.71 (m, 2H), 2.60 (m, 2H), 2.39 (m, 1H), 1.68 (m, 2H), 1.52 (m, 2H), 1.29 (m, 2H), 0.93 (t, 3H).

Example 24

(S)—N-(5-Cyano-3-(2-ethoxypyridin-3-yl)-1-((5-fluoro-2,4-dimethoxyphenyl)sulfonyl)-2-oxoindolin-3-yl)-3-(4-morpholinopiperidin-1-yl)azetidine-1-carboxamide (compound of formula I.1, wherein $R^1$ is methoxy, $R^2$ is methoxy, $R^3$ is 5-F (relative to the 2- and 4-positions of $R^1$ and $R^2$), $R^6$ is CN, $R^7$ is H, and $R^8$ and $R^9$, together with the nitrogen atom they are bound to, form morpholin-4-yl)

a. To a solution of (S)-3-amino-3-(2-ethoxypyridin-3-yl)-2-oxoindoline-5-carbonitrile (1.0 g, 3.40 mmol) in DMF (12 ml) at 5° C. sodium hydride (55%: 0.22 g, 5.04 mmol) was added. After stirring for 20 min 5-fluoro-2,4-dimethoxybenzene-1-sulfonyl chloride (1.0 g, 3.93 mmol) was added and stirring continued for 1 hr at 5° C. After completion of the reaction 30 ml of water were added dropwise, the mixture digested 3× with dichloromethane, the combined organic layers washed with brine, dried over MgSO$_4$, filtered and concentrated to leave a brown oil, which was purified by flash chromatography (silica gel/gradient from 0 to 15% methanol in dichloromethane) to yield 1.5 g; ESI-MS [M+H+]=513.2.

b. To a solution of (S)-3-amino-3-(2-ethoxypyridin-3-yl)-1-((5-fluoro-2,4-dimethoxyphenyl)sulfonyl)-2-oxoindoline-5-carbonitrile (1.5 g, 2.63 mmol) in dichloromethane (50 ml) at 5° C. were added dropwise pyridine (2.3 ml, 28.4 mmol) and phenylchloroformate (0.8 ml, 6.37 mmol), and the mixture stirred over night at room temperature. The mixture was diluted with dichloromethane, digested twice with water, the organic layer washed subsequently with 10% NaHCO3-solution and brine, dried over MgSO4, filtered and concentrated to give 2.1 g of a yellow oil, which was further purified by flash chromatography (silica gel/gradient from 0 to 15% methanol in dichloromethane) to give 0.7 g of a yellow amorphous solid; ESI-MS [M+H+]=633.9.

c. To a solution of (S)-phenyl (5-cyano-3-(2-ethoxypyridin-3-yl)-1-((5-fluoro-2,4-dimethoxyphenyl)sulfonyl)-2-oxoindolin-3-yl)carbamate (80 mg, 0,126 mmol) and 4-(1-(azetidin-3-yl)piperidin-4-yl)morpholine×3TFA (70 mg, 0,123 mmol) in DMF (3 ml) at 5° C. Et3N (120 μl, 0,861 mmol) was added and then stirred for 4 h at room temperature. The mixture was concentrated, diluted with dichloromethane, washed with water and brine, dried over MgSO$_4$, filtered and evaporated to leave 210 mg of a brown oil. Flash chromatography (silica gel/gradient from 0 to 20% methanol in dichloromethane) yielded 52 mg of the title compound as white solid.

ESI-MS [M+H+]=764.3.

$^1$H NMR (600 MHz, DMSO) δ 8.13 (dd, 1H), 7.89 (d, 1H), 7.74 (dd, 1H), 7.62 (dd, 1H), 7.48 (s, 1H), 7.34 (m, 1H), 7.02 (dd, 1H), 6.70 (dd, 1H), 6.67 (d, 1H), 4.11 (q, 2H), 3.86 (s, 3H), 3.75 (m broad, 2H), 3.70-3.55 (m, 6H), 3.50 (s, 3H), 2.94 (m, 1H), 2.71 (m, 2H), 2.42 (m, 4H), 2.08 (m, 1H), 1.71 (m, 4H), 1.34 (m, 2H), 1.01 (t, 3H).

Example 25

(S)—N-(5-Cyano-3-(2-ethoxypyridin-3-yl)-1-((4-methoxyphenyl)sulfonyl)-2-oxoindolin-3-yl)-3-(4-morpholinopiperidin-1-yl)azetidine-1-carboxamide (compound of formula I.1, wherein $R^1$ is H, $R^2$ is methoxy, $R^3$ is H, $R^6$ is CN, $R^7$ is H, and $R^8$ and $R^9$, together with the nitrogen atom they are bound to, form morpholin-4-yl)

Prepared according to the procedure described for EXAMPLE 25:

ESI-MS [M+H+]=716.3.

Example 26

(S)—N-(5-Cyano-1-((2,4-difluorophenyl)sulfonyl)-3-(2-ethoxypyridin-3-yl)-2-oxoindolin-3-yl)-3-(4-morpholinopiperidin-1-yl)azetidine-1-carboxamide (compound of formula I. 1, wherein $R^1$ is F, $R^2$ is F, $R^3$ is H, $R^6$ is CN, $R^7$ is H, and $R^8$ and $R^9$, together with the nitrogen atom they are bound to, form morpholin-4-yl)

To a solution of (S)—N-(5-cyano-3-(2-ethoxypyridin-3-yl)-2-oxoindolin-3-yl)-3-(4-morpholinopiperidin-1-yl)azetidine-1-carboxamide (200 mg, 0,367 mmol) in THF (3 ml) at 5° C. potassium tert-butoxide (60 mg, 0,535 mmol) and after 30 min 2,4-diflurobenzenesulfonylchloride (90 mg, 0,423 mmol) were added, and the mixture stirred over night at room temperature. The mixture was diluted with 20 ml of water, digested 3× with dichloromethane, and the combined organic layers washed with brine, dried over MgSO4, filtered and concentrated to give 300 mg of a clear oil. Flash chromatography (silica gel/gradient from 0 to 20% methanol in dichloromethane) yielded 115 mg of the title compound as white solid.

ESI-MS [M+H+]=716.3.

$^1$H NMR (600 MHz, DMSO) δ 8.30 (dd, 1H), 8.10 (m, 2H), 7.88 (m, 2H), 7.57 (s, 2H), 7.50 (m, 1H), 7.34 (m, 1H), 7.12 (dd, 1H), 4.09 (q, 2H), 3.80-3.50 (m, 7H), 2.93 (m, 1H), 2.71 (m, 2H), 2.39 (m, 4H), 2.08 (m, 1H), 1.71 (m, 4H), 1.4 (m, 2H), 0.98 (t, 3H).

The following compounds were prepared according to the procedure as described for EXAMPLE 27

Example 27

(S)—N-(5-cyano-3-(2-ethoxypyridin-3-yl)-1-((2-fluoro-4-methoxyphenyl)sulfonyl)-2-oxoindolin-3-yl)-3-(4-morpholinopiperidin-1-yl)azetidine-1-carboxamide (compound of formula I.1, wherein $R^1$ is F, $R^2$ is methoxy, $R^3$ is H, $R^6$ is CN, $R^7$ is H, and $R^8$ and $R^9$, together with the nitrogen atom they are bound to, form morpholin-4-yl)

ESI-MS [M+H+]=734.3.

$^1$H NMR (600 MHz, DMSO) δ 8.14 (dd, 1H), 8.01 (dd, 1H), 7.94 (t, 1H), 7.85 (m, 2H), 7.61 (s, 1H), 7.58 (s, 1H), 7.10 (dd, 1H), 7.05 (dd, 1H), 6.98 (dd, 1H), 4.05 (m, 2H), 3.86 (s, 3H), 3.75 (m broad, 2H), 3.60-3.50 (m, 5H), 2.93 (m, 1H), 2.71 (m, 2H), 2.39 (m, 4H), 2.09 (m, 1H), 1.72 (m, 4H), 1.35 (m, 2H), 0.93 (t, 3H).

Example 28

(S)—N-(5-cyano-3-(2-ethoxypyridin-3-yl)-1-((4-fluoro-2-methoxyphenyl)sulfonyl)-2-oxoindolin-3-yl)-3-(4-morpholinopiperidin-1-yl)azetidine-1-carboxamide (compound of formula I.1, wherein $R^1$ is methoxy, $R^2$ is F, $R^3$ is H, $R^6$ is CN, $R^7$ is H, and $R^8$ and $R^9$, together with the nitrogen atom they are bound to, form morpholin-4-yl)

ESI-MS [M+H+]=734.3.

1H NMR (600 MHz, DMSO) δ 8.14 (dd, 1H), 8.01 (dd, 1H), 7.94 (dd, 1H), 7.86 (m, 2H), 7.64 (s, 1H), 7.56 (s, 1H), 7.15 (dd, 1H), 7.09 (dd, 1H), 6.98 (td, 1H), 4.10 (m, 2H), 3.74 (m broad, 2H), 3.62-3.50 (m, 6H), 3.49 (s, 3H), 2.94 (m, 1H), 2.71 (m, 2H), 2.39 (m, 4H), 2.08 (m, 1H), 1.71 (m, 4H), 1.34 (m, 2H), 0.98 (t, 3H).

Example 29

(S)—N-(5-Cyano-1-((2-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein $R^1$ is methoxy, $R^2$ is H, $R^3$ is H, $R^6$ is CN, $R^7$ is H, $R^8$ is methyl, and $R^9$ is oxetan-3-yl)

ESI-MS [M+H+]=702.2.

$^1$H NMR (600 MHz, DMSO) δ 8.13 (dd, 1H), 7.98 (d, 1H), 7.87 (d, 1H), 7.82 (m, 2H), 7.71 (m, 2H), 7.69 (s, 1H), 7.24 (d, 1H), 7.16 (m, 1H), 7.06 (m, 1H), 4.44 (m, 4H), 3.84 (q, 2H), 3.75 (m broad, 2H), 3.63 (s, 3H), 3.54 (s, 3H, overlapped with m broad, 2H), 2.92 (m, 1H), 2.69 (m, 2H), 2.19 (m, 1H), 1.66 (m, 2H), 1.49 (m, 2H), 1.37 (m, 2H).

Example 30

(S)—N-(5-Cyano-1-((4-fluoro-2-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein $R^1$ is methoxy, $R^2$ is F, $R^3$ is H, $R^6$ is CN, $R^7$ is H, $R^8$ is methyl, and $R^9$ is oxetan-3-yl)

ESI-MS [M+H+]=720.2.

$^1$H NMR (600 MHz, DMSO) δ 8.16 (dd, 1H), 8.04 (dd, 1H), 7.91 (dd, 1H), 7.87 (d, 1H), 7.83 (dd, 1H), 7.69 (d, 1H), 7.60 (s, 3H), 7.17 (dd, 1H), 7.10 (dd, 1H), 7.00 (td, 1H), 4.45 (m, 4H), 3.83-3.50 (m broad, 5H) overlapped with 3.65 (s, 3H), 2.92 (m, 1H), 2.71 (m, 2H), 2.19 (m, 1H), 1.66 (m, 2H), 1.50 (m, 2H), 1.36 (m, 2H).

Example 31

(S)—N-(5-Cyano-1-((4-fluorophenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein $R^1$ is H, $R^2$ is F, $R^3$ is H, $R^6$ is CN, $R^7$ is H, $R^8$ is methyl and $R^9$ is oxetan-3-yl)

ESI-MS [M+H+]=690.2.

$^1$H NMR (600 MHz, DMSO) δ 8.16 (m, 3H), 8.05 (dd, 1H), 7.88 (d, 1H), 7.83 (dd, 1H), 7.65 (d, 2H), 7.53 (m, 2H), 7.13 (dd, 1H), 4.45 (m, 4H), 3.92-3.47 (m, 5H), 3.42 (s, 3H), 2.93 (m, 1H), 2.72 (m, 2H), 2.20 (m, 1H), 2.06 (s, 3H), 1.67 (m, 2H), 1.51 (m, 2H), 1.36 (m, 2H).

Example 32

(S)—N-(5-Cyano-1-((2-fluoro-4-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein $R^1$ is F, $R^2$ is methoxy, $R^3$ is H, $R^6$ is CN, $R^7$ is H, $R^8$ is methyl, and $R^9$ is oxetan-3-yl)

ESI-MS [M+H+]=720.3.

$^1$H NMR (600 MHz, DMSO) δ 8.16 (dd, 1H), 8.0 (m, 1H), 7.98 (m, 1H), 7.85 (m, 2H), 7.67 (s, 1H), 7.62 (s, 1H), 7.11 (m 2H), 7.0 (dd, 1H), 4.46 (m, 4H), 3.87 (s, 3H), 3.79-3.60 (m, 5H), 3.57 (s, 3H), 2.92 (m, 1H), 2.71 (m, 2H), 2.20 (m, 1H), 2.10 (s, 3H), 1.67 (m, 2H), 1.51 (m, 2H), 1.36 (m, 2H).

Example 33

(S)—N-(5-Cyano-1-((2,4-difluorophenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein $R^1$ is F, $R^2$ is F, $R^3$ is H, $R^6$ is CN, $R^7$ is H, $R^8$ is methyl, and $R^9$ is oxetan-3-yl)

ESI-MS [M+H+]=708.2.

$^1$H NMR (600 MHz, DMSO) δ 8.17 (dd, 1H), 8.14 (m, 1H), 8.06 (dd, 1H), 7.86 (m, 2H), 7.68 (s, 1H), 7.65 (s, 1H), 7.60 (m, 1H), 7.37 (m, 1H), 7.14 (dd, 1H), 4.46 (m, 4H), 3.90-3.55 (m, 5H), overlapped with 3.60 (s, 3H), 2.932 (m, 1H), 2.70 (m, 2H), 2.19 (m, 1H), 2.19 (s, 3H), 1.67 (m, 2H), 1.51 (m, 2H), 1.35 (m, 2H).

Example 34

(S)—N-(5-Cyano-1-((5-fluoro-2,4-dimethoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein $R^1$ is methoxy, $R^2$ is methoxy, $R^3$ is 5-F (relative to the 2- and 4-positions of $R^1$ and $R^2$), $R^6$ is CN, $R^7$ is H, $R^8$ is methyl, and $R^9$ is oxetan-3-yl)
ESI-MS [M+H+]=750.3.
$^1$H NMR (600 MHz, DMSO) δ 8.16 (dd, 1H), 7.87 (m, 2H), 7.82 (dd, 1H), 7.75 (dd, 1H), 7.70 (d, 1H), 7.62 (s, 1H), 7.09 (dd, 1H), 6.92 (d, 1H), 4.46 (m, 4H), 3.96 (s, 3H), 3.85 (m broad, 2H), 3.66 and 3.58 (each s, 3H) overlapped with 3.70-3.50 (m, 3H), 2.93 (m, 1H), 2.71 (m, 2H), 2.20 (m, 1H), 2.15 (s, 3H), 1.67 (m, 2H), 1.51 (m, 2H), 1.36 (m, 2H).

Example 35

(S)—N-(5-cyano-1-((4-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide (compound of formula I.6, wherein $R^1$ is H, $R^2$ is methoxy, $R^3$ is H, $R^6$ is CN, $R^7$ is H, $R^8$ is methyl, and $R^9$ is oxetan-3-yl)
ESI-MS [M+H+]=702.3.
$^1$H NMR (600 MHz, DMSO) δ 8.14 (dd, 1H), 8.00 (dd, 1H), 7.85 (d, 1H), 7.82 (dd, 1H), 7.63 (m, 2H), 7.18 (m, 2H), 7.10 (dd, 1H), 4.45 (m, 4H), 3.86 (s, 3H), 3.75-3.65 (m, 3H), 3.59 (m broad, 2H), 2.93 (m, 1H), 2.72 (m, 2H), 2.20 (m, 1H), 2.09 (s, 3H), 1.68 (m, 2H), 1.52 (m, 2H), 1.37 (m, 2H).

Example 36

(S)—N-(5-Cyano-3-(2-ethoxypyridin-3-yl)-1-((5-methoxypyridin-2-yl)sulfonyl)-2-oxoindolin-3-yl)-3-(4-morpholinopiperidin-1-yl)azetidine-1-carboxamidexTFA (compound of formula I.21, wherein $R^2$ is methoxy, $R^3$ is H, $R^6$ is CN, $R^7$ is H, and $R^8$ and $R^9$, together with the nitrogen atom they are bound to, form morpholin-4-yl)
ESI-MS [M+H+]=717.3.

Example 37

(S)—N-(5-Cyano-3-(2-ethoxypyridin-3-yl)-1-((2-methoxyphenyl)sulfonyl)-2-oxoindolin-3-yl)-3-(4-morpholinopiperidin-1-yl)azetidine-1-carboxamide (compound of formula I.1, wherein $R^1$ is methoxy, $R^2$ is H, $R^3$ is H, $R^6$ is CN, $R^7$ is H, and $R^8$ and $R^9$, together with the nitrogen atom they are bound to, form morpholin-4-yl)
ESI-MS [M+H+]=716.3
$^1$H NMR (600 MHz, DMSO) δ 8.14 (dd, 1H), 7.97 (dd, 1H), 7.85 (m, 3H), 7.71 (m, 1H), 7.67 (s, 1H), 7.56 (s, 1H), 7.20 (d, 1H), 7.14 (m, 1H), 7.06 (dd, 1H), 4.08 (q, 2H), 3.81 (m broad, 2H), 3.75-3.50 (m, 5H), 3.49 (s, 1H), 2.93 (m, 1H), 2.70 (m, 2H), 2.40 (m, 4H), 2.08 (m, 1H), 1.71 (m, 4H), 1.34 (m, 2H), 0.94 (t, 3H).

Example 38

(S)—N-(5-Cyano-1-((2,4-dimethoxyphenyl)sulfonyl)-3-(2-methoxypyridin-3-yl)-2-oxoindolin-3-yl)-3-(4-(isopropyl(oxetan-3-yl)amino)piperidin-1-yl)azetidine-1-carboxamide (compound of formula I.6, wherein $R^1$ is methoxy, $R^2$ is methoxy, $R^3$ is H, $R^6$ is CN, $R^7$ is H, $R^8$ is isopropyl, and $R^9$ is oxetan-3-yl)
ESI-MS [M+H+]=760.3
$^1$H NMR (600 MHz, DMSO) δ 8.15 (dd, 1H), 7.91 (d, 1H), 7.86 (d, 1H), 7.81 (m, 2H), 7.69 (d, 1H), 7.58 (s, 1H), 7.06 (dd, 1H), 6.72 (dd, 1H), 6.68 (d, 1H), 4.47 (m, 4H), 4.23 (m, 1H), 3.87 (s, 4H), 3.75 (m broad, 2H), 3.65 (s, 3H), 3.58 (m broad, 2H) 3.53 (s, 3H), 3.03 (m, 1H), 2.93 (m, 1H), 2.71 (m, 2H), 2.59 (m, 1H), 1.74 (m, 2H), 1.42 (m, 4H), 0.94 (d, 3H), 0.93 (d, 3H).

Example 39

(S)—N-(5-Cyano-1-((2,4-dimethoxyphenyl)sulfonyl)-3-(2-ethoxypyridin-3-yl)-2-oxoindolin-3-yl)-3-(4-(3,3-difluoroazetidin-1-yl)piperidin-1-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 3,3-difluoroazetidin-1-yl)
ESI-MS [M+H+]=752.3
$^1$H NMR (600 MHz, DMSO) δ 8.13 (dd, 1H), 7.88 (d, 1H), 7.86-7.80 (m, 3H), 7.66 (s, 1H), 7.54 (s, 1H), 7.05 (dd, 1H), 6.70 (dd, 1H), 6.66 (d, 1H), 4.09 (q, 2H), 3.86 (s, 4H), 3.78 (m broad, 2H), 3.66-3.53 (m, 6H), 3.52 (s, 3H), 2.98 (m, 1H), 2.57 (m, 2H), 2.16 (d, 1H), 1.83 (d, 2H), 1.62 (d, 2H), 1.19 (m, 2H), 0.95 (t, 3H).

Example 40

(S)—N-(5-Cyano-1-((2,4-dimethoxyphenyl)sulfonyl)-3-(2-ethoxypyridin-3-yl)-2-oxoindolin-3-yl)-3-(4,4-difluoro-[1,4'-bipiperidin]-1'-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 4,4-difluoropiperidin-1-yl)
ESI-MS [M+H+]=780.3
$^1$H NMR (600 MHz, DMSO) δ 8.14 (dd, 1H), 7.88 (d, 1H), 7.83 (m, 3H), 7.66 (s, 1H), 7.55 (s, 1H), 7.05 (dd, 1H), 6.70 (dd, 1H), 6.66 (d, 1H), 4.09 (q, 2H), 3.86 (s, 3H), 3.73 (m broad, 2H), 3.58 (m broad, 2H), 3.46 (s, 3H), 2.95 (m, 1H), 2.73 (m, 2H), 2.55 (m, 4H), 2.32 (m, 1H), 1.90 (m, 4H), 1.68 (m, 4H), 1.42 (m, 2H), 0.95 (t, 3H).

Example 41

(S)—N-(5-Cyano-1-((2,4-dimethoxyphenyl)sulfonyl)-3-(2-ethoxypyridin-3-yl)-2-oxoindolin-3-yl)-3-(4-(3-methoxyazetidin-1-yl)piperidin-1-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 3-methoxyazetidin-1-yl)

ESI-MS [M+H+]=746.3

$^1$H NMR (600 MHz, DMSO) δ 8.13 (dd, 1H), 7.88 (d, 1H), 7.83 (m, 3H), 7.66 (s, 1H), 7.54 (s, 1H), 7.05 (dd, 1H), 6.70 (dd, 1H), 6.66 (d, 1H), 4.07 (q, 2H), 3.89 (m, 1H), 3.86 (s, 3H), 3.76 (m broad, 2H), 3.58 (m broad, 2H), 3.46 (s, 3H), 3.42 (m, 2H), 3.13 (s, 3H), 2.95 (m, 1H), 2.69 (m, 2H), 2.51 (m, overlapped with DMSO, 2H), 1.94 (m, 1H), 1.79 (m, 2H), 1.59 (d, 2H), 1.14 (m, 2H), 0.95 (t, 3H).

Example 42

(S)—N-(5-Cyano-1-((2,4-dimethoxyphenyl)sulfonyl)-3-(2-ethoxypyridin-3-yl)-2-oxoindolin-3-yl)-3-(4-methoxy-[1,4'-bipiperidin]-1'-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 4-methoxypiperidin-1-yl)

ESI-MS [M+H+]=774.3

$^1$H NMR (600 MHz, DMSO) δ 8.14 (dd, 1H), 7.88 (d, 1H), 7.83 (m, 3H), 7.66 (s, 1H), 7.54 (s, 1H), 7.05 (dd, 1H), 6.70 (dd, 1H), 6.66 (d, 1H), 4.09 (q, 2H), 3.86 (s, 3H), 3.76 (m broad, 2H), 3.58 (m broad, 2H), 3.46 (s, 3H), 3.20 (s, 3H), 3.10 (m, 1H), 2.93 (m, 1H), 2.70 (m, 4H), 2.17 (m, 3H), 1.80 (m, 2H), 1.68 (m, 4H), 1.37 (m, 4H), 0.95 (t, 3H).

Example 43

(S)—N-(5-Cyano-1-((2,4-dimethoxyphenyl)sulfonyl)-3-(2-ethoxypyridin-3-yl)-2-oxoindolin-3-yl)-3-(4-(3-hydroxyazetidin-1-yl)piperidin-1-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 3-hydroxyazetidin-1-yl)

ESI-MS [M+H+]=732.3

$^1$H NMR (600 MHz, DMSO) δ 8.13 (dd, 1H), 7.87 (d, J=11.1 Hz, 1H), 7.83 (m, 3H), 7.66 (s, 1H), 7.53 (s, 1H), 7.05 (dd, 1H), 6.70 (dd, 1H), 6.66 (d, 1H), 5.23 (d, 1H), 4.09 (q, 2H), 3.86 (s, 3H), 3.76 (m broad, 2H), 3.58 (m broad, 2H), 3.45 (s, 3H), 3.41 (m, 3H), 2.95 (m, 1H), 2.60 (m, 2H), 2.52 (m overlapped with DMSO), 1.91 (m, 1H), 1.78 (s, 2H), 1.58 (m, 2H), 1.11 (m, 2H), 0.95 (t, 3H).

Example 44

(S)—N-(5-Cyano-1-((2,4-dimethoxyphenyl)sulfonyl)-3-(2-ethoxypyridin-3-yl)-2-oxoindolin-3-yl)-3-(4-hydroxy-[1,4'-bipiperidin]-1'-yl)azetidine-1-carboxamide (compound of formula I.1, wherein $R^1$ is methoxy, $R^2$ is methoxy, $R^3$ is H, $R^6$ is CN, $R^7$ is H, and $R^8$ and $R^9$, together with the nitrogen atom they are bound to, form 4-hydroxypiperidin-1-yl)

ESI-MS [M+H+]=760.3

$^1$H NMR (600 MHz, DMSO) δ 8.13 (dd, 1H), 7.88 (d, 1H), 7.83 (m, 3H), 7.66 (s, 1H), 7.54 (s, 1H), 7.05 (dd, 1H), 6.70 (dd, 1H), 6.66 (d, 1H), 4.51 (d, 1H), 4.08 (q, 2H), 3.86 (s, 3H), 3.73 (m broad, 2H), 3.54 (m broad, 2H), 3.46 (s, 3H), 3.40 (m, overlapped with DMSO), 2.93 (m, 1H), 2.71 (m, 4H), 2.14 (m, 3H), 1.67 (m, 6H), 1.33 (m, 4H), 0.95 (t, 3H).

Example 45

(S)—N-(5-Cyano-3-(2,5-dimethoxyphenyl)-1-((2,4-dimethoxyphenyl)sulfonyl)-2-oxoindolin-3-yl)-3-(4-morpholinopiperidin-1-yl)azetidine-1-carboxamide (compound of formula I.16, wherein $R^1$ is methoxy, $R^2$ is methoxy, $R^3$ is H, $R^6$ is CN, $R^7$ is H, and $R^8$ and $R^9$, together with the nitrogen atom they are bound to, form morpholin-4-yl)

ESI-MS [M+H+]=761.2

$^1$H NMR (600 MHz, DMSO) δ 7.90 (d, 1H), 7.84 (d, 1H), 7.77 (dd, 1H), 7.69 (d, 1H), 7.48 (s, 1H), 7.07 (d, 1H), 6.95-6.86 (m, 2H), 6.70 (dd, 1H), 6.66 (d, 1H), 3.90 (s, 3H), 3.86 (s, 3H), 3.70-3.55 (m, 11H), 3.50 (s, 3H), 2.90 (m, 1H), 2.70 (m, 2H), 2.40 (m, 4H), 2.07 (m, 1H), 1.70 (m, 4H), 1.35 (m, 2H).

Example 46

(S)—N-(5-Cyano-3-(2,5-dimethoxyphenyl)-1-((2,4-dimethoxyphenyl)sulfonyl)-2-oxoindolin-3-yl)-3-(4-(methyl(oxetan-3-yl)amino)piperidin-1-yl)azetidine-1-carboxamide (compound of formula I.16, wherein $R^1$ is methoxy, $R^2$ is methoxy, $R^3$ is H, $R^6$ is CN, $R^7$ is H, $R^8$ is methyl, and $R^9$ is oxetan-3-yl)

ESI-MS [M+H+]=761.3

$^1$H NMR (600 MHz, DMSO) δ 7.90 (d, 1H), 7.84 (d, 1H), 7.77 (dd, 1H), 7.68 (d, 1H), 7.48 (s, 1H), 7.07 (d, 1H), 6.96-6.87 (m, 2H), 6.69 (m, 1H), 6.66 (d, 1H), 4.53-4.41 (m, 4H), 3.90-3.81 (m, 5H), 3.74 (s, 3H), 3.64-3.56 (m, 3H), 3.53 (s, 3H), 3.49 (s, 3H), 2.91 (m, 1H), 2.70 (m, 2H), 2.19 (m, 1H), 2.08 (s, 3H), 1.66 (m, 2H), 1.50 (m, 2H), 1.35 (m, 2H).

III. Determination of the Biological Activity

1. Vasopressin V1b Receptor Binding Assay:

Substances:

The test substances were dissolved in a concentration of 5 mM in 100% DMSO and further diluted to $5\times10^{-4}$M to $5\times10^{-9}$ M. These serial DMSO predilutions were diluted 1:10 with assay buffer. The substance concentration was further diluted 1:5 in the assay mixture resulting in 2% DMSO in the mixture. All dilutions were performed in a Biomek NX automation workstation (Beckman)

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (2000), membranes (26 µg protein in incubation buffer) from CHO-K1 cells with stably expressed human V1b receptors (cell line hV1b_3H2_CHO) were incubated with 1.5 nM $^3$H-AVP (8-Arg-vasopressin, PerkinElmer, NET 800) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Fluka 94836). All determinations were carried out as duplicate determinations. After incubation (60 minutes at room temperature), the free radioligand was filtered off by vacuum filtration (Tomtec Mach III) through Wathman GF/B glass fiber filter plates (UniFilter, PerkinElmer 6005177). The liquid scintillation measurement took place in a Microbeta TriLux 12 (Wallac).

Analysis:

The binding parameters were calculated by nonlinear regression in SAS. The algorithms of the program operate in analogy to the LIGAND analysis program (Munson P T and Rodbard D, Analytical Biochem. 107, 220-239 (1980)). The Kd of $^3$H-AVP for the recombinant human V1b receptors is 0.4 nM and was used to determine the Ki.

2. Vasopressin V1a Receptor Binding Assay:

Substances:

The test substances were dissolved in a concentration of 5 mM M in DMSO. Further dilution of these DMSO solutions took place as described for V1b.

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized in a High-Pressure-Homogenizer, Polytec 50K at 1500 PSI (Heinemann, Germany) and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (200 µl), membranes (40 µg protein in incubation buffer) from CHO-K1 cells with stably expressed human V1a receptors (cell line hV1a_5_CHO) were incubated with 0.04 nM $^{125}$I-AVP (8-Arg-vasopressin, PerkinElmer NEX 128) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Fluka 94836). Duplicate determinations were carried out.

After incubation (60 minutes at room temperature), the samples were processed as described for V1b.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.

3. Oxytocin Receptor Binding Assay

Substances:

The substances were dissolved in a concentration of 5 mM in DMSO and diluted further as described for V1b.

Membrane Preparation:

Confluent HEK-293 cells with transiently expressing recombinant human oxytocin receptors were harvested and centrifuged at 750×g at room temperature for 5 minutes. The pellet was taken up in ice-cold lysis buffer (50 mM Tris-HCl, 10% glycerol, pH 7.4 and Roche complete protease inhibitor) and thereby subjected to an osmotic shock at 4° C. for 20 minutes. Lysed cells were then centrifuged at 750×g at 4° C. for 20 minutes, the pellet was taken up in incubation buffer (50 mM Tris, 10 mM $MgCl_2$, 0.1% BSA, pH 7.4), and aliquots corresponding to $10^7$ cells/ml were prepared. The aliquots were frozen at −80° C. until use.

Binding Assay:

On the day of the experiment, the cell lysate was thawed, homogenized, and diluted with incubation buffer (50 mM Tris, 10 mM $MgCl_2$, 0.1% BSA, pH 7.4) to the desired concentration. The reaction mixture of 0.200 ml was composed of cell lysate corresponding to $5 \times 10^4$ cells (HEK-293 cells expressing transiently human OT receptors) and 1 nM 3H-oxytocin (PerkinElmer NET858) in the presence of test substance (displacement experiment) or incubation buffer only (total binding). The nonspecific binding was determined in the presence of 1 µM oxytocin (Bachem AG, H2510). Determinations were carried out in duplicates. After 60 minutes incubation at room temperature, bound and free radioligand were separated by filtration under vacuum on GF/B UniFilter plates (Perkin Elmer #6005177) pre-incubated with 0.3% PEI. The bound radioactivity was determined by liquid scintillation measurement in a Microbeta (Perkin Elmer) plate counter.

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant hOT receptors was 7.6 nM and was used to calculate the Ki from competition binding experiments.

4. Determination of the Microsomal Half-Life:

The metabolic stability of the compounds of the invention was determined in the following assay.

The test substances were incubated in a concentration of 0.5 µM as follows: 0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/ml)×1000 [ml/min/mg] (modified from references: Di, The Society for Biomoleculur Screening, 2003, 453-462; Obach, D M D, 1999 vol 27. N 11, 1350-1359).

5. Methods for In Vitro Determination of the Cytochrome P450 (CYP) Inhibition
Luminescent Substrates for 2C9 and 3A4:

0.4 mg/ml human liver microsomes are preincubated with the test substances to be investigated (0-20 μM), the CYP-specific substrates, in 0.05 M potassium phosphate buffer of pH 7.4 at 37° C. for 10 min. The Cyp-specific substrate for CYP 2C9 is lucifer-luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam CYP 3A4 Time-Dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 μM (or 50 μM) test substance in 50 mM potassium phosphate buffer for 5 min. The reaction is started with NADPH. After 30 min 4 μM midazolam (final concentration) are added, and incubation is continued for 10 min. 75 μl of the reaction solution are removed after 10 min, and stopped with 150 μl of acetonitrile solution.

Coincubation:

0.05 mg/ml microsomal protein (human liver microsomes) are preincubated with 4 μm midazolam (final concentration) and 0-10 μM (or 50 0\4) test substance in 50 mM potassium phosphate buffer for 5 min. The reaction is started with NADPH. 75 μl of the reaction solution are removed after 10 min and stopped with 150 μl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

6. Method for Determining the Solubility in Water (in Mg/Ml)

The solubility in water of the compounds of the invention can be determined for example by the so-called shake flask method (as specified in *ASTM International: E* 1148-02, *Standard test methods for measurement of aqueous solubility, Book of Standards Volume* 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

7. Results

The results of the receptor binding investigations are expressed as receptor binding constants [$K_i$(V1b)] or selectivities [$K_i$(V1a)/$K_i$(V1b)]. The results of the investigation of the metabolic stability are indicated as microsomal clearance (mCl).

The compounds of the invention show very high affinities for the V1b receptor in these assays (maximally 100 nM, or maximally 10 nM, frequently <1 nM). The compounds also show high selectivities vis-à-vis the V1a receptor and a good metabolic stability, measured as microsomal clearance.

The results are listed in table C. The numbers of the compounds refer to the synthesis examples.

TABLE C

| Example | $K_i$(h-V1b)* [nM] | $K_i$(h-V1a)/$K_i$(h-V1b) |
|---|---|---|
| 1 | +++ | +++ |
| 2 | +++ | +++ |
| 3 | +++ | +++ |
| 4 | ++ | +++ |
| 5 | ++ | +++ |
| 6 | ++ | +++ |
| 8 | +++ | ++ |
| 9 | +++ | ++ |
| 10 | +++ | +++ |
| 11 | ++ | ++ |
| 13 | +++ | +++ |
| 14 | +++ | ++ |
| 15 | ++ | +++ |
| 17 | + | +++ |
| 18 | +++ | +++ |
| 19 | +++ | +++ |
| 20 | ++ | + |
| 21 | +++ | + |
| 23 | ++ | ++ |
| 24 | ++ | +++ |
| 25 | +++ | ++ |
| 26 | ++ | +++ |
| 27 | +++ | +++ |
| 28 | ++ | +++ |
| 29 | ++ | + |
| 30 | ++ | + |
| 31 | ++ | + |
| 32 | ++ | + |
| 33 | + | + |
| 35 | ++ | ++ |
| 36 | ++ | + |
| 37 | ++ | +++ |
| 38 | + | + |
| 39 | + | +++ |
| 40 | +++ | +++ |
| 41 | ++ | +++ |
| 42 | ++ | +++ |
| 43 | ++ | +++ |
| 44 | +++ | +++ |
| 45 | +++ | + |
| 46 | +++ | ++ |

* h = human

Key:

| | $K_i$(h-V1b) | $K_i$(h-V1a)/$K_i$(h-V1b) |
|---|---|---|
| + | >10-100 nM | 10-<25 |
| ++ | 1-10 nM | 25-75 |
| +++ | <1 nM | >75 |

The invention claimed is:
1. A compound of formula (I)

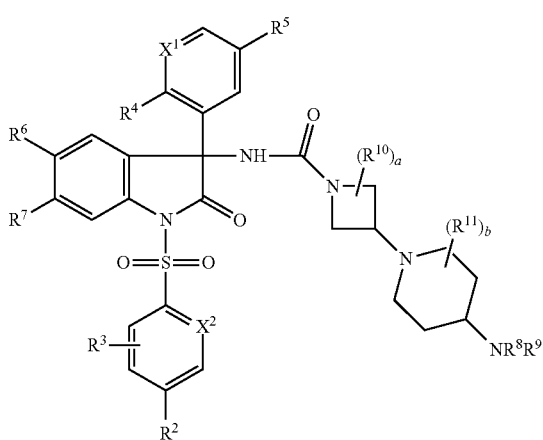

wherein
$X^1$ is N or CH;
$X^2$ is C—$R^1$ or N;
$R^1$ and $R^2$, independently of each other, are selected from the group consisting of hydrogen, halogen, cyano, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;
$R^3$ is selected from the group consisting of hydrogen, halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;
$R^4$ is $C_1$-$C_3$-alkoxy;
$R^5$ is selected from the group consisting of hydrogen and $C_1$-$C_3$-alkoxy;
$R^6$ is selected from the group consisting of cyano and halogen;
$R^7$ is selected from the group consisting of hydrogen, halogen and cyano;
$R^8$ is selected from the group consisting of hydrogen, cyano, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_7$-cycloalkyl, $C_3$-$C_7$-halocycloalkyl and phenyl which may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;
$R^9$ is selected from the group consisting of $C_1$-$C_4$-alkoxy-$C_1$-$C_4$-alkyl, $C_1$-$C_4$-haloalkoxy-$C_1$-$C_4$-alkyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, phenoxy, wherein the phenyl moiety may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, wherein the heterocyclic ring may carry 1 or 2 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or $R^8$ and $R^9$, together with the nitrogen atom they are bound to, form a 3-, 4-, 5-, 6- or 7-membered saturated, partially unsaturated or maximally unsaturated heterocyclic ring, wherein the heterocyclic ring may contain 1 or 2 further heteroatoms or heteroatom groups selected from the group consisting of O, N, S, NO, SO and $SO_2$ as ring members, and wherein the heterocyclic ring may carry 1 or 2 substituents $R^{12}$ and/or 1 or 2 substituents $R^{13}$; wherein in case that the heterocyclic ring does not contain 1 or 2 further heteroatoms or heteroatom groups as ring members, the heterocyclic ring carries 1 or 2 substituents $R^{12}$ and optionally 1 or 2 substituents $R^{13}$;
$R^{10}$ and $R^{11}$, independently of each other and independently of each occurrence, are selected from the group consisting of halogen, $C_1$-$C_4$-alkyl, $C_1$-$C_4$-haloalkyl, $C_1$-$C_4$-alkoxy and $C_1$-$C_4$-haloalkoxy, with the proviso that $R^{10}$ and $R^{11}$ are not halogen, $C_1$-$C_4$-alkoxy or $C_1$-$C_4$-haloalkoxy if they are bound to a carbon atom in α-position to a nitrogen ring atom; or
two non-geminal radicals $R^{10}$ form together a group —$(CH_2)_n$—, wherein n is 1, 2, 3 or 4, wherein 1 or 2 hydrogen atoms in this group may be replaced a methyl group; or
two non-geminal radicals $R^{11}$ form together a group —$(CH_2)_n$—, wherein n is 1, 2, 3 or 4, wherein 1 or 2 hydrogen atoms in this group may be replaced a methyl group;
each $R^{12}$ is independently selected from the group consisting of halogen, hydroxyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, phenoxy, benzyloxy, wherein the phenyl moiety in the two last-mentioned radicals may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or
two radicals $R^{12}$, together with the atom(s) they are bound to, form a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;
each $R^{13}$ is independently selected from the group consisting of halogen, hydroxyl, cyano, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_7$-cycloalkyl, $C_3$-$C_7$-halocycloalkyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, phenyl, phenoxy and a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, wherein the phenyl moieties or the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

a is 0, 1 or 2; and b is 0, 1, 2, 3 or 4;

or a N-oxide, stereoisomer, or pharmaceutically acceptable salt thereof; or the above compound, wherein at least one of the atoms has been replaced by its stable, non-radioactive isotope.

2. The compound of claim 1, wherein at least one hydrogen atom has been replaced by a deuterium atom.

3. The compound of claim 1, wherein $X^2$ is C—$R^1$ and $R^1$, $R^2$ and $R^3$, independently of each other, are selected from the group consisting of hydrogen, halogen, $C_1$-$C_3$-alkyl, fluorinated $C_1$-$C_3$-alkyl, $C_1$-$C_3$-alkoxy and fluorinated $C_1$-$C_3$-alkoxy.

4. The compound of claim 3, wherein $R^1$, $R^2$ and $R^3$, independently of each other, are selected from the group consisting of hydrogen, fluorine and methoxy.

5. The compound of claim 4, wherein $R^1$ is selected from the group consisting of hydrogen, fluorine and methoxy.

6. The compound of claim 4, wherein $R^2$ is selected from the group consisting of hydrogen, fluorine and methoxy.

7. The compound of claim 4, wherein $R^3$ is hydrogen or fluorine.

8. The compound of claim 1, wherein $X^2$ is N and $R^2$ and $R^3$, independently of each other, are selected from the group consisting of hydrogen, halogen, $C_1$-$C_3$-alkyl, fluorinated $C_1$-$C_3$-alkyl, $C_1$-$C_3$-alkoxy and fluorinated $C_1$-$C_3$-alkoxy.

9. The compound of claim 8, wherein $R^2$ is selected from the group consisting of hydrogen, fluorine and methoxy.

10. The compound of claim 8, wherein $R^3$ is selected from the group consisting of hydrogen, fluorine and methoxy.

11. The compound of claim 1, wherein $R^4$ is selected from the group consisting of methoxy and ethoxy.

12. The compound of claim 1, wherein $R^5$ is hydrogen or methoxy.

13. The compound of claim 1, wherein $R^6$ is selected from the group consisting of cyano, fluorine and chlorine.

14. The compound of claim 1, wherein $R^7$ is hydrogen or fluorine.

15. The compound of claim 1, wherein $R^8$ is selected from the group consisting of hydrogen, $C_1$-$C_4$-alkyl, $C_1$-$C_4$-haloalkyl, $C_3$-$C_6$-cycloalkyl and $C_3$-$C_6$-halocycloalkyl;

$R^9$ is selected from the group consisting of $C_1$-$C_4$-alkoxy-$C_1$-$C_4$-alkyl, $C_1$-$C_4$-haloalkoxy-$C_1$-$C_4$-alkyl, $C_1$-$C_4$-alkoxy, $C_1$-$C_4$-haloalkoxy, $C_3$-$C_6$-cycloalkoxy, $C_3$-$C_6$-halocycloalkoxy, and a 3-, 4-, 5- or 6-membered saturated, partially unsaturated or maximally unsaturated heterocyclic ring containing 1 or 2 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or $R^8$ and $R^9$, together with the nitrogen atom they are bound to, form a 3-, 4-, 5- or 6-membered saturated, partially unsaturated or maximally unsaturated heterocyclic ring, wherein the heterocyclic ring may contain 1 or 2 further heteroatoms or heteroatom groups selected from the group consisting of O, N, S, NO, SO and $SO_2$ as ring members, and wherein the heterocyclic ring may carry 1 or 2 substituents $R^{12}$ and/or 1 substituent $R^{13}$; wherein in case that the heterocyclic ring does not contain 1 or 2 further heteroatoms or heteroatom groups as ring members, the heterocyclic ring carries 1 or 2 substituents $R^{12}$ and optionally 1 substituent $R^{13}$;

each $R^{12}$ is independently selected from the group consisting of halogen, hydroxyl, $C_1$-$C_4$-alkoxy, $C_1$-$C_4$-haloalkoxy, $C_3$-$C_6$-cycloalkoxy, $C_3$-$C_6$-halocycloalkoxy, and a 3-, 4-, 5- or 6-membered saturated, partially unsaturated or maximally unsaturated heterocyclic ring containing 1 or 2 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

or two radicals $R^{12}$, together with the atom(s) they are bound to, form a 3-, 4-, 5- or 6-membered saturated, partially unsaturated or maximally unsaturated heterocyclic ring containing 1 or 2 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and $R^{13}$ is selected from the group consisting of halogen, hydroxyl, cyano, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl, $C_3$-$C_6$-halocycloalkyl, $C_1$-$C_4$-alkoxy, $C_1$-$C_4$-haloalkoxy, $C_3$-$C_7$-cycloalkoxy, $C_3$-$C_7$-halocycloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, phenyl, phenoxy and a 3-, 4-, 5- or 6-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, wherein the phenyl moieties or the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy.

16. The compound of claim 15, wherein $R^8$ is selected from the group consisting of hydrogen, $C_1$-$C_4$-alkyl, fluorinated $C_1$-$C_4$-alkyl, $C_3$-$C_6$-cycloalkyl and fluorinated $C_3$-$C_6$-cycloalkyl;

$R^9$ is selected from the group consisting of $C_1$-$C_4$-alkoxy-$C_1$-$C_4$-alkyl, fluorinated $C_1$-$C_4$-alkoxy-$C_1$-$C_4$-alkyl, $C_1$-$C_4$-alkoxy, fluorinated $C_1$-$C_4$-alkoxy, and a 3-, 4-, 5- or 6-membered saturated heterocyclic ring containing 1 or 2 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; or $R^8$ and $R^9$, together with the nitrogen atom they are bound to, form a 3-, 4-, 5- or 6-membered saturated heterocyclic ring, wherein the heterocyclic ring may contain 1 or 2 further heteroatoms or heteroatom groups selected from the group consisting of O, N, S, NO, SO and $SO_2$ as ring members, and wherein the heterocyclic ring may carry 1 or 2 substituents and/or 1 substituent $R^{13}$; wherein in case that the heterocyclic ring does not contain 1 or 2 further heteroatoms or heteroatom groups as ring members, the heterocyclic ring carries 1 or 2 substituents $R^{12}$ and optionally 1 substituent $R^{13}$;

each $R^{12}$ is independently selected from the group consisting of halogen, hydroxyl, $C_1$-$C_4$-alkoxy, fluorinated $C_1$-$C_4$-alkoxy, and a 3-, 4-, 5- or 6-membered saturated heterocyclic ring containing 1 or 2 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-haloalkyl, $C_1$-$C_4$-alkoxy and $C_1$-$C_4$-haloalkoxy; or two radicals $R^{12}$, together with the atom(s) they are bound to, form a 3-, 4-, 5- or 6-membered saturated heterocyclic ring containing 1 or 2 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkoxy and $C_1$-$C_4$-haloalkoxy; and $R^{13}$ is selected from the group consisting of halogen, hydroxyl, cyano, fluorinated $C_1$-$C_4$-alkyl, $C_1$-$C_4$-alkoxy-$C_1$-$C_4$-alkyl, fluorinated $C_1$-$C_4$-alkoxy-$C_1$-$C_4$-alkyl, $C_3$-$C_6$-cycloalkyl, fluorinated $C_3$-$C_6$-cycloalkyl, $C_1$-$C_4$-alkoxy, fluorinated $C_1$-$C_4$-alkoxy, and a 3-, 4-, 5- or 6-membered saturated, partially unsaturated or maximally unsaturated heterocyclic ring containing 1 or 2 heteroatoms or heteroatom groups selected from the group consisting of O, N, S, NO, SO and $SO_2$ as ring members, wherein the heterocyclic ring may carry 1, 2 or 3 substituents selected from the group consisting of halogen, hydroxyl, cyano, $C_1$-$C_4$-alkoxy and $C_1$-$C_4$-haloalkoxy.

17. The compound of claim 16, wherein
$R^8$ is selected from the group consisting of hydrogen, $C_1$-$C_4$-alkyl and $C_3$-$C_6$-cycloalkyl;
$R^9$ is selected from the group consisting of $C_1$-$C_4$-alkoxy-$C_1$-$C_4$-alkyl, fluorinated $C_1$-$C_4$-alkoxy-$C_1$-$C_4$-alkyl, $C_1$-$C_4$-alkoxy, fluorinated $C_1$-$C_4$-alkoxy, and a 3-, 4-, 5- or 6-membered saturated heterocyclic ring containing 1 oxygen atom as ring member; or
$R^8$ and $R^9$, together with the nitrogen atom they are bound to form a 3-, 4-, 5- or 6-membered saturated heterocyclic ring, wherein the heterocyclic ring contains 1 further oxygen atom as ring member, and wherein the heterocyclic ring may carry 1 or 2 substituents $R^{12}$; or form a 3-, 4-, 5- or 6-membered saturated heterocyclic ring which carries 1 or 2 substituents $R^{12}$; and each $R^{12}$ is independently selected from the group consisting of halogen, hydroxyl, $C_1$-$C_4$-alkoxy, and a 3-, 4-, 5- or 6-membered saturated heterocyclic ring containing 1 oxygen atom as ring member; or
two radicals $R^{12}$ bound to the same carbon ring atom, together with this carbon atom they are bound to, form a 3-, 4-, 5- or 6-membered saturated heterocyclic ring containing 1 oxygen atom as ring member.

18. The compound of claim 17, wherein the saturated heterocyclic ring formed by $R^8$ and $R^9$ together with the nitrogen atom they are bound to is selected from the group consisting of azetidin-1-yl carrying in the 3-position (relative to the 1-position of the nitrogen ring atom) 1 or 2 substituents isoxazolidin-2-yl, piperidin-1-yl carrying in the 4-position (relative to the 1-position of the nitrogen ring atom) 1 or 2 substituents $R^{12}$; and morpholin-1-yl.

19. The compound of claim 17, wherein two radicals $R^{12}$ bound to the same carbon ring atom together form a group —$CH_2$—O—$CH_2$— (i.e. together with the carbon atom they are bound to form a spiro-bound oxetan-3-yl ring).

20. The compound of claim 1, wherein each $R^{10}$ is independently selected from the group consisting of halogen and $C_1$-$C_4$-alkyl with the proviso that $R^{10}$ is not halogen if it is bound to a carbon atom in α-position to a nitrogen ring atom.

21. The compound of claim 1, wherein each $R^{11}$ is independently selected from the group consisting of halogen and $C_1$-$C_4$-alkyl with the proviso that $R^{11}$ is not halogen if it is bound to a carbon atom in α-position to a nitrogen ring atom; or two non-geminal radicals $R^{11}$ form together a group —$CH_2$—.

22. The compound of claim 1, wherein $X^1$ is N.
23. The compound of claim 1, wherein $X^1$ is CH.
24. The compound of claim 1, wherein $X^2$ is C—$R^1$.
25. The compound of claim 1, wherein $X^2$ is N.
26. The compound of claim 1, wherein a is 0 or 1.
27. The compound of claim 1, wherein b is 0, 1 or 2.
28. A compound selected from the group consisting of
(S)—N-(5-cyano-1-((2,4-dimethoxyphenyl)sulfonyl)-3-(2-ethoxypyridin-3-yl)-2-oxoindolin-3-yl)-3-(4-morpholinopiperidin-1-yl)azetidine-1-carboxamide;

(S)—N-(5-cyano-1-((2,4-dimethoxyphenyl)sulfonyl)-3-(2-ethoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-morpholinopiperidin-1-yl)azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-(ethyl(oxetan-3-yl)amino)piperidin-1-yl)azetidine-1-carboxamide;

(S)-3-(4-(2-Oxa-7-Azaspiro[3.5]nonan-7-yl)piperidin-1-yl)-N-(5-cyano-1-((2,4-dimethoxyphenyl)sulfonyl)-3-(2-ethoxypyridin-3-yl)-2-oxoindolin-3-yl)azetidine-1-carboxamide;

N-[(3S)-5-Cyano-1-(2,4-dimethoxyphenyl)sulfonyl-3-(2-ethoxy-3-pyridyl)-2-oxo-indolin-3-yl]-3-[4-[cyclopropyl(oxetan-3-yl)amino]-1-piperidyl]azetidine-1-carboxamide;

(S)—N-(1-((2,4-Dimethoxyphenyl)sulfonyl)-3-(2-ethoxypyridin-3-yl)-5,6-difluoro-2-oxoindolin-3-yl)-3-(4-morpholinopiperidin-1-yl)azetidine-1-carboxamide;

(S)—N-(5-Cyano-1-((2,4-dimethoxyphenyl)sulfonyl)-3-(2-ethoxypyridin-3-yl)-6-fluoro-2-oxoindolin-3-yl)-3-(4-morpholinopiperidin-1-yl)azetidine-1-carboxamide;

(S)—N-(5-Cyano-1-((2,4-dimethoxyphenyl)sulfonyl)-3-(2-ethoxypyridin-3-yl)-6-fluoro-2-oxoindolin-3-yl)-3-(4-(methyl(oxetan-3-yl)amino)piperidin-1-yl)azetidine-1-carboxamide;

N-[(3S)-1-[(2,4-Dimethoxyphenyl)sulfonyl]-3-(2-ethoxypyridin-3-yl)-5,6-difluoro-2-oxo-2,3-dihydro- 1H-indol-3-yl]-3-{4-[methyl(oxetan-3-yl)amino]piperidin-1-yl}azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-(cyclopropyl(oxetan-3-yl)amino)piperidin-1-yl)azetidine-1-carboxamide;

(S)—N-(5-Chloro-1-((2,4-dimethoxyphenyl)sulfonyl)-3-(2-ethoxypyridin-3-yl)-2-oxoindolin-3-yl)-3-(4-morpholinopiperidin-1-yl)azetidine-1-carboxamide;

(S)—N-(5-Chloro-1-((2,4-dimethoxyphenyl)sulfonyl)-3-(2-ethoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-((2-methoxyethyl)(methyl)amino)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-(methoxy(methyl)amino)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-(isoxazolidin-2-yl)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-(3-(oxetan-3-yl)azetidin-1-yl)piperidin-1-yl)azetidine-1-carboxamide;

(S)-3-(4-(2-Oxa-6-azaspiro[3.3]heptan-6-yl)piperidin-1-yl)-N-(5-cyano-1-((2,4-dimethoxyphenyl)sulfonyl)-3-(2-ethoxypyridin-3-yl)-2-oxoindolin-3-yl)azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-(oxetan-3-ylamino)piperidin-1-yl)azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-(methyl(tetrahydro-2H-pyran-4-yl)amino)piperidin-1-yl)azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-(oxetan-3-yl(propyl)amino)piperidin-1-yl)azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-(ethyl(oxetan-3-yl)amino)piperidin-1-yl)azetidine-1-carboxamide;

(S)—N-(5-Cyano-3-(2-ethoxypyridin-3-yl)-1-((5-fluoro-2,4-dimethoxyphenyl)sulfonyl)-2-oxoindolin-3-yl)-3-(4-morpholinopiperidin-1-yl)azetidine-1-carboxamide;

(S)—N-(5-Cyano-3-(2-ethoxypyridin-3-yl)-1-((4-methoxyphenyl)sulfonyl)-2-oxoindolin-3-yl)-3-(4-morpholinopiperidin-1-yl)azetidine-1-carboxamide;

(S)—N-(5-Cyano-1-((2,4-difluorophenyl)sulfonyl)-3-(2-ethoxypyridin-3-yl)-2-oxoindolin-3-yl)-3-(4-morpholinopiperidin-1-yl)azetidine-1-carboxamide;

(S)—N-(5-cyano-3-(2-ethoxypyridin-3-yl)-1-((2-fluoro-4-methoxyphenyl)sulfonyl)-2-oxoindolin-3-yl)-3-(4-morpholinopiperidin-1-yl)azetidine-1-carboxamide;

(S)—N-(5-cyano-3-(2-ethoxypyridin-3-yl)-1-((4-fluoro-2-methoxyphenyl)sulfonyl)-2-oxoindolin-3-yl)-3-(4-morpholinopiperidin-1-yl)azetidine-1-carboxamide;

(S)—N-(5-Cyano-1-((2-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((4-fluoro-2-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((4-fluorophenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((2-fluoro-4-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((2,4-difluorophenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-Cyano-1-((5-fluoro-2,4-dimethoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-cyano-1-((4-methoxyphenyl)sulfonyl)-3-(2-methoxypyridin-3-yl)-2-oxoindolin-3-yl)-3-(4-(methyl(oxetan-3-yl)amino)piperidin-1-yl)azetidine-1-carboxamide;

(S)—N-(5-Cyano-3-(2-ethoxypyridin-3-yl)-1-((5-methoxypyridin-2-yl)sulfonyl)-2-oxoindolin-3-yl)-3-(4-morpholinopiperidin-1-yl)azetidine-1-carboxamide;

(S)—N-(5-Cyano-3-(2-ethoxypyridin-3-yl)-1-((2-methoxyphenyl)sulfonyl)-2-oxoindolin-3-yl)-3-(4-morpholinopiperidin-1-yl)azetidine-1-carboxamide;

(S)—N-(5-Cyano-1-((2,4-dimethoxyphenyl)sulfonyl)-3-(2-methoxypyridin-3-yl)-2-oxoindolin-3-yl)-3-(4-(isopropyl(oxetan-3-yl)amino)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-(3,3-difluoroazetidin-1-yl)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4,4-difluoro-[1,4'-bipiperidin]-1'-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-((3-methoxyazetidin-1-yl)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-methoxy-[1,4'-bipiperidin]-1'-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-(3-hydroxyazetidin-1-yl)piperidin-1-yl)azetidine-1-carboxamide;

(S)—N-(5-Cyano-1-((2,4-dimethoxyphenyl)sulfonyl)-3-(2-ethoxypyridin-3-yl)-2-oxoindolin-3-yl)-3-(4-hydroxy-[1,4'-bipiperidin]-1'-yl)azetidine-1-carboxamide;

(S)—N-(5-Cyano-3-(2, 5-dimethoxyphenyl)-1-((2,4-dimethoxyphenyl)sulfonyl)-2-oxoindolin-3-yl)-3-(4-morpholinopiperidin-1-yl)azetidine-1-carboxamide; and N-(5-Cyano-3-(2, 5-dimethoxyphenyl)-1-((2,4-dimethoxyphenyl)sulfonyl)-2-oxoindolin-3-yl)-3-(4-(methyl(oxetan-3-yl)amino)piperidin-1-yl)azetidine-1-carboxamide;

or a N-oxide, stereoisomer, or pharmaceutically acceptable salt thereof; or the above compound, wherein at least one of the atoms has been replaced by its stable, non-radioactive isotope.

29. A pharmaceutical composition comprising a compound of claim 1 or an N-oxide, a stereoisomer, or a pharmaceutically acceptable salt thereof and at least one pharmaceutically acceptable carrier.

\* \* \* \* \*